(12) United States Patent
Bondy-Denomy et al.

(10) Patent No.: US 11,485,760 B2
(45) Date of Patent: Nov. 1, 2022

(54) INHIBITORS OF CRISPR-CAS9

(71) Applicant: The Regents of the University of California, Oakland, CA (US)

(72) Inventors: Joseph Bondy-Denomy, Oakland, CA (US); Benjamin Rauch, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 496 days.

(21) Appl. No.: 16/349,253

(22) PCT Filed: Nov. 16, 2017

(86) PCT No.: PCT/US2017/061932
§ 371 (c)(1),
(2) Date: May 10, 2019

(87) PCT Pub. No.: WO2018/093990
PCT Pub. Date: May 24, 2018

(65) Prior Publication Data
US 2020/0087354 A1 Mar. 19, 2020

Related U.S. Application Data

(60) Provisional application No. 62/422,850, filed on Nov. 16, 2016.

(51) Int. Cl.
| | |
|---|---|
| C07K 14/195 | (2006.01) |
| A61K 35/14 | (2015.01) |
| A61K 35/28 | (2015.01) |
| C12N 15/85 | (2006.01) |

(52) U.S. Cl.
CPC ............ *C07K 14/195* (2013.01); *A61K 35/14* (2013.01); *A61K 35/28* (2013.01); *C12N 15/85* (2013.01)

(58) Field of Classification Search
CPC ...... C07K 14/195; C12N 15/85; A61K 35/14; A61K 35/28
See application file for complete search history.

(56) References Cited

U.S. PATENT DOCUMENTS

2006/0078901 A1    4/2006   Buchrieser et al.

FOREIGN PATENT DOCUMENTS

| JP | 2004507217 A | 3/2004 | | |
|---|---|---|---|---|
| WO | 2014093479 A1 | 6/2014 | | |
| WO | 2014/128659 A1 | 8/2014 | | |
| WO | WO-2018093990 A1 * | 5/2018 | ............. | A61K 35/14 |
| WO | 2019/034784 A1 | 2/2019 | | |
| WO | 2019/093479 A1 | 5/2019 | | |

OTHER PUBLICATIONS

Timme et al., "Listeria Monocytogenes anti-CRISPR Protein AcrIIA4," EMBL Database, Feb. 6, 2016, p. 143 XP055767976, (Internet ebi.ac.uk/ena/browser/api/embl/AMD24318.1?lineLimit-1000).
Borowsky et al., "Listeria Monocytogenes J0161 Hypothetical Protein," XX OS Listeria monocytogenes J0161 OC Bacteria, Sep. 8, 2011, XP055767859, (Internet ebi.ac.uk/ena/browser/api/embl/AE004689.1?lineLimit=1000).
Bondy-Denomy et al. Multiple mechanisms for CRISPR-Cas inhibition by anti-CRISPR proteins. Nature. Oct. 2015;526(7571):136-9.
Bondy-Denomy, et al. Bacteriophage genes that inactivate the CRISPR/Cas bacterial immune system. Nature. Jan. 2013;493(7432):429-32.
International Search Report in PCT/US2017/061932, dated Mar. 13, 2018, 2 pages.
Supplementary Partial European Search Report in EP 17 87 2333, dated Nov. 3, 2020, 13 pages.
Rauch, et al. Inhibition of CRISPR-Cas9 with bacteriophage proteins. Cell. Jan. 12, 2017;168(1-2):150-8.
Database EMBL, Dorscht et al, Bacteriophages of Listeria Monocytogenes, XP055744738, retrieved from EBI Database Accession No. A8ATW7, Oct. 23, 2007, 1 page.
Pawluk, et al. Inactivation of CRISPR-Cas systems by anti-CRISPR proteins in diverse bacterial species. Nature microbiology. Jun. 13, 2016;1(8):1-6.
Hypothetical Protein (Listeria Monocytogenes) NCBI Reference Sequence WP_0037225218.1, May 24, 2013.
"Conserved Hypothetical Protein Listeria Monocytogenes", DataBase: GenPept, CUL91420, Available Online at: https://www.ncbi.nlm.nih.gov/protein/CUL91420, Jan. 29, 2016, 1 page.
"Gp108", DataBase: UniProt, [online], Q30L37, Available Online at: https://www.uniprot.org/uniprot/Q30L37, Dec. 6, 2005, 1 page.
"Hypothetical Protein Listeria Monocytogenes", Database: GenPept, WP_046376634, Available Online at: https://www.ncbi.nlm.nih.gov/protein/814561750?sat=47&satkey=98889600, Apr. 23, 2015, 1 page.
"Hypothetical Protein Listeria Monocytogenes", Database: GenPept, WP_069001216, Available Online at: https://www.ncbi.nlm.nih.gov/protein/1059898626?sat=47&satkey=98904541, Aug. 26, 2016, 1 page.
"Hypothetical Protein Listeria Monocytogenes", DataBase GenPept, WP_060954847, Available Online at: https://www.ncbi.nlm.nih.gov/protein/988800496?sat=47&satkey=98899024, Feb. 10, 2016, 1 page.
"Hypothetical Protein Listeria Monocytogenes", DataBase GenPept, WP_061107115, Available Online at: https://www.ncbi.nlm.nih.gov/protein/1000359812?sat=47&satkey=98899140, Feb. 24, 2016, 1 page.
"Hypothetical Protein Listeria Monocytogenes", DataBase: GenPept, WP_061385557, Available Online at: https://www.ncbi.nlm.nih.gov/protein/1002432309?sat=47&satkey=98899318, Mar. 2, 2016, 1 page.

(Continued)

*Primary Examiner* — Karen Cochrane Carlson
(74) *Attorney, Agent, or Firm* — Kilpatrick Townsend & Stockton LLP

(57) ABSTRACT

Cas9-inhibiting polypeptide compositions and methods are provided.

19 Claims, 23 Drawing Sheets

Specification includes a Sequence Listing.

(56) References Cited

OTHER PUBLICATIONS

"Hypothetical Protein Listeria Monocytogenes", DataBase: GenPept, WP_003740262, Available Online at: https://www.ncbi.nlm.nih.gov/protein/489836546?sat=47&satkey=98854487, May 13, 2013, 1 page.
"Hypothetical Protein Listeria Monocytogenes", Database: GenPept, KLI10194, Available Online at: https://www.ncbi.nlm.nih.gov/protein/KLI10194, May 22, 2015, 1 page.
"Hypothetical Protein Listeria Monocytogenes", Database: GenPept, WP_003723290, Available Online at: https://www.ncbi.nlm.nih.gov/protein/489819479?sat=17&satkey=1 6991215, May 7, 2013, 1 page.
"Hypothetical Protein Listeria Monocytogenes", DataBase GenPept, WP_070295973, Available Online at: https://www.ncbi.nlm.nih.gov/protein/1079979452?sat=47&satkey=98909136, Oct. 14, 2016, 1 page.
"Hypothetical Protein Listeria Monocytogenes", Database: Genpept, WP_031667946, Available Online at: https://www.ncbi.nlm.nih.gov/protein/685935189?sat=47&satkey=98875473, Sep. 19, 2014, 1 page.
"Phage Protein, Putative Listeria Monocytogenes", DataBase: GenPept, CAR82813, Available Online at: https://www.ncbi.nlm.nih.gov/protein/CAR82813 > (Newly cited documents, Feb. 27, 2015, 1 page.
"Uncharacterized Protein", DataBase UniProt, A0A0E0UT28, Available Online at: https://www.uniprot.org/uniprot/A0A0E0UT28, May 27, 2015, 1 page.
"Uncharacterized Protein", DataBase: UniProt, M4H0H1, Available Online at: https://www.uniprot.org/uniprot/M4H0H1, May 29, 2013, 1 page.
"Uncharacterized Protein", DataBase: UniProt, A0A068CBP6, Available Online at: https://www.uniprot.org/uniprot/A0A068CBP6, Oct. 1, 2014, 1 page.
"Uncharacterized Protein", DataBase: UniProt, A0A068CCW6, Available Online at: https://www.uniprot.org/uniprot/A0A068CCW6, Oct. 1, 2014, 1 page.
"Uncharacterized Protein", DataBase: UniProt, A0A076G604, Available Online at: https://www.uniprot.org/uniprot/A0A076G604, Oct. 29, 2014, 1 page.
"Uncharacterized Protein", DataBase: UniProt, A0A059T5N9, Available Online at: https://www.uniprot.org/uniprot/A0A059T5N9, Sep. 3, 2014, 1 page.
"Uncharacterized Protein", DataBase: UniProt, A0A059T899, Available Online at: https://www.uniprot.org/uniprot/A0A059T899, Sep. 3, 2014, 1 page.
"Uncharacterized Protein", DataBase: UniProt, A0A060AFL3, Available Online at: https://www.uniprot.org/uniprot/A0A060AFL3, Sep. 3, 2014, 1 page.
"Uncharacterized Protein", DataBase: UniProt, A0A060ALR2, Available Online at: https://www.uniprot.org/uniprot/A0A060ALR2, Sep. 3, 2014, 1 page.
Application No. EP17872333.4, Extended European Search Report, dated Feb. 2, 2021, 12 pages.
Application No. PCT/US2017/061932, International Preliminary Report on Patentability, dated May 31, 2019, 10 pages.
PCT/US2017/061932, "Invitation to Pay Add'l Fees and Partial Search Report", dated Jan. 24, 2018, 2 pages.

\* cited by examiner

FIG. 1A
FIG. 1B
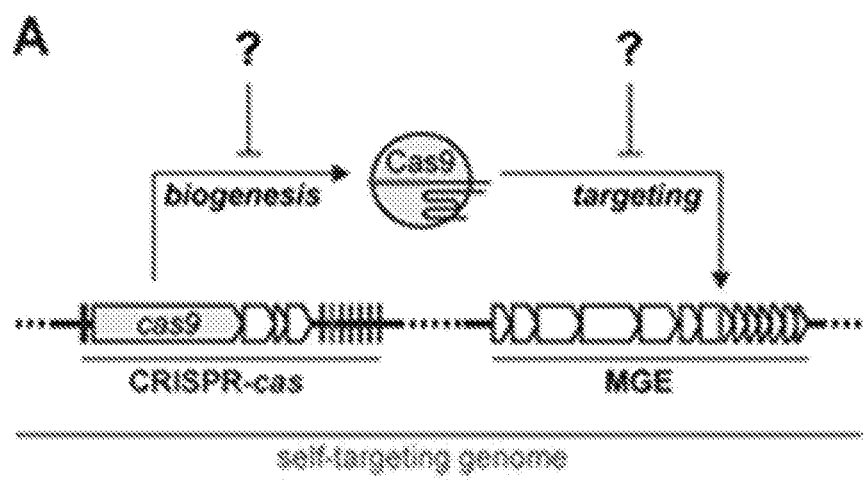
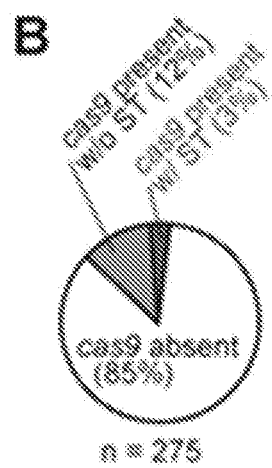
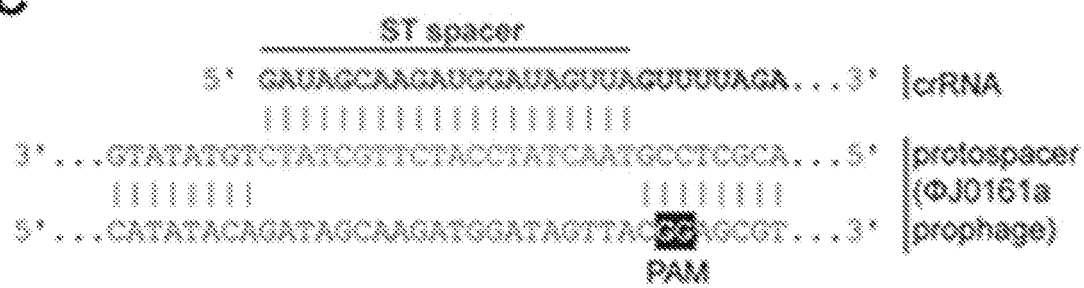
FIG. 1C

FIG. 2A
FIG. 2B
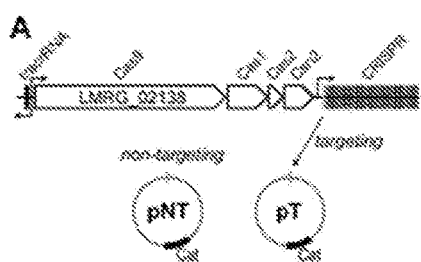
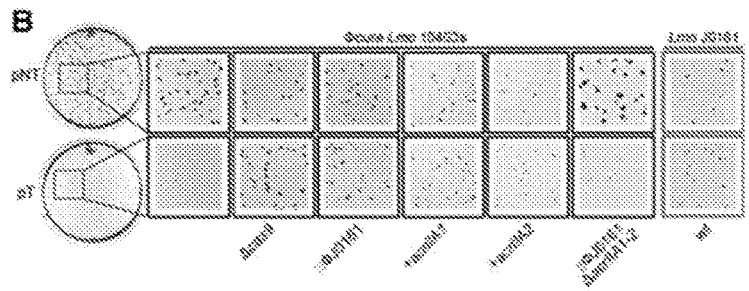
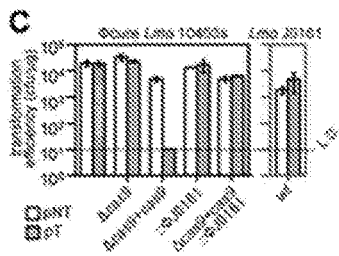
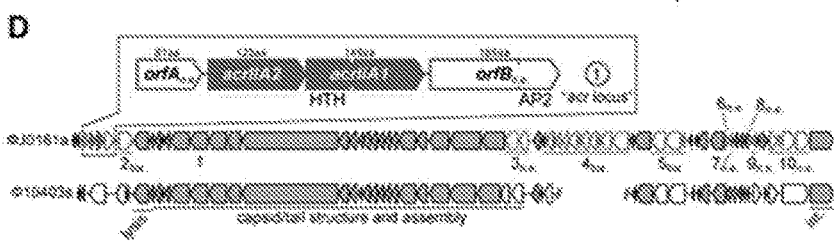
FIG. 2C
FIG. 2D

*FIG. 3A*
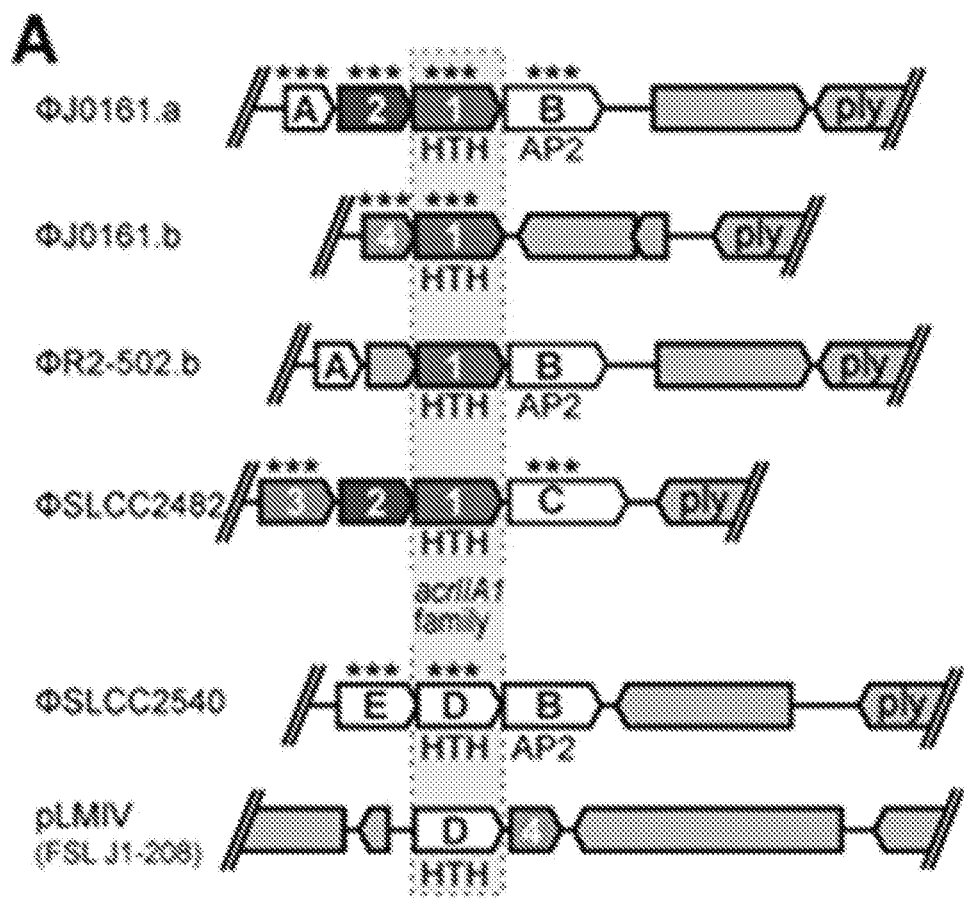
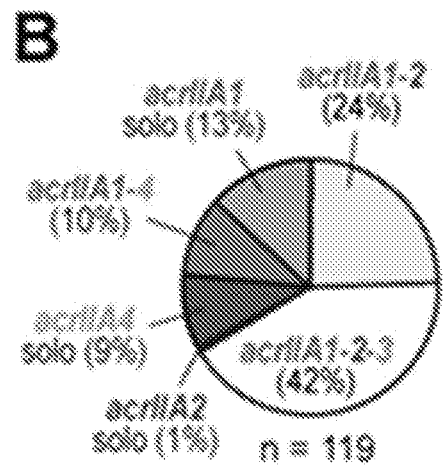
*FIG. 3B*
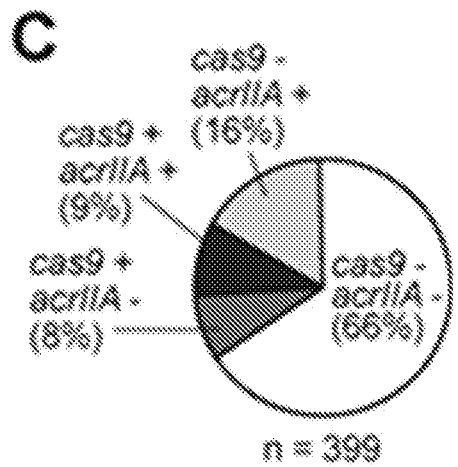
*FIG. 3C*

FIG. 7F (continued)

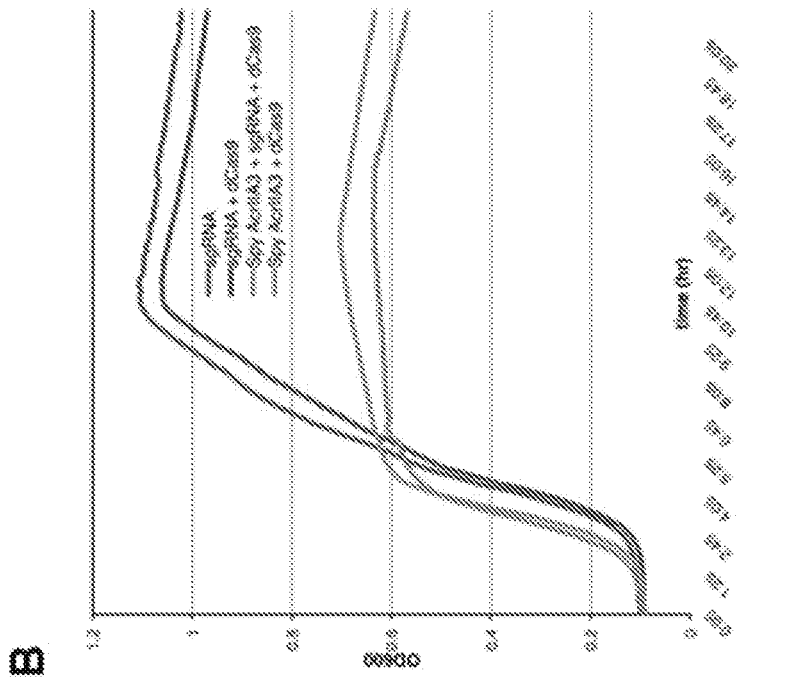
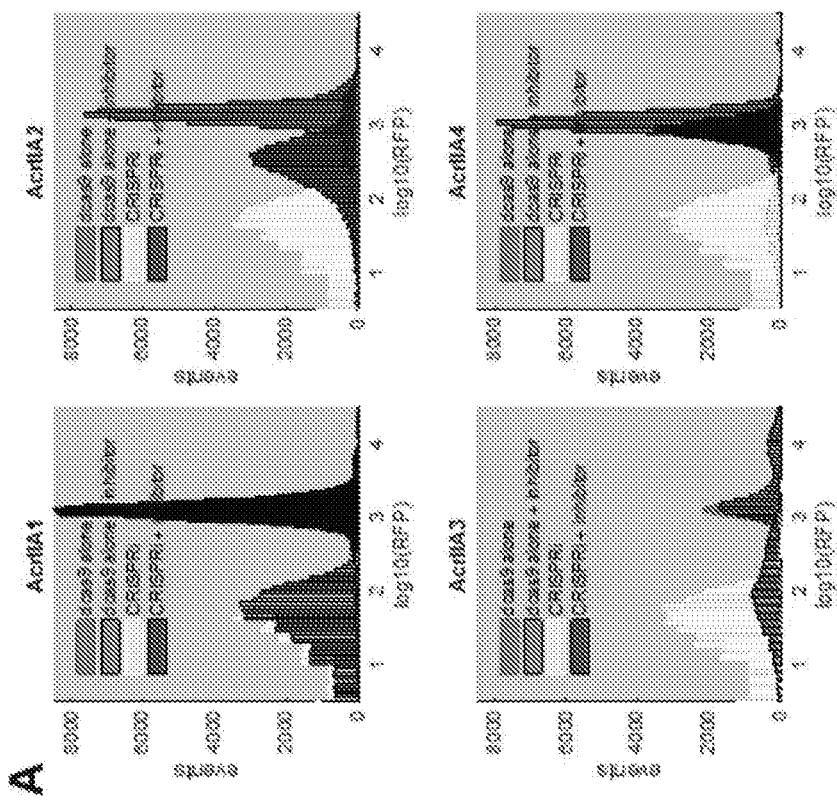
FIG. 11A
FIG. 11B

AcrIIA2 superfamily alignment

AcrIIA2a.1: Functions in Listeria, modest heterologous function
AcrIIA2b.1: Strong function in heterologous bacteria
AcrIIA2b.3: Strong function in heterologous bacteria
AcrIIA2c.1: Toxic in bacteria

*FIG. 15A*

| Name | % ID to AcrIIA2a.1 | Accession |
|---|---|---|
| AcrIIA2a.1 | 100 | WP_003722517.1 |
| AcrIIA2b.1 | 36 | WP_061112069.1 |
| AcrIIA2b.3 | 35 | KXX34219.1 |
| AcrIIA2c.1 | 50 | WP_015967155.1 |

53% ID (between WP_061112069.1 and KXX34219.1)

*FIG. 15B*

AcrIIA3 homolog searches

| Species | Cas9 %ID | acrIIA3 | Accession # | Acr %ID | Toxic? | Acr? |
|---|---|---|---|---|---|---|
| S. pyogenes | 100% | acrIIA3b.1 | WP_023611744.1 | 100% | YES | NA |
| S. phocae | 70% | acrIIA3b.2 | KGR72913.1 | 67% | NO | YES |
| S. cuniculi | 63% | acrIIA3b.3 | OLF47316.1 | 39% | NO | YES |
| S. pseudopneumo. | 63% | acrIIA3b.4 | WP_049537331.1 | 46% | NO | YES |
| L. monocytogenes | 53% | acrIIA3a.1 | WP_014930691.1 | 43% | YES | NA |

AcrIIA2

- Original gene (2a) has modest activity in *E. coli, P. aeruginosa*, human.
- New homolog (2b.1/2b.3) has enhanced activity in *P. aeruginosa*
- New homolog (2c) is toxic in *P. aeruginosa*

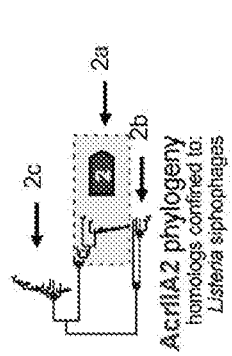

AcrIIA2 phylogeny
homologs confined to:
*Listeria* siphophages

AcrIIA3

- Original genes (3a, Lmo and 3b, Spy) were both toxic in *E. coli, P. aeruginosa* and non-toxic but non-functional in human
- New homologs (3b.2, 3b.3, 3b.4, all from Streptococcal species) are functional and non-toxic in *P. aeruginosa*

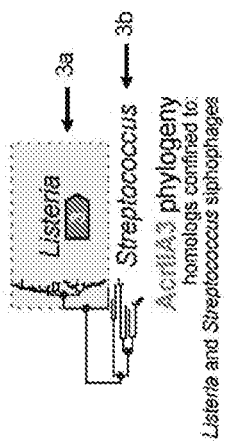

AcrIIA3 phylogeny
homologs confined to:
*Listeria* and *Streptococcus* siphophages

AcrIIA4

- Original gene (4a) functions in *E. coli, P. aeruginosa*, human cells.
- New homolog (4b) functional in *P. aeruginosa* but less active than 4a
- New homolog (4c) is toxic in *P. aeruginosa*

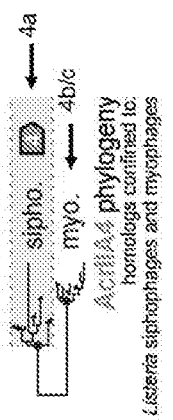

AcrIIA4 phylogeny
homologs confined to:
*Listeria* siphophages and myophages

*FIG. 19*

INHIBITORS OF CRISPR-CAS9

CROSS REFERENCE TO RELATED PATENT APPLICATIONS

The present application claims benefit of priority to U.S. Provisional Patent Application No. 62/422,850, filed Nov. 16, 2016, which is incorporated by referenced for all purposes.

BACKGROUND OF THE INVENTION

The ability to prevent attack from viruses is a hallmark of cellular life. Bacteria employ multiple mechanisms to resist infection by bacterial viruses (phages), including restriction enzymes and CRISPR-Cas systems (Labrie, S. J., Samson, J. E., and Mineau, S. (2010). Nat Rev Micro, 8, 317-327). CRISPR arrays possess the sequence-specific remnants of previous encounters with mobile genetic elements as small spacer sequences located between their clustered regularly interspaced short palindromic repeats (Mojica, F. J. M et al. (2005). J. Mol. Evol., 60, 174-182). These spacers are utilized to generate guide RNAs that facilitate the binding and cleavage of a programmed target (Brouns, S. J. J et al. (2008). Science, 321, 960-964; Garneau, J. E. et al. (2010). Nature, 468, 67-71). CRISPR-associated (cas) genes that are required for immune function are often found adjacent to the CRISPR array (Marraffini, L. A. (2015). CRISPR-Cas immunity in prokaryotes, Nature, 526, 55-61; Wright, A. V., Nuñez, J. K., and Doudna, J. A. (2016). Cell, 164, 29-44). Cas proteins not only carry out the destruction of a foreign genome (Garneau, J. E. et al, (2010). Nature, 468, 67-71), but also facilitate the production of mature CRISPR RNAs (crRNAs) (Deltcheva; Haurwitz, R. E et al. (2010). Science, 329, 1355-1358) and the acquisition of foreign sequences into the CRISPR array (Nuñez, J. K. et al. (2014). Nat. Struct. Mol. Biol, 21, 528-534; Yosef, I., Goren, M. G., and Qimron, U. (2012). Nucleic Acids Research, 40, 5569-5576).

CRISPR-Cas adaptive immune systems are common and diverse in the bacterial world. Six different types (I-VI) have been identified across bacterial genomes (Abudayyeh, O. O et al. (2016). Science aaf5573; Makarova, K. S. et al. (2015). Nat Rev Micro, 13, 722-736). Nat Rev Micro, 13, 722-736), with the ability to cleave target DNA or RNA sequences as specified by the RNA guide. The facile programmability of CRISPR-Cas systems has been widely exploited, opening up the door to many novel genetic technologies (Barrangou, R., and Doudna, J. A. (2016), Nature Biotechnology, 34, 933-941). Most of these technologies use Cas9 from *Streptococcus pyogenes* (Spy), together with an engineered single guide RNA as the foundation for such applications, including gene editing in animal cells (Cong, L. et al. (2013). Science 339, 819-823; Jinek, M. et al. (2012). Science, 337, 816-821; Mali, P, et al. (2013). Science, 339, 823-826; Qi, L. S. et al. (2013). Cell, 152, 1173-1183). Additionally, Cas9 orthologs within the II-A subtype have been investigated for gene editing applications (Ran, F. A. et al. (2015). Nature 520, 186-191), and new Class 2 CRISPR single protein effectors such as Cpf1 (Type V (Zetsche, B. et al. (2015). Cell, 163, 759-771)) and C2c2 (Type VI (Abudayyeh, O. O et al. (2016). Science aaf5573; East-Seletsky, A. et al. (2016). Nature 538, 270-273) are being characterized. Class 1 CRISPR-Cas systems (Type I, III, and IV) are RNA-guided multi-protein complexes and thus have been overlooked for most genomic applications due to their complexity. These systems are, however, the most common in nature being found in nearly half of all bacteria and 85% of archaea (Makarova, K. S. et al. (2015). Nat Rev Micro, 13, 722-736). Nat Rev Micro, 13, 722-736).

In response to the bacterial war on phage infection, phages, in turn, often encode inhibitors of bacterial immune systems that enhance their ability to lyse their host bacterium or integrate into its genome (Samson, J. E. et al. (2013). Nat Rev Micro, 11, 675-687). The first examples of phage-encoded "anti-CRISPR" proteins came for the (Class 1) type I-E and I-F systems in *Pseudomonas aeruginosa* (Bondy-Denomy et al. (2013). Nature, 493, 429-432; Pawluk, A. et al. (2014). mBio 5, e00896). Remarkably, ten type I-F anti-CRISPR and four type I-E anti-CRISPR genes have been discovered to date (Pawluk, A. et al. (2016). Nature Microbiology, 1, 1-6), all of which encode distinct, small proteins (50-150 amino acids), previously of unknown function. Our biochemical investigation of four I-F anti-CRISPR proteins revealed that they directly interact with different Cas proteins in the multi-protein CRISPR-Cas complex to prevent either the recognition or cleavage of target DNA (Bondy-Denomy, J et al. (2015). Nature, 526, 136-139). Each protein has a distinct sequence, structure, and mode of action (Maxwell, K. L. et al. (2016). Nature Communications, 7, 13134; Wang, X. (2016). Nat. Struct. Biol 23, 868-870). These findings support the independent evolution of CRISPR-Cas inhibitors and suggests that many more are yet to be discovered. In this light, a recent paper utilized the conservation of signature anti-CRISPR associated (aca) gene with a predicted helix-turn-helix (HTH) motif to identify anti-CRISPR genes outside of *P. aeruginosa*. This led to the authors finding anti-CRISPRs across proteobacteria, broadly spanning the type I-F CRISPR-Cas phylogeny (Pawluk, A. et al, (2016). Nature Microbiology, 1,1-6). This suggests that anti-CRISPRs may exist for all CRISPR systems, with methods needed to enable their discovery.

The type I anti-CRISPRs in *P. aeruginosa* are expressed from integrated phage genomes (prophages), leading to the constitutive inactivation of the host CRISPR-Cas system (Bondy-Denomy et al. (2013). Nature, 493,429-432. This can often lead to a situation where a prophage possesses a DNA target with perfect identity to a co-occurring CRISPR spacer in the same cell, called "self-targeting" (FIG. 1A). This situation makes CRISPR-Cas inactivation a requirement for survival, as in the absence of prophage anti-CRISPR genes, the host genome is cleaved in the act of targeting the prophage (Bondy-Denomy et al. (2013). Nature 493, 429-432; Edgar, R., and Qimron, U. (2010). J. Bacteriol 192, 6291-6294). Expression of an anti-CRISPR neutralizes this risk, however, allowing lysogen survival. We surmised that genomes possessing a CRISPR system with apparent self-targeting would be candidates for the identification of new CRISPR-Cas inhibitors. Here, we describe the identification of previously unknown phage-encoded CRISPR-Cas9 inhibitors in *Listeria monocytogenes* using a bioinformatics approach to identify incidents of self-targeting. We show that two of these inhibitors can also block the activity of *S. pyogenes* Cas9 in bacterial and human cells.

Definitions

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. The promoter can be a heterologous promoter.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. The promoter can be a heterologous promoter. In the context of promoters operably linked to a polynucleotide, a "heterologous promoter" refers to a promoter that would not be so operably linked to the same polynucleotide as found in a product of nature (e.g., in a wild-type organism).

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. In some cases, conservatively modified variants of Cas9 or sgRNA can have an increased stability, assembly, or activity as described herein.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or specified subsequences that are the same. Two sequences that are "substantially identical" have at least 60% identity, preferably 65%, 70%, 75%, 80%, 85%, 90%, 91%, 92%, 93, 94%, 95%, 96%, 97%, 98%, 99%, or 100% identity, when compared and aligned for maximum correspondence over a comparison window, or designated region as measured using a sequence comparison algorithm or by manual alignment and visual inspection where a specific region is not designated. With regard to polynucleotide sequences, this definition also refers to the complement of a test sequence. With regard to amino acid sequences, in some cases, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST 2.0 algorithm and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

An algorithm for determining percent sequence identity and sequence similarity is the BLAST 2.0 algorithm, which are described in Altschul el al., (1990) J. Mol. Biol. 215: 403-410. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The "CRISPR/Cas" system refers to a class of bacterial systems for defense against foreign nucleic acid. CRISPR/Cas systems are found in a wide range of eubacterial and archaeal organisms. CRISPR/Cas systems include type II, III, V, and VI sub-types. Wild-type type II CRISPR/Cas systems utilize the RNA-mediated nuclease, Cas9 in complex with guide and activating RNA to recognize and cleave foreign nucleic acid.

Cas9 homologs are found in a wide variety of eubacteria, including, but not limited to bacteria of the following taxonomic groups: *Actinobacteria, Aquificae, Bacteroidetes-Chlorobi, Chlamydia-Verrucomicrobia, Chlroflexi, Cyanobacteria, Firniicutes, Proteobacteria, Spirochaetes*, and *Thermotogae*. An exemplary Cas9 polyeptide is the *Streptococcus pyogenes* Cas9 polyeptide. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science, 2012 Aug. 17; 337(6096):816-21. The Cas9 protein can be nuclease defective. For example, the Cas9 protein can be a nicking endonuclease that nicks target DNA, but does not cause double strand breakage. Cas9 can also have both nuclease domains deactivated to generate "dead Cas9" (dCas9), a programmable DNA-binding protein with no nuclease activity. In some embodiments, dCas9 DNA-binding is inhibited by the polypeptides described herein.

BRIEF SUMMARY OF THE INVENTION

In one aspect, methods of inhibiting a Cas9 polypeptide in a cell are provided. In some embodiments, the method comprises, introducing a Cas9-inhibiting polypeptide into a cell, wherein: the Cas9-inhibiting polypeptide is heterologous to the cell, and the Cas9-inhibiting polypeptide is substantially (e.g., at least 60%, 70%, 80%, 90%, 95%) identical to any one or more of SEQ ID NO: 1-170, thereby inhibiting the Cas9 polypeptide in a cell. In sonic embodiments, the method comprises contacting the Cas9 inhibiting polypeptide with a Cas9 polypeptide in the cell. In some embodiments, the method comprises contacting the Cas9 inhibiting polypeptide with other components of the CRISPR-Cas9 system in the cell, thereby indirectly inhibiting Cas9 polypeptide activity.

In some embodiments, the Cas9-inhibiting polypeptide comprises one of SEQ ID NO: 1-170.

In some embodiments, the cell comprises the Cas9 polypeptide before the introducing. In some embodiments, the cell comprises an expression cassette comprising a promoter operably linked to a polynucleotide encoding the Cas9 polypeptide. In some embodiments, the promoter is inducible and the method comprises contacting the cell with an agent or condition that induces expression of the Cas9 polypeptide in the cell prior to the introducing.

In some embodiments, the cell comprises the Cas9 polypeptide after the introducing. In some embodiments, the promoter is inducible and the method comprises contacting the cell with an agent or condition that induces expression of the Cas9 polypeptide in the cell after to the introducing.

In some embodiments, the introducing comprises expressing the Cas9-inhibiting polypeptide in the cell from an expression cassette that is present in the cell and heterologous to the cell, wherein the expression cassette comprises a promoter operably linked to a polynucleotide encoding the Cas9-inhibiting polypeptide. In some embodiments, the promoter is an inducible promoter and the introducing comprises contacting the cell with an agent that induces expression of the Cas9-inhibiting polypeptide.

In some embodiments, the introducing comprises introducing an RNA encoding the Cas9-inhibiting polypeptide into the cell and expressing the Cas9-inhibiting polypeptide in the cell from the RNA.

In some embodiments, the introducing comprises inserting the Cas9-inhibiting polypeptide into the cell or contacting the cell with the Cas9-inhibiting polypeptide.

In some embodiments, the cell is a eukaryotic cell. In some embodiments, the cell is a mammalian cell. In some embodiments, the cell is a human cell. In some embodiments, the cell is a blood or an induced pluripotent stem cell. In some embodiments, the cell is a prokaryotic cell.

In some embodiments, the method occurs ex: vivo. In some embodiments, the cells are introduced into a mammal after the introducing and contacting. In some embodiments, the cells are autologous to the mammal.

Also provided is a cell (optionally isolated) comprising a Cas9-inhibiting polypeptide, wherein the Cas9-inhibiting polypeptide is heterologous to the cell and the Cas9-inhibiting polypeptide is substantially identical to any one or more of SEQ ID NO: 1-170. In some embodiments, the cell is a eukaryotic cell. In some embodiments, the cell is a mammalian cell. In some embodiments, the cell is a human cell In some embodiments, the cell is a prokaryotic cell.

Also provided is a polynucleotide comprising a nucleic acid encoding a Cas9-inhibiting polypeptide. In some embodiments, the Cas9-inhibiting polypeptide is substantially identical to any one or more of SEQ ID NO: 1-170. In some embodiments, the polynucleotide comprises an expression cassette, the expression cassette comprising a promoter operably linked to the nucleic acid. In some embodiments, the promoter is heterologous to the polynucleotide encoding the Cas9-inhibiting polypeptide. In some embodiments, the promoter is inducible. In some embodiments, the polynucleotide is DNA or RNA.

Also provided is a vector comprising the expression cassette as described above or elsewhere herein. In some embodiments, the vector is a viral vector.

Also provided is a (optionally isolated) Cas9-inhibiting polypeptide. In some embodiments, the Cas9-inhibiting polypeptide is substantially identical to any one or more of SEQ NO:1-170.

Also provided is a pharmaceutical composition comprising the polynucleotide or the polypeptide as described above or elsewhere herein.

Also provided is a delivery vehicle comprising the polynucleotide or the polypeptide as described above or elsewhere herein. In some embodiments, the delivery vehicle is a liposome or nanoparticle.

Other aspects are described in the remainder of this document.

BRIEF DESCRIPTION OF THE DRAWINGS

FIG. 1A-C. A survey for CRISPR-Cas9 genomic self-targeting (ST) in Listeria monocytogenes.

FIG. 1A A schematic depicting the principle of genomic self-targeting, where a mobile genetic element (MGE) possesses a target sequence for a spacer in a CRISPR array in the same genome. CRISPR-Cas9 function in this "self-targeting genome" is presumably inactive for continued cell viability.

FIG. 1B The abundance of genomes with cas9-linked self-targeting (red) and those without ST (grey), in L. monocytogenes genomes.

FIG. 1C An example of an ST event, where spacer 16 in the CRISPR array of strain J0161 has a perfect PAM and protospacer match with a resident prophage (φJ0161a) (spacer sequences: crRNA (SEQ ID NO:171), protospacer and protospacer complement (SEQ ID NOS:172-173)).

FIG. 2A-D. A prophage from L. monocytogenes J0161 contains two CRISPR-Cas9 inhibitor genes.

FIG. 2A The type II-A CRISPR-Cas locus in L. monocytogenes 10403s. Four cas genes are indicated, along with tracrRNA and CRISPR array, containing 30 spacers. The predicted direction of transcription is indicated with black arrows. Subsequent experiments utilize a non-targeted plasmid (pNT) and a targeted plasmid (pT) that has a protospacer matching spacer 1 in this strain.

FIG. 2B Representative pictures of transformed colonies after CRISPR-Cas-targeted (pT) or non-targeted (pNT) plasmids were electroporated into phage-cured (φcure) strains of L. monocytogenes 10403s and wild type (wt) J0161 (contains the φJ0161a prophage) shown in red to denote self-targeting. Analyzed φcure 10403s variants include a cas9-deletion strain (Δcas9), a lysogen of φJ0161a (::φJ0161a), strains constitutively expressing individual CRISPR-Cas9 inhibitor genes from φJ0161a (+acrIIA1, +acrIIA2) and a lysogen of φJ0161a with CRISPR-Cas9 inhibitor genes deleted (::φJ0161aΔacrIIA1-2). See FIG. 7 for a comparison of wt and φcure 10403s.

FIG. 2C 10403s φcure and wt J0161 strains were assessed for transformation efficiency. The 10403s φcure cas9-deletion strain (Δcas9), constitutively expressed cas9 (Δcas9+cas9) and φJ0161a lysogens of these strains (::φJ0161a) were analyzed. Error bars reflect the standard deviation of three biological replicates. L.D. limit of detection.

FIG. 2D Comparison of the open reading frames from two similar prophages from L. monocytogenes 10403s and J0161. Unique genes (red) comprising ten fragments of φJ0161 were tested for CRISPR-Cas9 inhibition in 10403s. n.e., No effect on CRISPR-Cas9 activity, tox., fragment toxic when expressed, t., location of self-targeted protospacer. The encircled fragment exhibited anti-CRISPR activity with two genes (acrAII1, acrAII2) independently capable of inhibiting CRISPR-Cas activity. Conserved (grey) genes were not tested. For reference, phage genes involved in cell lysis, capsid assembly and host integration (int.) are labeled.

FIG. 3A-C. Genomic organization and prevalence of acrII4 genes

FIG. 3A The genomic context of actIIA1 (1) and its homolog from L. monocytogenes (orfD) are depicted to scale as cartoons with acIIA1 homologs in vertical alignment. Typically, acrIIA genes are encoded within prophages adjacent to or near the phage lysin. (ply) gene. Genomic neighbors of acrIIA1 and orfD (acrIIA1-4, orfA-E) are shown. Individual genes (***) were assayed for CRISPR-Cas9 inhibition in L. monocytogenes 10403s (see FIG. 9). Helix-turn-helix (HUI) and AP2 DNA binding motifs were detected in some proteins using hidden markov model (HMM) prediction software (Soding, J., Siegert, A., and Lupas, A. N. (2005). Nucleic Acids Research, 33, W244-W248).

FIG. 3B Pie-graph representation of the frequency of each acrIIA gene co-occurrences FIG. 3C Pie-graph representation of the prevalence of acrIIA and cas9 genes in the L. monocytogenes pan-genome. See Supplementary Table 1 for relevant accession numbers.

Figure 4A:
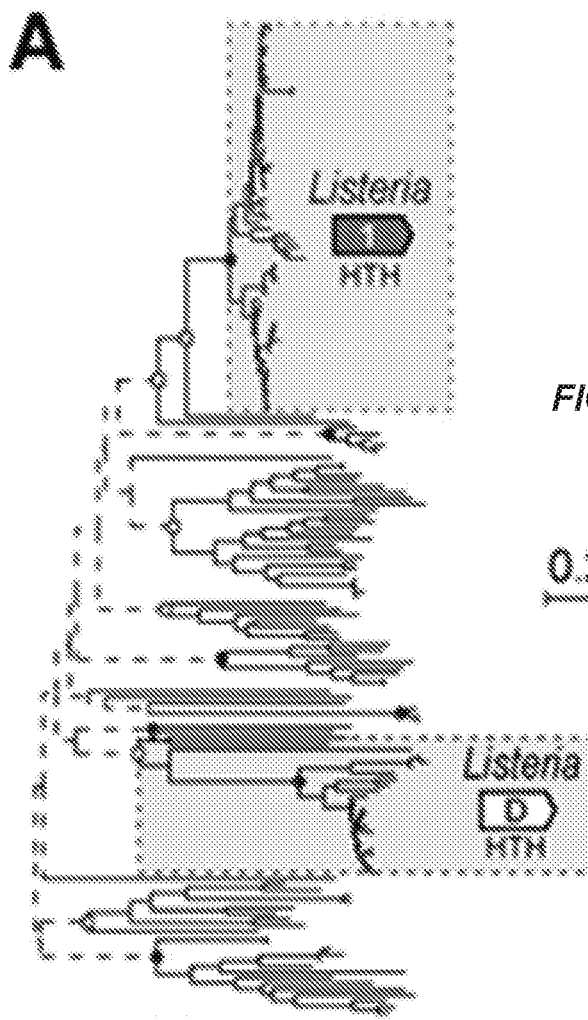
FIG. 4A. Phylogenetic analysis of AcrIIA1-4 homologs

A phylogenetic reconstruction of full-length protein sequences identified following an iterative psi-BLASTp search to query all non-redundant protein sequences within GenBank for (FIG. 4A)

Figure 4B:
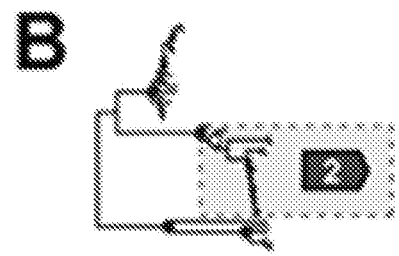
Figure 4C:
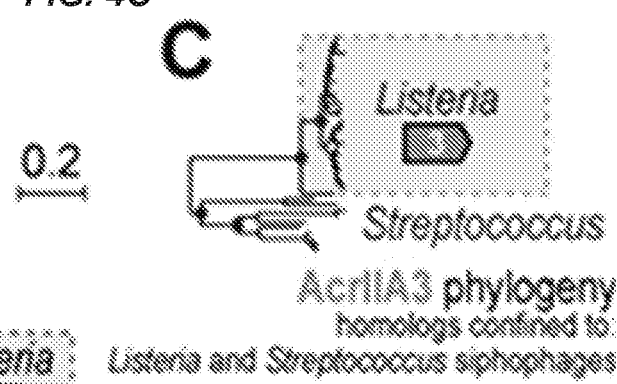
Figure 4D:

BLASTp was used to construct a similar tree for (FIG. 4B) AcrIIA2, (FIG. 4C) AcrIIA3, and FIG. 4D AcrIIA4 (see Methods). Selected bootstrapping support values are denoted with filled ovals (≥90%), open rectangles (≥70%) or dashed lines (<70%). The sequence family that is boxed-in represents the family that was tested for anti-CRISPR function. Other homologs reflect distinct sequence families present in the genotnes described under the tree.

FIG. 5A-D. Inhibition of *Streptococcus pyogenes* dCas9 and Cas9.

Figure 5A:
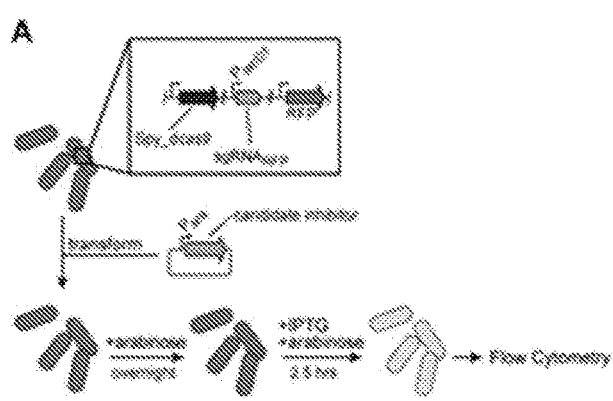

FIG. 5A A schematic outlining the experimental setup, where single-cell fluorescence of *E. coli* BW25113 with *Strepotococcus pyogenes* (Spy) dCas9 and a guide RNA targeted towards a chromosomal red fluorescent protein (RFR) gene was measured.

Figure 5B:
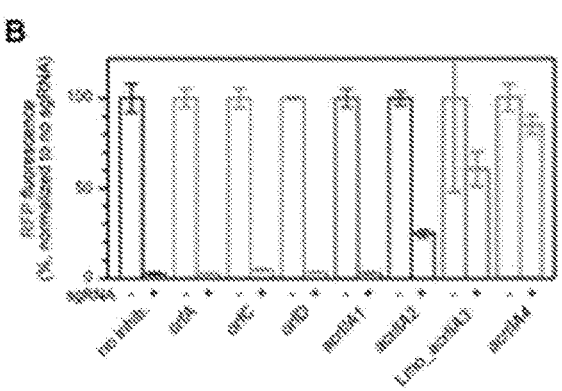

FIG. 5B Candidate (orf) and validated (act) acrIIA genes were tested for their ability to inhibit dCas9-based repression. Measurements taken reflect the median REP fluorescence value of a single cell in a unimodal population normalized for each candidate gene to a guide RNA-free control. Error bars represent the standard deviation of at least three biological replicates. See FIG. 2 and FIG. 9 for gene-identification information.

Figure 5C:
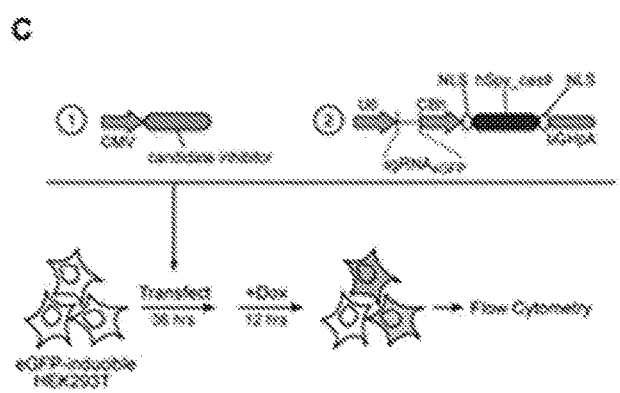

FIG. 5C A schematic outlining the experimental setup, where HEK293T cells with a doxycycline-inducible eGFP cassette were transfected with a plasmid encoding a single transcript tracrRNA/eGFP-targeting guide RNA and NLS-SpyCas9 alongside expression constructs encoding one of five codon-optimized phage genes at different ratios. The percent of eGFP positive cells was measured 12 hours after induction by flow cytometry.

Figure 5D:
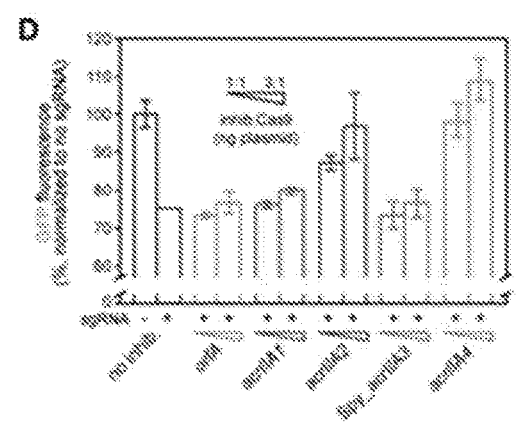

FIG. 5D Average percent of eGFP positive cells is depicted+/−standard deviation across biological triplicates. An increasing amount of inhibitor plasmid (in ng) was added from left to right, at a ratio to the Cas9/sgRNA plasmid of 1:1 and 3:1. Data were normalized to transfection with no phage ORF as the baseline.

Figure 6:
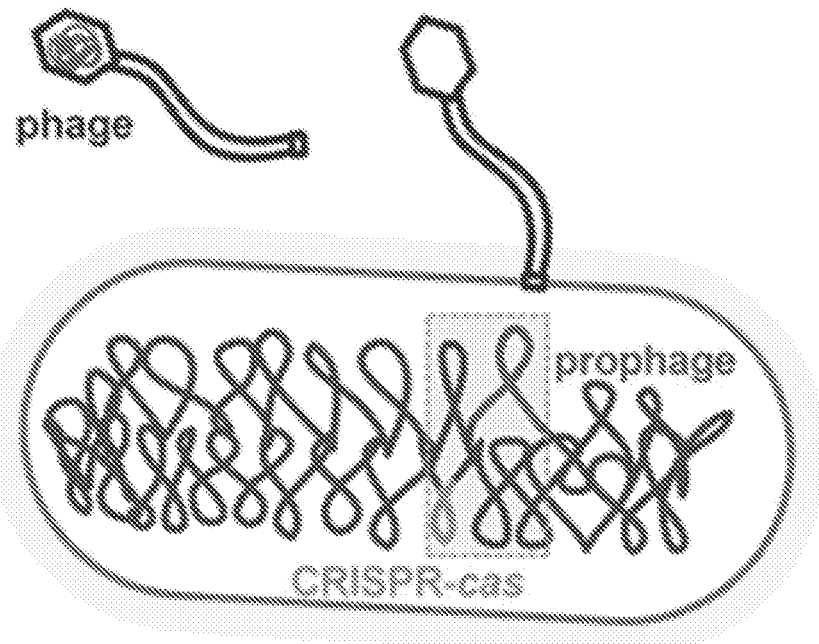
Figure 6:
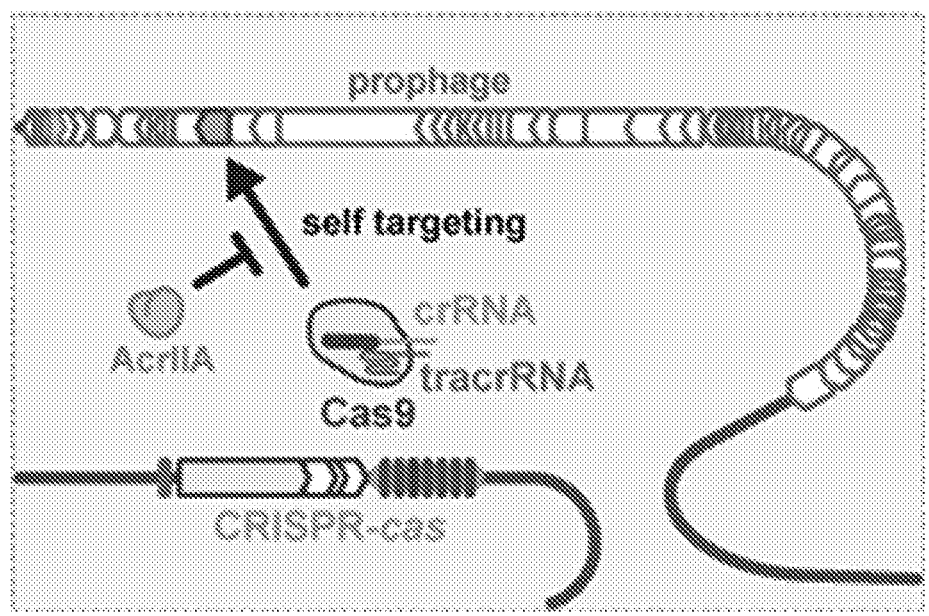

FIG. 6 is a cartoon depiction of AcrIIA-inhibition of Cas9.

FIG. 7A-F. Self-Targeting by CRISPR-Cas9 in *Listeria monocytogenes* J0161 is Not Associated with Loss-of-Function Mutations, Related to FIG. 1

Figure 7A:
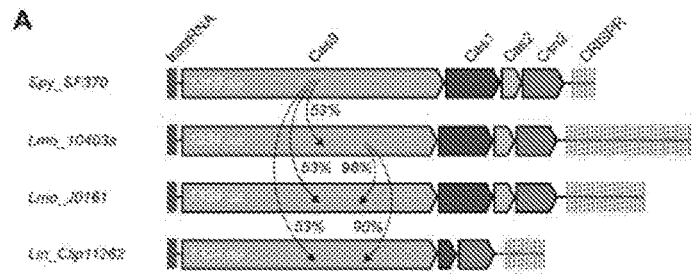

FIG. 7A Comparison of type II-A CRISPR-cas loci from *Streptococcus pyogenes* SF370 (Spy_SF370), *Listeria monocytogenes* 10403s (Lmo_10403s), *Listeria monocytogenes* J0161 (Lmo_J0161) and *Listeria innocua* (Lin_Clip11262). Percent identity between Cas9 protein sequences is shown.

Figure 7B:
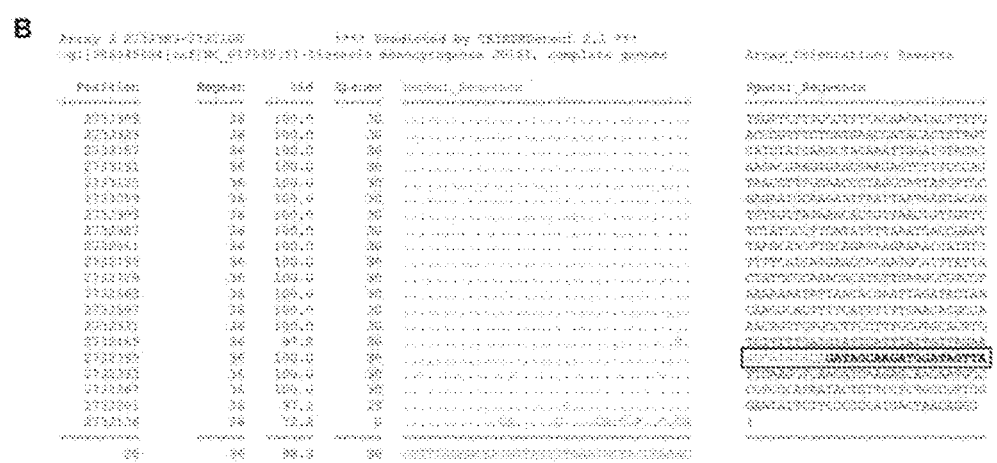

FIG. 7B The CRISPR array of self-targeting strain Lmo J0161. A type II-A CRISPR array, predicted by the CRISPRDetect web utility is shown (Spacer_Sequence: SEQ ID NOS:174-192, respectively; Repeat_Sequence: SEQ ID NO:193). The self-targeting spacer (number 16 (SEQ ID NO:189) is boxed. In bold, are the RNA-coding nucleotides responsible for target recognition.

Figure 7C:
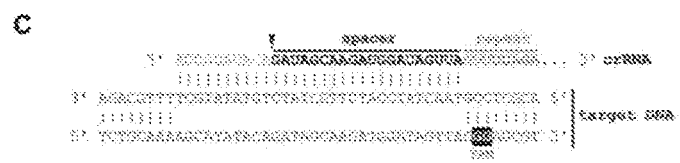

FIG. 7C A modified CRISPRtarget output, depicting self-targeting by *L. monocytogenes* J0161. The predicted crRNA processing site is identified by the wedge icon. (sequences: crRNA (SEQ ID NO:194), target DNA and target DNA complement (SEQ ID NOS:195-196)).

Figure 7D:
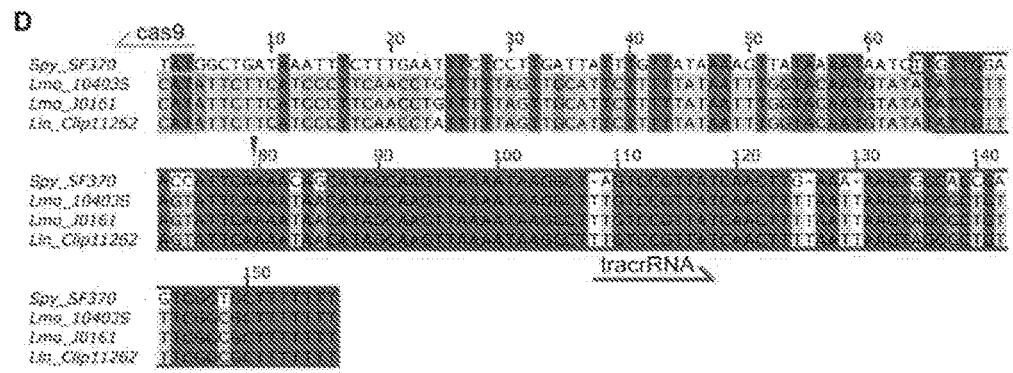

FIG. 7D Alignment of tracrRNA loci. (Spy_SF370 (SEQ ID NO:197); Lmo_10403s (SEQ ID NO:198); Lmo_J0161 (SEQ ID NO:199): Lin_Clip11262 (SEQ ID NO:200).

Figures 7E, 7F:
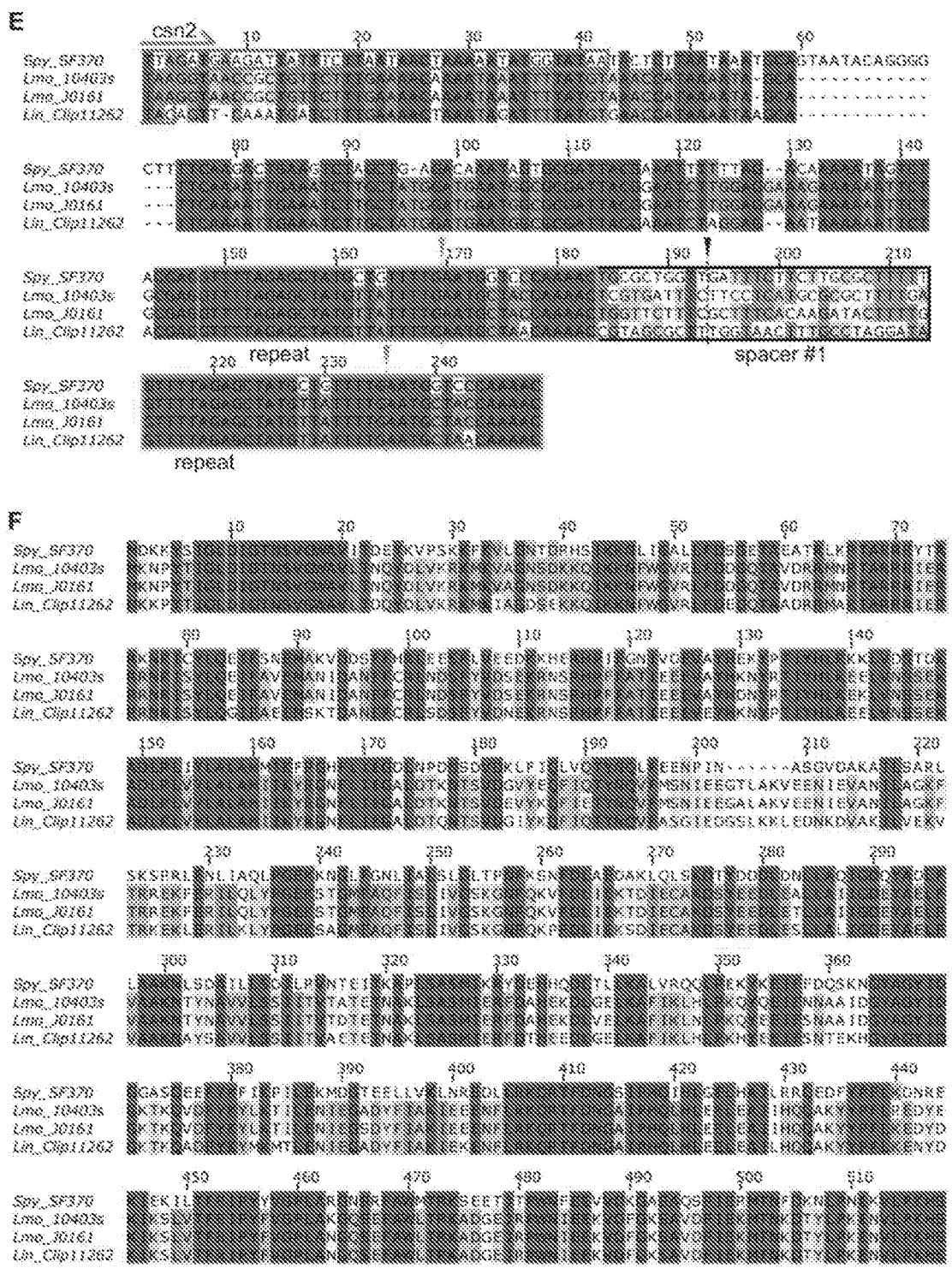
Figure 7F:
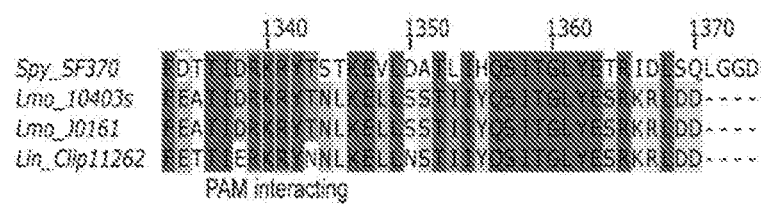

FIG. 7E Alignment of CRISPR loci. (Spy SF370 (SEQ ID NO:201); Lmo_10403s (SEQ ID NO:202); Lmo_J0161 (SEQ ID NO:203): Lin_Clip11262 (SEQ ID NO:204).

FIG. 7F Alignment of Cas9 protein sequences. Residues with essential chemical functionalities are boxed. (Spy_SF370 (SEQ ID NO:205); Lmo_10403s (SEQ ID NO:206); Lmo_J0161 (SEQ ID NO:207): Lin_Clip11262 (SEQ ID NO:208).

Figure 8:
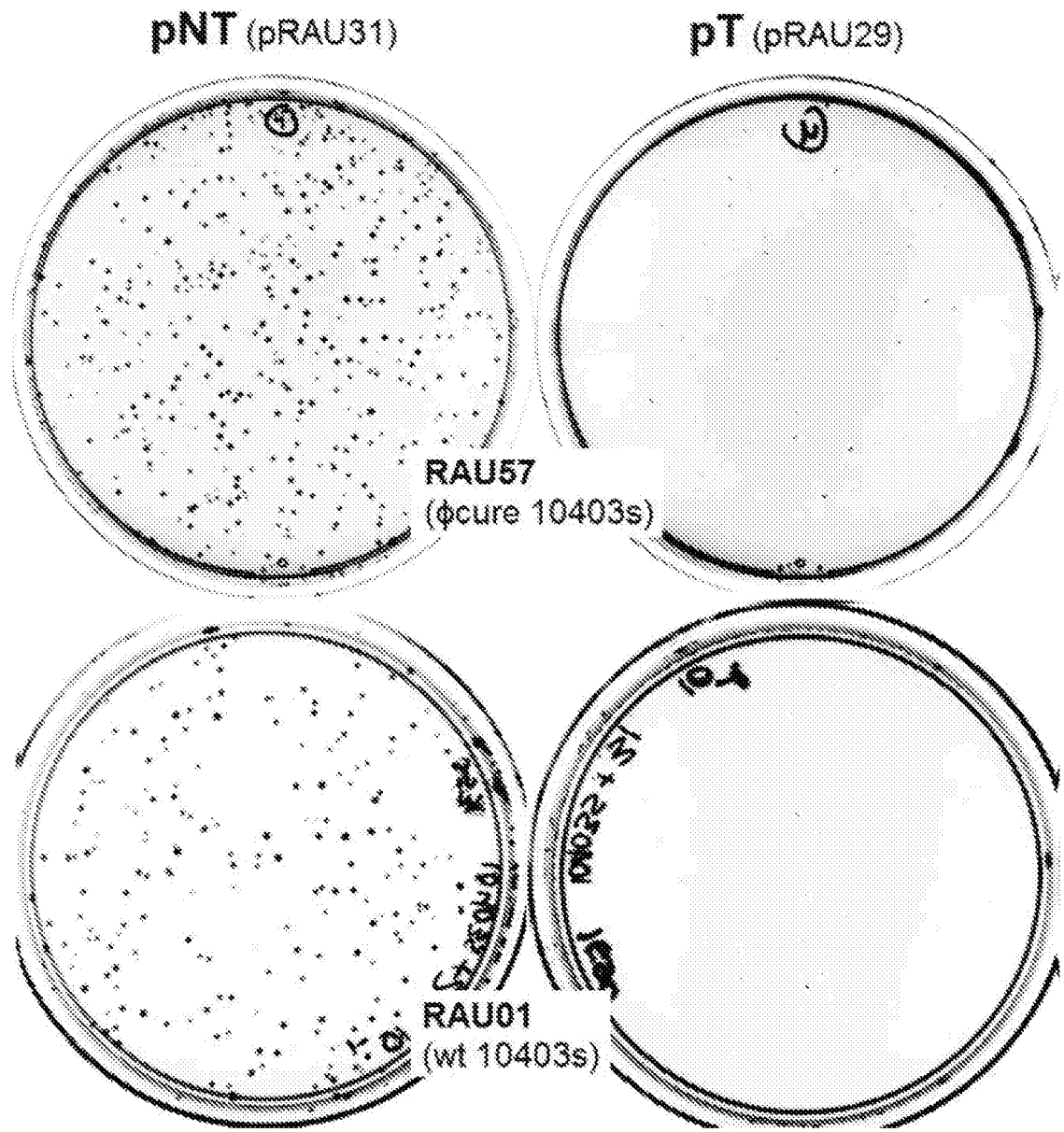

FIG. 8. The φ10403s Prophage Does Not Influence Plasmid Targeting in *L. monocytogenes* 10403s, Related to FIG. 2A-D. Representative plates depicting colonies after transformation and selection for targeted (pT; pRAU31) or non-targeted (pNT; pRAU29) plasmids. Wild type (wt) and nonlysogenic (φcure) strains of 10403s were analyzed. See Table S1 for additional information pertinent to plasmid and strain design and nomenclature.

Figure 9:
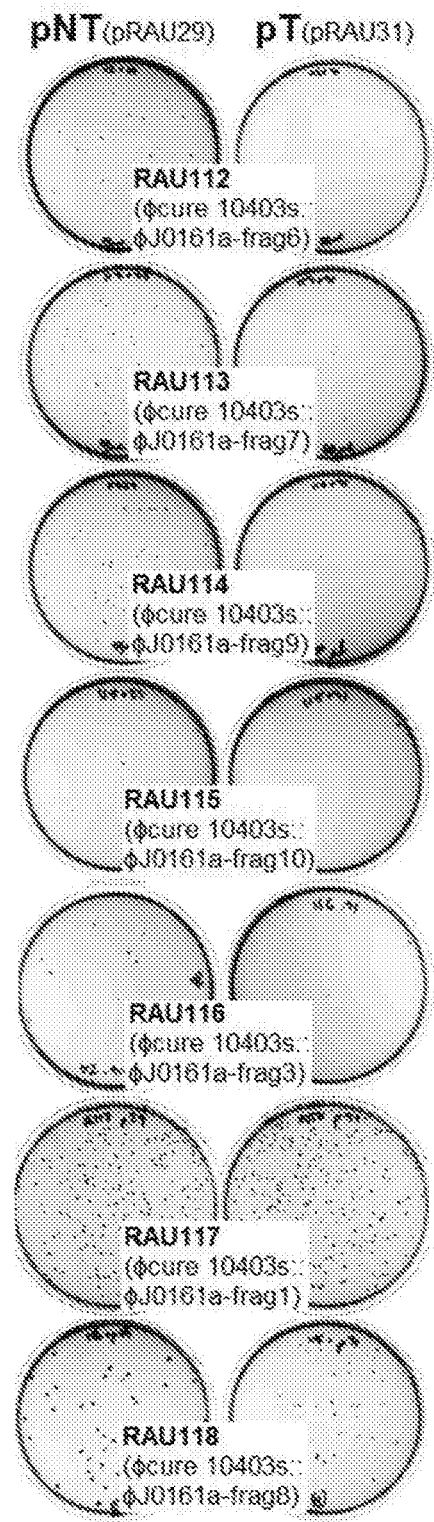

FIG. 9. Fragments of the φJ0161a Prophage that were Screened for CRISPR-Cas9 Inhibition Activity in *L. monocytogenes* 10403s, Related to FIG. 2. Representative plates depicting colonies after transformation and selection for targeted (pT; pRAU31) or non-targeted (pNT, pRAU29) plasmids. DNA sequence information is provided for all phage fragments as they are named in FIG. 2d. See Table 51 for additional information pertinent to plasmid and strain design and nomenclature.

Figure 10A:
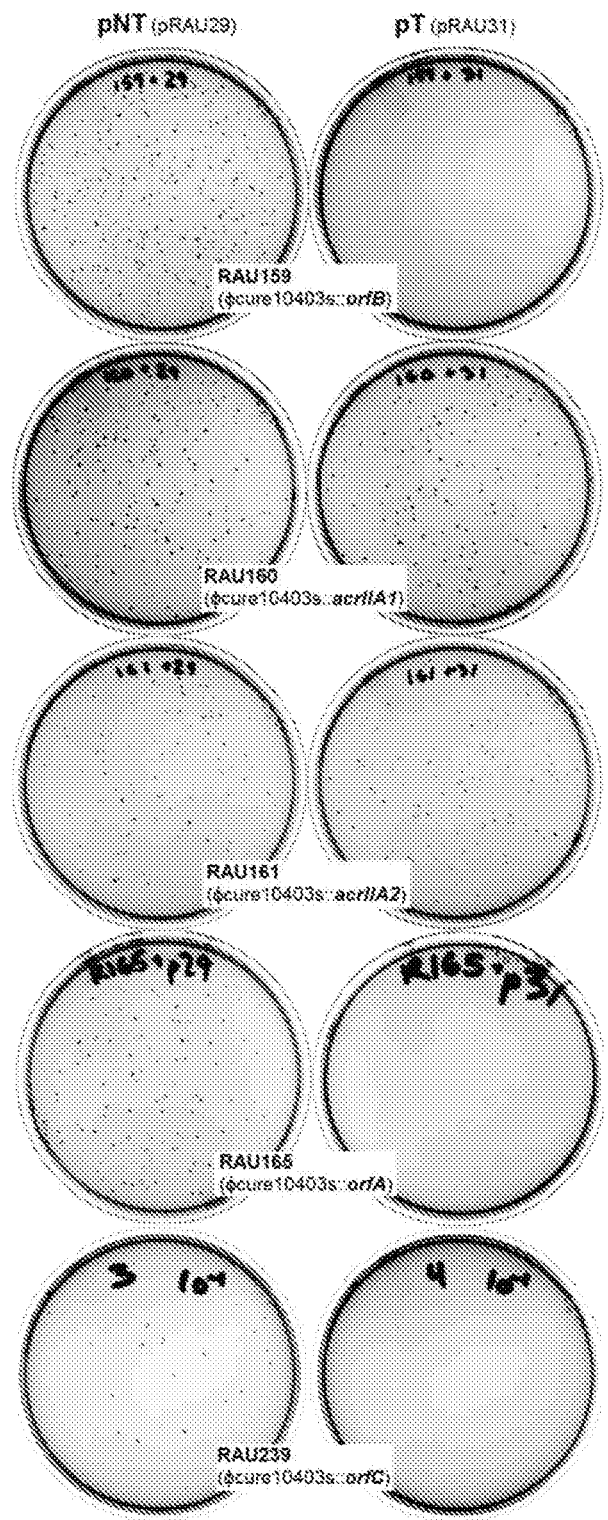
Figure 10B:
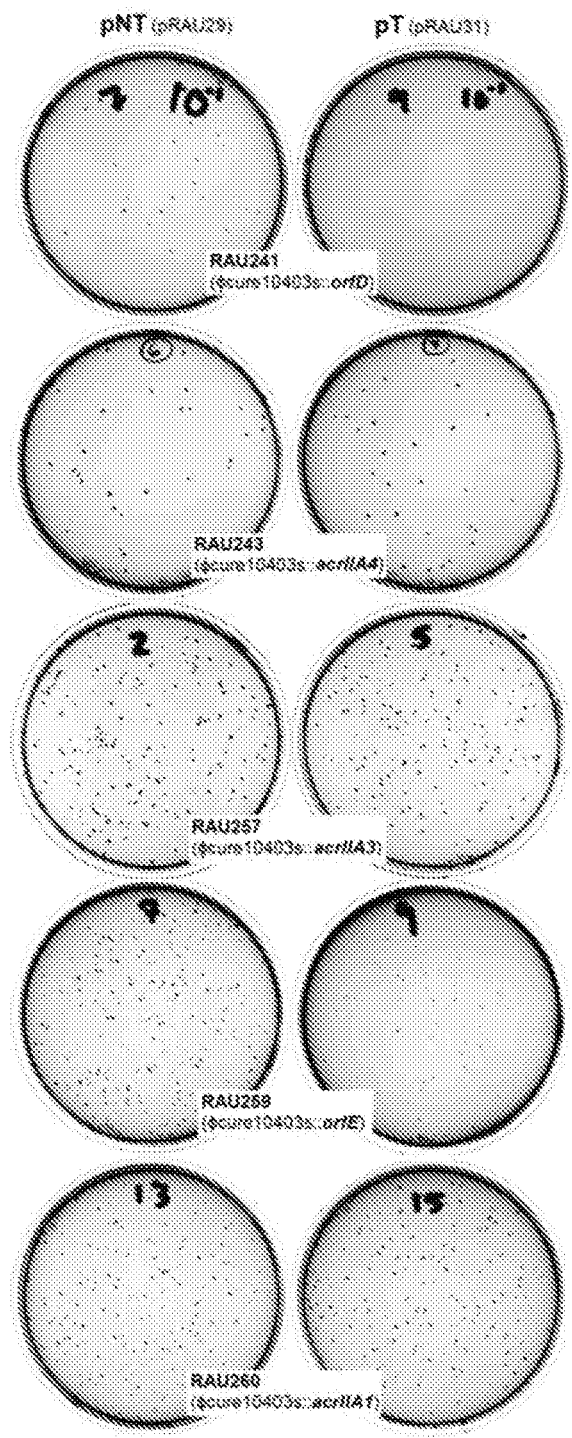

FIG. 10A-B. Individual Genes that were Screened for CRISPR-Cas9 Inhibition Activity in *L. monocytogenes* 10403s, Related to FIG. 2B and FIG. 3A. Representative plates depicting colonies after transformation and selection for targeted (pT; pRAU31) or non-targeted (pNT; pRAU29) plasmids. Given names, locus tags, accession numbers and DNA sequence information is provided for all candidate type II-A CRISPR-Cas inhibitors. See Table S1 for additional information pertinent to plasmid and strain design and nomenclature.

FIG. 11A-B. Toxicity of an AcrIIA3 Homolog from *S. pyogenes* in *E. coli*, Related to FIG. 5.

FIG. 11A Distribution of single-cell REP fluorescence values for *E. coli* CRISPRi reporter strains with and without expression of AcrIIA proteins. Expression of AcrIIA proteins leads to unimodal shift in population fluorescence towards the sgRNA (no CRISPRi knockdown) state, indicating a uniform disruption of CRISPRi activity. Strains were grown for 2.5 hr in the presence of IPTG to induce CRISPRi, with or without expression of the AcrIIA inhibitor.

FIG. 11B Expression of Spy AcrIIA3 is toxic in *E. coli*. In the presence of IPIG (CRISPRi induction) and arabinose (AcrIIA3 induction), Spy AcrIIA3 is toxic in the presence or absence of sgRNA, indicating that its toxicity is independent of CRISPRi activity.

Figure 12:
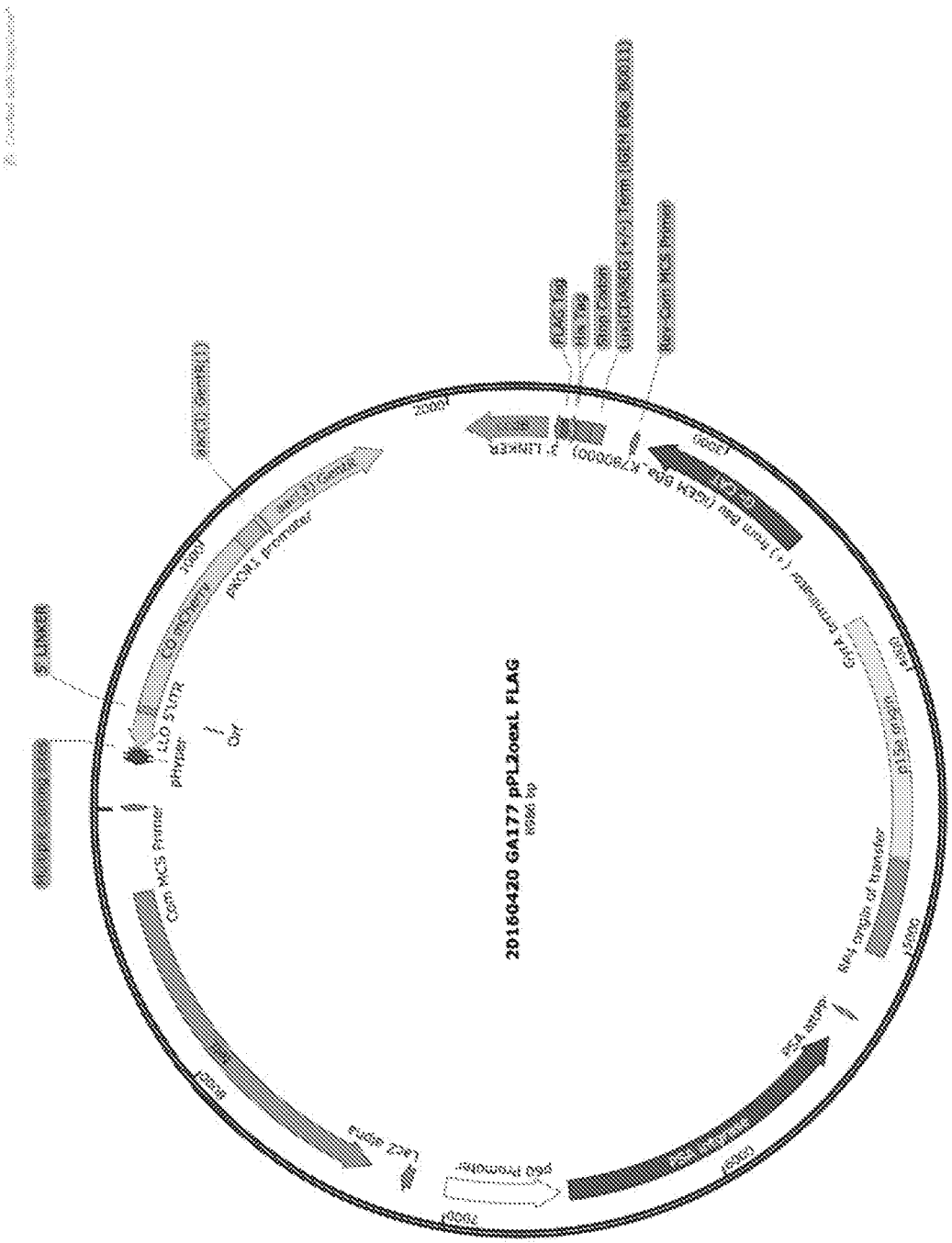

FIG. 12. Vector Map file for pPL2oexL, Related to FIG. 2 and FIG. 3. Genes and phage fragments to be tested for CRISPR-Cas9 inhibition in *L. monocytogenes* 10403s were cloned into pPL2oexL between pilyper and the FLAG tag. Native stop codons were included in pPL2oexL derivatives.

Figure 13:
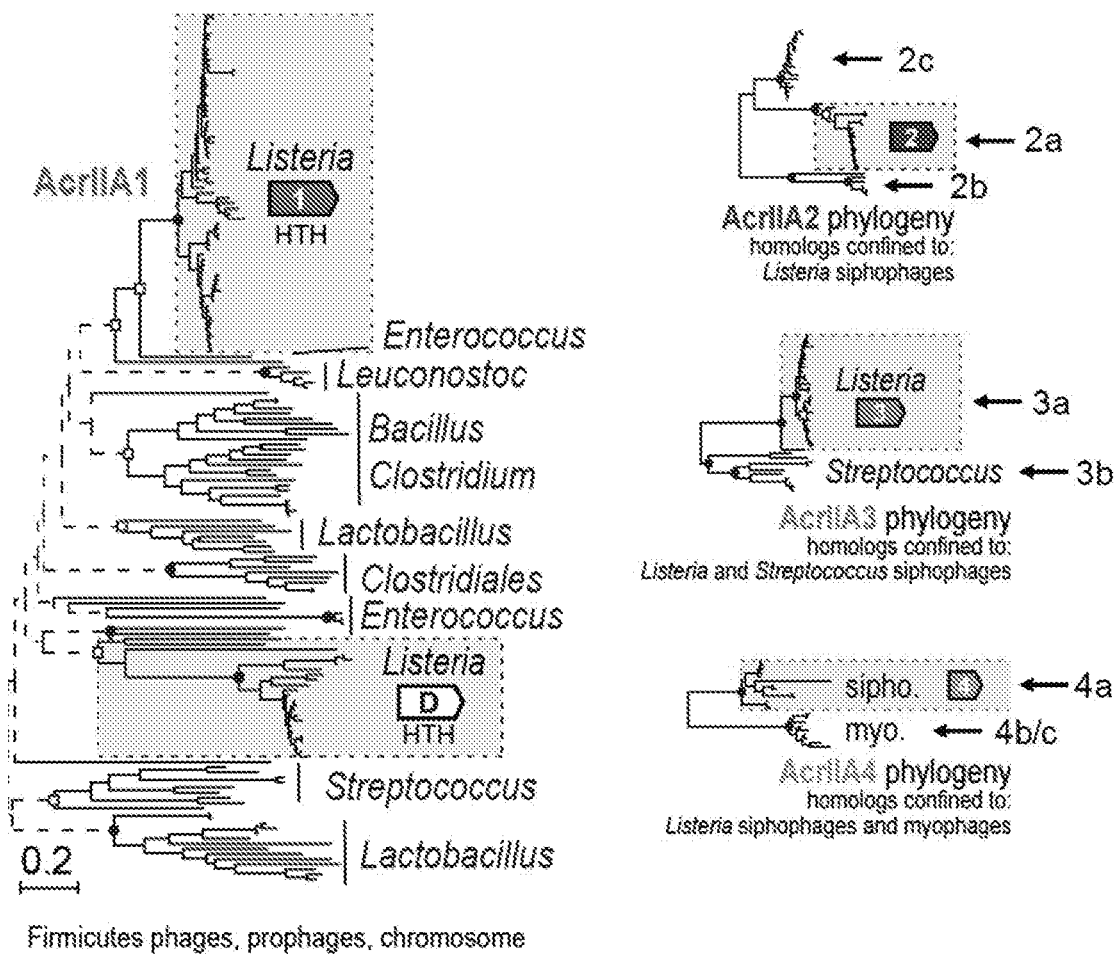

FIG. 13: acrIIA1 is very widespread across Firmicutes homologs are likely to inhibit Cas9 function in the organisms in which they are found. To identify new homologs of acrIIA genes with anti-CRISPR function, distinct members from the phylogenetic trees shown here were tested for anti-CRISPR activity in cell based assays. These homologs of known anti-CRISPR genes are being tested in a foreign bacterial system (*Pseudomonas aeruginosa*) to identify those with direct activity against SpyCas9.

Figure 14:
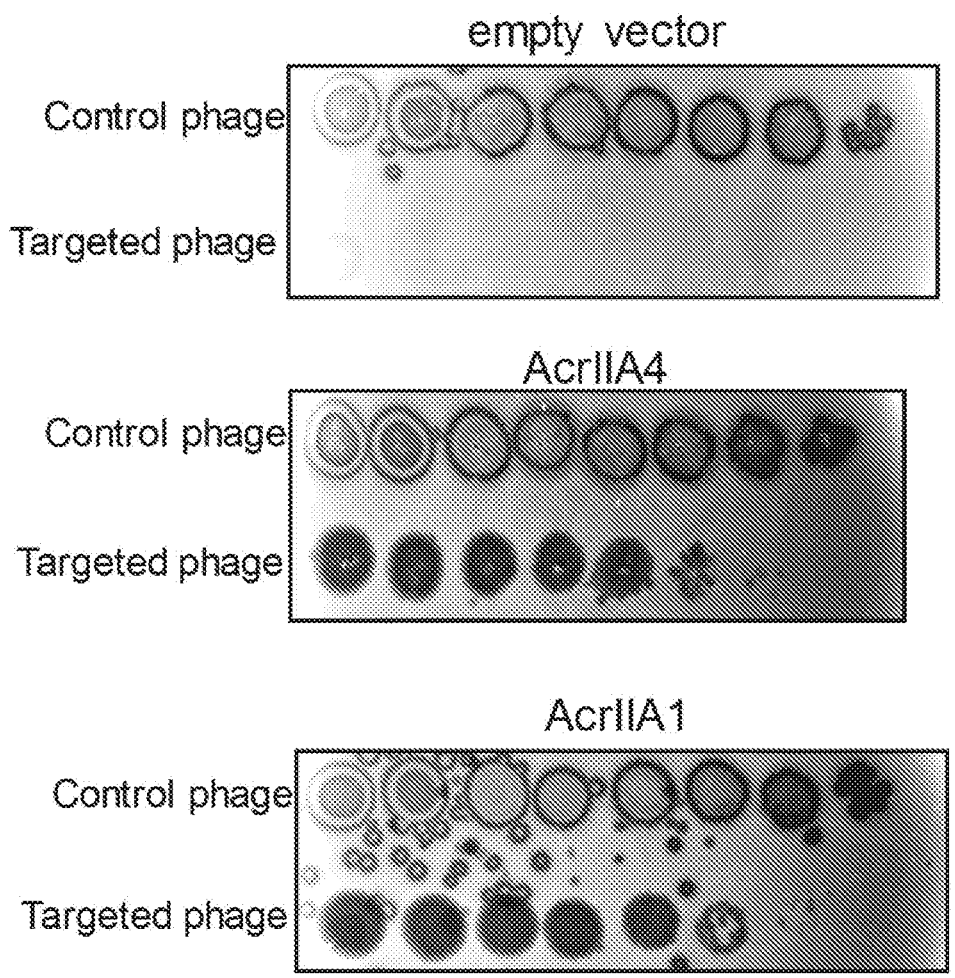

FIG. 14: Phage plaque assays showing ten-fold dilutions of a control phage (D3) or a phage targeted (JBD30) by SpyCas9 with a JBD30-specific sgRNA in a heterologous host (*Pseudomonas aeruginosa*). Expression of the indicated anti-CRISPR acrIIA4 (positive control) or acrIIA1 inactivates SpyCas9.

FIG. 15A-B: 15A) A multi-sequence alignment of acrIIA2 homologs found in different Listeria mobile elements. (AcrIIA2a.1 (SEQ ID NO:69), AcrIIA2a.2 (SEQ ID NO:84), AcrIIA2b.1 (SEQ ID NO:108); AcrIIA2b,3 (SEQ II) NO:209); AcrIIA2c.1 (SEQ ID NO:97): and AcrIIA2c.2

(SEQ ID NO:98)). Tested homologs are indicated with colored arrows and a summary of the results are shown below the alignment, 15B) A table summarizing the sequence identity (at the amino acid level) between the different homologs and their accession numbers.

Figure 16:
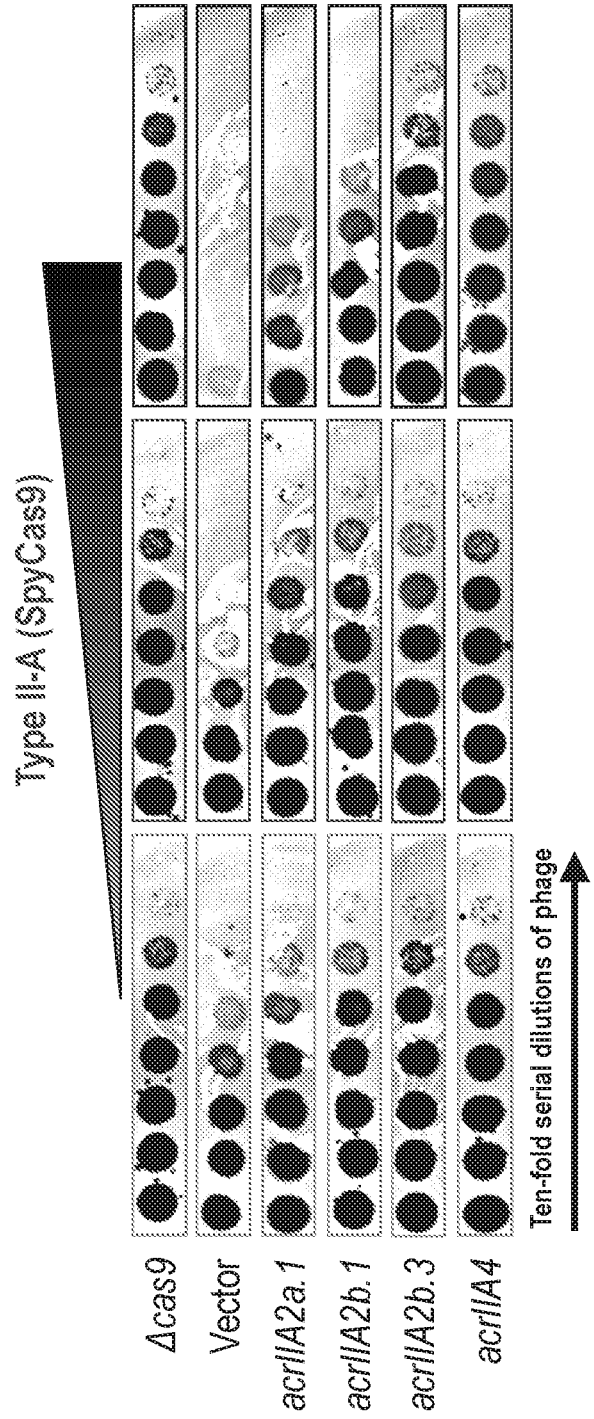

FIG. 16: Bacteriophage plaque assays with ten-fold serial dilutions phage JBD30 spotted on top of a lawn of *P. aeruginosa* expressing SpyCas9 and a sgRNA targeting phage JBD30. Phages will plaque in the absence of CRISPR activity. Cas9 and the sgRNA are induced with increasing amounts of arabinose from left to right (0.001%, 0.01%, 0.1%). In the absence of Cas9 (Acas9), the phages plaque fully, but in the present of Cas9 but no anti-CRISPR (vector), plaquing is reduced as Cas9 is induced. The provision of acriiA4 (positive control) fully blocks Cas9 at all levels. Only acrIIA2b.3 is comparable to acrIIA4 for its activity. The original acrIIA2a.1 is only partially active, with a slight improvement seen with acrIIA2b.1.

Figure 17:
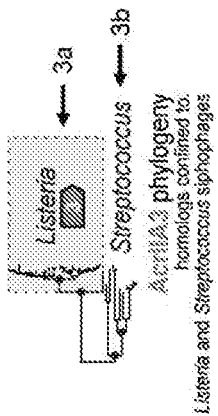

FIG. 17: Homologs of acrIIA3b found in *Streptococcus* species were tested for anti-CRISPR activity in heterologous system (*P. aeruginosa*) expressing SpyCas9 and an sgRNA. A summary of the results (data in FIG. 6) are shown in the table, indicating the species of origin for the anti-CRISPR, the sequence identity of Cas9 in that species to *S. pyogenes*, and similar information for the anti-CRISPR. Given the previously observed toxicity of acrIIA3a and acrIIA3b, these new proteins were assessed for toxicitiy (toxic?) and anti-CRISPR function (acr?).

Figure 18:
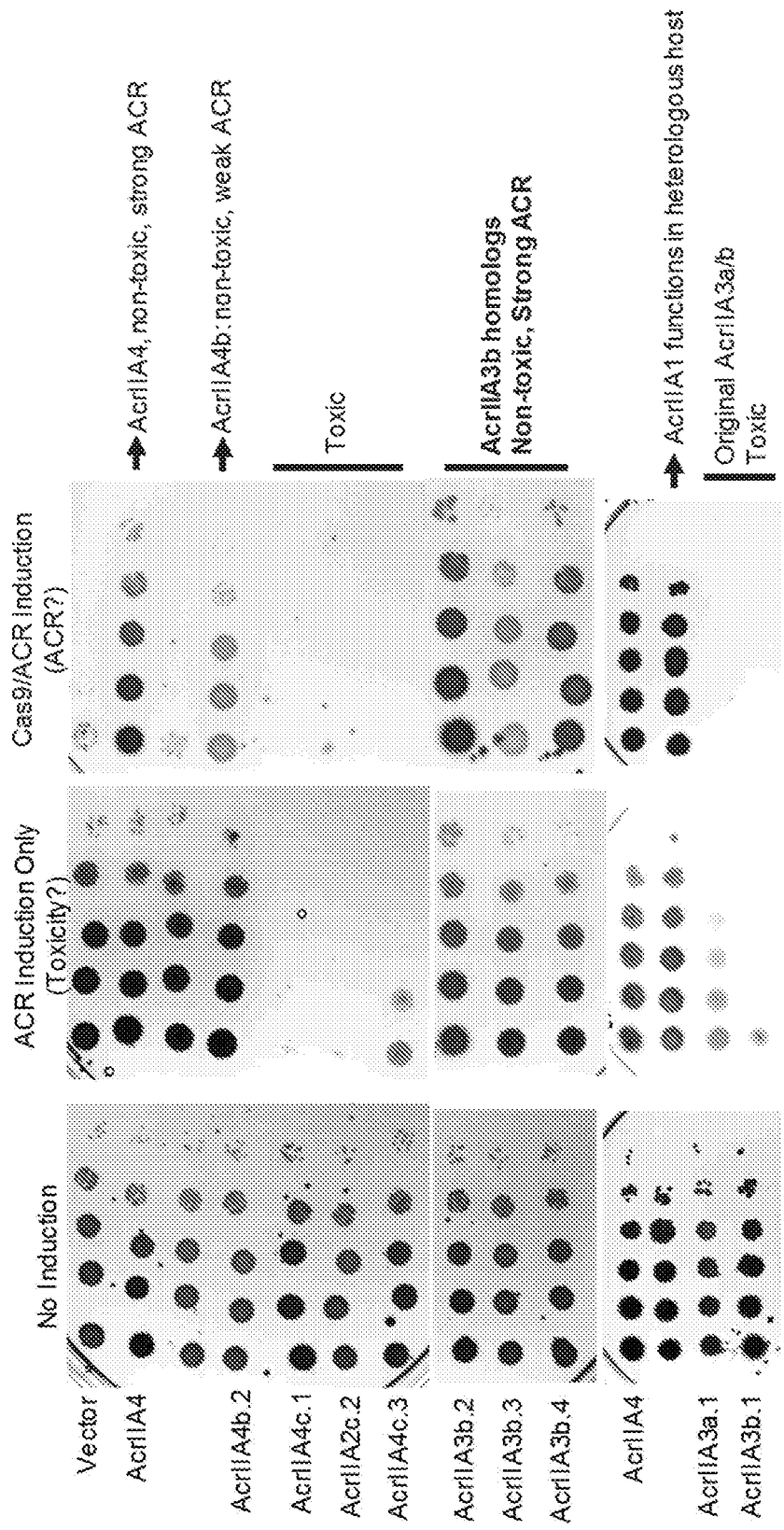

FIG. 18: Spot titration of bacterial cells on LB agar plates. SpyCas9 was programmed with an sgRNA targeting the *P. aeruginosa* genome, thus killing the cell. Cells only survive if the anti-CRISPR is functional. Plates are showing 10-fold serial dilutions of cells plated on non-inducing (left column), ACR inducing only (middle column, to test ACR toxicity), or Cas9/sgRNA/ACR inducing plates (right column, to test ACR function). Genome being cleaved by Cas9 leads to death, unless anti-CRIS:PR blocks Cas9 function. Colonies on right-most panels indicate ACR activity.

FIG. 19: Summary of some of the data from Example 2.

DETAILED DESCRIPTION OF THE INVENTION

Several polypeptide inhibitors ("Cas9-inhibiting polypeptides") of Cas9 nuclease have been identified from phage. The Cas9-inhibiting polypeptides initially discovered from phage were designated AcrIIA1, AcrIIA2, AcrIIA3, and AcrIIA4.

The Cas9-inhibiting polypeptides described herein can be used in many aspects to inhibit unwanted Cas9 activity. For example, one or more Cas9-inhibiting polypeptide can be used to regulate Cas9 in genome editing, thereby allowing for some Cas9 activity prior to introduction of the Cas9-inhibiting polypeptide. This can be helpful, for example, in limiting off-target effects of Cas9. This and other uses are described in more detail below.

As set forth in the examples and sequence listing, a large number of Cas9-inhibiting polypeptides have been discovered. Examples of exemplary Cas9-inhibiting polypeptides include proteins comprising any of SEQ ID NOs: 1-169, or substantially (e.g., at least 50, 60, 70, 75, 80, 85, 90, 95, or 98%) identical amino acid sequences. In some embodiments, the polypeptides, in addition to having one of the above-listed sequences, will include other amino acid sequences or other chemical moieties (e.g., detectable labels) at the amino terminus, carboxyl terminus, or both. Additional amino acid sequences can include, but are not limited to tags, detectable markers, or nuclear localization signal sequences.

As noted in the examples, a number of the Cas9-inhibiting polypeptides have been shown to inhibit *L. monocytogenes* Cas9 as well as *S. pyogenes* (Spy) Cas9. It is believed and expected that the Cas9-inhibiting polypeptides described herein will also similarly inhibit other block II-A Cas9 proteins. As used herein, a "Cas9-inhibiting polypeptide" is a protein that inhibits function of the Cas9 enzyme in *L. monocytogenes* during a transformation efficiency assay. When a plasmid bearing a targeted DNA sequence and protospacer adjacent motif (PAM) is used to transform a strain with intact Cas9 function, the transformation event is prevented by Cas9, generating miniscule colonies under selection. This is compared to a plasmid with a non-targeted DNA sequence, which produces normal sized colonies when used to transform *L. monocytogenes*. The expression of a Cas9 inhibitor neutralizes Cas9 activity and leads to transformed, normal sized colonies of both the targeted and non-targeted plasmid. While it is believed the Cas9-inhibiting polypeptides' inhibitory activity can be measured in other ways, the above assay, presented in more detail in the Examples, is the assay for determining whether the Cas9-inhibiting polypeptide have activity.

The Cas9-inhibiting polypeptides can be introduced into any cell to inhibit Cas9 in that cell. In some embodiments, the cell contains Cas9 protein when the Cas9-inhibiting polypeptide is introduced into the cell. In other embodiments, the Cas9-inhibiting polypeptide is introduced into the cell and then Cas9 polypeptide is introduced into the cell.

Introduction of the Cas9-inhibiting polypeptides into the cell can take different forms. For example, in some embodiments, the Cas9-inhibiting polypeptides themselves are introduced into the cells. Any method for introduction of polypeptides into cells can be used. For example, in some embodiments, electroporation, or liposomal or nanoparticle delivery to the cells can be employed. In other embodiments, a polynucleotide encoding a Cas9-inhibiting polypeptide is introduced into the cell and the Cas9-inhibiting polypeptide is subsequently expressed in the cell. In some embodiments, the polynucleotide is an RNA. In some embodiments, the polynucleotide is a DNA.

In some embodiments, the Cas9-inhibiting polypeptide is expressed in the cell from RNA encoded by an expression cassette, wherein the expression cassette comprises a promoter operably linked to a polynucleotide encoding the Cas9-inhibiting polypeptide. In some embodiments, the promoter is heterologous to the polynucleotide encoding the Cas9-inhibiting polypeptide. Selection of the promoter will depend on the cell in which it is to be expressed and the desired expression pattern. In sonic embodiments, promoters are inducible or repressible, such that expression of a nucleic acid operably linked to the promoter can be expressed under selected conditions. In some examples, a promoter is an inducible promoter, such that expression of a nucleic acid operably linked to the promoter is activated or increased.

An inducible promoter may be activated by presence or absence of a particular molecule, for example, doxycycline, tetracycline, metal ions, alcohol, or steroid compounds. In some embodiments, an inducible promoter is a promoter that is activated by environmental conditions, for example, light or temperature. In further examples, the promoter is a repressible promoter such that expression of a nucleic acid operably linked to the promoter can be reduced to low or undetectable levels, or eliminated. A repressible promoter may be repressed by direct binding of a repressor molecule (such as binding of the trp repressor to the trip operator in the presence of tryptophan). In a particular example, a repressible promoter is a tetracycline repressible promoter. In other examples, a repressible promoter is a promoter that is repressible by environmental conditions, such as hypoxia or exposure to metal ions.

In some embodiments, the polynucleotide encoding the Cas9-inhibiting polypeptide (e.g., as part of an expression cassette) is delivered to the cell by a vector. For example, in some embodiments, the vector is a viral vector. Exemplary viral vectors can include, but are not limited to, adenoviral vectors, adeno-associated viral (AAV) vectors, and lentiviral vectors.

in some embodiments, the Cas9-inhibiting polypeptide or a polynucleotide encoding the Cas9-inhibiting polypeptide is delivered as part of or within a cell delivery system. Various delivery systems are known and can be used to administer a composition of the present disclosure, for example, encapsulation in liposomes, microparticles, microcapsules, or receptor-mediated delivery.

Exemplary liposomal delivery methodologies are described in Metselaar et al., Mini Rev. Med. Chem. 2(4): 319-29 (2002); O'Haggen et al., Expert Rev. Vaccines 2(2):269-83 (2003); O'Hagan, Curr. Drug Targets Infjct. Disord. 1(3):273-86 (2001); Zho et al., Biosci Rep. 22(2): 355-69 (2002); Chikh et al., Biosci Rep. 22(2):339-53 (2002); Bungener et al., Biosci. Rep. 22(2):323-38 (2002); Park, Biosci Rep. 22(2):267-81 (2002); Ulrich, Biosci. Rep. 22(2):129-50; Lofthouse, Adv. Drug Deliv. Rev. 54(6):863-70 (2002); Zhou et al., J. Inmunmunother. 25(4):289-303 (2002); Singh et al., Pharm Res. 19(6):715-2.8 (2002); Wong et al., Curr. Med. Chem. 8(9):1123-36 (2001); and Zhou et al., Immunonmethods (3):229-35 (1994).

Exemplary nanoparticle delivery methodologies, including gold, iron oxide, titanium, hydrogel, and calcium phosphate nanoparticle delivery methodologies, are described in Wagner and Bhaduri, Tissue Engineering 18(1): 1-14 (2012) (describing inorganic nanoparticles); Ding et al., Mol Ther e-pub (2014) (describing gold nanoparticles); Zhang et al., Langmuir 30(3):839-45 (2014) (describing titanium dioxide nanoparticles); Xie et al., Curr Pharm Biotechnol 14(10): 918-25 (2014) (describing biodegradable calcium phosphate nanoparticles); and Sizovs et al., J Am Chem Soc 136(1): 234-40 (2014).

Introduction of a Cas9-inhibiting polypeptide as described herein into a prokaryotic cell can be achieved by any method used to introduce protein or nuclei acids into a prokaryote. In some embodiments, the Cas9-inhibiting polypeptide is delivered to the prokaryotic cell by a delivery vector (e.g., a bacteriophage) that deliver a polynucleotide encoding the Cas9-inhibiting polypeptide. In some embodiments, inhibiting Cas9 in the prokaryote could either help that phage kill the bacterium or help other phages kill it.

A Cas9-inhibiting polypeptide as described herein can be introduced into any cell that contains, expresses, or is expected to express, Cas9. Exemplary cells can be prokaryotic or eukaryotic cells. Exemplary prokaryotic cells can include but are not limited to, those used for biotechnological purposes, the production of desired metabolites, *E. coli* and human pathogens. Examples of such prokaryotic cells can include, for example, *Escherichia coli, Pseudomonas* sp., *Corynebacterium* sp., *Bacillus subtitis, Streptococcus pneumonia, Pseudomonas aeruginosa, Staphylococcus aureus, Campylobacter jejuni, Francisella novicida, Corynebacterium diphtheria, Enterococcus* sp., *Listeria monocytogenes, Mycoplasma gallisepticum, Streptococcus* sp., or *Treponema denticola*. Exemplary eukaryotic cells can include, for example, animal (e.g., mammalian) or plant cells. Exemplary mammalian cells include but are not limited to human, non-human primates, mouse, and rat cells. Cells can be cultured cells or primary cells. Exemplary cell types can include, but are not limited to, induced pluripotent cells, stem cells or progenitor cells, and blood cells, including but not limited to T-cells or B-cells.

In some embodiments, the cells are removed from an animal (e.g., a human, optionally in need of genetic repair), then Cas9, and optionally guide RNAs, for gene editing are introduced into the cell ex vivo, and a Cas9-inhibiting polypeptide is introduced into the cell. In some embodiments, the cell(s) is subsequently introduced into the same animal (autologous) or different animal (allogeneic).

In any of the embodiments described herein, a Cas9 polypeptide can be introduced into a cell to allow for Cas9 DNA binding and/or cleaving (and optionally editing), followed by introduction of a Cas9-inhibiting polypeptides as described herein. This timing of the presence of active Cas9 in the cell can thus be controlled by subsequently supplying Cas9-inhibiting polypeptides to the cell, thereby inactivating Cas9. This can be useful, for example, to reduce Cas9 "off-target" effects such that non-targeted chromosomal sequences are bound or altered. By limiting Cas9 activity to a limited "burst" that is ended upon introduction of the Cas9-inhibiting polypeptide, one can limit off-target effects. In some embodiments, the Cas9 polypeptide and the Cas9-inhibiting polypeptide are expressed from different inducible promoters, regulated by different inducers. These embodiments allow for first initiating expression of the Cas9 polypeptide followed later by induction of the Cas9-inhibiting polypeptide, optionally while removing the inducer of Cas9 expression.

In some embodiments, a Cas9-inhibiting polypeptide as described herein can be introduced (e.g., administered) to an animal (e.g., a human) or plant. This can be used to control in vivo Cas9 activity, for example in situations in which CRISPR/Cas9 gene editing was performed in vivo, or in circumstances in which an individual is exposed to unwanted Cas9, for example where a bioweapon comprising Cas9 is released.

In some embodiments, the Cas9-inhibiting polypeptides or a polynucleotide encoding the Cas9-inhibiting polypeptide, in administered as a pharmaceutical composition. In some embodiments, the composition comprises a delivery system such as a liposome, nanoparticle or other delivery vehicle as described herein or otherwise known, comprising the Cas9-inhibiting polypeptides or a polynucleotide encoding the Cas9-inhibiting polypeptide. The compositions can be administered directly to a mammal (e.g., human) to inhibit Cas9 using any route known in the art, including e.g., by injection (e.g., intravenous, intraperitoneal, subcutaneous, intramuscular, or intrademal), inhalation, transdermal application, rectal administration, or oral administration.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

EXAMPLES

Example 1

Results
CRISPR-Cas9 in *Listeria monocytogenes* Targets Foreign DNA

*Listeria monocytogenes* is a facultative intracellular food-borne pathogen with a well characterized phage population. Many *L. monocytogenes* isolates have type II-A CRISPR-Cas systems (Sesto, N. et al. (2014). *PLoS Genet*, 10, e1004065) and their CRISPR spacers possess identity to many virulent, temperate, and integrated phages (Di, H. et al, (2014) *Biochem Biophys Res Commun.*, 454, 399-403; Sesto, N. et al. (2014). *PLoS Genet*, 10, e1004065). However, there is no experimental evidence of canonical CRISPR-Cas function. We analyzed 275 genomes of *L. monocytogenes* and identified typeII-A CRISPR-Cas9 systems (Lmo Cas9) in 15% (n=41) of genomes (FIG. 1B). Interestingly, we found eight genomes (3% of the total), with examples of self-targeting (FIG. 1B and 1C) although CRISPR-cas9 is anticipated to be functional as the CRISPR repeat, PAM, tracrRNA, Cas9, and the associated promoters lack obvious inactivating mutations (FIG. 6A-E), We predicted that these strains possess inhibitors of CRISPR-Cas9 that allow the stable co-existence of a spacer-protospacer pair.

To test whether inhibitors were encoded by the prophages of *L. monocytogenes*, we first established the functionality of uninhibited CRISPR-Cas9 in an *L. monocytogenes* strain (10403s) that does not exhibit self-targeting. To test the activity of this system we designed a plasmid (pT) possessing a targeted protospacer (i.e. a sequence that is complementary to a natural spacer in the CRISPR array) along with a cognate protospacer adjacent motif (PAM), a three base motif that is necessary for Cas9 binding (FIG. 2A). We measured the transformation efficiency of 10403s with either pT or a control plasmid possessing a non-targeted sequence with an identical plasmid backbone (pNT). To simplify downstream analysis, a prophage cured version of 10403s (cure) was used for all downstream experiments since it was indistinguishable from wt10403s in this assay (FIG. 7). Transformation with pT yielded miniscule colonies relative to pNT (FIG. 2B, leftmost panel), although the number of colonies that emerged upon prolonged incubation were the same (FIG. 2C, see Discussion for further analysis). To confirm that this phenotype was the result of CRISPR-Cas9 interference, we constructed a cas9-deletion strain. Transformation of this strain with pT and pNT produced colonies of indistinguishable size (FIG. 2B $2^{nd}$ left panel). However, adding back cas9 to the *L. monocytogenes* chromosome under a constitutively active promoter completely inhibited transformation with pT (FIG. 2C). Together, these experiments demonstrate that Cas9 is functional in the *L. monocytogenes* strain 10403s at both endogenous and overexpressed levels, and limits transformation with a plasmid bearing a protospacer.

Resident Prophages Inactivate CRISPR-Cas9 in *L. monocytogenes*

To determine whether CRISPR-Cas9 may be disabled in a strain with self-targeting spacers, we examined immunity function in *L. monocytogenes* strain J0161, whose spacer 16 perfectly matches a prophage (ϕJ0161a) in the same genome (FIG. 1C). We could not detect any clearly deleterious CRISPR-Cas mutations in J0161, suggesting that this self-targeting scenario was the result of inhibition and not loss of function (FIG. 6B-F). Since the type II-A CRISPR array of J0161 is distinct from that of 10403s, a J0161-specific targeted plasmid ($pT_{J0161}$) was used to test the function CRISPR-Cas9 in J0161. Consistent with the inactivation implied by self-targeting, there was no significant difference in transformation efficiency or colony size to distinguish $pT_{J0161}$ from pNT (FIGS. 2B and 2C, rightmost panel). Thus, we reasoned that that the J0161 genome may encode Cas9 inhibitors.

In search of the genetic basis for CRISPR-Cas9 inactivation in J0161, we focused on the prophage ϕJ0161a as a likely source of an inhibitor gene because it contained the self-targeted sequence in this strain. To determine whether ϕJ0161a contained an inhibitor, the prophage-cured strain of 10403s was lysogenized with ϕJ0161a and assayed for CRISPR-Cas9 functionality by plasmid transformation. While ϕcure10403s strain targeted pT, the acquisition of ϕJ0161a was sufficient to inactivate CRISPR-Cas9 function (FIGS. 2B, $3^{rd}$ panel from left and 2C, $4^{th}$ from left), suggesting that this prophage encodes an inhibitor of CRISPR-Cas9. The ϕJ0161a prophage also inactivated plasmid targeting in a strain constitutively expressing cas9, suggesting that the inhibitory mechanism does not operate by disrupting natural regulation of the cas9 promoter (FIG. 2C. $5^{th}$ from left).

Given that ϕJ0161a inhibited CRISPR-Cas9 function, and the endogenous prophage ϕ10403s did not, we compared the genomes of these two closely related phages to identify the regions of difference (FIG. 2D). In addition to sharing 39 core phage genes with >40% protein sequence identity, ten non-overlapping unique dusters of genes were identified (cluster boundaries were chosen based on predicted operon structure, with 1-12 genes per cluster). Each cluster was cloned and integrated into the genome of prophage-cured 10403s and assayed for CRISPR-Cas9 function. Of the ten fragments, seven were successfully introduced into *L. monocytogenes*, while three fragments could not be inserted in the *L. monocytogenes* genome and were presumably toxic in isolation. Plasmid transformation assays revealed that ϕJ0161a fragment 1 was the only fragment capable of inhibiting CRISPR-Cas9, indicating that his fragment encoded at least one CRISPR-Cas9 inhibitor (FIG. 2D, FIG. 8). Expressing the individual genes from this four-gene fragment led to the conclusive identification of two anti-CRISPR genes, LMO_03146 and LMOG_03147 (herein referred to as acrIIA1 and acrIIA2, respectively; FIGS. 2B and 2D). Deletion of both acrIIA1 and acrIIA2 from a 10403s::ϕJ0161a lysogen restored CRISPR-Cas9 function, confirming that these are the only anti-CRISPR genes in ϕJ0161a (FIG. 2B).

Anti-CRISPR Loci are Widespread in *L. monocrytogenes*

To identify additional type II-A anti-CRISPRs, the genomic position analogous to that of acrIIA1 and acrIIA2 in related *L. monocytogenes* prophages was examined. A recurring anti-CRISPR (acr) locus containing acrIIA1 within in a small operon (2-5 genes) of highly conserved gene order was identified between the left integration site and the genes involved in cell lysis (FIG. 3A). We identified five novel protein families conserved within acr loci. To test these, we cloned and integrated representatives into the 10403s genome and assayed the transformation efficiency of pT and pNT. Two new genes were identified that were capable of CRISPR inactivation (acrIIA$^3$ and acrIIA4), while the remaining three (orfC, D, E) were not (FIG. 3A, FIG. 9).

To determine whether CRISPR-Cas9 inactivation in *L. monocytogenes* is pervasive, we next analyzed the conservation pattern for each anti-CRISPR. Although each acrIIA gene was sufficient to inactivate CRISPR-Cas9 in isolation, we observed a common presence of acrIIA1 in most acr loci. Nearly all instances (91%) of acrIIA2-4 were found upstream of the helix-turn-helix (HTH) motif-containing acrIIA1, suggesting that this gene may be a marker for acr loci (FIG. 3B). The most common scenario we observed in 119 acr loci were either acIIA1-2 or acrIIA1-2-3, representing 66% of acr loci. In total, acrIIA genes were identified in 25% of *L. monocytogenes* genomes, with approximately 50% oft monocytogenes cas9-containing strains possessing at least one anti-CRISPR in the same genome (FIG. 3C). Many instances of *L. monocytogenes* genomes possessing multiple acrIIA-encoding prophages were also identified (Supplementary Table 1). Furthermore, at least one acrIIA gene was found in the genomes of all eight instances of self-targeting that were initially identified (FIG. 1B, Supplementary Table 1), explaining how these scenarios are stable. Together, these data suggest widespread prophage-mediated inactivation of CRISPR-Cas9 in *L. monocytogenes*.

TABLE S1

| acrIIA Gene Conservation, Related to FIGS. 1B 4B and 4C | |
|---|---|
| genomes that lack cas9 and all known acrIIA genes | 264 |
| genomes that contain cas9 but lack all known acrIIA genes | 33 |
| genomes contain cas9 and acrIIA genes | 37 |
| genomes that lack cas9, but contain acrIIA genes | 65 |
| unpaired acr genes | |

| control (cysS) | acrIIA3 | acrIIA2 | acrIIA1 | acrIIA4 | Cas9 | ST strains |
|---|---|---|---|---|---|---|
| AEO05249.1 | | | | | AEO07576.1 | |
| AKI48207.1 | | | | | AKI50529.1 | |
| AMD50972.1 | | | | | AMD53187.1 | |
| AMR52783.1 | | | | | AMR55031.1 | |
| EEW14429.1 | | | | | EEW14776.1 | |
| KES84268.1 | | | | | KES86621.1 | |
| KET22766.1 | | | | | KET25022.1 | |
| KET54818.1 | | | | | KET56390.1 | |
| KEU03893.1 | | | | | KEU00315.1 | |
| KEU81061.1 | | | | | KEU82991.1 | |
| KEU92860.1 | | | | | KEU94779.1 | |
| KEV01501.1 | | | | | KEV04018.1 | |
| KEV13316.1 | | | | | KEV15767.1 | |
| KEV34890.1 | | | | | KEV37443.1 | |
| KEV87445.1 | | | | | KEV88657.1 | |
| KEW12308.1 | | | | | KEW13456.1 | |
| KEW54858.1 | | | | | KEW57091.1 | |
| KEX56334.1 | | | | | KEX57585.1 | |
| KEX62909.1 | | | | | KEX64108.1 | |
| KEX85751.1 | | | | | KEX84898.1 | |
| KFL18307.1 | | | | | KFL20187.1 | |
| KHK15389.1 | | | | | KHK15281.1 | |
| KPV81115.1 | | | | | KPV80639.1 | |
| KTA33634.1 | | | | | KTA27954.1 | |
| KTA40577.1 | | | | | KTA36142.1 | |
| KTA59125.1 | | | | | KTA59526.1 | |
| KTE88758.1 | | | | | KTE86646.1 | |
| KXS69410.1 | | | | | KXS73069.1 | |
| KXX03397.1 | | | | | KXX04680.1 | |
| KXX27153.1 | | | | | KXX27120.1 | |
| KYH47795.1 | | | | | KYH48716.1 | |
| KEX06234.1 | | | | | KEX03765.1 | |
| AGR07328.1 | | | | | AGR09779.1 | |
| EFG02722.1 | EFG02166.1 | EFG02165.1 | FG02164.1 | | EFG02048.1 | FSL J1-194 |
| AEO02308.1 | | AEO04363.1 | AEO04364.1 | AEO04689.1 | AEO04756.1 | J0161 |
| | | | AEO04690.1 | | | |
| AKI51021.1 | AKI52063.1 | AKI52062.1 | AKI52061.1 | | AKI53425.1 | L1846 |
| | AKI53105.1 | AKI53106.1 | AKI53107.1 | | | |
| AKI41163.1 | AKI40129.1 | AKI40130.1 | AKI40131.1 | | AKI42028.1 | L2626 |
| AGR26778.1 | AGR27459.1 | AGR27460.1 | AGR27297.1 | | AGR27343.1 | R2-502 |
| | | | AGR27461.1 | | | |
| EEW19474.1 | | | EEW20426.1 | | EEW20201.1 | R2-503 |
| AHJ04747.1 | AHJ02948.1 | AHJ02947.1 | AHJ02946.1 | | AHJ04249.1 | WSLC1001 |
| AKI42516.1 | AKI43551.1 | AKI43550.1 | AKI43549.1 | | AKI44910.1 | |
| EXL23533.1 | EXL25968.1 | | | | EXL23613.1 | |
| EZH70416.1 | EZH69742.1 | EZH71062.1 | EZH69029.1 | | EZH69562.1 | |
| | | | EZH71063.1 | | | |
| KEU59490.1 | KEU52815.1 | KEU52814.1 | KEU52813.1 | | KEU61049.1 | |
| KHK05112.1 | KHK09045.1 | KHK09044.1 | KHK04755.1 | | KHK11936.1 | |
| | | | KHK09043.1 | | | |
| KID24070.1 | KID23649.1 | KID23650.1 | KID23651.1 | | KID22034.1 | |
| | | KID25721.1 | KID25720.1 | | | |
| KKB89786.1 | KKB89545.1 | KKB87491.1 | KKB87492.1 | | KKB87210.1 | |
| | | KKB89544.1 | KKB89543.1 | | | |
| KTA33603.1 | KTA31236.1 | KTA31235.1 | KTA28092.1 | | KTA28352.1 | |
| | | | KTA31234.1 | | | |

TABLE S1-continued acrIIA Gene Conservation, Related to FIGS. 1B 4B and 4C

| | | | | | |
|---|---|---|---|---|---|
| KTA58546.1 | KTA51620.1 | KTA51621.1 | KTA51622.1 | | KTA50572.1 |
| KXS57839.1 | KXS58608.1 | KXS58607.1 | KXS58606.1 | KXS56938.1 | KXS59964.1 |
| EAL04996.1 | | EAL06504.1 | EAL05810.1 | EAL05809.1 | EAL05449.1 |
| | | | EAL06505.1 | | |
| EEW23167.1 | | EEW22373.1 | EEW22374.1 | EEW23439.1 | EEW22432.1 |
| | | | EEW23440.1 | | |
| EFF99811.1 | | EFG00297.1 | EFG00298.1 | EFG00182.1 | EFF99171.1 |
| | | | EFG00183.1 | | |
| EHY63973.1 | | | | EHY61390.1 | EHY61427.1 |
| EXL17326.1 | | | EXL17712.1 | EXL17711.1 | EXL16255.1 |
| KTA40536.1 | | KTA33666.1 | KTA31190.1 | KTA31189.1 | KTA29552.1 |
| | | | KTA33667.1 | | |
| KXS59387.1 | | KXS56902.1 | KXS64534.1 | KXS57719.1 | KXS62773.1 |
| KXW90032.1 | | KXW85500.1 | KXW85495.1 | KXW85912.1 | KXW90865.1 |
| | | | KXW85497.1 | | |
| KTA67982.1 | | | KTA68177.1 | | KTA68618.1 |
| AGR14764.1 | | | AGR15693.1 | | AGR15756.1 |
| ALU77418.1 | | | ALU78083.1 | | ALU77910.1 |
| EFK41798.1 | | | EFK41083.1 | | EFK42981.1 |
| KHK20071.1 | | | KHK19909.1 | | KHK21360.1 |
| KHK20265.1 | | | KHK17523.1 | | KHK22389.1 |
| KHK26884.1 | | KHK28212.1 | KHK28213.1 | | KHK29000.1 |
| KHK32359.1 | | KHK33774.1 | KHK33773.1 | | KHK34506.1 |
| KID12814.1 | | KID20146.1 | KID20145.1 | | KID19562.1 |
| KID16736.1 | | KID21567.1 | KID21568.1 | | KID14794.1 |
| KID25109.1 | | KID27661.1 | KID27662.1 | | KID22855.1 |
| KXX34587.1 | | KXX34834.1 | KXX34335.1 | | KXX35452.1 |
| | | KXX34219.1 | | | |
| ACK40737.1 | ACK39691.1 | ACK39692.1 | ACK39693.1 | ACK40885.1 | |
| AEH91268.1 | AEH92315.1 | AEH92314.1 | AEH92313.1 | AEH91120.1 | |
| ALU81417.1 | ALU80614.1 | ALU80615.1 | ALU80616.1 | | |
| EXL28212.1 | EXL28247.1 | EXL28248.1 | EXL28249.1 | | |
| KES32042.1 | KES29691.1 | KES29690.1 | KES29689.1 | | |
| KES38767.1 | KES36191.1 | KES36190.1 | KES36189.1 | | |
| KES64642.1 | KES69056.1 | KES69057.1 | KES69058.1 | | |
| KET22488.1 | KET20225.1 | KET20226.1 | KET20227.1 | | |
| KET33547.1 | KET33008.1 | KET33009.1 | KET33010.1 | | |
| KET65150.1 | KET67219.1 | KET67220.1 | KET67221.1 | | |
| KEU38314.1 | KEU32638.1 | KEU32639.1 | KEU32640.1 | | |
| KEU70290.1 | KEU73964.1 | KEU69222.1 | KEU69221.1 | | |
| KEU77521.1 | KEU79801.1 | KEU73965.1 | KEU73966.1 | | |
| | | KEU79802.1 | KEU79803.1 | | |
| KEU85819.1 | KEU87627.1 | KEU87628.1 | KEU87629.1 | | |
| KEW39277.1 | KEW37877.1 | KEW37876.1 | KEW37875.1 | | |
| KEW47138.1 | KEW38798.1 | KEW38797.1 | KEW38796.1 | | |
| KEW52188.1 | KEW54596.1 | KEW54597.1 | KEW54598.1 | | |
| KEW87000.1 | KEW91381.1 | KEW91380.1 | KEW91379.1 | | |
| KEX05231.1 | KEX03851.1 | KEX03850.1 | KEX03849.1 | | |
| KEX16623.1 | KEX13878.1 | KEX13879.1 | KEX13880.1 | | |
| KEX48257.1 | KEX45733.1 | KEX45732.1 | KEX45731.1 | | |
| KEX44142.1 | KEX49273.1 | KEX49272.1 | KEX49271.1 | | |
| KHK37385.1 | KHK39424.1 | KHK39423.1 | KHK39422.1 | | |
| KLI10624.1 | KLI10452.1 | KLI10451.1 | KLI10195.1 | KLI10194.1 | |
| | KLI12476.1 | KLI12475.1 | KLI10251.1 | | |
| KNX95479.1 | KNX95907.1 | KNX95906.1 | | | |
| | KNX94640.1 | KNX94641.1 | | | |
| KPJ28401.1 | KPJ30389.1 | KPJ30390.1 | KPJ30391.1 | | |
| KPV83306.1 | KPV85471.1 | KPV85472.1 | KPV85473.1 | | |
| KTA46249.1 | KTA44520.1 | KTA44521.1 | KTA44522.1 | | |
| | | | KTA45326.1 | | |
| KTA51238.1 | KTA50253.1 | KTA50252.1 | KTA50251.1 | | |
| | | | KTA50988.1 | | |
| KTA64947.1 | KTA62142.1 | KTA62143.1 | KTA62144.1 | | |
| KXS86581.1 | KXS85159.1 | KXS85158.1 | KXS85157.1 | | |
| KXX46503.1 | KXX46300.1 | KXX46299.1 | KXX46298.1 | | |
| KXX49128.1 | KXX48607.1 | KXX48606.1 | KXX48605.1 | | |
| KXX50214.1 | KXX49264.1 | KXX49263.1 | KXX49262.1 | | |
| AKI55317.1 | | | AKI56173.1 | AKI56172.1 | |
| AMD23307.1 | | | AMD24317.1 | AMD24318.1 | |
| KKD52037.1 | | | KKD49091.1 | KKD49092.1 | |
| KTA47721.1 | | | KTA46387.1 | KTA46388.1 | |
| KTA50332.1 | | | KTA52328.1 | KTA52327.1 | |
| KXS77556.1 | | | | KXS77365.1 | |
| KXS79013.1 | | | | KXS78354.1 | |
| KXX11384.1 | | | | KXX11218.1 | |
| KXX17306.1 | | | | KXX17138.1 | |
| KXX19133.1 | | | | KXX18287.1 | |
| KES91745.1 | | KES96882.1 | KES96881.1 | | |

TABLE S1-continued acrIIA Gene Conservation, Related to FIGS. 1B 4B and 4C

| | | |
|---|---|---|
| KET71424.1 | KET73263.1 | KET73262.1 |
| KET90504.1 | KET94691.1 | KET94692.1 |
| KEV66815.1 | KEV69928.1 | KEV69929.1 |
| KEV93156.1 | KEV93282.1 | KEV93281.1 |
| KEW04107.1 | KEW08181.1 | KEW08182.1 |
| KEW04863.1 | KEW09554.1 | KEW09555.1 |
| KEW11516.1 | KEW17021.1 | KEW17020.1 |
| KEW59026.1 | KEW65182.1 | KEW65181.1 |
| KEX05590.1 | KEX05985.1 | KEX05984.1 |
| KHK13841.1 | | KHK12400.1 |
| KJJ91084.1 | KJJ91611.1 | KJJ91612.1 |
| KJQ95289.1 | KJQ94313.1 | KJQ94314.1 |
| KJQ98292.1 | KJQ95811.1 | KJQ95812.1 |
| KJR57725.1 | KJR51141.1 | KJR51140.1 |
| KJR58524.1 | KJR60208.1 | KJR60209.1 |
| KKD51859.1 | | KKD43688.1 |
| KTA41666.1 | | KTA35071.1 |
| KTA65269.1 | | KTA63900.1 |
| KXF69083.1 | KXF66382.1 | KXF66381.1 |
| AGR12413.1 | AGR07062.1 | AGR07061.1 |
| AAT03038.1 | | |
| ADB67037.1 | | |
| ADB70126.1 | | |
| AEO24539.1 | | |
| AEO37792.1 | | |
| AFH78832.1 | | |
| AGR02736.1 | | |
| AGR04913.1 | | |
| AGR16038.1 | | |
| AGR21403.1 | | |
| AGR21930.1 | | |
| AGR32499.1 | | |
| AHF28095.1 | | |
| AHF30972.1 | | |
| AHF33963.1 | | |
| AHF36954.1 | | |
| AHF39945.1 | | |
| AHF42886.1 | | |
| AHI68925.1 | | |
| AHJ37147.1 | | |
| AHN31516.1 | | |
| AHY99532.1 | | |
| AIL67941.1 | | |
| AIZ37538.1 | | |
| AJA81957.1 | | |
| AJT44045.1 | | |
| AKG84402.1 | | |
| AKG87228.1 | | |
| AKI45409.1 | | |
| AKP37411.1 | | |
| AKS52855.1 | | |
| ALQ13660.1 | | |
| ALQ15375.1 | | |
| ALQ19576.1 | | |
| ALQ21479.1 | | |
| ALQ25193.1 | | |
| ALU83475.1 | | |
| ALX67727.1 | | |
| AMD26187.1 | | |
| ANE38117.1 | | |
| EAL07955.1 | | |
| EFD91450.1 | | |
| EFF96046.1 | | |
| EFR95169.1 | | |
| EGF38890.1 | | |
| EGJ23745.1 | | |
| ERH76184.1 | | |
| ERH76295.1 | | |
| ERH77379.1 | | |
| ERH83604.1 | | |
| ERH85425.1 | | |
| EUJ16754.1 | | |
| EXL13590.1 | | |
| EXL14999.1 | | |
| EXL25668.1 | | |
| KEK05609.1 | | |
| KEK07032.1 | | |
| KES28051.1 | | |

TABLE S1-continued acrIIA Gene Conservation, Related to FIGS. 1B 4B and 4C

KES28301.1
KES38071.1
KES42071.1
KES42797.1
KES48493.1
KES50725.1
KES54322.1
KES54965.1
KES55696.1
KES63074.1
KES63309.1
KES72038.1
KES79358.1
KES79767.1
KES80806.1
KES82973.1
KES86788.1
KES92539.1
KET00546.1
KET04697.1
KET06207.1
KET08149.1
KET08880.1
KET13375.1
KET15678.1
KET17220.1
KET30859.1
KET35076.1
KET38677.1
KET39554.1
KET41316.1
KET44817.1
KET47850.1
KET53482.1
KET55834.1
KET60044.1
KET62217.1
KET69318.1
KET74754.1
KET76626.1
KET81048.1
KET85737.1
KET86860.1
KET91339.1
KET98444.1
KEU01781.1
KEU03644.1
KEU06655.1
KEU10723.1
KEU12483.1
KEU18590.1
KEU21146.1
KEU23067.1
KEU24780.1
KEU30341.1
KEU36177.1
KEU37301.1
KEU43040.1
KEU43555.1
KEU46678.1
KEU51513.1
KEU55425.1
KEU55498.1
KEU58686.1
KEU64129.1
KEU68275.1
KEU69241.1
KEU77548.1
KEU86942.1
KEU90182.1
KEV00307.1
KEV00562.1
KEV06907.1
KEV11638.1
KEV12282.1
KEV14240.1
KEV21793.1
KEV22298.1

TABLE S1-continued acrIIA Gene Conservation, Related to FIGS. 1B 4B and 4C

KEV26044.1
KEV32026.1
KEV32063.1
KEV35626.1
KEV42967.1
KEV44621.1
KEV49515.1
KEV49947.1
KEV52716.1
KEV53451.1
KEV60716.1
KEV63470.1
KEV71076.1
KEV74160.1
KEV76378.1
KEV76776.1
KEV79179.1
KEV81224.1
KEV88927.1
KEV93759.1
KEV95283.1
KEW03640.1
KEW09573.1
KEW18769.1
KEW19179.1
KEW21604.1
KEW27010.1
KEW31226.1
KEW33386.1
KEW36305.1
KEW42387.1
KEW44715.1
KEW57718.1
KEW65692.1
KEW66741.1
KEW71344.1
KEW71596.1
KEW72422.1
KEW77363.1
KEW79497.1
KEW80113.1
KEW84366.1
KEW93848.1
KEW95807.1
KEW96317.1
KEX09756.1
KEX11628.1
KEX19359.1
KEX20220.1
KEX23616.1
KEX29531.1
KEX29582.1
KEX33273.1
KEX39294.1
KEX42941.1
KEX46988.1
KEX50326.1
KEX51799.1
KEX64668.1
KEX68538.1
KEX69000.1
KEX72953.1
KEX73328.1
KEX77547.1
KEX82199.1
KFZ71375.1
KGJ75182.1
KGJ80867.1
KGR20308.1
KHK07430.1
KHK19170.1
KHK26142.1
KHK36612.1
KHQ60145.1
KHQ69332.1
KHS60750.1
KHS61164.1
KID14246.1

TABLE S1-continued acrIIA Gene Conservation, Related to FIGS. 1B 4B and 4C

KJH24122.1
KJJ89955.1
KJQ79905.1
KJQ83378.1
KKF72182.1
KKO43304.1
KNX50880.1
KNX54024.1
KNX58068.1
KNX62105.1
KNX63287.1
KNX66597.1
KNX70553.1
KNX72130.1
KOX87096.1
KPJ27561.1
KQC81886.1
KQC82004.1
KRJ93270.1
KRW87784.1
KSZ43192.1
KSZ44687.1
KSZ45883.1
KSZ48351.1
KTA43969.1
KXF63597.1
KXS57277.1
KXS68541.1
KXS69730.1
KXS75040.1
KXS83236.1
KXW87734.1
KXW89246.1
KXW94597.1
KXW97284.1
KXX00507.1
KXX03707.1
KXX09006.1
KXX14888.1
KXX23313.1
KXX28906.1
KXX32727.1
KXX35528.1
KXX37642.1
KXX42799.1
KYB35881.1
KYB36139.1
KYB36717.1
KYB42077.1
KYB43947.1

SLCC5850 was no included in the conservation pattern analysis

| CBY50703.1 | CBY51763.1 | CBY51762.1 | CBY51761.1 | CBY53074.1 | slcc5850 |
|---|---|---|---|---|---|

Previous HTH-containing anti-CRISPR associated (aca) genes were used as markers to identify novel type I anti-CRISPR genes (Pawluk, A. et al. (2016). *Nature Microbiology*, 1, 1-6), although the aca genes did not have anti-CRISPR activity themselves. We hypothesized that acrIIA1 could fulfill the role of such a marker. A comprehensive phylogenetic analysis of acrIIA1 was conducted, revealing homologs detected widely across Firmicutes, in both mobile elements and core genomes (FIG. 4A). A family of distantly related acrIIA1 homologs were identified in *Listeria* genomes, exemplified by orfD, an HTH-containing gene that had been independently identified as an acr locus member (FIG. 3A). While this gene lacked anti-CRISPR activity in a functional assay, its co-occurrence with acrIIA4 in plasmid pLMIV suggests that the broad acrIIA1/orfD superfamily could be used as a marker to identify new acr genes (FIG. 3A). Future work will be necessary to determine whether the HTH-containing genes in these systems serve as effective markers for novel anti-CRISPR discovery.

To determine the homology landscape of acrIIA2-4, similar phylogenetic analyses were performed. Unlike acrIIA1, which was widespread across Firmicutes core genomes, these other three acr genes were mostly restricted to prophages in *Listeria*. Three distinct sequence families of acrIIA2 were identified, found only within *Listeria* siphophages (a family of long tailed, non-contractile phages) (FIG. 4B), while two acrIIA3 families were observed in the genomes of siphophages *Listeria* and *Streptococcus* (FIG. 4C). Lastly, acrIIA4 was observed in two distinct sequence families, one in *Listeria*, siphophages and plasmids, and the other in a group of obligate virulent myophages (long contractile tailed phages) (FIG. 4D). While acrIIA2 and acrIIA3 were nearly always found with acrIIA1, acrIIA4 often occurred in the absence of acrIIA1 homologs in phages and mobile elements of *Listeria*. For example, the family of acrIIA4 in virulent phages are distinct in that they have an ~70 amino acid C-terminal extension in the predicted protein and do not occur with the HTH-containing genes acrIIA1 or orfD, suggesting potential mechanistic and evolutionary distinctions between these acrIIA4 families. Together, these analyses reveal ample sequence space for surveying homologous acr genes for specificity determinants and suggest an active arms race between cas9 and mobile elements in L. monocytogenes.

AcrIIA2, AcrIIA3, and AcrIIA4 inhibit S. pyogenes Cas9

To determine the versatility of the Lmo Cas9 AcrIIA proteins, we asked whether these inhibitors were functional on the related Cas9 protein from S. pyogenes (Spy, 53% identical to Lmo Cas9). This ortholog has been used widely for biotechnological applications as an RNA-guided nuclease (Barrangou, R., and Doudna, J. A. (2016), Nature Biotechnology, 34, 933-941), as well as for programmable gene repression by a catalytically deactivated mutant (dCas9) for programmable gene repression (Gilbert, L. A. et al. (2013). Cell 154, 442-451; Qi, L. S. et al. (2013). Cell, 152, 1173-1183). Using an E. coli strain that carries Spy dCas9, we tested whether AcrIIA proteins block dCas9 from interfering with transcription of a chromosomal RFP reporter gene (FIG. 5A). In a genetic background lacking inhibitors, the presence of an sgRNA and dCas9 reduced RFP fluorescence to 2.6% relative to a strain with no guide RNA. acrIIA2 partially blocked dCas9 function with fluorescence rising to 25%, while acrIIA4 nearly completely blocked dCas9, with fluorescence at 85% of the no guide control (FIG. 5B). We could not obtain meaningful data from acrIIA3 because the protein was toxic to E. coli. This lowered the recorded cell count during flow cytometry (see FIG. 10a) and lead to large variability in the fluorescence measurements. A homolog of AcrIIA3 from S. pyogenes (accession number: AND04610.1) with 45% sequence identity to Lmo_acrIIA3 was also tested, but resulted in impaired growth of E. coli (FIG. 10b). The mechanism of acrIIA3 toxicity remains to be determined. We conclude the acrIIA2 and acrIIA4 inhibit Spy dCas9 in E. coil to different degrees.

Given the common application of Spy Cas9 in eukaryotic cells, we next tested the AcrIIA proteins for their ability to block gene editing in human cells. HEK293T cells with an inducible eGFP reporter gene were transiently transfected with a plasmid expressing both Spy Cas9 and an sgRNA targeting eGFP in the presence or absence of vectors expressing human codon optimized AcrIIA proteins. After allowing gene editing to proceed for 36 h, eGFP was induced for 12 h, and cellular fluorescence was then measured by flow cytometry (FIG. 5C). In the presence of Cas9 and the eGFP sgRNA, gene editing resulted in a 25% decrease in the number of GFP positive cells, while co-expression with acrIIA2 or acrIIA4 prevented Cas9-based gene editing (FIG. 5D). We additionally tested the S. pyogenes homolog of acrIIA3 (Spy_acrIIA3) in this assay, which was not toxic in human cells, but had no impact on Cas9 function. acrIIA1 was non-functional in human cells, as was orfA, a negative control that has no anti-CRISPR activity in L. monocytogenes. Taken together with dCas9 experiments in E. coli, these data demonstrate the utility of the AcrIIA2 and AcrIIA4 proteins to inhibit the function of an orthologous Cas9 in heterologous hosts. These reagents, therefore, represent new tools in the CRISPR-Cas9 genome engineering toolkit.

Discussion

Phage-encoded inhibitors of bacterial immune systems emerge due to the strong selective pressures in the evolutionary arms race between these two entities (Samson, J. E. et al. (2013). Nat Rev Micro, 11, 675-687). The first identification of phage encoded anti-CRISPRs in type I CRISPR-Cas systems hinted that more CRISPR inhibitors existed, but methods were lacking for their discovery. Here, we present a bioinformatics strategy that uses "self-targeting" as a genomic marker for CRISPR-Cas inhibitor genes (FIG. 1A). This approach led to the identification of four different type II-A CRISPR-Cas9 inhibitors (FIG. 3A), which are collectively present in half of all Cas9-encoding L. monocytogenes genomes, including all genomes with self-targeting (FIG. 3C). We anticipate that this approach will be helpful for identifying acr genes in other CRISPR-Cas systems, although a distinct mechanism for tolerance of self-targeting has been described for type III systems (Goldberg, G. W. et al. (2014). Nature 514, 633-637; Samai, P. et al. (2015). Cell, 161, 1164-1174).

To facilitate the identification of AcrIIA proteins, we first demonstrate a functional CRISPR-Cas9 system in L. monocytogenes (FIG. 2B). Previous studies of CRISPR-Cas in this organism have focused on the type I-B system and an associated I-B derived CRISPR orphan array lacking cas genes (Mandin, P. et al. (2007). Nucleic Acids Research, 35, 962-974; Sesto, N. et al. (2014). PLoS Genet, 10, e1004065). Although no canonical CRISPR-Cas function had been established for either system previously, the orphan array was shown to be processed by a host ribonuclease to generate non coding RNAs (Mandin, P, et al. (2007). Nucleic Acids Research, 35, 962-974; Sesto, N. et al. (2014). PLoS Genet, 10, e1004065). To observe function for the II-A CRISPR-Cas system, we used a standard transformation efficiency assay, showing that Cas9 function in strain 10403s is sufficient to limit transformation of a plasmid in a sequence specific manner (FIG. 2A-C). Given the small colony phenotype observed during transformation of 10403s with pT, we suspect that endogenous levels of cas9 expression are not sufficient to totally clear the plasmid, leading to maintained plasmid in a tiny colony. Confirming this, increased expression of cas9 resulted in a complete elimination of transformants in this assay (FIG. 2C). Given that ϕJ0161a can inhibit this overexpressed CRISPR-Cas9 system (FIG. 2C), we conclude that the identified inhibitors are able to block both endogenous and overexpressed Cas9 function.

To identify candidate anti-CRISPR genes, related prophages from CRISPR-active strain 10403s to a prophage that inhibits CRISPR from strain J0161 were compared, and a process of elimination cloning approach was taken (FIG. 2D). The identification of two isolated acr genes was confirmed for acrIIA1 and acrIIA2 genes that are present in ϕJ0161. In searching for more anti-CRISPRs, we find that conserved genomic positioning in related. phages is a good proxy for identifying distinct type II-A Cas9 inhibitor proteins, despite a lack of sequence conservation between the proteins themselves (FIG. 3A). This has been observed previously in studies of Type I-F and I-E anti-CRISPRs (Bondy-Denomy et al. (2013). Nature, 493, 429-432; Pawluk, A. et al. (2014). mBio 5, e00896). In L. monocytogenes, the high prevalence of Cas9 inhibitors in prophages suggests the widespread inactivation of CRISPR-Cas9 function (FIG. 3C). At present, we do not understand whether there is a mechanistic link to explain the common co-occurrence of acIIA1 with other anti-CRISPRs (FIGS. 3A and 3B). Although this gene is sufficient to inactivate CRISPR-Cas9 function in a plasmid challenge assay, we speculate that it could act as a co-factor or regulator of other acrII4 genes during infection or lysogeny, thus explaining the genomic associations observed. Future work will be necessary to understand whether AcrIIA1 is, in fact, a bi-functional protein in this regard and more broadly, whether the superfamily is a marker for acr genes.

Phylogenetic analyses demonstrate common occurrences of acrIIA2-4 in mobile elements in *Listeria* mobile elements (FIG. 4). This likely facilitates horizontal gene transfer in this organism by blocking Cas9-based targeting and adaptation (Heler, R. et al. (2015) *Nature* 519, 199-202). In addition to the family of prophages where these acrIIA genes were first identified, homologs were also found in distant siphophages, myophages and plasmids. Most notably, the acrIIA4 homologs encoded by virulent myophages did not have acrIIA1 superfamily homologs in their vicinity. Furthermore, the presence of acrIIA1 and acrIIA3 homologs in genera outside of *Listeria* demonstrates that CRISPR-Cas9 inactivation may be common-place in the Firmicutes.

To inactivate CRISPR-Cas9 function, many mechanisms are possible, in theory. By demonstrating the efficacy of acrIIA2 and acrIIA4 in heterologous hosts with engineered elements (i.e. cas9 promoter, sgRNA design and promoter) we conclude that transcriptional repression is unlikely. Type I anti-CRISPRs function by binding directly to the Cas proteins required for interference and preventing DNA binding or DNA cleavage (Bondy-Denomy, J et al. (2015). *Nature,* 526, 136-139). By extension, we expect a similar mechanism for acrIIA2 and acrIIA4, given their ability to function in human cells. The enhanced efficacy of acrIIA2 in the cleavage-based Cas9 assay in human cells relative to the dCas9 based assay suggests that it may inhibit both binding and cleavage to some degree, with cleavage inhibition manifesting as a full inactivation of Cas9 function. In the case of acrIIA4, DNA-binding is clearly inhibited, although whether this is through a direct interaction with Cas9 remains to be seen.

The identification and future mechanistic dissection of type II-A inhibitors will provide valuable new reagents for studying canonical CRISPR-Cas9 function in natural and engineered settings. The ability of AcrIIA proteins to block Spy Cas9 in *E. coli* and human cells suggests that these proteins can provide a post-translational "off-switch" for Cas9. This could add a layer of regulation on this powerful system that can be applied in eukaryotic systems to control genome engineering. This new addition to the CRISPR-Cas9 toolbox could enable new applications, such as specifically reversing the effects of dCas9 binding to a genomic locus, or limiting the amount of time that Cas9 is active in the nucleus to reduce off-target gene editing. It will be important to expand the search for inhibitor proteins to continue to exploit the abundant tools provided to us from the phage-bacteria arms race.

| REAGENT or RESOURCE | SOURCE | IDENTIFIER |
|---|---|---|
| Experimental Models: Cell Lines | | |
| HEK293T | ATCC | N/A |
| Experimental Models: Organisms/Strains | | |
| *Listeria monocytogenes* 10403s | Laboratory of Daniel Portnoy | ncbi.nlm.nih.gov/Taxonomy/Browser/wwwtax.cgi?mode=Info&id=393133&lvl=3&lin=f&keep=1&srchmode=1&unlock |
| *Listeria monocytogenes* 10403s derivatives | this paper | see Table S2 |
| *Listeria monocytogenes* J0161 | Laboratory of Martin Wiedmann | ncbi.nlm.nih.gov/Taxonomy/Browser/wwwtax.cgi?id=393130 |
| *Listeria monocytogenes* SLCC2482 | Ariane Pietzka | ncbi.nlm.nih.gov/Taxonomy/Browser/wwwtax.cgi?id=863767 |
| *Lisieria mortoeytogenes* SLCC2540 | Ariane Pietzka | ncbi.nlm.nih.gov/Taxonomy/Browser/wwwtax.cgi?id=879089 |
| *Escherichia coli* BW25113 derivatives | this paper | see Table S2 |
| Recombinant DNA | | |
| pBAD24 | Laboratory of Carol Gross | ncbi.nlm.nih.gov/nuccore/X81837.1 |
| pBAD24-derivative plasmids | this paper | see Table S2 |
| pdCas9-bacteria | Addgene | addgene.org/vector-database/44249/ |
| pLVX-TetOne-Puro | Ciontech | clontech.com/US/Products/Inducible_Systems/TetSystems_Product_Overview/Tet-One_Overview |
| pMD2.G | Addgene | addgene.org/12259/ |
| pX330 | Addgene | addgene.org/vector-database/42230/ |
| pcDNA3.1(+) | Addgene | addgene.org/vector-database/2093/ |
| pKSV7 | Laboratory of Daniel Portnoy | addgene.org/26686/ |
| pKSV7-derivative plasmids | this paper | see Table S2 |
| pPL2oexL | Laboratory of Daniel Portnoy | see FIG. 11 |
| pPL2oexL-derivative plasmids | this paper | see Table S2 |

| REAGENT or RESOURCE | SOURCE | IDENTIFIER |
|---|---|---|
| Sequence-Based Reagents | | |
| I. GeneBlocks for HEK293T expression of phage proteins | IDT | II. see Table S3 |
| Software and Algorithms | | |
| Prism 5 | GraphPad | graphpad.com/scientific-software/prism/ |
| CRISPRfinder | I2BC | crispr.i2bc.paris-saclay.fr/Server/ |
| CRISPRDetect | Univsersity of Otago | brownlabtools.otago.ac.nz/CRISPRDetect/predict_crispr_array.html |
| CRISPRtarget | Univsersity of Otago | bioanatysis.otago.ac.nz/CRISPRTarget/crispr_analysis.html |
| illustrator | adobe | adobe.com/Illlustrator |
| MEGA6 | MEGA | megasoftware.net/ |
| Image Lab 5.2.1 | BioRad | bio-rad.com/en-cn/product/image-lab-software |
| FlowJo | FlowJo LLC | flowjo.com/ |

TABLE S2

Strains and Plasmids, strain ID

| strain ID (RAU###, pRAU###) | species | strain | genotype | plasmid | drug res, |
|---|---|---|---|---|---|
| 1 | Lmo | 10403S | wt | — | — |
| 3 | E. coli | DH5a | — | pKSV7 | $amp_{100}$ |
| 13 | Lmo | SLCC2482 | wt | — | — |
| 14 | Lmo | SLCC2540 | wt | — | — |
| 19 | Lmo | J0161 | wt | — | — |
| 29 | E. coli | DH5a | — | pKSV7-S1$_{J0161}$ | $amp_{100}$ |
| 31 | E. coli | DH5a | — | pKSV7-S1$_{104036}$ | $amp_{100}$ |
| 57 | Lmo | 10403S | Φ10403S cure (ComK$^+$) | — | — |
| 46 | E. coli | DB3.1 | — | pPL2xoeL | $chlor_{34}$ |
| 71 | Lmo | 10403S | ΔComK::ΦJ0161a | — | — |
| 100 | E. coli | NEB5alpha | — | pPL2xoeL-ΦJ0161a-frag6 | $chlor_{34}$ |
| 101 | E. coli | NEB5alpha | — | pPL2xoeL-ΦJ0161a-frag7 | $chlor_{34}$ |
| 102 | E. coli | NEB5alpha | — | pPL2xoeL-ΦJ0161a-frag9 | $chlor_{34}$ |
| 103 | E. coli | NEB5alpha | — | pPL2xoeL-ΦJ0161a-frag10 | $chlor_{34}$ |
| 104 | E. coli | NEB5alpha | — | pPL2xoeL-ΦJ0161a-frag5 | $chlor_{34}$ |
| 105 | E. coli | NEB5alpha | — | pPL2xoeL-ΦJ0161a-frag3 | $chlor_{34}$ |
| 106 | E. coli | NEB5alpha | — | pPL2xoeL-ΦJ0161a-frag1 | $chlor_{34}$ |
| 107 | E. coli | DH5a | — | pKSV7-ΔCas9 | $amp_{100}$ |
| 109 | E. coli | NEB5alpha | — | pPL2xoeL-ΦJ0161a-frag8 | $chlor_{34}$ |
| 111 | E. coli | NEB5alpha | — | pPL2xoeL-ΦJ0161a-frag2 | $chlor_{34}$ |
| 112 | Lmo | 10403S | ComK$^+$, ΔtRNA$^{Arg}$::pRAU100 | — | $tet_2$ |
| 113 | Lmo | 10403S | ComK$^+$, ΔtRNA$^{Arg}$::pRAU101 | — | $tet_2$ |
| 114 | Lmo | 10403S | ComK$^+$, ΔtRNA$^{Arg}$::pRAU102 | — | $tet_2$ |
| 115 | Lmo | 10403S | ComK$^+$, ΔtRNA$^{Arg}$::pRAU103 | — | $tet_2$ |
| 116 | Lmo | 10403S | ComK$^+$, ΔtRNA$^{Arg}$::pRAU105 | — | $tet_2$ |
| 117 | Lmo | 10403S | ComK$^+$, ΔtRNA$^{Arg}$::pRAU106 | — | $tet_2$ |
| 118 | Lmo | 10403S | ComK$^+$, ΔtRNA$^{Arg}$::pRAU109 | — | $tet_2$ |
| 120 | E. coli | NEB5alpha | — | pPL2oexL-Cas9 | $chlor_{34}$ |
| 123 | E. coli | NEB5alpha | — | pPL2xoeL-ΦJ0161a-frag4 | $chlor_{34}$ |
| 128 | Lmo | 10403S | ComK$^+$, ΔtRNA$^{Thr}$::pRAU104 | — | $tet_2$ |
| 130 | Lmo | 10403S | ComK$^+$, ΔCas9 | — | — |
| 142 | Lmo | 10403S | ComK$^+$, ΦJ0161 ΔCas9 | — | — |
| 144 | Lmo | 10403S | ComK$^+$, ΔCas9 ΔtRNA$^{Arg}$::pRAU120 | — | $tet_2$ |
| 151 | Lmo | 10403S | ΔComK::ΦJ0161 ΔCas9 ΔtRNAArg:pRAU120 | — | $tet_2$ |
| 153 | E. coli | NEB5alpha | — | pPL2xoeL-LMOG_03145 | $chlor_{34}$ |
| 155 | E. coli | NEB5alpha | — | pPL2xoeL-LMOG_03146 | $chlor_{34}$ |
| 157 | E. coli | NEB5alpha | — | pPL2xoeL-LMOG_03147 | $chlor_{34}$ |
| 159 | Lmo | 10403S | ComK$^+$, ΔtRNA$^{Arg}$::pRAU153 | — | $tet_2$ |
| 160 | Lmo | 10403S | ComK$^+$, ΔtRNA$^{Arg}$::pRAU155 | — | $tet_2$ |
| 161 | Lmo | 10403S | ComK$^+$, ΔtRNA$^{Arg}$::pRAU157 | — | $tet_2$ |
| 162 | E. coli | NEB5alpha | — | pPL2xoeL-LMOG_03148 | $chlor_{34}$ |
| 165 | Lmo | 10403S | ComK$^+$, ΔtRNAArg:pRAU162 | — | $tet_2$ |
| 167 | E. coli | DH5a | — | pBAD24 | $amp_{100}$ |
| 168 | E. coli | NEB5alpha | — | pBAD24-LMOG_03146 | $amp_{100}$ |
| 171 | E. coli | NEB5alpha | — | pBAD24-LMOG_03147 | $amp_{100}$ |

TABLE S2-continued

Strains and Plasmids, strain ID

| | species | strain | genotype | plasmid | drug res, |
|---|---|---|---|---|---|
| 173 | E. coli | NEB5alpha | — | pBAD24-LMOG_03148 | amp$_{100}$ |
| 233 | E. coli | NEB5alpha | — | pKSV7-ΔLMOG_03146-7 | amp$_{100}$ |
| 239 | Lmo | 10403S | ComK$^+$, ΔtRNAArg::pCW3 | — | tet$_2$ |
| 241 | Lmo | 10403S | ComK$^+$, ΔtRNAArg::pCW7 | — | tet$_2$ |
| 243 | Lmo | 10403S | ComK$^+$, ΔtRNAArg::pCSW9 | — | tet$_2$ |
| 246 | Lmo | 10403S | ΔComK::phi_J0161a ΔacrIIAl-2 | — | — |
| 257 | Lmo | 10403S | ComK$^+$, tRNAArg::pCSW29 | — | tet$_2$ |
| 259 | Lmo | 10403S | ComK$^+$, tRNAArg::pCSW33 | — | tet$_2$ |
| 260 | Lmo | 10403S | ComK$^+$, tRNAArg::pCSW35 | — | tet$_2$ |
| (CSW##, pCS##) | | | | | |
| 3 | E. coli | NEB5alpha | — | pPL2oexL-lmoslcc2482_0685 | chlor$_{34}$ |
| 7 | E. coli | NEB5alpha | — | pPL2oexL-lmoslcc2540_1277 | chlor$_{34}$ |
| 9 | E. coli | NEB5alpha | — | pPL2oexL-LMOG_02993 | chlor$_{34}$ |
| 13 | E. coli | NEB5alpha | — | pBAD24-lmoslcc2482_0685 | amp$_{100}$ |
| 18 | E. coli | NEB5alpha | — | pBAD24-lmoslcc2540_1277 | amp$_{100}$ |
| 21 | E. coli | NEB5alpha | — | pBAD24-LMOG_02993 | amp$_{100}$ |
| 26 | E. coli | NEB5alpha | — | pBAD24-Axk13_03345 | amp$_{100}$ |
| 29 | E. coli | NEB5alpha | — | pPL2oexL-lmoslcc2482_0688 | chlor$_{34}$ |
| 33 | E. coli | NEB5alpha | — | pPL2oexL-lmoslcc2540_1278 | chlor$_{34}$ |
| 35 | E. coli | NEB5alpha | — | pPL2oexL-LMOG_02992 | chlor$_{34}$ |
| 65 | E. coli | NEB5alpha | — | pBAD24-lmoslcc2482_0688 | amp$_{100}$ |
| (MS##) | | | | | |
| 101 | E. coli | BW25113 | — | — | — |
| 161 | E. coli | BW25113 | nfsA::mrfp | — | kan$_{30}$ |
| 243 | E. coli | BW25113 | nfsA::mrfp, λatt::pCs550-r | — | kan$_{30}$,chlor$_{20}$ |
| 270 | E. coli | BW25113 | nfsA::mrfp, Tn7att::spy-dcas9 | — | kan$_{30}$,gent$_{10}$ |
| 271 | E. coli | BW25113 | nfsA::mrfp, λatt::pCs550-r, Tn7att::spy-dcas9 | — | kan$_{30}$,chlor$_{20}$,gent$_{10}$ |
| 270-262 | E. coli | BW25113 | nfsA::mrfp, Tn7att::spy-dcas9 | pBAD24 | kan$_{30}$,gent$_{10}$,amp$_{100}$ |
| 270-168 | E. coli | BW25113 | nfsA::mrfp, Tn7att::spy-dcas9 | pRAU168 | kan$_{30}$,gent$_{10}$,amp$_{100}$ |
| 270-171 | E. coli | BW25113 | nfsA::mrfp, Tn7att::spy-dcas9 | pRAU171 | kan$_{30}$,gent$_{10}$,amp$_{100}$ |
| 270-173 | E. coli | BW25113 | nfsA::mrfp, Tn7att::spy-dcas9 | pRAU173 | kan$_{30}$,gent$_{10}$,amp$_{100}$ |
| 270-13 | E. coli | BW25113 | nfsA::mrfp, Tn7att::spy-dcas9 | pCSW13 | kan$_{30}$,gent$_{10}$,amp$_{100}$ |
| 270-18 | E. coli | BW25113 | nfsA::mrfp, Tn7att::spy-dcas9 | pCSW18 | kan$_{30}$,gent$_{10}$,amp$_{100}$ |
| 270-21 | E. coli | BW25113 | nfsA::mrfp, Tn7att::spy-dcas9 | pCSW21 | kan$_{30}$,gent$_{10}$,amp$_{100}$ |
| 270-26 | E. coli | BW25113 | nfsA::mrfp, Tn7att::spy-dcas9 | pCSW26 | kan$_{30}$,gent$_{10}$,amp$_{100}$ |
| 270-65 | E. coli | BW25113 | nfsA::mrfp, Tn7att::spy-dcas9 | pCSW29 | kan$_{30}$,gent$_{10}$,amp$_{100}$ |
| 271-262 | E. coli | BW25113 | nfsA::mrfp, λatt::pCs550-r, Tn7att::spy-dcas9 | pBAD24 | kan$_{30}$,chlor$_{20}$,gent$_{10}$, amp$_{100}$ |
| 271-168 | E. coli | BW25113 | nfsA::mrfp, λatt::pCs550-r, Tn7att::spy-dcas9 | pRAU168 | kan$_{30}$,chlor$_{20}$,gent$_{10}$, amp$_{100}$ |
| 271-171 | E. coli | BW25113 | nfsA::mrfp, λatt::pCs550-r, Tn7att::spy-dcas9 | pRAU171 | kan$_{30}$,chlor$_{20}$,gent$_{10}$, amp$_{100}$ |
| 271-173 | E. coli | BW25113 | nfsA::mrfp, λatt::pCs550-r, Tn7att::spy-dcas9 | pRAU173 | kan$_{30}$,chlor$_{20}$,gent$_{10}$, amp$_{100}$ |
| 271-13 | E. coli | BW25113 | nfsA::mrfp, λatt::pCs550-r, Tn7att::spy-dcas9 | pCSW13 | kan$_{30}$,chlor$_{20}$,gent$_{10}$, amp$_{100}$ |
| 271-18 | E. coli | BW25113 | nfsA::mrfp, λatt::pCs550-r, Tn7att::spy-dcas9 | pCSW18 | kan$_{30}$,chlor$_{20}$,gent$_{10}$, amp$_{100}$ |
| 271-21 | E. coli | BW25113 | nfsA::mrfp, λatt::pCs550-r, Tn7att::spy-dcas9 | pCSW21 | kan$_{30}$,chlor$_{20}$,gent$_{10}$, amp$_{100}$ |

TABLE S2-continued

Strains and Plasmids, strain ID

| | species | strain | genotype | plasmid | drug res, |
|---|---|---|---|---|---|
| 271-26 | E. coli | BW25113 | nfsA::mrfp, λatt::pCs550-r, Tn7att::spy-dcas9 | pCSW26 | $kan_{30}$, $chlor_{20}$, $gent_{10}$, $amp_{100}$ |
| 271-65 | E. coli | BW25113 | nfsA::mrfp, λatt::pCs550-r, Tn7att::spy-dcas9 | pCSW29 | $kan_{30}$, $chlor_{20}$, $gent_{10}$, $amp_{100}$ | by genome

| 1 alone | 2 alone | 4 alone | 3 alone | 1 + 2 | 1 + 2 + 3 | 1 + 4 |
|---|---|---|---|---|---|---|
| 8 | 2 | 11 | 1 | 28 | 48 | 12 | by neighborhood

| 1 + 2 + 3 | 1 + 2 | 1 alone | 1 + 4 | 4 alone | 2 alone | 4 alone |
|---|---|---|---|---|---|---|
| 50 | 29 | 16 | P | 11 | 1 | 0 | all isolated acrIIA3

| EXL25968.1 | cut off | | prophage |
|---|---|---|---| all isolated acrIIA2

| KXS56902.1 | cut off | | |
|---|---|---|---|
| KXX34219.1 | | context unknown; prob not phage | | all isolated acrIIA4

| EHY61390.1 | arr1a | plasmid (FSL J1208) |
|---|---|---|
| KXS57719.1 | arr1a | genome |
| KXW85912.1 | arr1a | genome |
| KXS77365.1 | arr1b | genome |
| KXS78354.1 | arr1b | genome |
| KXX11218.1 | arr1b | genome |
| KXX17138.1 | arr1b | genome |
| KXX18287.1 | arr1b | genome |
| KXS56935.1 | arr1c | genome |
| AEH91120.1 | arr2 | prophage |
| ACK40885.1 | arr2 | prophage | all isolated acrIIA1

| KTA68177.1 | upstr-orf5 | prophage |
|---|---|---|
| AGR15693.1 | upstr-orf5 | prophage |
| AGR27297.1 | upstr-orf5 | prophage |
| ALU78083.1 | upstr-orf5 | prophage |
| EEW20426.1 | upstr-orf5 | prophage |
| EFK41083.1 | upstr-orf5 | prophage |
| EZH69029.1 | contig cut off | |
| KHK04755.1 | upstr-orf5 | |
| KHK19909.1 | upstr-orf5 | prophage |
| KHK17523.1 | upstr-orf5 | |
| KTA28092.1 | upstr-orf5 | |
| KXS64534.1 | contig cut off | prophage |
| KHK12400.1 | upstr-orf5 | |
| KKD43688.1 | upstr-orf5 | |
| KLH0251.1 | contig cut off | prophage |
| KTA35071.1 | upstr-orf5 | |
| KTA45326.1 | upstr-orf5 | |
| KTA50988.1 | upstr-orf5 | |
| KTA63900.1 | upstr-orf5 | |

EXPERIMENTAL MODEL AND SUBJECT DETAILS

Microbes.

*Listeria monocytogenes* strains were cultured on Brain-Heart Infusion (BHI) medium. *Escherichia coli* strains were cultured on LB medium.

Cell Lines

Human Embryonic Kidney 293 plus T cell antigen (HEK293T, CRL-3216, ATCC) cells were cultured in Dulbecco's Modified Eagle's Medium (DMEM) supplemented with 10% fetal bovine serum (FBS, Atlanta Biologicals) and 50 μg/mL penicillin/streptomycin (P/S, UCSF CCF).

EXAMPLE 2

We sought to identify homologs of acrIIA1-4 (FIG. 13) that possess anti-CRISPR function against the *Streptococcus pyogenes* ortholog of Cas9, which is widely used for gene editing.

FIG. 14: AcrIIA1 possesses anti-Cas9 activity in a heterologous system (i.e. outside of natural organism). Previously, this protein did not have anti-Cas9 function in *E. coli* or human cells. The reason for this discrepancy is not yet known, but compared to positive control AcrIIA4, AcrIIA1 functions very well in this heterologous system (*P. aeruginosa*), while targeting Cas9.

FIG. 15: AcrIIA2 homologs were identified via sequence alignments, to broadly sample the natural sequence space. Three homologs were tested in addition to the original protein, and as shown using phage plaque assays in FIG. 16: AcrIIA2b.1 and AcrIIA2b.3 have strong anti-SpyCas9 activity compared to the original protein, AcrIIA2a.

FIG. 17: Similar homology searches were performed to identify AcrIIA3 homologs, AcrIIA3b.2, 3b.3, 3b.4. As shown in FIG. 18 with an assay where bacteria spotted on a plate, these three new anti-CRISPR proteins are not toxic and work robustly in bacteria. AcrIIA4, as identified in the paper is a strong and broad spectrum Cas9 inhibitor that binds tightly to Cas9 (see Dong et al Nature, and Shin et al Science Advances). One homolog (AcrIIA4b) was identified to have modest anti-Cas9 activity.

FIG. 19 summarizes the results described in Example 2.

REFERENCES

Abudayyeh, O. O et al. (2016). *Science aaf*5573
Barrangou, R., and Doudna, J. A. (2016), *Nature Biotechnology*, 34, 933-941
Biswas, A. et al. (2013). *RNA Biol*, 10, 817-827
Biswas, A et al. (2016). *BMC Genomics*, 17, 356
Bondy-Denomy et al, (2013). *Nature*, 493, 429-432
Bondy-Denomy, J et al. (2015). *Nature*, 526, 136-139
Brouns, S. J. J et at. (2008). *Science*, 321, 960-964
Camilli, A., Tilney, L G., and Portnoy, D. A. (1993). *Molecular Microbiology*, 43-157
Choi, K.-H. et al. (2005). *Nat. Methods*, 2, 443-448
Cong, L. et al. (2013). *Science* 339, 819-823
Deltcheva, E. et al. (2011). *Nature* 471, 602-607
Di, H. et al. (2014) *Biochem Biophys Res commun*, 454, 399-403
East-Seletsky, A. et al. (2016). *Nature* 538, 270-273
Edgar, R., and Qimron, U. (2010). 192, 6291-6294
Edgar, R. C. (2004). *Nucleic Acids Research*, 32, 1792-1797
Garneau, J. E. et al. (2010). *Nature*, 468, 67-71
Gilbert, L. A. et al. (2013). *Cell* 154, 442-451
Goldberg, G. W. et al. (2014). *Nature* 514, 633-637
Grissa, I., Vergnaud, G., and Pourcel, C. (2007). *Nucleic Acids Research*, 35, W52-W57
Guzman, L. M. et al. (1995). *J. Bacteria*, 177, 4121-4130
Halditnann, A., and Wanner, B. L. (2001), *J. Bacteriol.*, 183, 6384-6393
Haurwitz, R. E et al. (2010). *Science*, 329, 1355-1358
Heler, R. et at. (2015). *Nature* 519, 199-202
Jinek, M, et al. (2012). *Science*, 337, 816-821
Labrie, S. J., Samson, J. E., and Moineau, S. (2010). *Nat Rev Micro*, 8, 317-327
Lauer, P. et al. (2002). *J. Bacteriol.*, 184, 4177-4186
Loessner, M. J., and Busse, M. (1990). *Applied and Environmental Microbiology*, 56, 1912-1918
Makarova, K. S. et al. (2015). *Nat Rev Micro*, 13, 722-736
Mali, P. et al. (2013). *Science*, 339, 823-826
Mandin, P. et al. (2007). *Nucleic Acids Research*, 35, 962-974
Marraffini, L. A. (2015). CRISPR-Cas immunity in prokaryotes. *Nature*, 526, 55-61
Maxwell, K. L. et al. (2016). *Nature Communications*, 7, 13134
Mojica, F. J. M. et al. (2005), *J. Mol. Evol.*, 60, 174-182
Nuñez, J. K. et al. (2014). *Nat. Struct. Mol. Biol* 21, 528-534
Park, S. F., and Stewart, G. S. (1990). *Gene*, 94, 129-132
Pawluk, A. et al. (2014). *mBio* 5, e00896
Pawluk, A. et al. (2016). *Nature Microbiology*, 1, 1-6
Qi, L. S. et al. (2013). *Cell*. 152, 1173-1183
Ran, F. A. et al, (2015). *Cas9*. 520, 186-191
Samai, P. et al. (2015). *Cell*, 161, 1164-1174
Samson, J. E. et al. (2013). *Nat Rev Micro*, 11, 675-687
Sesto, N. et al, (2014). *PLoS Genet*, 10, e1004065
Söding, J., Biegert, A., and Lupas, A. N. (2005). *Nucleic Acids Research*, 33, W244-W248
Tamura, K. et al. (2013). *Mol. Biol. Evol*, 30, 2725-2729
Typas, A. et al. (2008). *Nat. Methods*, 5, 781-787
Volz, S. E. et al. (2015). *Cell*, 163, 759-771
Wang, X. (2016). *Nat. Struct. Mol. Biol* 23, 868-870
Wright, A. V., Nuñez, J. K., and Doudna, J. A. (2016). *Cell*, 164, 29-44
Yosef, I., Goren, M. G., and Qimron, U. (2012). *Nucleic Acids Research*, 40, 5569-5576
Zemansky, J. et al. (2009). *J. Bacteria*, 191, 3950-3964
Zetsche, B. et al. (2015). *Cell*, 163, 759-771

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

```
AcrIIA1 protein sequences
>WP_003722518.1 (LMOG_03146)
                                    SEQ ID NO: 1
MTIKLLDEFLKKHDLTRYQLSKLTGISQNTLKDQNEKPLNKYTVSIL

RSLSLISGLSVSDVLFELEDIEKNSDDLAGFKHLLDKYKLSFPAQEF

ELYCLIKEFESANIEVLPFTFNRFENEEHVNIKKDVCKALENAITVL

KEKKNELL

>WP_060571535.1
                                    SEQ ID NO: 2
MTIKLLDEFLKKHDLTRYQLSKLTGISQNTLKDQNEKPLNKYTVSIL

RSLSLISGLSVSDVLFELEDIEKNSDDLAGFKHLLDKYKLSFPAQEF

ELYCLIKEFESTNIEVLPFTFNRFENEEHVNIKKDVCKALENAITVL

KEKKNELL

>WP_070783094.1
                                    SEQ ID NO: 3
MTIKLLDEFLKKHDLTRYQLSKLTGISQNTLKDQNEKPLNKYTVSIL

RSLSLISGLSVSDVLFELEDIEKNSDDLAGFKHLLDKYKLSFPAQEF

ELYCLIKEFESNIEVLPFTFNRFENEEHVNIGKDVCKALENAITVLK

EKKNELL

>WP_031669445.1
                                    SEQ ID NO: 4
MTIKLLDEFLKKHDLTRYQLSKLTGISQNTLKDQNEKPLNKYTVSIL

RSLSLISGLSVSDVLFELEDIEKNSDDLAGFKHLLDKYKLSFPAQEF

ELYCLIKEFESANIEVLPFTFNRFENEEHVNIEKDVCKALENAITVL

KEKKNELL
```

```
>WP_070286809.1
                                              SEQ ID NO: 5
MTIKLLDEFLKKHDLTRYQLSKLTGISQNTLKDQNEKPLNKYTVSIL
RSLSLISGLSVSDVLFELEDIEKNSDDLAGFKHLLDKYKLSFPAQEF
ELYCLIKEFESNIEVLPFTFNRFENEKHVNIKKDVCKALENAITVLK
EKKNELL

>WP_070213372.1
                                              SEQ ID NO: 6
MTIKLLDEFLKKHDLTRYQLSKLTGISQNTLKDQNEKPLNKYTVSIL
RSLSLISGLSVSDVLFELEDIEKNSDDLAGFKHLLNKYKLSFPAQEF
ELYCLIKEFESANIEVLPFTFNRFENEEHVNIEKDVCKALENAITVL
KEKKNELL

>WP_003731275.1
                                              SEQ ID NO: 7
MAIKLLDEFLKKHDLTRYQLSKLTGISQNTLKDQNEKPLNKYTVSIL
RSLSLISGLSVSDVLFELEDIEKNSDDLAGFKHLLDKYKLSFPAQEF
ELYCLIKEFESANIEVLPFTFNRFENEKHVNIKKDVCKALENAITVL
KEKKNELL

>WP_010989942.1
                                              SEQ ID NO: 8
MSIKLLDEFLKKHNKTRYQLSKLTGISQNTLKDQNEKPLNKYTVSIL
RSLSLISGLSVSDVLFELEDIEKNSDDLAGFKHLLDKYKLSFPAQEF
ELYCLIKEFESANIEVLPFTFNRFENEEHVNIEKDVCKALENAITVL
KEKKNELL

>WP_070286796.1
                                              SEQ ID NO: 9
MKLLDEFLKKHDLTRYQLSKLTGISQNTLKDQNEKPLNKYTVSILRS
LSLISGLSVSDVLFELEDIEKNSDDLAGFKHLLDKYKLSFPAQEFEL
YCLSKEFESANIEVLPFTFNRFENEKHVNIKKDVCKALENAITVLKE
KKNELL

>WP_038409766.1
                                              SEQ ID NO: 10
MTIKLLDEFLKKHDLTRYQLSKLTGISQNTLKDQNEKPLNKYTVSIL
RSLSLISGLSVSDVLFELEDIEKNSDDLAGFKHLLNKYKLSFPAQEF
ELYCLIKEFESANIEVLPFTFNRFENETHVDIEKDVRKALENAITVL
KEKKNELL

>WP_060595919.1
                                              SEQ ID NO: 11
MTIKLLDEFLKKHDLTRYQLSKLTGISQNTLKDQNEKPLNKYTVSIL
RSLSLISGLSVSDVLFELEDIEKNSDDLAGFKHLLDKYKLSFPAQEF
ELYCLIKEFESANIEVLPFTFNRFENETHVDIEKDVRKALENAITVL
KEKKNELI

>WP_047934203.1
                                              SEQ ID NO: 12
MTIKILDEFLKKHDLTRYQLSKLTGISQNTLKDQNEKSLNKYTVSIL
RSLSLISGLSVSDVLFELEDIEKNSDDLAGFKHLLGKYKLSFPAQEF
ELYCLIKEFESANIEVLPFTFNRFENETHVDIEKDVRKALENAITVL
KEKKNELI

>YP_009044824.1
                                              SEQ ID NO: 13
MTIKLLDEFLKKHDLTRYQLSKLTGISQNTLKDQNEKPLNKYTVSIL
RSLSLISGLSVSDVLFELEDIEKNSDDLAGFKHLLDKYKLSFPAQEF
ELYCLIKEFESANSEVLTFTFNRFENEEHADIEKDVKKALNNAIAVL
KEKKEELL

>WP_061396064.1
                                              SEQ ID NO: 14
MTIKLLDEFLKKHDLTRYQLSKLTGISQNTLKDQNEKSLNKYTVSIL
RSLSLISGLSVSDVLFELEDIEKNSDDLAGFKHLLGKYKLSFPAQEF
ELYCLIKEFESANIEVLTFTFNRFENEEHADIEKDVKKALNNAIAVL
KEKKEELL

>WP_014930689.1
                                              SEQ ID NO: 15
MTIKLLDEFLKKHDLTRYQLSKLTGISQNTLKDQNEKSLNKYTVSIL
RSLSLISGLSVSDVLFELEDIEKNSDDLAGFKHLLGKYKLSFPAQEF
ELYCLIKEFESANIEVLTFTFNRFENEEHADIEKDVKKALNNAIAVL
KAKKEELL

>WP_061105218.1
                                              SEQ ID NO: 16
MTIKLLDEFLKKHDLTRYQLSKLTGISQNTLKDQNEKSLNKYTVSIL
RSLSLISGLSVSDVLFELEDIEKNSDDLAGFKHLLGKYKLSFPAQEF
ELYCLIKEFESANSEVLTFTFNRFENEEHADIEKDVKKTLNNAIAVL
KEKKEELL

>WP_070216262.1
                                              SEQ ID NO: 17
MTIKLLDEFLKKHDLTRYQLSKLTGISQNTLKDQNEKPLNKYTVSIL
RSLSLISGLSVSDVLFELEDIEKNSDDLAGFKHLLDKYKLSFPAQEF
ELYCLIKEFESANIEVLTFTFNRFENEEHADIEKDVKKALNNAIAVL
KEK

>WP_070761486.1
                                              SEQ ID NO: 18
MTSKLLDEFLKKHDLTRYQLSKLTGISQNTLKDQNEKSLNKYTVSIL
RSLSLISGLSVSDVLFELEDIEKNSDDLAGFKHLLGKYKLSFPAQEF
ELYCLIKEFESANIEVLTFTFNRFENEEHADIEKDVKKALNNAIAVL
KEKKKNCYKNY

>WP_070005110.1
                                              SEQ ID NO: 19
MSIKLLDEFLKKHDLTRYQLSKLTGISQNTLKDQNEKSLNKYTVSIL
RALALITGMPISDVLFELEDLEKNADDLAGFKHLLDTYKLSFPAQEF
ELYCLIKEFESANIEVLPFTFNRFESETHVDIEKDVRKALENAITVL
KEKKNEFM

>WP_070784182.1
                                              SEQ ID NO: 20
MTIKLLDEFLKKHDLTRYQLSKLTGISQNTLKDQNEKPLNKYTVSIL
RSLSLISGLSVSDVLFELEDIEKNSDDLAGFKHLLDKYKLSFPAQEF
ELYCLIKEFESANIEVLPFTFNRFENEEHVNIEKDVCKA
```

>WP_070776459.1
SEQ ID NO: 21
MSIKLLDEFLKKHDLTRYGLSKLTGISGNTLKDGNEKTLNKYTVSIL
RALALITGMPISDVLFELEDLEKNADDLAGFKHLLDTYKLSFPAQEF
ELYCLIKEFESANIEVLPFTFNRFESETHVDIEKDVQKALENAITVL
KEKKNEFM

>WP_003737351.1
SEQ ID NO: 22
MSIKLLDEFLKKHDLTRYGLSKLTGISGNTLKDGNEKTLNKYTVSIL
RALALITGMPISDVLFELEDLEKNADDLAGFKGLLDTHKLSFPAHEF
ELYCLIKEFESVNIEVLPFTFNRFESETHVDIEKDVRKALENAITVL
KEKKNEFM

>WP_010991654.1
SEQ ID NO: 23
MSIKLLDEFLKKHDLTRYGLSKLTGISGNTLKDGNEKTLNKYTVSIL
RALALITGMPISDVLFELEDLEKNADDLAGFKGLLDTHKLSFPAHEF
ELYCLIKEFESVNIEVLPFTFNRFESETHVDIEKDVRKALENAITVL
KEKKNEFI

>WP_070295945.1
SEQ ID NO: 24
MSIKLLDEFLKKHDLTRYQLSKLTGISQNTLKDQNEKTLNKYTVSIL
RALALITGMPSSDVLFELEDLEKNADDLAGFKQLLDTHKLSFPAHEF
ELYCLIKEFESVNIEVLPFTFNRFESETHVDIEKDVQKALENAIAVL
KEKKEELL

>WP_061662200.1
SEQ ID NO: 25
MTIKLLDEFLKKHDLTRYQLSKLTGISQNTLKDQNEKPLNKYTVSIL
RSLSLISGLSVSDVLFELEDIEKNSDDLAGFKHLLDKYKLSFPAQEF
ELYCLIKEFESANIEVLPFTFNRFENEEHVN

>WP_061665494.1
SEQ ID NO: 26
MSIKLLDEFLKKHNKTRYQLSKLTGISQNTLNDYNKKELNKYSVSFL
RALSMCAGISTFDVFIELAELEKSYDDLAGFKHLLDKYKLSFPAQEF
ELYCLIKEFESANIEVLPFTFNRFENEEHVNIKKDVCKALENAITVL
KEKKNELL

>WP_061107167.1
SEQ ID NO: 27
MSIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFESANIEVLPFTFNRFENEEHVNIKKDVCKALENAITVL
KEKKNELL

>WP_070005290.1
SEQ ID NO: 28
MSIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFESANIEVLPFTFNRFENEEHVNIEKDVCKALENAITVL
KEKKNELL

>WP_039385152.1
SEQ ID NO: 29
MSIKLLDEFLKKHNKTRYQLSKLTGISQNTLNDYNKKELNKYSVSFL
RALSMCTGISTFDVFIELAELEKSYDDLAGFKHLLNKYKLSFPAQEF
ELYCLIKEFDSANIEVLPFTFNRFENEEHVNIEKDVCKALENAITVL
KEKKNELL

>WP_015967154.1
SEQ ID NO: 30
MSIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFESANIEVLPFTFNRFENEEHVNIEKDVCKALENAITVL
KEKKNELI

>WP_069001242.1
SEQ ID NO: 31
MNIKLLDEFLKKHNKTRYQLSKLTGISQNTLNDYNKKELNKYSVSFL
RALSMCTGISTFDVFIELAELEKSHDDLAGFKHLLDKHKLSFPAQEF
ELYCLIKEFESANIEVLPFTFNRFENEEHVNIEKDVCKALENAITVL
KEKKNELL

>WP_070040173.1
SEQ ID NO: 32
MSIKLLDEFLKKHDLTRYQLSKLTGISQNTLNDYNKKELNKYSVSFL
RALSMCTGISTFDVLIELAELEKSYDDLAGFKHLLDKYKLSFPAQEF
ELYCLIKEFESANIEVLPFTFNRFENETHVDIEKDVRKALENAITVL
KEKKNELI

>WP_068999238.1
SEQ ID NO: 33
MTSKLLDEFLKKHSLTRYQLSKLTGISQNTLNDYNKKELNKYSVSFL
RALSMCAGISTFDVLIELAELEKSYDDLAGFKHLLDKYKLSFPAQEF
ELYCLIKEFESANIEVLPFTFNRFENETHVDIEKDVRKALENAITVL
KEKKNELI

>WP_070784648.1
SEQ ID NO: 34
MSIKLLDEFLKKHNKTRYQLSKLTGISQNTLNDYNKKELNKYSVSFL
RALSMCAGISTFDVLIELAELEKSYDDLAGFKHLLDKYKLSFPAQEF
ELYCLIKEFESANIEVLPFTFNRFENETHVDIEKDVRKALENAITVL
KEKKNELI

>WP_070777825.1
SEQ ID NO: 35
MSIKLLDEFLKKHNKTRYQLSKLTGISQNTLNDYNKKELNKYSVSFL
RALSMCAGISTFDVLIELAELEKSYDDLAGFKHLLDKYKLSFPAQEF
ELYCLIKEFECANIEVLPFTFNRFENETHVDIEKDVRKALENAITVL
KEKKNELI

>WP_047934326.1
SEQ ID NO: 36
MSIKLLDEFLKKHNKTRYQLSKLTGISQNTLNDYNKKELNKYSVSFL
RALSMCAGiSTFDVFIELAELEKSYDDLAGFKHLLDKYKLSFPAQEF
ELYCLIKEFESANIEVLPFTFNRFENETHVDIEKDVRKALENAITVL
KEKKNELI

>WP_003727802.1
                               SEQ ID NO: 37
MSIKLLDEFLKKHNKTRYQLSKLTGISQNTLNDYNKKELNKYSVSFL
RALSMCTGISTFDVFIELAELEKNYDDLAGFKHLLDKYKLSFPAQEF
ELYCLIKEFECANIEVLPFTFNRFENETHVDIEKDVRKALENAITVL
KEKKNELI

>WP_003723291.1 (LMOG_02992)
                               SEQ ID NO: 38
MSIKLLDEFLKKHNKTRYQLSKLTGISQNTLNDYNKKELNKYSVSFL
RALSMCAGSTFDVFNELEELEKNYDDLAGFKHLLDKYKLSFSAQEFE
LYCLIKEFESANIEVLPFTFNRFENETHVDIEKDVRKALENAITVLK
EKKNELI

>WP_069027465.1
                               SEQ ID NO: 39
MTIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFECANIEVLPFTFNRFENETHVDIEKDVRKALENAITVL
KEKKNELI

>WP_047933338.1
                               SEQ ID NO: 40
MSIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFESANIEVLPFTFNRFENETHVDIEKDVRKALENAITVL
KEKKNELI

>WP_060579665.1
                               SEQ ID NO: 41
MSIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFECANIEVLPFTFNRFENETHVDIEKDVRKALENAITVL
KEKKNELL

>WP_031646274.1
                               SEQ ID NO: 42
MTIKLLDEFLKKHDLTRYQLSKLTGISQNTLNDYNKKELNKYSVSFL
RALSMCTGISTFDVFIELAELEKSYDDLAGFKHLLDKYKLSFPAQEF
ELYCLIKEFESANIEVLPFTFNRFENEEHTDIEKDVKKTLNNAIAVL
KEKKEELL

>WP_070776287.1
                               SEQ ID NO: 43
MSIKLLDEFLKKHNKTRYQLSKLTGISQNTLNDYNKKELNKYSVSFL
RALSMCAGISTFDVFIELAELEKSYDDLAGFKHLLDKYKLSFPAQEF
ELYCLIKEFECANSEVLPFTFNRFENETHVDIEKDVRKALENAITVL
KEKKNELI

>WP_031645842.1
                               SEQ ID NO: 44
MSIKLLDEFLKKHSKTRYQLSKLTGISQNTLNDYNKKELNKYSVSFM
RALSMCAGISTFDVFIELAELEKSYDDLAGFKHLLDKYKLSFPAQEF
ELYCLIKEFESANIEVLPFTFNRFENETHVDIEKDVRKALENAITVL
KEKKNELI

>WP_046376633.1
                               SEQ ID NO: 45
MSIKLLDEFLKKHNKTRYQLSKLTGISQNTLNDYNKKELNKYSVSFL
RALSMCAGISTFDVFKELEELEKNYDDLAGFKHLLDKYKLSFSAQEF
ELYCLIKEFESANIEVLPFTFNRFENETHVDIEKDVRKALENAITVL
KEKKNELI

>WP_070242402.1
                               SEQ ID NO: 46
MSIKLLDEFLKKHSKTRYQLSKLTGISQNTLNDYNKKELNKYSVSFL
RALSMCAGISTFDVFIELAELEKSYDDLSGFKHLLDKYKLSFPAQEF
ELYCLIKEFESANIEVLPFTFNRFENETHVDIEKDVRKALENAITVL
KEKKNELI

>WP_047923954.1
                               SEQ ID NO: 47
MSIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFESASIEVLPFTFNRFENETHVDIEKDVRKALENAITVL
KEKKNELI

>WP_031668927.1
                               SEQ ID NO: 48
MSIKLLDEFLKKHNKTRYQLSKLTGISQNTLNDYNKKELNKYSVSFL
RALSMCTGISTFDVFIELAELEKSHDDLAGFKHLLDKHKLSFPAQEF
ELYCLIKEFESANIEVLPFTFNRFENETHVDIEKDVRKALENAITVL
KEKKNELI

>WP_012581438.1
                               SEQ ID NO: 49
MSIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFECANIEVLPFTFNRFENETHVDIEKDVRKALENAITVL
KEKKNELI

>WP_031667947.1
                               SEQ ID NO: 50
MSIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFECANIEVLPFTFNRFENETHVDIEKDIRKALENAITVL
KEKKNELI

>WP_061107116.1
                               SEQ ID NO: 51
MSIKLLDEFLKKHNKTRYQLSKLTGISQNTLNDYNKKELNKYTVSFL
RTLSMCVGMSTVDVFIELAELEKNYDDLAGFKHLLDKYKLSFPAQEF
ELYCLSKEFESANIEVLPFTFNRFESETHVDIEKDVKKALNNAIAVL
KEKKEELL

>WP_070783481.1
                               SEQ ID NO: 52
MSIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFESANIEVLPFTFNRFENETHVDIEKDVRKALNNAIAVL
KEKKEELL

>WP_060577773.1

SEQ ID NO: 53

MSIKLLDEFLKKHNKTRYQLSKLTGISQNTLNDYNKKELNKYSVSFL
RALSMCAGISTFDVFIELAELEKSYDDLAGFKYLLDKHKLSFPAQEF
ELYCLIKEFESANIEVLPFTFNRFENETHVDIEKDVRKALENAITVL
KEKKNELI

>WP_039389295.1

SEQ ID NO: 54

MNIKLLDEFLKKHDLTRYQLSKLTGISQNTLNDYNKKELNKYSVSFL
RALSMCTGISTFDVFIELAELEKSYDDLAGFKHLLDKHKLSFPAQEF
ELYCLIKEFESANIEVLPFTFNRFENEEHADIEKDVKKALNNAIAVL
KAKKEELL

>WP_070295880.1

SEQ ID NO: 55

MSIKLLDEFLKKHDLTRYQLSKLTGISQNTLKDQNEKTLNKYTVSIL
RALALITGMPISDVLFELEDLEKNADDLAGFKQLLDTHKLSFPAHEF
ELYCLIKEFESVNIEVLPFTFNRFESETHVDIEKDV

>WP_061399219.1

SEQ ID NO: 56

TRYQLSKLTGISQNTLNDYNKKELNKYSVSFLRALSMCAGISTFDVF
IELAELEKSYDDLAGFKHLLDKYKLSFPAQEFELYCLIKEFESANIE
VLPFTFNRFENEEHVNIKKDVCKALENAITVLKEKKNELL

>WP_061112070.1

SEQ ID NO: 57

MKINLLDEFLKRHNITRYRLSKLAGISQNTLKDYNEKSLNKYTVSFL
RSLSFVTGEDVTDVLIELAELEKGYDDLAGFKYLLDKYKLSFPALEF
ELYCIIKEFESANIEISPFTFNRFENETHVDIEKDVKKALQNAVTVL
EERKEELL

>WP_070779352.1

SEQ ID NO: 58

MKNNLLDTFLKRHDITRYRLSKLAGISQNTLKDYNEKSLNKYTVSLL
RSLSFVTGESITDVLLELAEIEKDYDDLAGFKYLLDKYKLSFPALEF
ELYCIIKEFESANVEISPFTFNRFENETHADIEKDVKKALNNAITVL
KEKKEELL

>WP_014930929.1

SEQ ID NO: 59

MSIKLLDEFLKKHNKTRYQLSKLTGISQNTLNDYNKKELNKYSVSFL
RALSMCAGISTFDVFIELAELEKSYDDLAGFKYLLDKHKLSFPTQEF
ELYCLIKEFESANIEVLPFTFNRFENETHADIEKDVKKALNNAIAVL
EEKKEELL

>WP_069001897.1

SEQ ID NO: 60

MKINLLDAFLKRHNITRYRLSKLAGISGNTLKDYNEKSLNKYTVSFL
RSLSFVTGEDVTDVLIELAELEKGYDDLAGFKYLLDKYKLAFPALEF
ELYCLIKEFEAANIEVSPFTFNRFENETHADIEKDVKKALKNAIIVL
KEKKEELL

>WP_070784143.1

SEQ ID NO: 61

MSIKLLDEFLKKHSKTRYQLSKLTGISQNTLNDYNKKELNKYSVSFL
RALSMCAGISTFDVFIELAELEKSYDDLAGFKHLLDKYKLSFPAQEF
ELYCLIKEFESANIEVLPFTFNRFENEEHVNIEKDVCKA

>EFS02359.1

SEQ ID NO: 62

MKINLLDEFLKRHNITRYRLSKLAGISQNTLKDYTEKSLNKYTVSFL
RSLSFATGESVTDILLELAELEKDYDDLAGFKYLLDKYKLAFPALEF
ELYCLSKEFESANIEISPFTFNRFESETHTDIEKDVKKALQNAVTVL
EERKEELL

>WP_061128861.1

SEQ ID NO: 63

MSIKLLDEFLKKHSKTRYQLSKLTGISQNTLNDYNKKELNKYSVSFL
RSLSFATGESVTDILLELAELEKDYDDLAGFKYLLDKYKLAFPALEF
ELYCLIKEFESANIEISPFTFNRFESETHTDIEKDVKKALQNAVTVL
EERKEELL

>KUG37233.1

SEQ ID NO: 64

MSIKLLDEFLKKHNKTRYQLSKLTGISQNTLNDYNKKELNKYSVSFL
RALSMCAGISTFDVFIELAELEKSYDDLAGFKYLLDKHKLSFPTQEF
ELYCLIKEFESANIEVLPFTFNRFENETHADIEKDVKKALNNAIAVL
EEKKRRTVIKTIDYYDYS

>WP_049955951.1

SEQ ID NO: 65

MNNFAFITSFNYQQPRYQLSKLTGISQNTLNDYNKKELNKYSVSFLR
ALSMCAGiSTFDVLIELAELEKSYDDLAGFKHLLDKYKLSFPAQEFE
LYCLIKEFESANIEVLPFTFNRFENETHVDIEKDVRKALENAITVLK
EKKNELI

>WP_009917642.1

SEQ ID NO: 66

MKTNLLDTFLKRHGITRYRLSKLAGISQNTLKDYTEKSLNKYTVSFL
RSLSFVTGEDVTDVLLELAEIENGYDDLAGFKYLLDKYKLSFPALEF
ELYCIIKEFESANIEISPFTFNRFENETHADIEKDVKKALKNAVTVL
EERKEELL

>WP_070777879.1

SEQ ID NO: 67

MNNFAFITSFNYQQPRYQLSKLTGISQNTLNDYNKKELNKYSVSFLR
ALSMCAGSSTFDVLIELAELEKSYDDLAGFKHLLDKYKLSFPAQEFE
LYCLIKEFECANIEVLPFTFNRFENETHVDIEKDVRKALENAITVLK
EKKNELI

>WP_061662201.1

SEQ ID NO: 68

MSIKLLDEFLKKHNKTRYQLSKLTGISQNTLNDYNKKELNKYSVSFL
RALSMCAGISTFDVFIELAELEKSYDDLAGFKHLLDKYKLSFPAQEF
ELYCLIKEFESANIEVLPFTFNRFENEEHVN

AcrIIA2 protein sequences
>WP_003722517.1
SEQ ID NO: 69
MTLTRAQKKYAEAMHEFINMVDDFEESTPDFAKEVLHDSDYVVITKN
EKYAVALCSLSTDECEYDTNLYLDEKLVDYSTVDVNGVTYYINIVET
NDIDDLEIATDEDEMKSGNQEIILKSELK >WP_031668925.1
SEQ ID NO: 70
MTLTRAQKKYAEAMHEFINMVDDFEESTPDFAKEVLHDSDYVVITKN
EKYAVALCSLSTDECEYDTNLYLDEKLVDYSTVDVNGVTYYINIVET
NDIDDLEIATDEDEMKSGNQEIILKSELN >WP_031646276.1
SEQ ID NO: 71
MTITRAQKKYAEAMHEFINMVDDFEESTPDFAKEVLHDSDYVVITKN
EKYAVALCSLSTDECEYDTNLYLDEKLVDYSTVDVNGVTYYINIVET
NDIDDLEIATDEDEMKSGNQEIILKSELK >EZH71062.1
SEQ ID NO: 72
KMTLTRAQKKYAEAMHEFINMVDDFEESTPDFAKEVLHDSDYVVITK
NEKYAVALCSLSTDECEYDTNLYLDEKLVDYSTVDVNGVTYYINIVE
TNDIDDLEIATDEDEMKSGNQEIILKSELN >WP_061662199.1
SEQ ID NO: 73
MTLTRAQKKYAEAMHEFINMVDDFEESTPDFAKEVLHDSDYVVITKN
EKYAVALCSLSTDECEYDTNLYLDEKLVDYSTVDVNGVTYYINIVET
NDIDDLEIATDEDEMKSGNQEIILKSEL >WP_070026783.1
SEQ ID NO: 74
MTLTRAQKKYAEAMHEFINMVDDFEESTPDFAKEVLHDSDYVVITKN
EKYAVALCSLSTDECEYDTNLYLDEKLVDYSTVDVNGVTYYINIVET
NDIDDLEIATDEDEMKSDNQEIILKSELK >WP_068996202.1
SEQ ID NO: 75
MTITRAQKKYAEAMHEFINMVDDFEESTPDFAKEVLHDSDYVVITKN
EKYAVALCSLSTDGCEYDTNLYLDEKLVDYSTVDVNGVTYYINIVET
NDIDDLEIATDEDEMKSGNQEIILKSELK >WP_009928183.1
SEQ ID NO: 76
MTLTRAQKKYAEAMHEFINMVDDFEESTPDFAKEVLHDSDYVVITKN
EKYAVALCSLSTDECEYDTNLYLDEKLVDYSTVDVNGVTYYINIVET
KDIDDLEIATDEDEMKSDNQEIILKSELK >WP_014930690.1
SEQ ID NO: 77
MTITTAQKKYAEAMHEFINMVDDFEESTPDFAKEVLHDSDYVVITKN
EKYAVALCSLSTDECEYDTNLYLDEKLVDYSTVDVNGVTYYINIVET
NDIDDLEIATDEDEMKSGNQEIILKSELK >WP_061394923.1
SEQ ID NO: 78
MTITTAQRKYNEAMHEFINMVDDFEESTPDFAKEVLHDSDYVVITKN
EKYAVALCSLSTDECEYDTNLYLDEKLVDYSTVDVNGVTYYINIVET
NDIDDLEIATDEDEMKSGNQEIILKSELK >WP_069001241.1
SEQ ID NO: 79
MTITTAQRKYNEAMHEFINMVDDFEESTPDFAKEVLHDCDYVVVTKN
EKYAVALCTLSTDECEYDTNLYLDEKLVDYSTVNVNGVTYYINIVET
NDIDDLEIATDEDEMKSDNQEIILKSELK >WP_039389299.1
SEQ ID NO: 80
MTITTAQRKYNEAMHEFINMVDDFEESTPDFAKEVLHDCDYVVVTKN
EKYAVALCTLSTDECEYDTNLYLDEKLVDYSTVNVNGVTYYINIVET
NDIDDLEIATDEDEMKSDNQKIILKSELK >WP_039385155.1
SEQ ID NO: 81
MTLTRAQKKYAEAMHEFINMVDDFEESTPDFAKEVLHDSDYVVITKN
EKYAVALCSLSTDECEYDTNLYLDEKLVDYSTVDVNGVTYYINIVET
KDIDDLEIATDEDKEKHDKQEVIIKSELN >WP_003733874.1
SEQ ID NO: 82
MHEFINMVDDFEESTPDFAKEVLHDSDYVVITKNEKYAVALCSLSTD
ECEYDTNLYLDEKLVDYSTVDVNGVTYYINIVETNDIDDLEIATDED
EMKSGNQEIILKSELK >WP_070294198.1
SEQ ID NO: 83
MTLTRAQKKYAEAMHEFINMVDDFEESKPNFAKEVLHDSDYVVITKN
EKYAVALCSLSTDECEYDTNLYLDEKLVDYSTVDVNGVTYYINIVVT
NEDDFKLATDKDKEKHDKQEVIVKSELN >WP_031649390.1
SEQ ID NO: 84
MTLTTAQRKYNEAMHEFINMVDDFEESTPEFSKEVLNDSDYVVITKN
EKYAGALCHVSTDECEDGSNLYIDEKLIDYSTLNVGGVTYYINIVER
CEDDLEIATDEDKMKSDNQEIILKNELN >EFR93689.1
SEQ ID NO: 85
MVDDFEESTPEFSKEVLNDSDYVVITKNEKYAGALCHVSTDECEDGS
NLYIDEKLIDYSTLNVGGVTYYINIVERCEDDLEIATDEDKMKSDNQ
EIILKNELN >WP_070295879.1
SEQ ID NO: 86
MTLTTAQKRYYDAMNEFEAITSKKLEQTPEFSQDLLNDSDYLVITKN
EAYAVALCMLDDDKLYLDETLVQSTCLDVEGETYYINFVVTNEDDFK
LATDEDKEKHDKQEVIVKSELN >WP_070776458.1
SEQ ID NO: 87
MTLTTAQKRYYDAMNEFEAITSKELEQTPEFSQDLLNDSDYLVITKN
EAYAVALCMLDDDKLYLDETLVQSTCLDVEGETYYINFVVTNEDDFK
LATDEDKEKHDKQEVIVKSELN >WP_070005111.1
SEQ ID NO: 88
MTLTTAQKRYYDAMNEFEAITSKELEQTPEFSQDLLNDSDYLVITKN
EAYAVALCMLDDDKLYLDETLVQSTCLDVEGETYYINFVVTNEDDFK
LATDKDKEKHDKQEVIVKSELN

\>WP_023553814.1

SEQ ID NO: 89
MTITTAQKRYYDAMNEFEAIISKELEQTPAFSQDLLNDSDYLVITKN
EAYAVALCMLDDDKLYLDETLVQSTRLDIEDETYYINFVVTNEDDFK
LATDEDEKEHDKQEVIIKSELN

\>WP_031645843.1

SEQ ID NO: 90
MTITTAQKRYYDAMNEFEAITSKELEQTPEFSQDLLNDSDYLVITKN
EAYAVALCMLDDDKLYIDETLVQSTCLDVEGETYYINFVVTNEDDFK
LATDKDKEKHDKQEVIIKSELN

\>WP_014930930.1

SEQ ID NO: 91
MTLTTAQKRYYDAMNEFEAIISKELEQTRAFSQDLLNDSDYLVITKN
EAYAVDLCMLDDDKLYLDETLVQSTRLDIEDETYYINFVVTNEDDFK
LATDEDEKEHDRQEVIIKSELN

\>WP_070783480.1

SEQ ID NO: 92
MTITTAQKRYYDAMNEFEAITSKELEQTPEFSQDLLNDSDYLVVTKN
EAYAAALCMLDDDKLYLDETLVQSTCLDVEGEIYYINFVVTNEDDFK
LATDKDKEKHDKQEVIVKSELN

\>WP_070040172.1

SEQ ID NO: 93
MTITTAQKRYYDAMNEFEAITSKGLEQTPEFSQDLLNDFDYLVITKN
EAYAAALCMLDDEKLYLDETLVHSTRLDIEDDTYYINFVVTNEDDFK
LATDEDKEKHDKQEVIIKRELN

\>WP_012581437.1

SEQ ID NO: 94
MTITTAQKRYYDAMNEFEAIISKELEQTPAFSQDLLNDSDYLVITKN
EAYAVALCLLDDDKLYLDETLVHSTRLDIEDETYYINFVVTNEDDFK
LATDEDKEKHDKQEVIIKSELN

\>WP_061107168.1

SEQ ID NO: 95
MTITTAQKRYYDAMNEFEAIISKELEQTPAFSQNLLNDSDYLVITKN
EAYAVALCLLDDDKLYLDETLVHSTRLDIEDETYYINFVVTNEDDFK
LATDEDKEKHDKQEVIIKSELN

\>WP_070243058.1

SEQ ID NO: 96
MTITTAQKRYYDAMNEFEAITSKELEQTPAFSQDLLNDSDYLVITKN
EAYAVALCLLDDDKLYLDETLVHSTRLDIEDETYYINFVVTNEDDFK
LATDEDKEKHDKQEVIVKSELN

\>WP_015967155.1

SEQ ID NO: 97
MTITTAQKRYYDAMNEFEAIISKELEQTPAFSQDLLNDSDYLVITKN
EAYAVALCLLDDDKLYLDETLVHSTRLNIEDETYYINFVVTNEDDFK
LATDEDKEKHDKQEVIIKSEFN

\>WP_010989941.1

SEQ ID NO: 98
MTLTTAQKRYYDAMNEFEAITSKELEQTPEFSQDLLNDSDYLAVTKN
EAYAVALCLLDDDKLYLDETLVHSTRLDIEDETYYINFVVTNEDDFK
LATDEDKEKHDKQEVIIKSGLN

\>WP_010991653.1

SEQ ID NO: 99
MTVTTAQKRYYDAMNEFEAITSKELEQTPEFSQDLLNDSDYLAVTKN
EAYAVALCLLDDDKLYLDETLVHSTRLDIEDETYYINFVVTNEDDFK
LATDEDKEKHDKQEVIIKSELN

\>WP_068996515.1

SEQ ID NO: 100
MTLTTVQKRYYDAMNEFEAITSKELEQTPEFSQDLLNDSDYLAVTKN
EAYAVALCLLDDDKLYLDETLVHSTRFDIEDETYYINFVVTNEDDFK
LATDEDKEKHDKQEVIIKSELN

\>WP_047934322.1

SEQ ID NO: 101
MTLTTVQKRYYDAMNEFEAITSKELEQTPEFSQDSLNDSDYLAVTKN
EAYAVALCLLDDDKLYLDETLVHSTRFDIEDETYYINFVVTNEDDFK
LATDEDKEKHDKQEVIIKSELN

\>WP_003727803.1

SEQ ID NO: 102
MTITTAQKRYYDAMNEFEAIISKELEQTPAFSQDLLNDSDYLAVTKN
EAYAVALCLLDDDKLYLDETLVHSTRLDIEDETYYINFVVTNEDDFK
LATDEDKEKHDKQEVIIKSGLN

\>WP_061114505.1

SEQ ID NO: 103
MTITTAQKRYYDAMNEFEAITSKELEQTPAFSQDLLNDSDYLAVTKN
EAYAVALCLLDDDKLYLDETLVHSTRLDIEDETYYINFVVTNEDDFK
LATDEDKEKHDKQEVIIKSGLN

\>EFS02358.1

SEQ ID NO: 104
MAITLSQRKFYEAINEFEEMTENEVVTSPRIPQDYLNDGDYVVITKS
ENYALNLCTTNLEGFEDRHFLDEKLIYSTFVETYSGETYYIYITQTA
EFDEDDAVEFLATQEQIYEYHKQEEQKTVILKMELS

\>WP_069001896.1

SEQ ID NO: 105
MAQTEAQKIFYEAINEFEEMTNEEVVTSPRIPQDYLNDGDYVVITKS
ENYALNLCTTDLEGFEDRYFLDEKLIYSTSVETYTDETYYIYITQTT
EFEEDNAVEFLATQEQIYEYHKQEEQKTVILKMELS

\>WP_061665680.1

SEQ ID NO: 106
MTTARKKFYQAISEFEAMTGKDVERTPQIADEVLNDAEYIAFTKTEK
YALYLCTSNVEGLEDRYFLDEECLDSTFLETEDNETYYIHFLQETEF
SEDDNEDELPLATEEQIEAYDKQEELKAVILKKELN

\>WP_009917643.1

SEQ ID NO: 107
MRTTAQERLDNAINEFEEITNEEVVTSPRIPQDYLNDGDYVVITKSE
NYALNLCTTNLEGFEDRHFLDEKLIYSTFVETYSGETYYIYITQTAE
FDEDDAVEFLATQEQIYEYHKQEEQKTVILKMELS

\>WP_061112069.1

SEQ ID NO: 108
MRTTAQERLDNAINEFEEITNEEVVTSPRIPQDYLNDGDYVVITKSE
NYALNLCTTNLEGFEDRHFLDEKLIYSTFVETYAGETYYIYITQTAE
FDEDDAVEFLATQEQIYEYHKQEEQKTVILKMELS

```
>WP_003745974.1
                                    SEQ ID NO: 109
MRTTAQERLDNAINEFEEITNEEVVTSPLIPQDYLNDGDYVVITKSE

NYALNLCTTNLEGFEDRHFLDEKLIYSTFVETYSGETYYIYITQTAE

FDEDDAVEFLATQEQIYEYHKQEEQKTVILKMELS

AcrIIA3 protein sequences
>WP_014930691.1 (Listeria)
                                    SEQ ID NO: 110
MFNKAEIMKQAWNWFNDSNIWLSDIEWVSYTDKEKSFSVCLKAAWSK

AKEEVEESKKESKHIAKSEELKAWNWAERKLGLHFNISDDEKFTSVK

DETKINFGLSVWACAMKAVKLHNDLFPQTAA

>WP_068996201.1
                                    SEQ ID NO: 111
MYNKAEIMKQAWNWFNDSNIWLSDSEWVSYTDKEKSFSVCLKAAWSK

AKEEVEESKKESKHIAKSEELKAWNWAERKLGLHFNISDDEKFTSVK

DETKINFGLSVWACAMKAVKLHNDLFPQTAA

>WP_031646277.1
                                    SEQ ID NO: 112
MYNKAEIMKQAWNWFNDSNIWLSDIEWVSYTDKEKSFSVCLKGAWSK

AKEEVEESKKESKHIAKSEELKAWNWAERKLGLHFNISDDEKFTSVK

DETKINFGLSWVACAMKAVKLHNDLFPQTAA

>WP_003727804.1
                                    SEQ ID NO: 113
MYNKAEIMKQAWNWFNDSNIWLSDIEWVSYTDKEKSFSVCLKAAWSK

AKEEVEESKKESKHIAKSEELKAWNWAERKLGLHFNISDDEKFTSVK

DETKINFGLSLWACAMKAVKLHNDLFPQTAA

>WP_070776457.1
                                    SEQ ID NO: 114
MYNKAEIMKQAWNWFNDSNVWLSDIEWISYTDKEKTFSVCLKAAWSK

AKEEVEESKKESKHIAKSEELKAWNWAERKLGLHFNISDDEKFTSVK

DETKINFGLSVWACAMKAVKLHNDLFPQTAA

>WP_015455142.1
                                    SEQ ID NO: 115
MYNKAEIMKQAWNWFNDSNIWLSDIEWVSYTDKEKSFSVCLKAAWSK

AKEEVEESKKESKYIAKSEELKAWNWAERKLGLRFNISDDEKFTSVK

DETKINFGLSVWACAMKAVKLHNDLFPQTAA

>WP_070005112.1
                                    SEQ ID NO: 116
MFNKAEIMKQAWNWFTDSNVWLSDIEWASYTDKEKSFSVCLKAAWSK

AKEEVEESKKESKHIAKSEELKAWNWAERKLGLHFNISDDEKFTSVK

DETKINFGLSVWACAMKAVKLHNDLFPQTAA

>WP_068996392.1
                                    SEQ ID NO: 117
MYNKAEIMKQAWNWFNDSNIWLSDIEWVSYTDKEKSFSVCLKAAWSK

AKEEVEEFKKESKYIAKSEELKAWNWAERKLGLRFNISDDEKFTSVK

DETKINFGLSVWACAMKAVKLHNDLFPQTAA

>CUK89695.1
                                    SEQ ID NO: 118
MKQAWNWFNDSNIWLSDIEWVSYTDKEKSFSVCLKAAWSKAKEEVEE

SKKESKYIAKSEELKAWNWAERKLGLRFNISDDEKFTSVKDETKINF

GLSVWACAMKAVKLHNDLFPQTAA

>WP_060577772.1
                                    SEQ ID NO: 119
MYNKAEIMKQAWNWFNNSNVWLSDIEWVSYTDKEKTFSVCLKAAWSK

AKEEVEESKKESKHIAKSEELKAWNWAERKLGLHFNISDDEKFTSVK

DETKINFGLSVWACAMKAVKLHNDLFPQTAA

>WP_070295878.1
                                    SEQ ID NO: 120
MYNKAEIMKQAWNWFNNSNVWLSDIEWVSYTDKEKTFSVCLRAAWSK

AKEEVEESKEESKHIAKSEELKAWNWAERKLGLHFNISDDEKFTSVK

DETKINFGLSVWACAMKAVKLHNDLFPQTAA

>WP_061396065.1
                                    SEQ ID NO: 121
MFNKAEIMKQAWNWFTDSNVWLSDIEWVSYTDKEKTFSVCLKAAWSK

AKEEVKEVEKEIKHISKSEELKAWNWAERKLGLHFNISDDEKFTSVK

DETKINFGLSVWACAMKAVKLHNDLFPQTAA

>WP_039389302.1
                                    SEQ ID NO: 122
MYNKAEIMKQAWNWFNDSNVWLSDIEWASYTDKEKTFSVCLKAAWSK

AKEEVKEVEKEIKHISKSEELKAWNWAERKLGLHFNISDDEKFTSVK

DETKINFGLSVWACAMKAVKLHNDLFPQTAA

>WP_047934319.1
                                    SEQ ID NO: 123
MFNKAEIMKQAWNWFTDSNVWLSDIEWASYTDKEKTFSVCLKAAWSK

AKEEVKEVEKEIKHISKSEELKAWNWAERKLGLHFNISDDEKFTSVK

DETKINFGLSVWACAMKAVKLHNDLFPQTAA

>WP_069001240.1
                                    SEQ ID NO: 124
MYNKAEIMKQAWNWFTDSNVWLSDIEWASYTDKEKTFSVCLKAAWSK

AKEEVKEVEKEIKHISKSEELKAWNWAERKLGLHFNISDDEKFTSVK

DETKINFGLSVWACAMKAVKLHNDLFPQTAA

>WP_010991652.1
                                    SEQ ID NO: 125
MFNKAEIMKQAWNWFTDSNVWLSDIEWVSYTDKEKTFSVCLKAAWSK

AKEEFKEVEKEIKHISKSEELKAWNWAERKLGLHFNISDDEKFTSVK

NETKMNFGLSVWACAMKAVKLHNDLFPQTAA

>WP_061114504.1
                                    SEQ ID NO: 126
MYNKAEIMKQAWNWFTDSNVWLSDIEWASYTDKEKTFSVCLKAAWSK

AKEEVKEVEKEIKHISKSEELKAWNWAERKLGLHFNISDDEKFTSVK

DETKINFGLSVWACAMKAVKLHNDLFPQTVA

>WP_014930931.1
                                    SEQ ID NO: 127
MYNKAEIMKQAWNWFNDSNVWLSDiEWASYTDKEKTFSVCLKAAWSK

AKEEVKEVEKEIKHISKSEELKAWNWAERKLGLHFNISDDEKFTSVK

DETKINFGLSVWACAMKAVKLHSHLFPQTAA

>WP_069002681.1
                                    SEQ ID NO: 128
MYNKAEIMKQAWNWFTDSNVWLSDIEWASYTDKEKTFSVCLKAAWSK

AKEEVKEVEKEIKHISKREELKAWNWAERKLGLHFNISDDEKFTSVK

DETKINFGLSVWACAMKAVKLHNDLFPQTVA
```

>WP_012581436.1
SEQ ID NO: 129
MFNKAEIMKQAWNWFTDSNVWLSDIEWVSYTDKEKTFSVCLKAAWSK
AKEEVKEVEKEIKHISKSEELKAWNWAERKLGLRFNISDDEKFTSVK
DETKQHFGLSVWACAMKAVKLHNDLFPQTAA

>WP_010989940.1
SEQ ID NO: 130
MYNKAEIMKQAWNWFNDSNIWLSDIEWVSYTDKEKSFSVCLKAAWSK
AKEEVEESKKESKHIAKSEELKAWNWAESKLGLRFNISDDEKFTSVK
DETKMNFDLNVWACAMKAVKLHNDLFPQTAA

>WP_015967156.1
SEQ ID NO: 131
MYNKAEIMKQAWNWFTDSNVWLSDIEWVSYTDKEKTFSVCLKAAWSK
AKEEVKEVEKEIKHISKSEELKAWNWAERKLGLRFNSSDDEKFTSVK
DETKQHFGLSVWACAMKAVKLHNDLFPQTAA

>WP_031645844.1
SEQ ID NO: 132
MYNKAEIMKQAWNCFNDSNVWLSDIEWVSYTDKEKTFSVCLKAAWSK
AKEEIEKSKKESKHIAKSEELKAWNWAERKLGLRFNISDDEKFTSVK
DETKQHFGLSVWACAMKAVKLHNDLFPQTAA

>WP_031691597.1
SEQ ID NO: 133
MYNKAEIMKQAWNCFNDSNVWLSDIEWVSYTDKEKTFSVCLKAAWSK
AKEEIEESKKESKHIAKSEELKAWNWAERKLGLRFNISDDEKFTSVK
DETKQHFGLSVWACAMKAVKLHNDLFPQTAA

>WP_023553812.1
SEQ ID NO: 134
MYNKSEIMGQAWNWFRDSSVWLSDIEVWSYTDKEKTFSVCLKAAWSK
AKEEVEESKKESKHIAKSEELKAWNWAESKLGLRFNISDDEKFTSVK
DETKINFGLSVWACAMKAVKLHNDLFPQTAA

>WP_069029656.1
SEQ ID NO: 135
MYNKAEIMKQAWNWFTDSNVWLSDIEWASYTDKEKTFSVCLKAAWSK
AKEEVKEVEKEIKHISKREELKAWNLAERKLGLHFNISDDEKFTSVK
DETKINFGLSVWACAMKAVKLHNDLFPQTVA

>WP_069001927.1
SEQ ID NO: 136
MFNKAEIMKQAWNWFTDSNVWLSDIEWASYTDKEKTFSVCLKAAWSK
AKEEVKEVEKEIKHISKSEELKAWNWAERKLGLHFNISDDEKFTSVK
DETKINFGLSVWACAMKAVKLHN

>WP_064659125.1
SEQ ID NO: 137
MKKVTYDKSGIMKEAWNLFNNDDITLADFEHLGWMEWKSEKTFALCL
KEAWGREKEVVERVNQKFANAETSEEAKAWDWACKKLGVAFEMDAYT
KMTNVEDMEKEAWPGTSVWSLAMRAVKLHMEVAA

>WP_012678885.1
SEQ ID NO: 138
MRYNKSEIMKNAWAMFNSCNWGAENFKFVSVEEKTFAACLKEAWAEE
KEYVEEKIKESANAPKSEEAKAWDWACRKLNANKLQNVEATDKVAWV
SEMAKEMWSSNIWAQAIKAVKLHIKLFAA

>WP_037595340.1
SEQ ID NO: 139
MKYNKSEIMKNAWTMFNDDNFDTSYYEYATAEVYGQKTFSECLKESW
GREKAYQEEKEKRLVDAPKSEEAKAWDWACRKLNVNELQNIDATDKV
FYVEGMAKEMWSSNVWAQAIKAVKLHIELFVA

>WP_009730539.1
SEQ ID NO: 140
MKKVAYDKSGIMKEAWEMFNRNYQICDFEYADFSGREYFEYASFADC
LKEAWAHEKEVVERVNQKYADAETSEEVKAWDWACKKLGVAFEMDAY
TKITNVEGMEKEAWPGTSVWSLAMRAVKLHMEVAA

>WP_071127625.1
SEQ ID NO: 141
MAKYNKSEIMTQAWTLFNSDNFDTCDYEYTTALVYGQKNFSDCLKEA
WGREKAIVERMAEQEANAPLSEEAKAWDWACRKLGVTAEVTAVEKVR
YVDDMAKEMWSANVWKQAIKAVQLYATVA

>AGM98706.1
SEQ ID NO: 142
MAKYNKSEIMTQAWTLFNSDNFDTCDYEYATALVYGQKTFSDCLKEA
WGREKAIVERMAEKEANAPLSEEAKAWDWACRKLGVTAEVTAVEKVR
YVDDMAKEMWSTNVWKQAIKAVQLYATVA

>WP_012767357.1
SEQ ID NO: 143
MAKYNKSEIMKNAWAMFNSYEWDVENFKFVSAENKTFSNCLKEAWAE
EKEYVERKAKETAEAPKSEEAKAWDWACRKLNVNDLQNIDATDKVFY
VVDMQKEMWTSNVWAQAIKAVELYVKLGLA

>WP_023611744.1 (Streptococcus)
SEQ ID NO: 144
MTKYNKSEIMKNAWAMFNSYEWDVENFKFVSAENKTFSNCLKEAWAE
EKEYVERKAKETAEAPRSEEAKAWDWACRKLNVNDLQNIDATDKVFY
VVDMQKEMWTSNVWAQAIKAVELYVKLGLA >WP_066028552.1
SEQ ID NO: 145
MTKYNKSEIMKNAWAMFNSYEWDVENFKFVSAENKTFSNCLKEAWAE
EKEYVERKAKETAEAPKSEEAKAWDWACRKLNVNDLQNIDATDKVFY
VVDMQKEMWTSNIWAQAIKAVELYVKLGLA >WP_003055844.1
SEQ ID NO: 146
MTKYNKSEIMKNAWAMFNSYEWDVENFKFVSAENKTFSNCLKEAWAE
EKEYVERKAKEAAEASKSEEAKAWDWACRKLNVNDLQNIDATNKVFY
VVDMQKEMWTSNWVAQAIKAVELYVKLGLA AcrIIA4 protein sequences
>WP_003723290.1
SEQ ID NO: 147
MNINDLIREIKNKDYTVKLSGTDSNSITQLIIRVNNDGNEYVISESE
NESIVEKFISAFKNGWNQEYEDEEEFYNDMQTITLKSELN >WP_046376634.1
SEQ ID NO: 148
MNINELIREIKNKDYTAKLSGTDSNSITQLIIRVNNDGNEYVISESE
NESIVEKFISAFKNGWNQEYEDEEEFYNDMQTITLKSELN >WP_069001216.1
SEQ ID NO: 149
MNINELIREVKNKDYTAKLSGTDSNSITQLIIRVNNDGNEYVISESE
NESIVEKFISAFKNGWNQEYEDEEEFYNDMQTITLKSELN >KLI10194.1
SEQ ID NO: 150
MNINELIREIKNKDYTAKLSGTDSNSIAQLIIRVNNDGNEYVISESE
NESIVEKFISAFKNGWNQEYEDEEEFYNDMQTITLKSELN >WP_031667946.1
SEQ ID NO: 151
MNINELIREIKNKDY7AKLSGTDSNSITQLIIHVNNDGNEYVISESE
NESIVEKFISAFKNGWNQEYEDEEEFYNDMQTITLKSELN >WP_070295973.1
SEQ ID NO: 152
MNINDLIREIKNKDYTVKLSGTDSNSITQLIINVNNDGNEYGISESN
FESIVEKFVSNFENGWDGAYEDEEEFYNDMQAISLKSELN >WP_061107115.1
SEQ ID NO: 153
MNINDLIREIKNKDYTVKLSGTDSNSITQLIINVNNDGNEYGISESN
FESIVEKFVSNFENGWDGAYEDEEEFYNDMQAIILKSESN >WP_060954847.1
SEQ ID NO: 154
MNISELIREIKNKDYTVRLEGTDDNSITKLIIDVDNDGNEYVISESK
NESIAEKFASTFKNGWNKEYEDEEEFYNDMQSIILKSELN >WP_012582157.1
SEQ ID NO: 155
MNISELSREIKNKDYAVRLEGTDDNSITKLIIDVDNDGNEYVISESK
NESIAEKFASTFKNGWNKEYEDEEEFYNDMQSIILKSELN >CAR82813.1
SEQ ID NO: 156
MAGYLKRYAEDRGWTLYRLAKESHLSDSTLRTADLTTLNKLSVINIK
KISEAVGETPGEVLDDLIKFEERVEKMNISELIREIKNKDYAVRLEG
TDDNSITKLIIDVDNDGNEYVISESKNESIAEKFASTFKNGWNKEYE
DEEEFYNDMQSIILKSELN >WP_003740262.1
SEQ ID NO: 157
MNLKELVREIKNKDYTAKLSGTDSNSITQLIIHVNNDGNEYGISESN
FESIVEKFVSTFENGWDGAYEDEEEFYNDMQDIVNRHFK >WP_061385557.1
SEQ ID NO: 158
MNLKELVREIKNKDYTAKLSGTDSNSITQLIIHVNNDGNEYGISESN
FESIVEKFVSNFENGWDGAYEDEEEFYNDMQDIVNRHFK >CUL91420.1
SEQ ID NO: 159
MKINELVREIKSRDYTVRLNGTDSNSITKLIIDVNNDGNEYVISERQ
DTSIVESFADSFIDGWTGTYEDEEDFYNDMQEIAQDIILETLKEAFE
NNNYNTDEVDTDLFDGYQIKLAMEYDNIGELATSVNKTKHFTAYMDA
STDFMIIEKY >YP_008239985.1
SEQ ID NO: 160
MSIIAIKKEIHAKGYKVTGTHQGYIAQINFDGTGNEYPLPATWDEFI
ETFKDGWNGTYEDEQAFFNDMQEVALKEILDELTGALFCQDITTYDF
TIDDVKKKVITLDKPTFEEDAEDLIIEFDSTCFWDATVENDKIKITV
RNKSRY >AII27415.1
SEQ ID NO: 161
MSIIAIKKEIHAKGYKVTGTHQGYIAQINFDGTGNEYPLPATWDEFI
ETFKDGWNGTYEDEQAFFNDMQEIALDEILDELIDVLYNLDITTYNF
TIDDS >YP_001468568.1
SEQ ID NO: 162
MSIIAIKKEIHAKGYKVTGTHQGYIAGINFDGTGNEYPLPATWDEFI
ETFKDGWNGTYEDEQAFFNDMQEIALEEILDELTGALFCQDITTYDF
TIDDVKKKVITLDKPTFEEDAEDLISEFDSTCFWDATVENDKSKITV
RNKSRY >YP_009043548.1
SEQ ID NO: 163
MSIIAINKEIRAKGYKVTGTHQGYIAQINFEGTGNEYPLPATWDEFI
ETFKDGWNGTYEDEQAFFNDMQEIALDEILDELIDVLYNLDITTYNF
TIDDVKKKVITLNKPIDEEETEDLVQEFNVTCFWDATVEDDKVKVTI
RNKNRAIS >AID17477.1
SEQ ID NO: 164
MSTTAINKEIHAKGYKVTGTHQGYIAQINFDGTGNEYPLPATWEKFI
ETFKDGWDGTYEDEQAFFNDMQEIALDEILDELIDVLYNLDITTYNF
TIDDVKKKVITLNKPIDEEETEDLVQEFNVTCFWNAIVEDDKVKITV
RNKSK >YP_009043010.1
SEQ ID NO: 165
MSTTAINKEIHAKGYKVTGTHQGYIAQINFDGTGNEYPLPATWEEFI
ETFKDGWDGTYEDEQAFFNDMQEIALDEILDELIDVLYNLDITTYNF
TIDDVKKKVITLNKPIDEEETEDLVQEFNVTCFWNAIVEDDKVKITV
RNKSK >AID17274.1
SEQ ID NO: 166
MSTTAINKEIHAKGYKVTGTHQGYVAQINFDGTGNEYPLPATWEEFI
ETFKDGWDGTYKDEQAFFNDMQEIALDEILDELIDTLYNLDITTYDF
TIDDIKKKVITLDKPTDREETEDLVQEFNVTCFWNAIVEDDKVKVTV
RNKSK >AAY53411.1
SEQ ID NO: 167
MTGTHQGYIAQINFDGTGNEYPLPATWDEFIETFKDGWNGTYEDEQA
FFNDMQEVALKEILDELIDVLYNLDITTYNFTIDDVKKKVITLNKPT
DEEDAEDLVIEFDSTCFXDATVENDKIKVTVRNKSK >YP_009044467.1
SEQ ID NO: 168
MSTTAINKEIHAKGYKVTGTHQGYMAQINFDGTGNEFPLPATWEEFI
ETFKDGWDGTYEDEQAFFNDMQEVALEELLDELTDVFYNLDITAYDF
TVDDVKKKVITLDKPTDREETEDLVQEFKATCFWNAVVEDDKVKVTI
RNKNRAIS Additional protein sequences
AcrIIA3b.3; OLF47316.1
SEQ ID NO: 169

MQFVVTNKSELFKFAWKIFKANKDIAFSECLQNAWFQYKRYLNREAI

KAAQQRKLAKFIADTENEEVKAWNWAEKKLGVALNLTDAEKERNVRN

MYKEMWNANVWATAIKAVKLHMEIG

AcrIIA4b.2, YP 008240385.1
SEQ ID NO: 170

MNELRSLEMSINAKKYDTRLESGNRVLNIGFGDGEDYPVCSSSRYSL

KESFIECFKDGWSGTYRDEKELMEDMQEIAQELILEELTDIFEYYEF

NTDEIDTDLFKGFTFDVDSDLEDSMALMKAINATKYFEARSSSWYAS

FEVSYIG

---

What is claimed is:

1. A polynucleotide comprising a promoter operably linked to a nucleic acid encoding a Cas9-inhibiting polypeptide, wherein the Cas9-inhibiting polypeptide has at least 95% identity to SEQ ID NO: 147, and wherein the promoter is heterologous to the nucleic acid.

2. A vector comprising the polynucleotide of claim 1.

3. A pharmaceutical composition comprising the polynucleotide of claim 1.

4. A delivery vehicle comprising the polynucleotide of claim 1.

5. The delivery vehicle of claim 4, wherein the delivery vehicle is a liposome or nanoparticle.

6. A method of expressing a Cas9-inhibiting polypeptide in a cell, the method comprising introducing into the cell a polynucleotide comprising a promoter operably linked to a nucleic acid encoding a Cas9-inhibiting polypeptide, wherein the encoded Cas9-inhibiting polypeptide has at least 95% identity to SEQ ID NO: 147, and wherein said promoter is heterologous to the nucleic acid encoding the Cas9-inhibiting polypeptide, and wherein the Cas9-inhibiting polypeptide is expressed in the cell.

7. The method of claim 6, wherein the Cas9-inhibiting polypeptide comprises SEQ ID NO: 147.

8. The method of claim 6, wherein the promoter that is operably linked to a nucleic acid encoding a Cas9-inhibiting polypeptide is an inducible promoter and the cell is contacted with an agent that induces expression of the Cas9-inhibiting polypeptide.

9. The method of claim 6, further comprising introducing a Cas9 polypeptide into the cell before introducing the polynucleotide comprising the promoter operably linked to a nucleic acid encoding a Cas9-inhibiting polypeptide, wherein the expressed Cas9-inhibiting polypeptide inhibits the introduced Cas9 polypeptide.

10. The method of claim 6, further comprising introducing a Cas9 polypeptide into the cell after introducing the polynucleotide comprising the promoter operably linked to a nucleic acid encoding a Cas9-inhibiting polypeptide, wherein the expressed Cas9-inhibiting polypeptide inhibits the introduced Cas9 polypeptide.

11. The method of claim 6, further comprising introducing a polynucleotide encoding a Cas9 polypeptide into the cell before introducing the polynucleotide comprising the promoter operably linked to a nucleic acid encoding a Cas9-inhibiting polypeptide, wherein the Cas9 polypeptide is expressed in said cell, wherein the expressed Cas9-inhibiting polypeptide inhibits the expressed Cas9 polypeptide.

12. The method of claim 11, wherein the polynucleotide encoding a Cas9 polypeptide is operably linked to an inducible promoter and the cell is contacted with an agent or condition that induces expression of the Cas9 polypeptide in the cell.

13. The method of claim 6, further comprising introducing a polynucleotide encoding a Cas9 polypeptide into the cell after introducing the polynucleotide comprising the promoter operably linked to a nucleic acid encoding a Cas9-inhibiting polypeptide, wherein the Cas9 polypeptide is expressed in said cell, wherein the expressed Cas9-inhibiting polypeptide inhibits the expressed Cas9 polypeptide.

14. The method of claim 13, wherein the polynucleotide encoding a Cas9 polypeptide is operably linked to an inducible promoter and the cell is contacted with an agent or condition that induces expression of the Cas9 polypeptide in the cell.

15. The method of claim 6, wherein the cell is a eukaryotic cell.

16. The cell of claim 15, wherein the cell is selected from the group consisting of a mammalian cell and a human cell.

17. The method of claim 15 wherein the method occurs ex vivo in a cell that is removed from an animal.

18. The method of claim 17, wherein the cell is introduced into a mammal.

19. The method of claim 6, wherein the cell is a prokaryotic cell.

* * * * *

SEQUENCE LISTING

```
<160> NUMBER OF SEQ ID NOS: 209

<210> SEQ ID NO 1
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 1

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Pro Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Glu His Val Asn Ile Lys Lys
        115                 120                 125

Asp Val Cys Lys Ala Leu Glu Asn Ala Ile Thr Val Leu Lys Glu Lys
    130                 135                 140

Lys Asn Glu Leu Leu
145

<210> SEQ ID NO 2
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 2

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Pro Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60
```

```
Leu Glu Asp Ile Glu Lys Asn Ser Asp Asp Leu Ala Gly Phe Lys His
 65                  70                  75                  80

Leu Leu Asp Lys Tyr Lys Leu Ser Phe Pro Ala Gln Glu Phe Glu Leu
                 85                  90                  95

Tyr Cys Leu Ile Lys Glu Phe Glu Ser Thr Asn Ile Glu Val Leu Pro
            100                 105                 110

Phe Thr Phe Asn Arg Phe Glu Asn Glu Glu His Val Asn Ile Lys Lys
        115                 120                 125

Asp Val Cys Lys Ala Leu Glu Asn Ala Ile Thr Val Leu Lys Glu Lys
    130                 135                 140

Lys Asn Glu Leu Leu
145

<210> SEQ ID NO 3
<211> LENGTH: 148
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 3

Met Thr Ile Lys Leu Leu Asp Glu Phe Leu Lys Lys His Asp Leu Thr
  1               5                  10                  15

Arg Tyr Gln Leu Ser Lys Leu Thr Gly Ile Ser Gln Asn Thr Leu Lys
                 20                  25                  30

Asp Gln Asn Glu Lys Pro Leu Asn Lys Tyr Thr Val Ser Ile Leu Arg
            35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
 65                  70                  75                  80

Leu Leu Asp Lys Tyr Lys Leu Ser Phe Pro Ala Gln Glu Phe Glu Leu
                 85                  90                  95

Tyr Cys Leu Ile Lys Glu Phe Glu Ser Asn Ile Glu Val Leu Pro Phe
            100                 105                 110

Thr Phe Asn Arg Phe Glu Asn Glu Glu His Val Asn Ile Gly Lys Asp
        115                 120                 125

Val Cys Lys Ala Leu Glu Asn Ala Ile Thr Val Leu Lys Glu Lys Lys
    130                 135                 140

Asn Glu Leu Leu
145

<210> SEQ ID NO 4
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 4

Met Thr Ile Lys Leu Leu Asp Glu Phe Leu Lys Lys His Asp Leu Thr
  1               5                  10                  15

Arg Tyr Gln Leu Ser Lys Leu Thr Gly Ile Ser Gln Asn Thr Leu Lys
                 20                  25                  30

Asp Gln Asn Glu Lys Pro Leu Asn Lys Tyr Thr Val Ser Ile Leu Arg
            35                  40                  45
```

Ser Leu Ser Leu Ile Ser Gly Leu Ser Val Ser Asp Val Leu Phe Glu
        50                  55                  60

Leu Glu Asp Ile Glu Lys Asn Ser Asp Asp Leu Ala Gly Phe Lys His
 65                  70                  75                  80

Leu Leu Asp Lys Tyr Lys Leu Ser Phe Pro Ala Gln Glu Phe Glu Leu
                 85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Glu His Val Asn Ile Glu Lys
        115                 120                 125

Asp Val Cys Lys Ala Leu Glu Asn Ala Ile Thr Val Leu Lys Glu Lys
    130                 135                 140

Lys Asn Glu Leu Leu
145

<210> SEQ ID NO 5
<211> LENGTH: 148
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 5

Met Thr Ile Lys Leu Leu Asp Glu Phe Leu Lys Lys His Asp Leu Thr
 1               5                  10                  15

Arg Tyr Gln Leu Ser Lys Leu Thr Gly Ile Ser Gln Asn Thr Leu Lys
                 20                  25                  30

Asp Gln Asn Glu Lys Pro Leu Asn Lys Tyr Thr Val Ser Ile Leu Arg
            35                  40                  45

Ser Leu Ser Leu Ile Ser Gly Leu Ser Val Ser Asp Val Leu Phe Glu
        50                  55                  60

Leu Glu Asp Ile Glu Lys Asn Ser Asp Asp Leu Ala Gly Phe Lys His
 65                  70                  75                  80

Leu Leu Asp Lys Tyr Lys Leu Ser Phe Pro Ala Gln Glu Phe Glu Leu
                 85                  90                  95

Tyr Cys Leu Ile Lys Glu Phe Glu Ser Asn Ile Glu Val Leu Pro Phe
            100                 105                 110

Thr Phe Asn Arg Phe Glu Asn Glu Lys His Val Asn Ile Lys Lys Asp
        115                 120                 125

Val Cys Lys Ala Leu Glu Asn Ala Ile Thr Val Leu Lys Glu Lys Lys
    130                 135                 140

Asn Glu Leu Leu
145

<210> SEQ ID NO 6
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 6

Met Thr Ile Lys Leu Leu Asp Glu Phe Leu Lys Lys His Asp Leu Thr
 1               5                  10                  15

Arg Tyr Gln Leu Ser Lys Leu Thr Gly Ile Ser Gln Asn Thr Leu Lys
                 20                  25                  30

```
Asp Gln Asn Glu Lys Pro Leu Asn Lys Tyr Thr Val Ser Ile Leu Arg
            35                  40                  45

Ser Leu Ser Leu Ile Ser Gly Leu Ser Val Ser Asp Val Leu Phe Glu
 50                  55                  60

Leu Glu Asp Ile Glu Lys Asn Ser Asp Asp Leu Ala Gly Phe Lys His
 65                  70                  75                  80

Leu Leu Asn Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
               100                 105                 110

Phe Thr Phe Asn Arg Phe Glu Asn Glu Glu His Val Asn Ile Glu Lys
               115                 120                 125

Asp Val Cys Lys Ala Leu Glu Asn Ala Ile Thr Val Leu Lys Glu Lys
           130                 135                 140

Lys Asn Glu Leu Leu
145
```

<210> SEQ ID NO 7
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 7

```
Met Ala Ile Lys Leu Leu Asp Glu Phe Leu Lys His Asp Leu Thr
 1               5                  10                  15

Arg Tyr Gln Leu Ser Lys Leu Thr Gly Ile Ser Gln Asn Thr Leu Lys
                20                  25                  30

Asp Gln Asn Glu Lys Pro Leu Asn Lys Tyr Thr Val Ser Ile Leu Arg
            35                  40                  45

Ser Leu Ser Leu Ile Ser Gly Leu Ser Val Ser Asp Val Leu Phe Glu
 50                  55                  60

Leu Glu Asp Ile Glu Lys Asn Ser Asp Asp Leu Ala Gly Phe Lys His
 65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
               100                 105                 110

Phe Thr Phe Asn Arg Phe Glu Asn Glu Lys His Val Asn Ile Lys Lys
               115                 120                 125

Asp Val Cys Lys Ala Leu Glu Asn Ala Ile Thr Val Leu Lys Glu Lys
           130                 135                 140

Lys Asn Glu Leu Leu
145
```

<210> SEQ ID NO 8
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 8

```
Met Ser Ile Lys Leu Leu Asp Glu Phe Leu Lys Lys His Asn Lys Thr
 1               5                  10                  15
```

-continued

Arg Tyr Gln Leu Ser Lys Leu Thr Gly Ile Ser Gln Asn Thr Leu Lys
            20                  25                  30

Asp Gln Asn Glu Lys Pro Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Glu His Val Asn Ile Glu Lys
        115                 120                 125

Asp Val Cys Lys Ala Leu Glu Asn Ala Ile Thr Val Leu Lys Glu Lys
    130                 135                 140

Lys Asn Glu Leu Leu
145

<210> SEQ ID NO 9
<211> LENGTH: 147
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 9

Met Lys Leu Leu Asp Glu Phe Leu Lys Lys His Asp Leu Thr Arg Tyr
1               5                   10                  15

Gln Leu Ser Lys Leu Thr Gly Ile Ser Gln Asn Thr Leu Lys Asp Gln
            20                  25                  30

Asn Glu Lys Pro Leu Asn Lys Tyr Thr Val Ser Ile Leu Arg Ser Leu
        35                  40                  45

Ser Leu Ile Ser Gly Leu Ser Val Ser Asp Val Leu Phe Glu Leu Glu
    50                  55                  60

Asp Ile Glu Lys Asn Ser Asp Asp Leu Ala Gly Phe Lys His Leu Leu
65                  70                  75                  80

Asp Lys Tyr Lys Leu Ser Phe Pro Ala Gln Glu Phe Glu Leu Tyr Cys
                85                  90                  95

Leu Ile Lys Glu Phe Glu Ser Ala Asn Ile Glu Val Leu Pro Phe Thr
            100                 105                 110

Phe Asn Arg Phe Glu Asn Glu Lys His Val Asn Ile Lys Lys Asp Val
        115                 120                 125

Cys Lys Ala Leu Glu Asn Ala Ile Thr Val Leu Lys Glu Lys Asn
    130                 135                 140

Glu Leu Leu
145

<210> SEQ ID NO 10
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 10

```
Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Pro Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
65                  70                  75                  80

Leu Leu Asn Lys Tyr Lys Leu Ser Phe Pro Ala Gln Glu Phe Glu Leu
            85                  90                  95

Tyr Cys Leu Ile Lys Glu Phe Glu Ser Ala Asn Ile Glu Val Leu Pro
        100                 105                 110

Phe Thr Phe Asn Arg Phe Glu Asn Glu Thr His Val Asp Ile Glu Lys
        115                 120                 125

Asp Val Arg Lys Ala Leu Glu Asn Ala Ile Thr Val Leu Lys Glu Lys
        130                 135                 140

Lys Asn Glu Leu Leu
145

<210> SEQ ID NO 11
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 11

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Pro Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
65                  70                  75                  80

Leu Leu Asp Lys Tyr Lys Leu Ser Phe Pro Ala Gln Glu Phe Glu Leu
            85                  90                  95

Tyr Cys Leu Ile Lys Glu Phe Glu Ser Ala Asn Ile Glu Val Leu Pro
        100                 105                 110

Phe Thr Phe Asn Arg Phe Glu Asn Glu Thr His Val Asp Ile Glu Lys
        115                 120                 125

Asp Val Arg Lys Ala Leu Glu Asn Ala Ile Thr Val Leu Lys Glu Lys
        130                 135                 140

Lys Asn Glu Leu Ile
145

<210> SEQ ID NO 12
<211> LENGTH: 149
<212> TYPE: PRT
<213> ORGANISM: Unknown
<220> FEATURE:
<223> OTHER INFORMATION: Unknown bacterial, unknown viral (phage), or
``` synthetic Cas9-inhibiting polypeptide

<400> SEQUENCE: 12

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Ser Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Leu Ala Gly Phe Lys His
65                  70                  75                  80

Leu Leu Gly Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Thr His Val Asp Ile Glu Lys
        115                 120                 125

Asp Val Arg Lys Ala Leu Glu Asn Ala Ile Thr Val Leu Lys Glu Lys
    130                 135                 140

Lys Asn Glu Leu Ile
145

<210> SEQ ID NO 13
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 13

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Pro Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Thr
            100                 105                 110

Phe Thr Phe Asn Arg Phe Glu Asn Glu His Ala Asp Ile Glu Lys
        115                 120                 125

Asp Val Lys Lys Ala Leu Asn Asn Ala Ile Ala Val Leu Lys Glu Lys
    130                 135                 140

Lys Glu Glu Leu Leu
145

<210> SEQ ID NO 14
<211> LENGTH: 149
<212> TYPE: PRT

<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 14

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Ser Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
65                  70                  75                  80

Leu Leu Gly Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Thr
            100                 105                 110

Phe Thr Phe Asn Arg Phe Glu Asn Glu His Ala Asp Ile Glu Lys
        115                 120                 125

Asp Val Lys Lys Ala Leu Asn Asn Ala Ile Ala Val Leu Lys Glu Lys
    130                 135                 140

Lys Glu Glu Leu Leu
145

<210> SEQ ID NO 15
<211> LENGTH: 149
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 15

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Ser Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
65                  70                  75                  80

Leu Leu Gly Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Thr
            100                 105                 110

Phe Thr Phe Asn Arg Phe Glu Asn Glu His Ala Asp Ile Glu Lys
        115                 120                 125

Asp Val Lys Lys Ala Leu Asn Asn Ala Ile Ala Val Leu Lys Ala Lys
    130                 135                 140

Lys Glu Glu Leu Leu
145

```
<210> SEQ ID NO 16
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 16

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Ser Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
65                  70                  75                  80

Leu Leu Gly Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Thr
            100                 105                 110

Phe Thr Phe Asn Arg Phe Glu Asn Glu Glu His Ala Asp Ile Glu Lys
        115                 120                 125

Asp Val Lys Lys Thr Leu Asn Asn Ala Ile Ala Val Leu Lys Glu Lys
    130                 135                 140

Lys Glu Glu Leu Leu
145

<210> SEQ ID NO 17
<211> LENGTH: 144
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 17

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Pro Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Thr
            100                 105                 110

Phe Thr Phe Asn Arg Phe Glu Asn Glu Glu His Ala Asp Ile Glu Lys
        115                 120                 125

Asp Val Lys Lys Ala Leu Asn Asn Ala Ile Ala Val Leu Lys Glu Lys
    130                 135                 140
```

```
<210> SEQ ID NO 18
<211> LENGTH: 152
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 18

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Ser Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
65                  70                  75                  80

Leu Leu Gly Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Thr
            100                 105                 110

Phe Thr Phe Asn Arg Phe Glu Asn Glu Glu His Ala Asp Ile Glu Lys
        115                 120                 125

Asp Val Lys Lys Ala Leu Asn Asn Ala Ile Ala Val Leu Lys Glu Lys
    130                 135                 140

Lys Lys Asn Cys Tyr Lys Asn Tyr
145                 150

<210> SEQ ID NO 19
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 19

Met Ser Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Ser Leu Asn Lys Tyr Thr Val Ser Ile Leu Arg
        35                  40                  45

Ala Leu Ala Leu Ile Thr Gly Met Pro Ile Ser Asp Val Leu Phe Glu
    50                  55                  60

Leu Glu Asp Leu Glu Lys Asn Ala Asp Asp Leu Ala Gly Phe Lys His
65                  70                  75                  80

Leu Leu Asp Thr Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Ser Glu Thr His Val Asp Ile Glu Lys
        115                 120                 125

Asp Val Arg Lys Ala Leu Glu Asn Ala Ile Thr Val Leu Lys Glu Lys
    130                 135                 140

Lys Asn Glu Phe Met
```

<210> SEQ ID NO 20
<211> LENGTH: 133
<212> TYPE: PRT
<213> ORGANISM: Unknown
<220> FEATURE:
<223> OTHER INFORMATION: Unknown bacterial, unknown viral (phage), or
synthetic Cas9-inhibiting polypeptide

<400> SEQUENCE: 20

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Pro Leu Asn Lys Tyr Thr Val Ser Ile Leu Arg
        35                  40                  45

Ser Leu Ser Leu Ile Ser Gly Leu Ser Val Ser Asp Val Leu Phe Glu
    50                  55                  60

Leu Glu Asp Ile Glu Lys Asn Ser Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Glu His Val Asn Ile Glu Lys
        115                 120                 125

Asp Val Cys Lys Ala
        130

<210> SEQ ID NO 21
<211> LENGTH: 149
<212> TYPE: PRT
<213> ORGANISM: Unknown
<220> FEATURE:
<223> OTHER INFORMATION: Unknown bacterial, unknown viral (phage), or
synthetic Cas9-inhibiting polypeptide

<400> SEQUENCE: 21

Met Ser Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Thr Leu Asn Lys Tyr Thr Val Ser Ile Leu Arg
        35                  40                  45

Ala Leu Ala Leu Ile Thr Gly Met Pro Ile Ser Asp Val Leu Phe Glu
    50                  55                  60

Leu Glu Asp Leu Glu Lys Asn Ala Asp Asp Leu Ala Gly Phe Lys His
65                  70                  75                  80

Leu Leu Asp Thr Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Ser Glu Thr His Val Asp Ile Glu Lys
        115                 120                 125

Asp Val Gln Lys Ala Leu Glu Asn Ala Ile Thr Val Leu Lys Glu Lys
    130                 135                 140

Lys Asn Glu Phe Met
            145

```
<210> SEQ ID NO 22
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 22

Met Ser Ile Lys Leu Leu Asp Glu Phe Leu Lys His Asp Leu Thr
1               5                   10                  15

Arg Tyr Gln Leu Ser Lys Leu Thr Gly Ile Ser Gln Asn Thr Leu Lys
                20                  25                  30

Asp Gln Asn Glu Lys Thr Leu Asn Lys Tyr Thr Val Ser Ile Leu Arg
            35                  40                  45

Ala Leu Ala Leu Ile Thr Gly Met Pro Ile Ser Asp Val Leu Phe Glu
        50                  55                  60

Leu Glu Asp Leu Glu Lys Asn Ala Asp Asp Leu Ala Gly Phe Lys Gln
65                  70                  75                  80

Leu Leu Asp Thr His Lys Leu Ser Phe Pro Ala His Glu Phe Glu Leu
                85                  90                  95

Tyr Cys Leu Ile Lys Glu Phe Glu Ser Val Asn Ile Glu Val Leu Pro
                100                 105                 110

Phe Thr Phe Asn Arg Phe Glu Ser Glu Thr His Val Asp Ile Glu Lys
            115                 120                 125

Asp Val Arg Lys Ala Leu Glu Asn Ala Ile Thr Val Leu Lys Glu Lys
        130                 135                 140

Lys Asn Glu Phe Met
145

<210> SEQ ID NO 23
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 23

Met Ser Ile Lys Leu Leu Asp Glu Phe Leu Lys His Asp Leu Thr
1               5                   10                  15

Arg Tyr Gln Leu Ser Lys Leu Thr Gly Ile Ser Gln Asn Thr Leu Lys
                20                  25                  30

Asp Gln Asn Glu Lys Thr Leu Asn Lys Tyr Thr Val Ser Ile Leu Arg
            35                  40                  45

Ala Leu Ala Leu Ile Thr Gly Met Pro Ile Ser Asp Val Leu Phe Glu
        50                  55                  60

Leu Glu Asp Leu Glu Lys Asn Ala Asp Asp Leu Ala Gly Phe Lys Gln
65                  70                  75                  80

Leu Leu Asp Thr His Lys Leu Ser Phe Pro Ala His Glu Phe Glu Leu
                85                  90                  95

Tyr Cys Leu Ile Lys Glu Phe Glu Ser Val Asn Ile Glu Val Leu Pro
                100                 105                 110

Phe Thr Phe Asn Arg Phe Glu Ser Glu Thr His Val Asp Ile Glu Lys
            115                 120                 125

Asp Val Arg Lys Ala Leu Glu Asn Ala Ile Thr Val Leu Lys Glu Lys
```

```
                130                 135                 140
Lys Asn Glu Phe Ile
145

<210> SEQ ID NO 24
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 24

Met Ser Ile Lys Leu Leu Asp Glu Phe Leu Lys His Asp Leu Thr
1               5                   10                  15

Arg Tyr Gln Leu Ser Lys Leu Thr Gly Ile Ser Gln Asn Thr Leu Lys
                20                  25                  30

Asp Gln Asn Glu Lys Thr Leu Asn Lys Tyr Thr Val Ser Ile Leu Arg
            35                  40                  45

Ala Leu Ala Leu Ile Thr Gly Met Pro Ile Ser Asp Val Leu Phe Glu
        50                  55                  60

Leu Glu Asp Leu Glu Lys Asn Ala Asp Asp Leu Ala Gly Phe Lys Gln
65                  70                  75                  80

Leu Leu Asp Thr His Lys Leu Ser Phe Pro Ala His Glu Phe Glu Leu
                85                  90                  95

Tyr Cys Leu Ile Lys Glu Phe Glu Ser Val Asn Ile Glu Val Leu Pro
            100                 105                 110

Phe Thr Phe Asn Arg Phe Glu Ser Glu Thr His Val Asp Ile Glu Lys
        115                 120                 125

Asp Val Gln Lys Ala Leu Glu Asn Ala Ile Ala Val Leu Lys Glu Lys
    130                 135                 140

Lys Glu Glu Leu Leu
145

<210> SEQ ID NO 25
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 25

Met Thr Ile Lys Leu Leu Asp Glu Phe Leu Lys His Asp Leu Thr
1               5                   10                  15

Arg Tyr Gln Leu Ser Lys Leu Thr Gly Ile Ser Gln Asn Thr Leu Lys
                20                  25                  30

Asp Gln Asn Glu Lys Pro Leu Asn Lys Tyr Thr Val Ser Ile Leu Arg
            35                  40                  45

Ser Leu Ser Leu Ile Ser Gly Leu Ser Val Ser Asp Val Leu Phe Glu
        50                  55                  60

Leu Glu Asp Ile Glu Lys Asn Ser Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Glu His Val Asn
```

<210> SEQ ID NO 26
<211> LENGTH: 149
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 26

Met Ser Ile Lys Leu Leu Asp Glu Phe Leu Lys Lys His Asn Lys Thr
1               5                   10                  15

Arg Tyr Gln Leu Ser Lys Leu Thr Gly Ile Ser Gln Asn Thr Leu Asn
                20                  25                  30

Asp Tyr Asn Lys Lys Glu Leu Asn Lys Tyr Ser Val Ser Phe Leu Arg
            35                  40                  45

Ala Leu Ser Met Cys Ala Gly Ile Ser Thr Phe Asp Val Phe Ile Glu
        50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
                100                 105                 110

Phe Thr Phe Asn Arg Phe Glu Asn Glu Glu His Val Asn Ile Lys Lys
            115                 120                 125

Asp Val Cys Lys Ala Leu Glu Asn Ala Ile Thr Val Leu Lys Glu Lys
        130                 135                 140

Lys Asn Glu Leu Leu
145

<210> SEQ ID NO 27
<211> LENGTH: 149
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 27

Met Ser Ile Lys Leu Leu Asp Glu Phe Leu Lys Lys His Ser Lys Thr
1               5                   10                  15

Arg Tyr Gln Leu Ser Lys Leu Thr Gly Ile Ser Gln Asn Thr Leu Asn
                20                  25                  30

Asp Tyr Asn Lys Lys Glu Leu Asn Lys Tyr Ser Val Ser Phe Leu Arg
            35                  40                  45

Ala Leu Ser Met Cys Ala Gly Ile Ser Thr Phe Asp Val Phe Ile Glu
        50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
                100                 105                 110

Phe Thr Phe Asn Arg Phe Glu Asn Glu Glu His Val Asn Ile Lys Lys
            115                 120                 125

Asp Val Cys Lys Ala Leu Glu Asn Ala Ile Thr Val Leu Lys Glu Lys

```
              130                 135                 140
Lys Asn Glu Leu Leu
145

<210> SEQ ID NO 28
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 28

Met Ser Ile Lys Leu Leu Asp Glu Phe Leu Lys His Ser Lys Thr
1               5                   10                  15

Arg Tyr Gln Leu Ser Lys Leu Thr Gly Ile Ser Gln Asn Thr Leu Asn
                20                  25                  30

Asp Tyr Asn Lys Lys Glu Leu Asn Lys Tyr Ser Val Ser Phe Leu Arg
            35                  40                  45

Ala Leu Ser Met Cys Ala Gly Ile Ser Thr Phe Asp Val Phe Ile Glu
        50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Glu His Val Asn Ile Glu Lys
        115                 120                 125

Asp Val Cys Lys Ala Leu Glu Asn Ala Ile Thr Val Leu Lys Glu Lys
    130                 135                 140

Lys Asn Glu Leu Leu
145

<210> SEQ ID NO 29
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 29

Met Ser Ile Lys Leu Leu Asp Glu Phe Leu Lys His Asn Lys Thr
1               5                   10                  15

Arg Tyr Gln Leu Ser Lys Leu Thr Gly Ile Ser Gln Asn Thr Leu Asn
                20                  25                  30

Asp Tyr Asn Lys Lys Glu Leu Asn Lys Tyr Ser Val Ser Phe Leu Arg
            35                  40                  45

Ala Leu Ser Met Cys Thr Gly Ile Ser Thr Phe Asp Val Phe Ile Glu
        50                  55                  60

Leu Ala Glu Leu Glu Lys Ser Tyr Asp Asp Leu Ala Gly Phe Lys His
65                  70                  75                  80

Leu Leu Asn Lys Tyr Lys Leu Ser Phe Pro Ala Gln Glu Phe Glu Leu
                85                  90                  95

Tyr Cys Leu Ile Lys Glu Phe Asp Ser Ala Asn Ile Glu Val Leu Pro
            100                 105                 110

Phe Thr Phe Asn Arg Phe Glu Asn Glu Glu His Val Asn Ile Glu Lys
```

```
                115                 120                 125
Asp Val Cys Lys Ala Leu Glu Asn Ala Ile Thr Val Leu Lys Glu Lys
            130                 135                 140

Lys Asn Glu Leu Leu
145

<210> SEQ ID NO 30
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 30

Met Ser Ile Lys Leu Leu Asp Glu Phe Leu Lys Lys His Ser Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu His Val Asn Ile Glu Lys
        115                 120                 125

Asp Val Cys Lys Ala Leu Glu Asn Ala Ile Thr Val Leu Lys Glu Lys
    130                 135                 140

Lys Asn Glu Leu Ile
145

<210> SEQ ID NO 31
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 31

Met Asn Ile Lys Leu Leu Asp Glu Phe Leu Lys Lys His Asn Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Thr Gly Ile Ser Thr Phe Asp Val Phe Ile Glu
    50                  55                  60

Leu Ala Glu Leu Glu Lys Ser His Asp Asp Leu Ala Gly Phe Lys His
65                  70                  75                  80

Leu Leu Asp Lys His Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
```

```
                    100                 105                 110

Phe Thr Phe Asn Arg Phe Glu Asn Glu Glu His Val Asn Ile Glu Lys
            115                 120                 125

Asp Val Cys Lys Ala Leu Glu Asn Ala Ile Thr Val Leu Lys Glu Lys
        130                 135                 140

Lys Asn Glu Leu Leu
145

<210> SEQ ID NO 32
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 32

Met Ser Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Thr Gly Ile Ser Thr Phe Asp Val Leu Ile Glu
    50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Thr His Val Asp Ile Glu Lys
        115                 120                 125

Asp Val Arg Lys Ala Leu Glu Asn Ala Ile Thr Val Leu Lys Glu Lys
    130                 135                 140

Lys Asn Glu Leu Ile
145

<210> SEQ ID NO 33
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 33

Met Thr Ile Lys Leu Leu Asp Glu Phe Leu Lys Lys His Ser Leu Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Leu Ile Glu
    50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
```

```
                    85                  90                  95

Tyr Cys Leu Ile Lys Glu Phe Glu Ser Ala Asn Ile Glu Val Leu Pro
                   100                 105                 110

Phe Thr Phe Asn Arg Phe Glu Asn Glu Thr His Val Asp Ile Glu Lys
           115                 120                 125

Asp Val Arg Lys Ala Leu Glu Asn Ala Ile Thr Val Leu Lys Glu Lys
       130                 135                 140

Lys Asn Glu Leu Ile
145

<210> SEQ ID NO 34
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 34

Met Ser Ile Lys Leu Leu Asp Glu Phe Leu Lys Lys His Asn Lys Thr
1               5                  10                  15

Arg Tyr Gln Leu Ser Lys Leu Thr Gly Ile Ser Gln Asn Thr Leu Asn
           20                  25                  30

Asp Tyr Asn Lys Lys Glu Leu Asn Lys Tyr Ser Val Ser Phe Leu Arg
       35                  40                  45

Ala Leu Ser Met Cys Ala Gly Ile Ser Thr Phe Asp Val Leu Ile Glu
   50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
               85                  90                  95

Tyr Cys Leu Ile Lys Glu Phe Glu Ser Ala Asn Ile Glu Val Leu Pro
                   100                 105                 110

Phe Thr Phe Asn Arg Phe Glu Asn Glu Thr His Val Asp Ile Glu Lys
           115                 120                 125

Asp Val Arg Lys Ala Leu Glu Asn Ala Ile Thr Val Leu Lys Glu Lys
       130                 135                 140

Lys Asn Glu Leu Ile
145

<210> SEQ ID NO 35
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 35

Met Ser Ile Lys Leu Leu Asp Glu Phe Leu Lys His Asn Lys Thr
1               5                  10                  15

Arg Tyr Gln Leu Ser Lys Leu Thr Gly Ile Ser Gln Asn Thr Leu Asn
           20                  25                  30

Asp Tyr Asn Lys Lys Glu Leu Asn Lys Tyr Ser Val Ser Phe Leu Arg
       35                  40                  45

Ala Leu Ser Met Cys Ala Gly Ile Ser Thr Phe Asp Val Leu Ile Glu
   50                  55                  60

Leu Ala Glu Leu Glu Lys Ser Tyr Asp Asp Leu Ala Gly Phe Lys His
```

```
                65                  70                  75                  80
Leu Leu Asp Lys Tyr Lys Leu Ser Phe Pro Ala Gln Glu Phe Glu Leu
                    85                  90                  95

Tyr Cys Leu Ile Lys Glu Phe Glu Cys Ala Asn Ile Glu Val Leu Pro
                100                 105                 110

Phe Thr Phe Asn Arg Phe Glu Asn Glu Thr His Val Asp Ile Glu Lys
                115                 120                 125

Asp Val Arg Lys Ala Leu Glu Asn Ala Ile Thr Val Leu Lys Glu Lys
                130                 135                 140

Lys Asn Glu Leu Ile
145

<210> SEQ ID NO 36
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 36

Met Ser Ile Lys Leu Leu Asp Glu Phe Leu Lys His Asn Lys Thr
1               5                   10                  15

Arg Tyr Gln Leu Ser Lys Leu Thr Gly Ile Ser Gln Asn Thr Leu Asn
                20                  25                  30

Asp Tyr Asn Lys Lys Glu Leu Asn Lys Tyr Ser Val Ser Phe Leu Arg
                35                  40                  45

Ala Leu Ser Met Cys Ala Gly Ile Ser Thr Phe Asp Val Phe Ile Glu
            50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                    85                  90                  95

Tyr Cys Leu Ile Lys Glu Phe Glu Ser Ala Asn Ile Glu Val Leu Pro
                100                 105                 110

Phe Thr Phe Asn Arg Phe Glu Asn Glu Thr His Val Asp Ile Glu Lys
                115                 120                 125

Asp Val Arg Lys Ala Leu Glu Asn Ala Ile Thr Val Leu Lys Glu Lys
                130                 135                 140

Lys Asn Glu Leu Ile
145

<210> SEQ ID NO 37
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 37

Met Ser Ile Lys Leu Leu Asp Glu Phe Leu Lys Lys His Asn Lys Thr
1               5                   10                  15

Arg Tyr Gln Leu Ser Lys Leu Thr Gly Ile Ser Gln Asn Thr Leu Asn
                20                  25                  30

Asp Tyr Asn Lys Lys Glu Leu Asn Lys Tyr Ser Val Ser Phe Leu Arg
                35                  40                  45

Ala Leu Ser Met Cys Thr Gly Ile Ser Thr Phe Asp Val Phe Ile Glu
```

```
                 50                  55                  60

Leu Ala Glu Leu Glu Lys Asn Tyr Asp Asp Leu Ala Gly Phe Lys His
 65                  70                  75                  80

Leu Leu Asp Lys Tyr Lys Leu Ser Phe Pro Ala Gln Glu Phe Glu Leu
                 85                  90                  95

Tyr Cys Leu Ile Lys Glu Phe Glu Cys Ala Asn Ile Glu Val Leu Pro
                100                 105                 110

Phe Thr Phe Asn Arg Phe Glu Asn Glu Thr His Val Asp Ile Glu Lys
            115                 120                 125

Asp Val Arg Lys Ala Leu Glu Asn Ala Ile Thr Val Leu Lys Glu Lys
            130                 135                 140

Lys Asn Glu Leu Ile
145

<210> SEQ ID NO 38
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 38

Met Ser Ile Lys Leu Leu Asp Glu Phe Leu Lys Lys His Asn Lys Thr
 1               5                  10                  15

Arg Tyr Gln Leu Ser Lys Leu Thr Gly Ile Ser Gln Asn Thr Leu Asn
                 20                  25                  30

Asp Tyr Asn Lys Lys Glu Leu Asn Lys Tyr Ser Val Ser Phe Leu Arg
             35                  40                  45

Ala Leu Ser Met Cys Ala Gly Ile Ser Thr Phe Asp Val Phe Asn Glu
         50                  55                  60

Leu Glu Glu Leu Glu Lys Asn Tyr Asp Asp Leu Ala Gly Phe Lys His
 65                  70                  75                  80

Leu Leu Asp Lys Tyr Lys Leu Ser Phe Ser Ala Gln Glu Phe Glu Leu
                 85                  90                  95

Tyr Cys Leu Ile Lys Glu Phe Glu Ser Ala Asn Ile Glu Val Leu Pro
                100                 105                 110

Phe Thr Phe Asn Arg Phe Glu Asn Glu Thr His Val Asp Ile Glu Lys
            115                 120                 125

Asp Val Arg Lys Ala Leu Glu Asn Ala Ile Thr Val Leu Lys Glu Lys
            130                 135                 140

Lys Asn Glu Leu Ile
145

<210> SEQ ID NO 39
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 39

Met Thr Ile Lys Leu Leu Asp Glu Phe Leu Lys Lys His Ser Lys Thr
 1               5                  10                  15

Arg Tyr Gln Leu Ser Lys Leu Thr Gly Ile Ser Gln Asn Thr Leu Asn
                 20                  25                  30

Asp Tyr Asn Lys Lys Glu Leu Asn Lys Tyr Ser Val Ser Phe Leu Arg
```

```
                35                  40                  45
Ala Leu Ser Met Cys Ala Gly Ile Ser Thr Phe Asp Val Phe Ile Glu
 50                  55                  60

Leu Ala Glu Leu Glu Lys Ser Tyr Asp Asp Leu Ala Gly Phe Lys His
 65                  70                  75                  80

Leu Leu Asp Lys Tyr Lys Leu Ser Phe Pro Ala Gln Glu Phe Glu Leu
                 85                  90                  95

Tyr Cys Leu Ile Lys Glu Phe Glu Cys Ala Asn Ile Glu Val Leu Pro
            100                 105                 110

Phe Thr Phe Asn Arg Phe Glu Asn Glu Thr His Val Asp Ile Glu Lys
        115                 120                 125

Asp Val Arg Lys Ala Leu Glu Asn Ala Ile Thr Val Leu Lys Glu Lys
    130                 135                 140

Lys Asn Glu Leu Ile
145

<210> SEQ ID NO 40
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 40

Met Ser Ile Lys Leu Leu Asp Glu Phe Leu Lys Lys His Ser Lys Thr
 1               5                  10                  15

Arg Tyr Gln Leu Ser Lys Leu Thr Gly Ile Ser Gln Asn Thr Leu Asn
                20                  25                  30

Asp Tyr Asn Lys Lys Glu Leu Asn Lys Tyr Ser Val Ser Phe Leu Arg
            35                  40                  45

Ala Leu Ser Met Cys Ala Gly Ile Ser Thr Phe Asp Val Phe Ile Glu
 50                  55                  60

Leu Ala Glu Leu Glu Lys Ser Tyr Asp Asp Leu Ala Gly Phe Lys His
 65                  70                  75                  80

Leu Leu Asp Lys Tyr Lys Leu Ser Phe Pro Ala Gln Glu Phe Glu Leu
                 85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Thr His Val Asp Ile Glu Lys
        115                 120                 125

Asp Val Arg Lys Ala Leu Glu Asn Ala Ile Thr Val Leu Lys Glu Lys
    130                 135                 140

Lys Asn Glu Leu Ile
145

<210> SEQ ID NO 41
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 41

Met Ser Ile Lys Leu Leu Asp Glu Phe Leu Lys Lys His Ser Lys Thr
 1               5                  10                  15

Arg Tyr Gln Leu Ser Lys Leu Thr Gly Ile Ser Gln Asn Thr Leu Asn
```

```
                20              25              30

Asp Tyr Asn Lys Lys Glu Leu Asn Lys Tyr Ser Val Ser Phe Leu Arg
            35                  40                  45

Ala Leu Ser Met Cys Ala Gly Ile Ser Thr Phe Asp Val Phe Ile Glu
        50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Cys Ala Asn Ile Glu Val Leu Pro
                100                 105                 110

Phe Thr Phe Asn Arg Phe Glu Asn Glu Thr His Val Asp Ile Glu Lys
            115                 120                 125

Asp Val Arg Lys Ala Leu Glu Asn Ala Ile Thr Val Leu Lys Glu Lys
        130                 135                 140

Lys Asn Glu Leu Leu
145

<210> SEQ ID NO 42
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 42

Met Thr Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Asn
                20                  25                  30

Asp Tyr Asn Lys Lys Glu Leu Asn Lys Tyr Ser Val Ser Phe Leu Arg
            35                  40                  45

Ala Leu Ser Met Cys Thr Gly Ile Ser Thr Phe Asp Val Phe Ile Glu
        50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
                100                 105                 110

Phe Thr Phe Asn Arg Phe Glu Asn Glu Glu His Thr Asp Ile Glu Lys
            115                 120                 125

Asp Val Lys Lys Thr Leu Asn Asn Ala Ile Ala Val Leu Lys Glu Lys
        130                 135                 140

Lys Glu Glu Leu Leu
145

<210> SEQ ID NO 43
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 43

Met Ser Ile Lys Leu Leu Asp Glu Phe Leu Lys Lys His Asn Lys Thr
```

```
1               5                   10                  15
Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
            35                  40                  45

Ala Leu Ser Met Cys Ala Gly Ile Ser Thr Phe Asp Val Phe Ile Glu
            50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
            85                  90                  95

Tyr Cys Leu Ile Lys Glu Phe Glu Cys Ala Asn Ile Glu Val Leu Pro
            100                 105                 110

Phe Thr Phe Asn Arg Phe Glu Asn Glu Thr His Val Asp Ile Glu Lys
            115                 120                 125

Asp Val Arg Lys Ala Leu Glu Asn Ala Ile Thr Val Leu Lys Glu Lys
            130                 135                 140

Lys Asn Glu Leu Ile
145

<210> SEQ ID NO 44
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 44

Met Ser Ile Lys Leu Leu Asp Glu Phe Leu Lys Lys His Ser Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Met Arg
            35                  40                  45

Ala Leu Ser Met Cys Ala Gly Ile Ser Thr Phe Asp Val Phe Ile Glu
            50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
            85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Thr His Val Asp Ile Glu Lys
            115                 120                 125

Asp Val Arg Lys Ala Leu Glu Asn Ala Ile Thr Val Leu Lys Glu Lys
            130                 135                 140

Lys Asn Glu Leu Ile
145

<210> SEQ ID NO 45
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide
```

```
<400> SEQUENCE: 45

Met Ser Ile Lys Leu Leu Asp Glu Phe Leu Lys Lys His Asn Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Lys Glu
    50                  55                  60

Leu Glu Glu Leu Glu Lys Asn Tyr Asp Asp Leu Ala Gly Phe Lys His
65                  70                  75                  80

Leu Leu Asp Lys Tyr Lys Leu Ser Phe Ser Ala Gln Glu Phe Glu Leu
                85                  90                  95

Tyr Cys Leu Ile Lys Glu Phe Glu Ser Ala Asn Ile Glu Val Leu Pro
                100                 105                 110

Phe Thr Phe Asn Arg Phe Glu Asn Glu Thr His Val Asp Ile Glu Lys
            115                 120                 125

Asp Val Arg Lys Ala Leu Glu Asn Ala Ile Thr Val Leu Lys Glu Lys
        130                 135                 140

Lys Asn Glu Leu Ile
145

<210> SEQ ID NO 46
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 46

Met Ser Ile Lys Leu Leu Asp Glu Phe Leu Lys Lys His Ser Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60

Leu Ala Glu Leu Glu Lys Ser Tyr Asp Asp Leu Ser Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
                100                 105                 110

Phe Thr Phe Asn Arg Phe Glu Asn Glu Thr His Val Asp Ile Glu Lys
            115                 120                 125

Asp Val Arg Lys Ala Leu Glu Asn Ala Ile Thr Val Leu Lys Glu Lys
        130                 135                 140

Lys Asn Glu Leu Ile
145

<210> SEQ ID NO 47
<211> LENGTH: 149
<212> TYPE: PRT
<213> ORGANISM: Unknown
<220> FEATURE:
```

<223> OTHER INFORMATION: Unknown bacterial, unknown viral (phage), or
      synthetic Cas9-inhibiting polypeptide

<400> SEQUENCE: 47

Met Ser Ile Lys Leu Leu Asp Glu Phe Leu Lys Lys His Ser Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Ser Ile Glu Val Leu Pro
            100                 105                 110

Phe Thr Phe Asn Arg Phe Glu Asn Glu Thr His Val Asp Ile Glu Lys
        115                 120                 125

Asp Val Arg Lys Ala Leu Glu Asn Ala Ile Thr Val Leu Lys Glu Lys
    130                 135                 140

Lys Asn Glu Leu Ile
145

<210> SEQ ID NO 48
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 48

Met Ser Ile Lys Leu Leu Asp Glu Phe Leu Lys Lys His Asn Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Thr Gly Ile Ser Thr Phe Asp Val Phe Ile Glu
    50                  55                  60

Leu Ala Glu Leu Glu Lys Ser His Asp Asp Leu Ala Gly Phe Lys His
65                  70                  75                  80

Leu Leu Asp Lys His Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Thr His Val Asp Ile Glu Lys
        115                 120                 125

Asp Val Arg Lys Ala Leu Glu Asn Ala Ile Thr Val Leu Lys Glu Lys
    130                 135                 140

Lys Asn Glu Leu Ile
145

<210> SEQ ID NO 49
<211> LENGTH: 149

```
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 49

Met Ser Ile Lys Leu Leu Asp Glu Phe Leu Lys Lys His Ser Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Cys Ala Asn Ile Glu Val Leu Pro
            100                 105                 110

Phe Thr Phe Asn Arg Phe Glu Asn Glu Thr His Val Asp Ile Glu Lys
        115                 120                 125

Asp Val Arg Lys Ala Leu Glu Asn Ala Ile Thr Val Leu Lys Glu Lys
    130                 135                 140

Lys Asn Glu Leu Ile
145

<210> SEQ ID NO 50
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 50

Met Ser Ile Lys Leu Leu Asp Glu Phe Leu Lys Lys His Ser Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Cys Ala Asn Ile Glu Val Leu Pro
            100                 105                 110

Phe Thr Phe Asn Arg Phe Glu Asn Glu Thr His Val Asp Ile Glu Lys
        115                 120                 125

Asp Ile Arg Lys Ala Leu Glu Asn Ala Ile Thr Val Leu Lys Glu Lys
    130                 135                 140

Lys Asn Glu Leu Ile
145
```

<210> SEQ ID NO 51
<211> LENGTH: 149
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 51

Met Ser Ile Lys Leu Leu Asp Glu Phe Leu Lys His Asn Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Thr Val Ser Phe Leu Arg
        35                  40                  45

Thr Leu Ser Met Cys Val Gly Met Ser Thr Val Asp Val Phe Ile Glu
    50                  55                  60

Leu Ala Glu Leu Glu Lys Asn Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Ser Glu Thr His Val Asp Ile Glu Lys
        115                 120                 125

Asp Val Lys Lys Ala Leu Asn Asn Ala Ile Ala Val Leu Lys Glu Lys
    130                 135                 140

Lys Glu Glu Leu Leu
145

<210> SEQ ID NO 52
<211> LENGTH: 149
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 52

Met Ser Ile Lys Leu Leu Asp Glu Phe Leu Lys Lys His Ser Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Thr His Val Asp Ile Glu Lys
        115                 120                 125

Asp Val Arg Lys Ala Leu Asn Asn Ala Ile Ala Val Leu Lys Glu Lys
    130                 135                 140

-continued

Lys Glu Glu Leu Leu
145

<210> SEQ ID NO 53
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 53

Met Ser Ile Lys Leu Leu Asp Glu Phe Leu Lys Lys His Asn Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60

Leu Ala Glu Leu Glu Lys Ser Tyr Asp Asp Leu Ala Gly Phe Lys Tyr
65                  70                  75                  80

Leu Leu Asp Lys His Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Thr His Val Asp Ile Glu Lys
        115                 120                 125

Asp Val Arg Lys Ala Leu Glu Asn Ala Ile Thr Val Leu Lys Glu Lys
    130                 135                 140

Lys Asn Glu Leu Ile
145

<210> SEQ ID NO 54
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 54

Met Asn Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Thr Gly Ile Ser Thr Phe Asp Val Phe Ile Glu
    50                  55                  60

Leu Ala Glu Leu Glu Lys Ser Tyr Asp Asp Leu Ala Gly Phe Lys His
65                  70                  75                  80

Leu Leu Asp Lys His Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Glu His Ala Asp Ile Glu Lys
        115                 120                 125

```
Asp Val Lys Lys Ala Leu Asn Asn Ala Ile Ala Val Leu Lys Ala Lys
    130                 135                 140

Lys Glu Glu Leu Leu
145

<210> SEQ ID NO 55
<211> LENGTH: 130
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 55

Met Ser Ile Lys Leu Leu Asp Glu Phe Leu Lys Lys His Asp Leu Thr
1               5                   10                  15

Arg Tyr Gln Leu Ser Lys Leu Thr Gly Ile Ser Gln Asn Thr Leu Lys
            20                  25                  30

Asp Gln Asn Glu Lys Thr Leu Asn Lys Tyr Thr Val Ser Ile Leu Arg
        35                  40                  45

Ala Leu Ala Leu Ile Thr Gly Met Pro Ile Ser Asp Val Leu Phe Glu
    50                  55                  60

Leu Glu Asp Leu Glu Lys Asn Ala Asp Asp Leu Ala Gly Phe Lys Gln
65                  70                  75                  80

Leu Leu Asp Thr His Lys Leu Ser Phe Pro Ala His Glu Phe Glu Leu
                85                  90                  95

Tyr Cys Leu Ile Lys Glu Phe Glu Ser Val Asn Ile Glu Val Leu Pro
            100                 105                 110

Phe Thr Phe Asn Arg Phe Glu Ser Glu Thr His Val Asp Ile Glu Lys
        115                 120                 125

Asp Val
    130

<210> SEQ ID NO 56
<211> LENGTH: 134
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 56

Thr Arg Tyr Gln Leu Ser Lys Leu Thr Gly Ile Ser Gln Asn Thr Leu
1               5                   10                  15

Asn Asp Tyr Asn Lys Lys Glu Leu Asn Lys Tyr Ser Val Ser Phe Leu
            20                  25                  30

Arg Ala Leu Ser Met Cys Ala Gly Ile Ser Thr Phe Asp Val Phe Ile
        35                  40                  45

Glu Leu Ala Glu Leu Glu Lys Ser Tyr Asp Asp Leu Ala Gly Phe Lys
    50                  55                  60

His Leu Leu Asp Lys Tyr Lys Leu Ser Phe Pro Ala Gln Glu Phe Glu
65                  70                  75                  80

Leu Tyr Cys Leu Ile Lys Glu Phe Glu Ser Ala Asn Ile Glu Val Leu
                85                  90                  95

Pro Phe Thr Phe Asn Arg Phe Glu Asn Glu Glu His Val Asn Ile Lys
            100                 105                 110

Lys Asp Val Cys Lys Ala Leu Glu Asn Ala Ile Thr Val Leu Lys Glu
        115                 120                 125
```

Lys Lys Asn Glu Leu Leu
    130

<210> SEQ ID NO 57
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 57

Met Lys Ile Asn Leu Leu Asp Glu Phe Leu Lys Arg His Asn Ile Thr
1               5                   10                  15

Arg Tyr Arg Leu Ser Lys Leu Ala Gly Ile Ser Gln Asn Thr Leu Lys
            20                  25                  30

Asp Tyr Asn Glu Lys Ser Leu Asn Lys Tyr Thr Val Ser Phe Leu Arg
        35                  40                  45

Ser Leu Ser Phe Val Thr Gly Glu Asp Val Thr Asp Val Leu Ile Glu
    50                  55                  60

Leu Ala Glu Leu Glu Lys Gly Tyr Asp Asp Leu Ala Gly Phe Lys Tyr
65                  70                  75                  80

Leu Leu Asp Lys Tyr Lys Leu Ser Phe Pro Ala Leu Glu Phe Glu Leu
                85                  90                  95

Tyr Cys Ile Ile Lys Glu Phe Glu Ser Ala Asn Ile Glu Ile Ser Pro
            100                 105                 110

Phe Thr Phe Asn Arg Phe Glu Asn Glu Thr His Val Asp Ile Glu Lys
        115                 120                 125

Asp Val Lys Lys Ala Leu Gln Asn Ala Val Thr Val Leu Glu Glu Arg
    130                 135                 140

Lys Glu Glu Leu Leu
145

<210> SEQ ID NO 58
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 58

Met Lys Asn Asn Leu Leu Asp Thr Phe Leu Lys Arg His Asp Ile Thr
1               5                   10                  15

Arg Tyr Arg Leu Ser Lys Leu Ala Gly Ile Ser Gln Asn Thr Leu Lys
            20                  25                  30

Asp Tyr Asn Glu Lys Ser Leu Asn Lys Tyr Thr Val Ser Leu Leu Arg
        35                  40                  45

Ser Leu Ser Phe Val Thr Gly Glu Ser Ile Thr Asp Val Leu Leu Glu
    50                  55                  60

Leu Ala Glu Ile Glu Lys Asp Tyr Asp Asp Leu Ala Gly Phe Lys Tyr
65                  70                  75                  80

Leu Leu Asp Lys Tyr Lys Leu Ser Phe Pro Ala Leu Glu Phe Glu Leu
                85                  90                  95

Tyr Cys Ile Ile Lys Glu Phe Glu Ser Ala Asn Val Glu Ile Ser Pro
            100                 105                 110

Phe Thr Phe Asn Arg Phe Glu Asn Glu Thr His Ala Asp Ile Glu Lys
        115                 120                 125

Asp Val Lys Lys Ala Leu Asn Asn Ala Ile Thr Val Leu Lys Glu Lys
    130                 135                 140

Lys Glu Glu Leu Leu
145

<210> SEQ ID NO 59
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 59

Met Ser Ile Lys Leu Leu Asp Glu Phe Leu Lys His Asn Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60

Leu Ala Glu Leu Glu Lys Ser Tyr Asp Asp Leu Ala Gly Phe Lys Tyr
65                  70                  75                  80

Leu Leu Asp Lys His Lys Leu Ser Phe Pro Thr Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu Thr His Ala Asp Ile Glu Lys
        115                 120                 125

Asp Val Lys Lys Ala Leu Asn Asn Ala Ile Ala Val Leu Glu Glu Lys
    130                 135                 140

Lys Glu Glu Leu Leu
145

<210> SEQ ID NO 60
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 60

Met Lys Ile Asn Leu Leu Asp Ala Phe Leu Lys Arg His Asn Ile Thr
1               5                   10                  15

Arg Tyr Arg Leu Ser Lys Leu Ala Gly Ile Ser Gln Asn Thr Leu Lys
            20                  25                  30

Asp Tyr Asn Glu Lys Ser Leu Asn Lys Tyr Thr Val Ser Phe Leu Arg
        35                  40                  45

Ser Leu Ser Phe Val Thr Gly Glu Asp Val Thr Asp Val Leu Ile Glu
    50                  55                  60

Leu Ala Glu Leu Glu Lys Gly Tyr Asp Asp Leu Ala Gly Phe Lys Tyr
65                  70                  75                  80

Leu Leu Asp Lys Tyr Lys Leu Ala Phe Pro Ala Leu Glu Phe Glu Leu
                85                  90                  95

Tyr Cys Leu Ile Lys Glu Phe Glu Ala Ala Asn Ile Glu Val Ser Pro
            100                 105                 110

```
Phe Thr Phe Asn Arg Phe Glu Asn Glu Thr His Ala Asp Ile Glu Lys
            115                 120                 125

Asp Val Lys Lys Ala Leu Lys Asn Ala Ile Ile Val Leu Lys Glu Lys
130                 135                 140

Lys Glu Glu Leu Leu
145

<210> SEQ ID NO 61
<211> LENGTH: 133
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 61

Met Ser Ile Lys Leu Leu Asp Glu Phe Leu Lys His Ser Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60

Leu Ala Glu Leu Glu Lys Ser Tyr Asp Asp Leu Ala Gly Phe Lys His
65                  70                  75                  80

Leu Leu Asp Lys Tyr Lys Leu Ser Phe Pro Ala Gln Glu Phe Glu Leu
                85                  90                  95

Tyr Cys Leu Ile Lys Glu Phe Glu Ser Ala Asn Ile Glu Val Leu Pro
            100                 105                 110

Phe Thr Phe Asn Arg Phe Glu Asn Glu His Val Asn Ile Glu Lys
        115                 120                 125

Asp Val Cys Lys Ala
    130

<210> SEQ ID NO 62
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 62

Met Lys Ile Asn Leu Leu Asp Glu Phe Leu Lys Arg His Asn Ile Thr
1               5                   10                  15

Arg Tyr Arg Leu Ser Lys Leu Ala Gly Ile Ser Gln Asn Thr Leu Lys
            20                  25                  30

Asp Tyr Thr Glu Lys Ser Leu Asn Lys Tyr Thr Val Ser Phe Leu Arg
        35                  40                  45

Ser Leu Ser Phe Ala Thr Gly Glu Ser Val Thr Asp Ile Leu Leu Glu
    50                  55                  60

Leu Ala Glu Leu Glu Lys Asp Tyr Asp Asp Leu Ala Gly Phe Lys Tyr
65                  70                  75                  80

Leu Leu Asp Lys Tyr Lys Leu Ala Phe Pro Ala Leu Glu Phe Glu Leu
                85                  90                  95

Tyr Cys Leu Ile Lys Glu Phe Glu Ser Ala Asn Ile Glu Ile Ser Pro
            100                 105                 110
```

```
Phe Thr Phe Asn Arg Phe Glu Ser Glu Thr His Thr Asp Ile Glu Lys
            115                 120                 125

Asp Val Lys Lys Ala Leu Gln Asn Ala Val Thr Val Leu Glu Glu Arg
        130                 135                 140

Lys Glu Glu Leu Leu
145

<210> SEQ ID NO 63
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 63

Met Ser Ile Lys Leu Leu Asp Glu Phe Leu Lys His Ser Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ser Leu Ser Phe Ala Thr Gly Glu Ser Val Thr Asp Ile Leu Leu Glu
    50                  55                  60

Leu Ala Glu Leu Glu Lys Asp Tyr Asp Leu Ala Gly Phe Lys Tyr
65                  70                  75                  80

Leu Leu Asp Lys Tyr Lys Leu Ala Phe Pro Ala Leu Glu Phe Glu Leu
                85                  90                  95

Tyr Cys Leu Ile Lys Glu Phe Glu Ser Ala Asn Ile Glu Ile Ser Pro
            100                 105                 110

Phe Thr Phe Asn Arg Phe Glu Ser Glu Thr His Thr Asp Ile Glu Lys
        115                 120                 125

Asp Val Lys Lys Ala Leu Gln Asn Ala Val Thr Val Leu Glu Glu Arg
    130                 135                 140

Lys Glu Glu Leu Leu
145

<210> SEQ ID NO 64
<211> LENGTH: 159
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 64

Met Ser Ile Lys Leu Leu Asp Glu Phe Leu Lys His Asn Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60

Leu Ala Glu Leu Glu Lys Ser Tyr Asp Asp Leu Ala Gly Phe Lys Tyr
65                  70                  75                  80

Leu Leu Asp Lys His Lys Leu Ser Phe Pro Thr Gln Glu Phe Glu Leu
                85                  90                  95
```

-continued

Tyr Cys Leu Ile Lys Glu Phe Glu Ser Ala Asn Ile Glu Val Leu Pro
                100                 105                 110

Phe Thr Phe Asn Arg Phe Glu Asn Glu Thr His Ala Asp Ile Glu Lys
        115                 120                 125

Asp Val Lys Lys Ala Leu Asn Asn Ala Ile Ala Val Leu Glu Glu Lys
    130                 135                 140

Lys Arg Arg Thr Val Ile Lys Thr Ile Asp Tyr Tyr Asp Tyr Ser
145                 150                 155

<210> SEQ ID NO 65
<211> LENGTH: 148
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 65

Met Asn Asn Phe Ala Phe Ile Thr Ser Phe Asn Tyr Gln Gln Pro Arg
1               5                   10                  15

Tyr Gln Leu Ser Lys Leu Thr Gly Ile Ser Gln Asn Thr Leu Asn Asp
            20                  25                  30

Tyr Asn Lys Lys Glu Leu Asn Lys Tyr Ser Val Ser Phe Leu Arg Ala
        35                  40                  45

Leu Ser Met Cys Ala Gly Ile Ser Thr Phe Asp Val Leu Ile Glu Leu
    50                  55                  60

Ala Glu Leu Glu Lys Ser Tyr Asp Asp Leu Ala Gly Phe Lys His Leu
65                  70                  75                  80

Leu Asp Lys Tyr Lys Leu Ser Phe Pro Ala Gln Glu Phe Glu Leu Tyr
                85                  90                  95

Cys Leu Ile Lys Glu Phe Glu Ser Ala Asn Ile Glu Val Leu Pro Phe
                100                 105                 110

Thr Phe Asn Arg Phe Glu Asn Glu Thr His Val Asp Ile Glu Lys Asp
        115                 120                 125

Val Arg Lys Ala Leu Glu Asn Ala Ile Thr Val Leu Lys Glu Lys Lys
    130                 135                 140

Asn Glu Leu Ile
145

<210> SEQ ID NO 66
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 66

Met Lys Thr Asn Leu Leu Asp Thr Phe Leu Lys Arg His Gly Ile Thr
1               5                   10                  15

Arg Tyr Arg Leu Ser Lys Leu Ala Gly Ile Ser Gln Asn Thr Leu Lys
            20                  25                  30

Asp Tyr Thr Glu Lys Ser Leu Asn Lys Tyr Thr Val Ser Phe Leu Arg
        35                  40                  45

Ser Leu Ser Phe Val Thr Gly Glu Asp Val Thr Asp Val Leu Leu Glu
    50                  55                  60

Leu Ala Glu Ile Glu Asn Gly Tyr Asp Asp Leu Ala Gly Phe Lys Tyr
65                  70                  75                  80

```
Leu Leu Asp Lys Tyr Lys Leu Ser Phe Pro Ala Leu Glu Phe Glu Leu
                85                  90                  95

Tyr Cys Ile Ile Lys Glu Phe Glu Ser Ala Asn Ile Glu Ile Ser Pro
            100                 105                 110

Phe Thr Phe Asn Arg Phe Glu Asn Glu Thr His Ala Asp Ile Glu Lys
        115                 120                 125

Asp Val Lys Lys Ala Leu Lys Asn Ala Val Thr Val Leu Glu Glu Arg
    130                 135                 140

Lys Glu Glu Leu Leu
145

<210> SEQ ID NO 67
<211> LENGTH: 148
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 67

Met Asn Asn Phe Ala Phe Ile Thr Ser Phe Asn Tyr Gln Gln Pro Arg
1               5                   10                  15

Tyr Gln Leu Ser Lys Leu Thr Gly Ile Ser Gln Asn Thr Leu Asn Asp
            20                  25                  30

Tyr Asn Lys Lys Glu Leu Asn Lys Tyr Ser Val Ser Phe Leu Arg Ala
        35                  40                  45

Leu Ser Met Cys Ala Gly Ile Ser Thr Phe Asp Val Leu Ile Glu Leu
    50                  55                  60

Ala Glu Leu Glu Lys Ser Tyr Asp Asp Leu Ala Gly Phe Lys His Leu
65                  70                  75                  80

Leu Asp Lys Tyr Lys Leu Ser Phe Pro Ala Gln Glu Phe Glu Leu Tyr
                85                  90                  95

Cys Leu Ile Lys Glu Phe Glu Cys Ala Asn Ile Glu Val Leu Pro Phe
            100                 105                 110

Thr Phe Asn Arg Phe Glu Asn Glu Thr His Val Asp Ile Glu Lys Asp
        115                 120                 125

Val Arg Lys Ala Leu Glu Asn Ala Ile Thr Val Leu Lys Glu Lys Lys
    130                 135                 140

Asn Glu Leu Ile
145

<210> SEQ ID NO 68
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 68

Met Ser Ile Lys Leu Leu Asp Glu Phe Leu Lys Lys His Asn Lys Thr
1               5                   10                  15

Arg Tyr Gln Leu Ser Lys Leu Thr Gly Ile Ser Gln Asn Thr Leu Asn
            20                  25                  30

Asp Tyr Asn Lys Lys Glu Leu Asn Lys Tyr Ser Val Ser Phe Leu Arg
        35                  40                  45

Ala Leu Ser Met Cys Ala Gly Ile Ser Thr Phe Asp Val Phe Ile Glu
    50                  55                  60
```

```
Leu Ala Glu Leu Glu Lys Ser Tyr Asp Asp Leu Ala Gly Phe Lys His
 65                  70                  75                  80

Leu Leu Asp Lys Tyr Lys Leu Ser Phe Pro Ala Gln Glu Phe Glu Leu
                 85                  90                  95

Tyr Cys Leu Ile Lys Glu Phe Glu Ser Ala Asn Ile Glu Val Leu Pro
                100                 105                 110

Phe Thr Phe Asn Arg Phe Glu Asn Glu Glu His Val Asn
            115                 120                 125
```

<210> SEQ ID NO 69
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 69

```
Met Thr Leu Thr Arg Ala Gln Lys Lys Tyr Ala Glu Ala Met His Glu
  1               5                  10                  15

Phe Ile Asn Met Val Asp Asp Phe Glu Glu Ser Thr Pro Asp Phe Ala
                 20                  25                  30

Lys Glu Val Leu His Asp Ser Asp Tyr Val Val Ile Thr Lys Asn Glu
                 35                  40                  45

Lys Tyr Ala Val Ala Leu Cys Ser Leu Ser Thr Asp Glu Cys Glu Tyr
             50                  55                  60

Asp Thr Asn Leu Tyr Leu Asp Glu Lys Leu Val Asp Tyr Ser Thr Val
 65                  70                  75                  80

Asp Val Asn Gly Val Thr Tyr Tyr Ile Asn Ile Val Glu Thr Asn Asp
                 85                  90                  95

Ile Asp Asp Leu Glu Ile Ala Thr Asp Glu Asp Glu Met Lys Ser Gly
                100                 105                 110

Asn Gln Glu Ile Ile Leu Lys Ser Glu Leu Lys
            115                 120
```

<210> SEQ ID NO 70
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 70

```
Met Thr Leu Thr Arg Ala Gln Lys Lys Tyr Ala Glu Ala Met His Glu
  1               5                  10                  15

Phe Ile Asn Met Val Asp Asp Phe Glu Glu Ser Thr Pro Asp Phe Ala
                 20                  25                  30

Lys Glu Val Leu His Asp Ser Asp Tyr Val Val Ile Thr Lys Asn Glu
                 35                  40                  45

Lys Tyr Ala Val Ala Leu Cys Ser Leu Ser Thr Asp Glu Cys Glu Tyr
             50                  55                  60

Asp Thr Asn Leu Tyr Leu Asp Glu Lys Leu Val Asp Tyr Ser Thr Val
 65                  70                  75                  80

Asp Val Asn Gly Val Thr Tyr Tyr Ile Asn Ile Val Glu Thr Asn Asp
                 85                  90                  95

Ile Asp Asp Leu Glu Ile Ala Thr Asp Glu Asp Glu Met Lys Ser Gly
                100                 105                 110
```

```
Asn Gln Glu Ile Ile Leu Lys Ser Glu Leu Asn
        115                 120
```

<210> SEQ ID NO 71
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 71

```
Met Thr Ile Thr Arg Ala Gln Lys Lys Tyr Ala Glu Ala Met His Glu
1               5                   10                  15

Phe Ile Asn Met Val Asp Asp Phe Glu Glu Ser Thr Pro Asp Phe Ala
            20                  25                  30

Lys Glu Val Leu His Asp Ser Asp Tyr Val Val Ile Thr Lys Asn Glu
        35                  40                  45

Lys Tyr Ala Val Ala Leu Cys Ser Leu Ser Thr Asp Glu Cys Glu Tyr
    50                  55                  60

Asp Thr Asn Leu Tyr Leu Asp Glu Lys Leu Val Asp Tyr Ser Thr Val
65                  70                  75                  80

Asp Val Asn Gly Val Thr Tyr Tyr Ile Asn Ile Val Glu Thr Asn Asp
                85                  90                  95

Ile Asp Asp Leu Glu Ile Ala Thr Asp Glu Asp Glu Met Lys Ser Gly
            100                 105                 110

Asn Gln Glu Ile Ile Leu Lys Ser Glu Leu Lys
        115                 120
```

<210> SEQ ID NO 72
<211> LENGTH: 124
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 72

```
Lys Met Thr Leu Thr Arg Ala Gln Lys Lys Tyr Ala Glu Ala Met His
1               5                   10                  15

Glu Phe Ile Asn Met Val Asp Asp Phe Glu Glu Ser Thr Pro Asp Phe
            20                  25                  30

Ala Lys Glu Val Leu His Asp Ser Asp Tyr Val Val Ile Thr Lys Asn
        35                  40                  45

Glu Lys Tyr Ala Val Ala Leu Cys Ser Leu Ser Thr Asp Glu Cys Glu
    50                  55                  60

Tyr Asp Thr Asn Leu Tyr Leu Asp Glu Lys Leu Val Asp Tyr Ser Thr
65                  70                  75                  80

Val Asp Val Asn Gly Val Thr Tyr Tyr Ile Asn Ile Val Glu Thr Asn
                85                  90                  95

Asp Ile Asp Asp Leu Glu Ile Ala Thr Asp Glu Asp Glu Met Lys Ser
            100                 105                 110

Gly Asn Gln Glu Ile Ile Leu Lys Ser Glu Leu Asn
        115                 120
```

<210> SEQ ID NO 73
<211> LENGTH: 122
<212> TYPE: PRT
<213> ORGANISM: Unknown
<220> FEATURE:

<223> OTHER INFORMATION: Unknown bacterial, unknown viral (phage), or
      synthetic Cas9-inhibiting polypeptide

<400> SEQUENCE: 73

Met Thr Leu Thr Arg Ala Gln Lys Lys Tyr Ala Glu Ala Met His Glu
1               5                   10                  15

Phe Ile Asn Met Val Asp Asp Phe Glu Glu Ser Thr Pro Asp Phe Ala
                20                  25                  30

Lys Glu Val Leu His Asp Ser Asp Tyr Val Val Ile Thr Lys Asn Glu
            35                  40                  45

Lys Tyr Ala Val Ala Leu Cys Ser Leu Ser Thr Asp Glu Cys Glu Tyr
        50                  55                  60

Asp Thr Asn Leu Tyr Leu Asp Glu Lys Leu Val Asp Tyr Ser Thr Val
65                  70                  75                  80

Asp Val Asn Gly Val Thr Tyr Tyr Ile Asn Ile Val Glu Thr Asn Asp
                85                  90                  95

Ile Asp Asp Leu Glu Ile Ala Thr Asp Glu Asp Glu Met Lys Ser Gly
            100                 105                 110

Asn Gln Glu Ile Ile Leu Lys Ser Glu Leu
        115                 120

<210> SEQ ID NO 74
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 74

Met Thr Leu Thr Arg Ala Gln Lys Lys Tyr Ala Glu Ala Met His Glu
1               5                   10                  15

Phe Ile Asn Met Val Asp Asp Phe Glu Glu Ser Thr Pro Asp Phe Ala
                20                  25                  30

Lys Glu Val Leu His Asp Ser Asp Tyr Val Val Ile Thr Lys Asn Glu
            35                  40                  45

Lys Tyr Ala Val Ala Leu Cys Ser Leu Ser Thr Asp Glu Cys Glu Tyr
        50                  55                  60

Asp Thr Asn Leu Tyr Leu Asp Glu Lys Leu Val Asp Tyr Ser Thr Val
65                  70                  75                  80

Asp Val Asn Gly Val Thr Tyr Tyr Ile Asn Ile Val Glu Thr Asn Asp
                85                  90                  95

Ile Asp Asp Leu Glu Ile Ala Thr Asp Glu Asp Glu Met Lys Ser Asp
            100                 105                 110

Asn Gln Glu Ile Ile Leu Lys Ser Glu Leu Lys
        115                 120

<210> SEQ ID NO 75
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 75

Met Thr Ile Thr Arg Ala Gln Lys Lys Tyr Ala Glu Ala Met His Glu
1               5                   10                  15

Phe Ile Asn Met Val Asp Asp Phe Glu Glu Ser Thr Pro Asp Phe Ala

-continued

```
                    20                  25                  30

Lys Glu Val Leu His Asp Ser Asp Tyr Val Val Ile Thr Lys Asn Glu
                35                  40                  45

Lys Tyr Ala Val Ala Leu Cys Ser Leu Ser Thr Asp Gly Cys Glu Tyr
        50                  55                  60

Asp Thr Asn Leu Tyr Leu Asp Glu Lys Leu Val Asp Tyr Ser Thr Val
65                  70                  75                  80

Asp Val Asn Gly Val Thr Tyr Tyr Ile Asn Ile Val Glu Thr Asn Asp
                85                  90                  95

Ile Asp Asp Leu Glu Ile Ala Thr Asp Glu Asp Glu Met Lys Ser Gly
            100                 105                 110

Asn Gln Glu Ile Ile Leu Lys Ser Glu Leu Lys
        115                 120

<210> SEQ ID NO 76
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 76

Met Thr Leu Thr Arg Ala Gln Lys Lys Tyr Ala Glu Ala Met His Glu
1               5                   10                  15

Phe Ile Asn Met Val Asp Asp Phe Glu Glu Ser Thr Pro Asp Phe Ala
                20                  25                  30

Lys Glu Val Leu His Asp Ser Asp Tyr Val Val Ile Thr Lys Asn Glu
                35                  40                  45

Lys Tyr Ala Val Ala Leu Cys Ser Leu Ser Thr Asp Glu Cys Glu Tyr
        50                  55                  60

Asp Thr Asn Leu Tyr Leu Asp Glu Lys Leu Val Asp Tyr Ser Thr Val
65                  70                  75                  80

Asp Val Asn Gly Val Thr Tyr Tyr Ile Asn Ile Val Glu Thr Lys Asp
                85                  90                  95

Ile Asp Asp Leu Glu Ile Ala Thr Asp Glu Asp Glu Met Lys Ser Asp
            100                 105                 110

Asn Gln Glu Ile Ile Leu Lys Ser Glu Leu Lys
        115                 120

<210> SEQ ID NO 77
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 77

Met Thr Ile Thr Thr Ala Gln Lys Lys Tyr Ala Glu Ala Met His Glu
1               5                   10                  15

Phe Ile Asn Met Val Asp Asp Phe Glu Glu Ser Thr Pro Asp Phe Ala
                20                  25                  30

Lys Glu Val Leu His Asp Ser Asp Tyr Val Val Ile Thr Lys Asn Glu
                35                  40                  45

Lys Tyr Ala Val Ala Leu Cys Ser Leu Ser Thr Asp Glu Cys Glu Tyr
        50                  55                  60

Asp Thr Asn Leu Tyr Leu Asp Glu Lys Leu Val Asp Tyr Ser Thr Val
```

```
                      65                  70                  75                  80

Asp Val Asn Gly Val Thr Tyr Tyr Ile Asn Ile Val Glu Thr Asn Asp
                    85                  90                  95

Ile Asp Asp Leu Glu Ile Ala Thr Asp Glu Asp Glu Met Lys Ser Gly
                100                 105                 110

Asn Gln Glu Ile Ile Leu Lys Ser Glu Leu Lys
            115                 120

<210> SEQ ID NO 78
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 78

Met Thr Ile Thr Thr Ala Gln Arg Lys Tyr Asn Glu Ala Met His Glu
1               5                   10                  15

Phe Ile Asn Met Val Asp Asp Phe Glu Glu Ser Thr Pro Asp Phe Ala
                20                  25                  30

Lys Glu Val Leu His Asp Ser Asp Tyr Val Val Ile Thr Lys Asn Glu
            35                  40                  45

Lys Tyr Ala Val Ala Leu Cys Ser Leu Ser Thr Asp Glu Cys Glu Tyr
        50                  55                  60

Asp Thr Asn Leu Tyr Leu Asp Glu Lys Leu Val Asp Tyr Ser Thr Val
65                  70                  75                  80

Asp Val Asn Gly Val Thr Tyr Tyr Ile Asn Ile Val Glu Thr Asn Asp
                    85                  90                  95

Ile Asp Asp Leu Glu Ile Ala Thr Asp Glu Asp Glu Met Lys Ser Gly
                100                 105                 110

Asn Gln Glu Ile Ile Leu Lys Ser Glu Leu Lys
            115                 120

<210> SEQ ID NO 79
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 79

Met Thr Ile Thr Thr Ala Gln Arg Lys Tyr Asn Glu Ala Met His Glu
1               5                   10                  15

Phe Ile Asn Met Val Asp Asp Phe Glu Glu Ser Thr Pro Asp Phe Ala
                20                  25                  30

Lys Glu Val Leu His Asp Cys Asp Tyr Val Val Thr Lys Asn Glu
            35                  40                  45

Lys Tyr Ala Val Ala Leu Cys Thr Leu Ser Thr Asp Glu Cys Glu Tyr
        50                  55                  60

Asp Thr Asn Leu Tyr Leu Asp Glu Lys Leu Val Asp Tyr Ser Thr Val
65                  70                  75                  80

Asn Val Asn Gly Val Thr Tyr Tyr Ile Asn Ile Val Glu Thr Asn Asp
                    85                  90                  95

Ile Asp Asp Leu Glu Ile Ala Thr Asp Glu Asp Glu Met Lys Ser Asp
                100                 105                 110

Asn Gln Glu Ile Ile Leu Lys Ser Glu Leu Lys
```

<210> SEQ ID NO 80
<211> LENGTH: 123
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 80

Met Thr Ile Thr Thr Ala Gln Arg Lys Tyr Asn Glu Ala Met His Glu
1               5                   10                  15

Phe Ile Asn Met Val Asp Asp Phe Glu Glu Ser Thr Pro Asp Phe Ala
            20                  25                  30

Lys Glu Val Leu His Asp Cys Asp Tyr Val Val Thr Lys Asn Glu
        35                  40                  45

Lys Tyr Ala Val Ala Leu Cys Thr Leu Ser Thr Asp Glu Cys Glu Tyr
    50                  55                  60

Asp Thr Asn Leu Tyr Leu Asp Glu Lys Leu Val Asp Tyr Ser Thr Val
65                  70                  75                  80

Asn Val Asn Gly Val Thr Tyr Tyr Ile Asn Ile Val Glu Thr Asn Asp
                85                  90                  95

Ile Asp Asp Leu Glu Ile Ala Thr Asp Glu Asp Glu Met Lys Ser Asp
            100                 105                 110

Asn Gln Lys Ile Ile Leu Lys Ser Glu Leu Lys
        115                 120

<210> SEQ ID NO 81
<211> LENGTH: 123
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 81

Met Thr Leu Thr Arg Ala Gln Lys Lys Tyr Ala Glu Ala Met His Glu
1               5                   10                  15

Phe Ile Asn Met Val Asp Asp Phe Glu Glu Ser Thr Pro Asp Phe Ala
            20                  25                  30

Lys Glu Val Leu His Asp Ser Asp Tyr Val Val Ile Thr Lys Asn Glu
        35                  40                  45

Lys Tyr Ala Val Ala Leu Cys Ser Leu Ser Thr Asp Glu Cys Glu Tyr
    50                  55                  60

Asp Thr Asn Leu Tyr Leu Asp Glu Lys Leu Val Asp Tyr Ser Thr Val
65                  70                  75                  80

Asp Val Asn Gly Val Thr Tyr Tyr Ile Asn Ile Val Glu Thr Lys Asp
                85                  90                  95

Ile Asp Asp Leu Glu Ile Ala Thr Asp Glu Asp Lys Glu Lys His Asp
            100                 105                 110

Lys Gln Glu Val Ile Ile Lys Ser Glu Leu Asn
        115                 120

<210> SEQ ID NO 82
<211> LENGTH: 110
<212> TYPE: PRT
<213> ORGANISM: Unknown
<220> FEATURE:
<223> OTHER INFORMATION: Unknown bacterial, unknown viral (phage), or -continued synthetic Cas9-inhibiting polypeptide

<400> SEQUENCE: 82

Met His Glu Phe Ile Asn Met Val Asp Asp Phe Glu Glu Ser Thr Pro
1               5                   10                  15

Asp Phe Ala Lys Glu Val Leu His Asp Ser Asp Tyr Val Val Ile Thr
            20                  25                  30

Lys Asn Glu Lys Tyr Ala Val Ala Leu Cys Ser Leu Ser Thr Asp Glu
        35                  40                  45

Cys Glu Tyr Asp Thr Asn Leu Tyr Leu Asp Glu Lys Leu Val Asp Tyr
50                  55                  60

Ser Thr Val Asp Val Asn Gly Val Thr Tyr Tyr Ile Asn Ile Val Glu
65                  70                  75                  80

Thr Asn Asp Ile Asp Asp Leu Glu Ile Ala Thr Asp Glu Asp Glu Met
                85                  90                  95

Lys Ser Gly Asn Gln Glu Ile Ile Leu Lys Ser Glu Leu Lys
            100                 105                 110

<210> SEQ ID NO 83
<211> LENGTH: 122
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 83

Met Thr Leu Thr Arg Ala Gln Lys Lys Tyr Ala Glu Ala Met His Glu
1               5                   10                  15

Phe Ile Asn Met Val Asp Asp Phe Glu Glu Ser Lys Pro Asn Phe Ala
            20                  25                  30

Lys Glu Val Leu His Asp Ser Asp Tyr Val Val Ile Thr Lys Asn Glu
        35                  40                  45

Lys Tyr Ala Val Ala Leu Cys Ser Leu Ser Thr Asp Glu Cys Glu Tyr
50                  55                  60

Asp Thr Asn Leu Tyr Leu Asp Glu Lys Leu Val Asp Tyr Ser Thr Val
65                  70                  75                  80

Asp Val Asn Gly Val Thr Tyr Tyr Ile Asn Ile Val Val Thr Asn Glu
                85                  90                  95

Asp Asp Phe Lys Leu Ala Thr Asp Lys Asp Lys Glu Lys His Asp Lys
            100                 105                 110

Gln Glu Val Ile Val Lys Ser Glu Leu Asn
        115                 120

<210> SEQ ID NO 84
<211> LENGTH: 122
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 84

Met Thr Leu Thr Thr Ala Gln Arg Lys Tyr Asn Glu Ala Met His Glu
1               5                   10                  15

Phe Ile Asn Met Val Asp Asp Phe Glu Glu Ser Thr Pro Glu Phe Ser
            20                  25                  30

Lys Glu Val Leu Asn Asp Ser Asp Tyr Val Val Ile Thr Lys Asn Glu
        35                  40                  45

```
Lys Tyr Ala Gly Ala Leu Cys His Val Ser Thr Asp Glu Cys Glu Asp
        50                  55                  60

Gly Ser Asn Leu Tyr Ile Asp Glu Lys Leu Ile Asp Tyr Ser Thr Leu
65                  70                  75                  80

Asn Val Gly Gly Val Thr Tyr Tyr Ile Asn Ile Val Glu Arg Cys Glu
                85                  90                  95

Asp Asp Leu Glu Ile Ala Thr Asp Glu Asp Lys Met Lys Ser Asp Asn
            100                 105                 110

Gln Glu Ile Ile Leu Lys Asn Glu Leu Asn
        115                 120

<210> SEQ ID NO 85
<211> LENGTH: 103
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 85

Met Val Asp Asp Phe Glu Glu Ser Thr Pro Glu Phe Ser Lys Glu Val
1               5                   10                  15

Leu Asn Asp Ser Asp Tyr Val Val Ile Thr Lys Asn Glu Lys Tyr Ala
            20                  25                  30

Gly Ala Leu Cys His Val Ser Thr Asp Glu Cys Glu Asp Gly Ser Asn
        35                  40                  45

Leu Tyr Ile Asp Glu Lys Leu Ile Asp Tyr Ser Thr Leu Asn Val Gly
    50                  55                  60

Gly Val Thr Tyr Tyr Ile Asn Ile Val Glu Arg Cys Glu Asp Asp Leu
65                  70                  75                  80

Glu Ile Ala Thr Asp Glu Asp Lys Met Lys Ser Asp Asn Gln Glu Ile
                85                  90                  95

Ile Leu Lys Asn Glu Leu Asn
            100

<210> SEQ ID NO 86
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 86

Met Thr Leu Thr Thr Ala Gln Lys Arg Tyr Tyr Asp Ala Met Asn Glu
1               5                   10                  15

Phe Glu Ala Ile Thr Ser Lys Lys Leu Glu Gln Thr Pro Glu Phe Ser
            20                  25                  30

Gln Asp Leu Leu Asn Asp Ser Asp Tyr Leu Val Ile Thr Lys Asn Glu
        35                  40                  45

Ala Tyr Ala Val Ala Leu Cys Met Leu Asp Asp Lys Leu Tyr Leu
    50                  55                  60

Asp Glu Thr Leu Val Gln Ser Cys Leu Asp Val Glu Gly Glu Thr
65                  70                  75                  80

Tyr Tyr Ile Asn Phe Val Val Thr Asn Glu Asp Phe Lys Leu Ala
                85                  90                  95

Thr Asp Glu Asp Lys Glu Lys His Asp Lys Gln Glu Val Ile Val Lys
            100                 105                 110
```

Ser Glu Leu Asn
        115

<210> SEQ ID NO 87
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 87

Met Thr Leu Thr Thr Ala Gln Lys Arg Tyr Tyr Asp Ala Met Asn Glu
1               5                   10                  15

Phe Glu Ala Ile Thr Ser Lys Glu Leu Glu Gln Thr Pro Glu Phe Ser
            20                  25                  30

Gln Asp Leu Leu Asn Asp Ser Asp Tyr Leu Val Ile Thr Lys Asn Glu
        35                  40                  45

Ala Tyr Ala Val Ala Leu Cys Met Leu Asp Asp Lys Leu Tyr Leu
    50                  55                  60

Asp Glu Thr Leu Val Gln Ser Thr Cys Leu Asp Val Glu Gly Glu Thr
65                  70                  75                  80

Tyr Tyr Ile Asn Phe Val Val Thr Asn Glu Asp Asp Phe Lys Leu Ala
                85                  90                  95

Thr Asp Glu Asp Lys Glu Lys His Asp Lys Gln Glu Val Ile Val Lys
            100                 105                 110

Ser Glu Leu Asn
        115

<210> SEQ ID NO 88
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 88

Met Thr Leu Thr Thr Ala Gln Lys Arg Tyr Tyr Asp Ala Met Asn Glu
1               5                   10                  15

Phe Glu Ala Ile Thr Ser Lys Glu Leu Glu Gln Thr Pro Glu Phe Ser
            20                  25                  30

Gln Asp Leu Leu Asn Asp Ser Asp Tyr Leu Val Ile Thr Lys Asn Glu
        35                  40                  45

Ala Tyr Ala Val Ala Leu Cys Met Leu Asp Asp Lys Leu Tyr Leu
    50                  55                  60

Asp Glu Thr Leu Val Gln Ser Thr Cys Leu Asp Val Glu Gly Glu Thr
65                  70                  75                  80

Tyr Tyr Ile Asn Phe Val Val Thr Asn Glu Asp Asp Phe Lys Leu Ala
                85                  90                  95

Thr Asp Lys Asp Lys Glu Lys His Asp Lys Gln Glu Val Ile Val Lys
            100                 105                 110

Ser Glu Leu Asn
        115

<210> SEQ ID NO 89
<211> LENGTH: 116
<212> TYPE: PRT
<213> ORGANISM: Unknown

```
<220> FEATURE:
<223> OTHER INFORMATION: Unknown bacterial, unknown viral (phage), or
      synthetic Cas9-inhibiting polypeptide

<400> SEQUENCE: 89

Met Thr Ile Thr Thr Ala Gln Lys Arg Tyr Tyr Asp Ala Met Asn Glu
1               5                   10                  15

Phe Glu Ala Ile Ile Ser Lys Glu Leu Glu Gln Thr Pro Ala Phe Ser
                20                  25                  30

Gln Asp Leu Leu Asn Asp Ser Asp Tyr Leu Val Ile Thr Lys Asn Glu
            35                  40                  45

Ala Tyr Ala Val Ala Leu Cys Met Leu Asp Asp Lys Leu Tyr Leu
50                  55                  60

Asp Glu Thr Leu Val Gln Ser Thr Arg Leu Asp Ile Glu Asp Glu Thr
65                  70                  75                  80

Tyr Tyr Ile Asn Phe Val Val Thr Asn Glu Asp Asp Phe Lys Leu Ala
                85                  90                  95

Thr Asp Glu Asp Lys Glu Lys His Asp Lys Gln Glu Val Ile Ile Lys
            100                 105                 110

Ser Glu Leu Asn
        115

<210> SEQ ID NO 90
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 90

Met Thr Ile Thr Thr Ala Gln Lys Arg Tyr Tyr Asp Ala Met Asn Glu
1               5                   10                  15

Phe Glu Ala Ile Thr Ser Lys Glu Leu Glu Gln Thr Pro Glu Phe Ser
                20                  25                  30

Gln Asp Leu Leu Asn Asp Ser Asp Tyr Leu Val Ile Thr Lys Asn Glu
            35                  40                  45

Ala Tyr Ala Val Ala Leu Cys Met Leu Asp Asp Lys Leu Tyr Ile
50                  55                  60

Asp Glu Thr Leu Val Gln Ser Thr Cys Leu Asp Val Glu Gly Glu Thr
65                  70                  75                  80

Tyr Tyr Ile Asn Phe Val Val Thr Asn Glu Asp Asp Phe Lys Leu Ala
                85                  90                  95

Thr Asp Lys Asp Lys Glu Lys His Asp Lys Gln Glu Val Ile Ile Lys
            100                 105                 110

Ser Glu Leu Asn
        115

<210> SEQ ID NO 91
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 91

Met Thr Leu Thr Thr Ala Gln Lys Arg Tyr Tyr Asp Ala Met Asn Glu
1               5                   10                  15
```

```
Phe Glu Ala Ile Ile Ser Lys Glu Leu Glu Gln Thr Arg Ala Phe Ser
                20                  25                  30

Gln Asp Leu Leu Asn Asp Ser Asp Tyr Leu Val Ile Thr Lys Asn Glu
            35                  40                  45

Ala Tyr Ala Val Asp Leu Cys Met Leu Asp Asp Asp Lys Leu Tyr Leu
 50                  55                  60

Asp Glu Thr Leu Val Gln Ser Thr Arg Leu Asp Ile Glu Asp Glu Thr
 65                  70                  75                  80

Tyr Tyr Ile Asn Phe Val Val Thr Asn Glu Asp Phe Lys Leu Ala
                85                  90                  95

Thr Asp Glu Asp Lys Glu Lys His Asp Arg Gln Glu Val Ile Ile Lys
            100                 105                 110

Ser Glu Leu Asn
        115

<210> SEQ ID NO 92
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 92

Met Thr Ile Thr Thr Ala Gln Lys Arg Tyr Tyr Asp Ala Met Asn Glu
 1               5                  10                  15

Phe Glu Ala Ile Thr Ser Lys Glu Leu Glu Gln Thr Pro Glu Phe Ser
                20                  25                  30

Gln Asp Leu Leu Asn Asp Ser Asp Tyr Leu Val Val Thr Lys Asn Glu
            35                  40                  45

Ala Tyr Ala Ala Ala Leu Cys Met Leu Asp Asp Asp Lys Leu Tyr Leu
 50                  55                  60

Asp Glu Thr Leu Val Gln Ser Thr Cys Leu Asp Val Glu Gly Glu Ile
 65                  70                  75                  80

Tyr Tyr Ile Asn Phe Val Val Thr Asn Glu Asp Phe Lys Leu Ala
                85                  90                  95

Thr Asp Lys Asp Lys Glu Lys His Asp Lys Gln Glu Val Ile Val Lys
            100                 105                 110

Ser Glu Leu Asn
        115

<210> SEQ ID NO 93
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 93

Met Thr Ile Thr Thr Ala Gln Lys Arg Tyr Tyr Asp Ala Met Asn Glu
 1               5                  10                  15

Phe Glu Ala Ile Thr Ser Lys Gly Leu Glu Gln Thr Pro Glu Phe Ser
                20                  25                  30

Gln Asp Leu Leu Asn Asp Phe Asp Tyr Leu Val Ile Thr Lys Asn Glu
            35                  40                  45

Ala Tyr Ala Ala Ala Leu Cys Met Leu Asp Asp Glu Lys Leu Tyr Leu
 50                  55                  60
```

```
Asp Glu Thr Leu Val His Ser Thr Arg Leu Asp Ile Glu Asp Asp Thr
 65                  70                  75                  80

Tyr Tyr Ile Asn Phe Val Val Thr Asn Glu Asp Asp Phe Lys Leu Ala
                 85                  90                  95

Thr Asp Glu Asp Lys Glu Lys His Asp Lys Gln Glu Val Ile Ile Lys
            100                 105                 110

Arg Glu Leu Asn
        115

<210> SEQ ID NO 94
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 94

Met Thr Ile Thr Thr Ala Gln Lys Arg Tyr Tyr Asp Ala Met Asn Glu
  1               5                  10                  15

Phe Glu Ala Ile Ile Ser Lys Glu Leu Glu Gln Thr Pro Ala Phe Ser
                 20                  25                  30

Gln Asp Leu Leu Asn Asp Ser Asp Tyr Leu Val Ile Thr Lys Asn Glu
             35                  40                  45

Ala Tyr Ala Val Ala Leu Cys Leu Leu Asp Asp Lys Leu Tyr Leu
     50                  55                  60

Asp Glu Thr Leu Val His Ser Thr Arg Leu Asp Ile Glu Asp Glu Thr
 65                  70                  75                  80

Tyr Tyr Ile Asn Phe Val Val Thr Asn Glu Asp Asp Phe Lys Leu Ala
                 85                  90                  95

Thr Asp Glu Asp Lys Glu Lys His Asp Lys Gln Glu Val Ile Ile Lys
            100                 105                 110

Ser Glu Leu Asn
        115

<210> SEQ ID NO 95
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 95

Met Thr Ile Thr Thr Ala Gln Lys Arg Tyr Tyr Asp Ala Met Asn Glu
  1               5                  10                  15

Phe Glu Ala Ile Ile Ser Lys Glu Leu Glu Gln Thr Pro Ala Phe Ser
                 20                  25                  30

Gln Asn Leu Leu Asn Asp Ser Asp Tyr Leu Val Ile Thr Lys Asn Glu
             35                  40                  45

Ala Tyr Ala Val Ala Leu Cys Leu Leu Asp Asp Lys Leu Tyr Leu
     50                  55                  60

Asp Glu Thr Leu Val His Ser Thr Arg Leu Asp Ile Glu Asp Glu Thr
 65                  70                  75                  80

Tyr Tyr Ile Asn Phe Val Val Thr Asn Glu Asp Asp Phe Lys Leu Ala
                 85                  90                  95

Thr Asp Glu Asp Lys Glu Lys His Asp Lys Gln Glu Val Ile Ile Lys
            100                 105                 110
```

Ser Glu Leu Asn
        115

<210> SEQ ID NO 96
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 96

Met Thr Ile Thr Thr Ala Gln Lys Arg Tyr Tyr Asp Ala Met Asn Glu
1               5                   10                  15

Phe Glu Ala Ile Thr Ser Lys Glu Leu Glu Gln Thr Pro Ala Phe Ser
            20                  25                  30

Gln Asp Leu Leu Asn Asp Ser Asp Tyr Leu Val Ile Thr Lys Asn Glu
        35                  40                  45

Ala Tyr Ala Val Ala Leu Cys Leu Leu Asp Asp Lys Leu Tyr Leu
    50                  55                  60

Asp Glu Thr Leu Val His Ser Thr Arg Leu Asp Ile Glu Asp Glu Thr
65                  70                  75                  80

Tyr Tyr Ile Asn Phe Val Val Thr Asn Glu Asp Asp Phe Lys Leu Ala
                85                  90                  95

Thr Asp Glu Asp Lys Glu Lys His Asp Lys Gln Glu Val Ile Val Lys
            100                 105                 110

Ser Glu Leu Asn
        115

<210> SEQ ID NO 97
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 97

Met Thr Ile Thr Thr Ala Gln Lys Arg Tyr Tyr Asp Ala Met Asn Glu
1               5                   10                  15

Phe Glu Ala Ile Ile Ser Lys Glu Leu Glu Gln Thr Pro Ala Phe Ser
            20                  25                  30

Gln Asp Leu Leu Asn Asp Ser Asp Tyr Leu Val Ile Thr Lys Asn Glu
        35                  40                  45

Ala Tyr Ala Val Ala Leu Cys Leu Leu Asp Asp Lys Leu Tyr Leu
    50                  55                  60

Asp Glu Thr Leu Val His Ser Thr Arg Leu Asn Ile Glu Asp Glu Thr
65                  70                  75                  80

Tyr Tyr Ile Asn Phe Val Val Thr Asn Glu Asp Asp Phe Lys Leu Ala
                85                  90                  95

Thr Asp Glu Asp Lys Glu Lys His Asp Lys Gln Glu Val Ile Ile Lys
            100                 105                 110

Ser Glu Phe Asn
        115

<210> SEQ ID NO 98
<211> LENGTH: 116
<212> TYPE: PRT
<213> ORGANISM: Unknown
<220> FEATURE:

<223> OTHER INFORMATION: Unknown bacterial, unknown viral (phage), or
synthetic Cas9-inhibiting polypeptide

<400> SEQUENCE: 98

Met Thr Leu Thr Thr Ala Gln Lys Arg Tyr Tyr Asp Ala Met Asn Glu
1               5                   10                  15

Phe Glu Ala Ile Thr Ser Lys Glu Leu Glu Gln Thr Pro Glu Phe Ser
            20                  25                  30

Gln Asp Leu Leu Asn Asp Ser Asp Tyr Leu Ala Val Thr Lys Asn Glu
        35                  40                  45

Ala Tyr Ala Val Ala Leu Cys Leu Leu Asp Asp Lys Leu Tyr Leu
    50                  55                  60

Asp Glu Thr Leu Val His Ser Thr Arg Leu Asp Ile Glu Asp Glu Thr
65                  70                  75                  80

Tyr Tyr Ile Asn Phe Val Val Thr Asn Glu Asp Phe Lys Leu Ala
                85                  90                  95

Thr Asp Glu Asp Lys Glu Lys His Asp Lys Gln Glu Val Ile Ile Lys
            100                 105                 110

Ser Gly Leu Asn
        115

<210> SEQ ID NO 99
<211> LENGTH: 116
<212> TYPE: PRT
<213> ORGANISM: Unknown
<220> FEATURE:
<223> OTHER INFORMATION: Unknown bacterial, unknown viral (phage), or
synthetic Cas9-inhibiting polypeptide

<400> SEQUENCE: 99

Met Thr Val Thr Thr Ala Gln Lys Arg Tyr Tyr Asp Ala Met Asn Glu
1               5                   10                  15

Phe Glu Ala Ile Thr Ser Lys Glu Leu Glu Gln Thr Pro Glu Phe Ser
            20                  25                  30

Gln Asp Leu Leu Asn Asp Ser Asp Tyr Leu Ala Val Thr Lys Asn Glu
        35                  40                  45

Ala Tyr Ala Val Ala Leu Cys Leu Leu Asp Asp Lys Leu Tyr Leu
    50                  55                  60

Asp Glu Thr Leu Val His Ser Thr Arg Leu Asp Ile Glu Asp Glu Thr
65                  70                  75                  80

Tyr Tyr Ile Asn Phe Val Val Thr Asn Glu Asp Phe Lys Leu Ala
                85                  90                  95

Thr Asp Glu Asp Lys Glu Lys His Asp Lys Gln Glu Val Ile Ile Lys
            100                 105                 110

Ser Glu Leu Asn
        115

<210> SEQ ID NO 100
<211> LENGTH: 116
<212> TYPE: PRT
<213> ORGANISM: Unknown
<220> FEATURE:
<223> OTHER INFORMATION: Unknown bacterial, unknown viral (phage), or
synthetic Cas9-inhibiting polypeptide

<400> SEQUENCE: 100

Met Thr Leu Thr Thr Val Gln Lys Arg Tyr Tyr Asp Ala Met Asn Glu
1               5                   10                  15

Phe Glu Ala Ile Thr Ser Lys Glu Leu Glu Gln Thr Pro Glu Phe Ser

```
                    20                  25                  30

Gln Asp Leu Leu Asn Asp Ser Asp Tyr Leu Ala Val Thr Lys Asn Glu
            35                  40                  45

Ala Tyr Ala Val Ala Leu Cys Leu Leu Asp Asp Asp Lys Leu Tyr Leu
        50                  55                  60

Asp Glu Thr Leu Val His Ser Thr Arg Phe Asp Ile Glu Asp Glu Thr
65                  70                  75                  80

Tyr Tyr Ile Asn Phe Val Val Thr Asn Glu Asp Asp Phe Lys Leu Ala
                85                  90                  95

Thr Asp Glu Asp Lys Glu Lys His Asp Lys Gln Glu Val Ile Ile Lys
            100                 105                 110

Ser Glu Leu Asn
        115

<210> SEQ ID NO 101
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 101

Met Thr Leu Thr Thr Val Gln Lys Arg Tyr Tyr Asp Ala Met Asn Glu
1               5                   10                  15

Phe Glu Ala Ile Thr Ser Lys Glu Leu Glu Gln Thr Pro Glu Phe Ser
                20                  25                  30

Gln Asp Ser Leu Asn Asp Ser Asp Tyr Leu Ala Val Thr Lys Asn Glu
            35                  40                  45

Ala Tyr Ala Val Ala Leu Cys Leu Leu Asp Asp Asp Lys Leu Tyr Leu
        50                  55                  60

Asp Glu Thr Leu Val His Ser Thr Arg Phe Asp Ile Glu Asp Glu Thr
65                  70                  75                  80

Tyr Tyr Ile Asn Phe Val Val Thr Asn Glu Asp Asp Phe Lys Leu Ala
                85                  90                  95

Thr Asp Glu Asp Lys Glu Lys His Asp Lys Gln Glu Val Ile Ile Lys
            100                 105                 110

Ser Glu Leu Asn
        115

<210> SEQ ID NO 102
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 102

Met Thr Ile Thr Thr Ala Gln Lys Arg Tyr Tyr Asp Ala Met Asn Glu
1               5                   10                  15

Phe Glu Ala Ile Ile Ser Lys Glu Leu Glu Gln Thr Pro Ala Phe Ser
                20                  25                  30

Gln Asp Leu Leu Asn Asp Ser Asp Tyr Leu Ala Val Thr Lys Asn Glu
            35                  40                  45

Ala Tyr Ala Val Ala Leu Cys Leu Leu Asp Asp Asp Lys Leu Tyr Leu
        50                  55                  60

Asp Glu Thr Leu Val His Ser Thr Arg Leu Asp Ile Glu Asp Glu Thr
```

```
                    65                  70                  75                  80
Tyr Tyr Ile Asn Phe Val Val Thr Asn Glu Asp Asp Phe Lys Leu Ala
                    85                  90                  95
Thr Asp Glu Asp Lys Glu Lys His Asp Lys Gln Glu Val Ile Ile Lys
                    100                 105                 110
Ser Gly Leu Asn
        115

<210> SEQ ID NO 103
<211> LENGTH: 116
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 103

Met Thr Ile Thr Thr Ala Gln Lys Arg Tyr Tyr Asp Ala Met Asn Glu
1               5                   10                  15
Phe Glu Ala Ile Thr Ser Lys Glu Leu Glu Gln Thr Pro Ala Phe Ser
                20                  25                  30
Gln Asp Leu Leu Asn Asp Ser Asp Tyr Leu Ala Val Thr Lys Asn Glu
                35                  40                  45
Ala Tyr Ala Val Ala Leu Cys Leu Leu Asp Asp Lys Leu Tyr Leu
        50                  55                  60
Asp Glu Thr Leu Val His Ser Thr Arg Leu Asp Ile Glu Asp Glu Thr
65                  70                  75                  80
Tyr Tyr Ile Asn Phe Val Val Thr Asn Glu Asp Asp Phe Lys Leu Ala
                    85                  90                  95
Thr Asp Glu Asp Lys Glu Lys His Asp Lys Gln Glu Val Ile Ile Lys
                    100                 105                 110
Ser Gly Leu Asn
        115

<210> SEQ ID NO 104
<211> LENGTH: 130
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 104

Met Ala Ile Thr Leu Ser Gln Arg Lys Phe Tyr Glu Ala Ile Asn Glu
1               5                   10                  15
Phe Glu Glu Met Thr Glu Asn Glu Val Val Thr Ser Pro Arg Ile Pro
                20                  25                  30
Gln Asp Tyr Leu Asn Asp Gly Asp Tyr Val Val Ile Thr Lys Ser Glu
                35                  40                  45
Asn Tyr Ala Leu Asn Leu Cys Thr Thr Asn Leu Glu Gly Phe Glu Asp
        50                  55                  60
Arg His Phe Leu Asp Glu Lys Leu Ile Tyr Ser Thr Phe Val Glu Thr
65                  70                  75                  80
Tyr Ser Gly Glu Thr Tyr Tyr Ile Tyr Ile Thr Gln Thr Ala Glu Phe
                    85                  90                  95
Asp Glu Asp Asp Ala Val Glu Phe Leu Ala Thr Gln Glu Gln Ile Tyr
                    100                 105                 110
Glu Tyr His Lys Gln Glu Glu Gln Lys Thr Val Ile Leu Lys Met Glu
```

```
                115                 120                 125

Leu Ser
    130

<210> SEQ ID NO 105
<211> LENGTH: 130
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 105

Met Ala Gln Thr Glu Ala Gln Lys Ile Phe Tyr Glu Ala Ile Asn Glu
1               5                   10                  15

Phe Glu Glu Met Thr Asn Glu Glu Val Val Thr Ser Pro Arg Ile Pro
                20                  25                  30

Gln Asp Tyr Leu Asn Asp Gly Asp Tyr Val Val Ile Thr Lys Ser Glu
            35                  40                  45

Asn Tyr Ala Leu Asn Leu Cys Thr Thr Asp Leu Glu Gly Phe Glu Asp
        50                  55                  60

Arg Tyr Phe Leu Asp Glu Lys Leu Ile Tyr Ser Thr Ser Val Glu Thr
65                  70                  75                  80

Tyr Thr Asp Glu Thr Tyr Tyr Ile Tyr Ile Thr Gln Thr Thr Glu Phe
                85                  90                  95

Glu Glu Asp Asn Ala Val Glu Phe Leu Ala Thr Gln Glu Gln Ile Tyr
            100                 105                 110

Glu Tyr His Lys Gln Glu Gln Lys Thr Val Ile Leu Lys Met Glu
        115                 120                 125

Leu Ser
    130

<210> SEQ ID NO 106
<211> LENGTH: 130
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 106

Met Thr Thr Ala Arg Lys Lys Phe Tyr Gln Ala Ile Ser Glu Phe Glu
1               5                   10                  15

Ala Met Thr Gly Lys Asp Val Glu Arg Thr Pro Gln Ile Ala Asp Glu
                20                  25                  30

Val Leu Asn Asp Ala Glu Tyr Ile Ala Phe Thr Lys Thr Glu Lys Tyr
            35                  40                  45

Ala Leu Tyr Leu Cys Thr Ser Asn Val Glu Gly Leu Glu Asp Arg Tyr
        50                  55                  60

Phe Leu Asp Glu Glu Cys Leu Asp Ser Thr Phe Leu Glu Thr Glu Asp
65                  70                  75                  80

Asn Glu Thr Tyr Tyr Ile His Phe Leu Gln Glu Thr Glu Phe Ser Glu
                85                  90                  95

Asp Asp Asn Glu Asp Glu Leu Pro Leu Ala Thr Glu Gln Ile Glu
            100                 105                 110

Ala Tyr Asp Lys Gln Glu Glu Leu Lys Ala Val Ile Leu Lys Lys Glu
        115                 120                 125

Leu Asn
```

<210> SEQ ID NO 107
<211> LENGTH: 129
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 107

Met Arg Thr Thr Ala Gln Glu Arg Leu Asp Asn Ala Ile Asn Glu Phe
1               5                   10                  15

Glu Glu Ile Thr Asn Glu Val Val Thr Ser Pro Arg Ile Pro Gln
            20                  25                  30

Asp Tyr Leu Asn Asp Gly Asp Tyr Val Val Ile Thr Lys Ser Glu Asn
        35                  40                  45

Tyr Ala Leu Asn Leu Cys Thr Thr Asn Leu Glu Gly Phe Glu Asp Arg
    50                  55                  60

His Phe Leu Asp Glu Lys Leu Ile Tyr Ser Thr Phe Val Glu Thr Tyr
65                  70                  75                  80

Ser Gly Glu Thr Tyr Tyr Ile Tyr Ile Thr Gln Thr Ala Glu Phe Asp
                85                  90                  95

Glu Asp Asp Ala Val Glu Phe Leu Ala Thr Gln Glu Gln Ile Tyr Glu
            100                 105                 110

Tyr His Lys Gln Glu Glu Gln Lys Thr Val Ile Leu Lys Met Glu Leu
        115                 120                 125

Ser

<210> SEQ ID NO 108
<211> LENGTH: 129
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 108

Met Arg Thr Thr Ala Gln Glu Arg Leu Asp Asn Ala Ile Asn Glu Phe
1               5                   10                  15

Glu Glu Ile Thr Asn Glu Val Val Thr Ser Pro Arg Ile Pro Gln
            20                  25                  30

Asp Tyr Leu Asn Asp Gly Asp Tyr Val Val Ile Thr Lys Ser Glu Asn
        35                  40                  45

Tyr Ala Leu Asn Leu Cys Thr Thr Asn Leu Glu Gly Phe Glu Asp Arg
    50                  55                  60

His Phe Leu Asp Glu Lys Leu Ile Tyr Ser Thr Phe Val Glu Thr Tyr
65                  70                  75                  80

Ala Gly Glu Thr Tyr Tyr Ile Tyr Ile Thr Gln Thr Ala Glu Phe Asp
                85                  90                  95

Glu Asp Asp Ala Val Glu Phe Leu Ala Thr Gln Glu Gln Ile Tyr Glu
            100                 105                 110

Tyr His Lys Gln Glu Glu Gln Lys Thr Val Ile Leu Lys Met Glu Leu
        115                 120                 125

Ser

<210> SEQ ID NO 109
<211> LENGTH: 129

<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 109

Met Arg Thr Thr Ala Gln Glu Arg Leu Asp Asn Ala Ile Asn Glu Phe
1               5                   10                  15

Glu Glu Ile Thr Asn Glu Val Val Thr Ser Pro Leu Ile Pro Gln
            20                  25                  30

Asp Tyr Leu Asn Asp Gly Asp Tyr Val Val Ile Thr Lys Ser Glu Asn
            35                  40                  45

Tyr Ala Leu Asn Leu Cys Thr Thr Asn Leu Glu Gly Phe Glu Asp Arg
50                  55                  60

His Phe Leu Asp Glu Lys Leu Ile Tyr Ser Thr Phe Val Glu Thr Tyr
65                  70                  75                  80

Ser Gly Glu Thr Tyr Tyr Ile Tyr Ile Thr Gln Thr Ala Glu Phe Asp
                85                  90                  95

Glu Asp Asp Ala Val Glu Phe Leu Ala Thr Gln Glu Gln Ile Tyr Glu
            100                 105                 110

Tyr His Lys Gln Glu Glu Gln Lys Thr Val Ile Leu Lys Met Glu Leu
            115                 120                 125

Ser

<210> SEQ ID NO 110
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 110

Met Phe Asn Lys Ala Glu Ile Met Lys Gln Ala Trp Asn Trp Phe Asn
1               5                   10                  15

Asp Ser Asn Ile Trp Leu Ser Asp Ile Glu Trp Val Ser Tyr Thr Asp
            20                  25                  30

Lys Glu Lys Ser Phe Ser Val Cys Leu Lys Ala Ala Trp Ser Lys Ala
            35                  40                  45

Lys Glu Glu Val Glu Glu Ser Lys Leu Glu Ser Lys His Ile Ala Lys
50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Ala Ala
            115                 120                 125

<210> SEQ ID NO 111
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 111

Met Tyr Asn Lys Ala Glu Ile Met Lys Gln Ala Trp Asn Trp Phe Asn
1               5                   10                  15

Asp Ser Asn Ile Trp Leu Ser Asp Ile Glu Trp Val Ser Tyr Thr Asp
                20                  25                  30

Lys Glu Lys Ser Phe Ser Val Cys Leu Lys Ala Ala Trp Ser Lys Ala
            35                  40                  45

Lys Glu Glu Val Glu Glu Ser Lys Lys Glu Ser Lys His Ile Ala Lys
        50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Ala Ala
        115                 120                 125

<210> SEQ ID NO 112
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 112

Met Tyr Asn Lys Ala Glu Ile Met Lys Gln Ala Trp Asn Trp Phe Asn
1               5                   10                  15

Asp Ser Asn Ile Trp Leu Ser Asp Ile Glu Trp Val Ser Tyr Thr Asp
                20                  25                  30

Lys Glu Lys Ser Phe Ser Val Cys Leu Lys Gly Ala Trp Ser Lys Ala
            35                  40                  45

Lys Glu Glu Val Glu Glu Ser Lys Lys Glu Ser Lys His Ile Ala Lys
        50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Ala Ala
        115                 120                 125

<210> SEQ ID NO 113
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 113

Met Tyr Asn Lys Ala Glu Ile Met Lys Gln Ala Trp Asn Trp Phe Asn
1               5                   10                  15

Asp Ser Asn Ile Trp Leu Ser Asp Ile Glu Trp Val Ser Tyr Thr Asp
                20                  25                  30

Lys Glu Lys Ser Phe Ser Val Cys Leu Lys Ala Ala Trp Ser Lys Ala
            35                  40                  45

```
Lys Glu Glu Val Glu Glu Ser Lys Lys Glu Ser Lys His Ile Ala Lys
        50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Leu Trp Ala Cys Ala Met Lys Ala
            100                 105                 110

Val Lys Leu His Asn Asp Leu Phe Pro Gln Thr Ala Ala
        115                 120                 125

<210> SEQ ID NO 114
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 114

Met Tyr Asn Lys Ala Glu Ile Met Lys Gln Ala Trp Asn Trp Phe Asn
1               5                   10                  15

Asp Ser Asn Val Trp Leu Ser Asp Ile Glu Trp Ile Ser Tyr Thr Asp
                20                  25                  30

Lys Glu Lys Thr Phe Ser Val Cys Leu Lys Ala Ala Trp Ser Lys Ala
            35                  40                  45

Lys Glu Glu Val Glu Glu Ser Lys Lys Glu Ser Lys His Ile Ala Lys
        50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Ala Ala
        115                 120                 125

<210> SEQ ID NO 115
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 115

Met Tyr Asn Lys Ala Glu Ile Met Lys Gln Ala Trp Asn Trp Phe Asn
1               5                   10                  15

Asp Ser Asn Ile Trp Leu Ser Asp Ile Glu Trp Val Ser Tyr Thr Asp
                20                  25                  30

Lys Glu Lys Ser Phe Ser Val Cys Leu Lys Ala Ala Trp Ser Lys Ala
            35                  40                  45

Lys Glu Glu Val Glu Glu Ser Lys Lys Glu Ser Lys Tyr Ile Ala Lys
        50                  55                  60

Ser Glu Glu Leu Lys Ala Trp Asn Trp Ala Glu Arg Lys Leu Gly Leu
65                  70                  75                  80

Arg Phe Asn Ile Ser Asp Asp Glu Lys Phe Thr Ser Val Lys Asp Glu
                85                  90                  95
```

Thr Lys Ile Asn Phe Gly Leu Ser Val Trp Ala Cys Ala Met Lys Ala
        100                 105                 110

Val Lys Leu His Asn Asp Leu Phe Pro Gln Thr Ala Ala
        115                 120                 125

<210> SEQ ID NO 116
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 116

Met Phe Asn Lys Ala Glu Ile Met Lys Gln Ala Trp Asn Trp Phe Thr
1               5                   10                  15

Asp Ser Asn Val Trp Leu Ser Asp Ile Glu Trp Ala Ser Tyr Thr Asp
            20                  25                  30

Lys Glu Lys Ser Phe Ser Val Cys Leu Lys Ala Ala Trp Ser Lys Ala
        35                  40                  45

Lys Glu Glu Val Glu Glu Ser Lys Lys Glu Ser Lys His Ile Ala Lys
    50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
        100                 105                 110

Val Lys Leu His Asn Asp Leu Phe Pro Gln Thr Ala Ala
        115                 120                 125

<210> SEQ ID NO 117
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 117

Met Tyr Asn Lys Ala Glu Ile Met Lys Gln Ala Trp Asn Trp Phe Asn
1               5                   10                  15

Asp Ser Asn Ile Trp Leu Ser Asp Ile Glu Trp Val Ser Tyr Thr Asp
            20                  25                  30

Lys Glu Lys Ser Phe Ser Val Cys Leu Lys Ala Ala Trp Ser Lys Ala
        35                  40                  45

Lys Glu Glu Val Glu Glu Phe Lys Lys Glu Ser Lys Tyr Ile Ala Lys
    50                  55                  60

Ser Glu Glu Leu Lys Ala Trp Asn Trp Ala Glu Arg Lys Leu Gly Leu
65                  70                  75                  80

Arg Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
        100                 105                 110

Val Lys Leu His Asn Asp Leu Phe Pro Gln Thr Ala Ala
        115                 120                 125

<210> SEQ ID NO 118

<211> LENGTH: 118
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 118

Met Lys Gln Ala Trp Asn Trp Phe Asn Asp Ser Asn Ile Trp Leu Ser
1               5                   10                  15
Asp Ile Glu Trp Val Ser Tyr Thr Asp Lys Glu Lys Ser Phe Ser Val
            20                  25                  30
Cys Leu Lys Ala Ala Trp Ser Lys Ala Lys Glu Glu Val Glu Glu Ser
        35                  40                  45
Lys Lys Glu Ser Lys Tyr Ile Ala Lys Ser Glu Glu Leu Lys Ala Trp
    50                  55                  60
Asn Trp Ala Glu Arg Lys Leu Gly Leu Arg Phe Asn Ile Ser Asp Asp
65                  70                  75                  80
Glu Lys Phe Thr Ser Val Lys Asp Glu Thr Lys Ile Asn Phe Gly Leu
                85                  90                  95
Ser Val Trp Ala Cys Ala Met Lys Ala Val Lys Leu His Asn Asp Leu
            100                 105                 110
Phe Pro Gln Thr Ala Ala
        115

<210> SEQ ID NO 119
<211> LENGTH: 125
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 119

Met Tyr Asn Lys Ala Glu Ile Met Lys Gln Ala Trp Asn Trp Phe Asn
1               5                   10                  15
Asn Ser Asn Val Trp Leu Ser Asp Ile Glu Trp Val Ser Tyr Thr Asp
            20                  25                  30
Lys Glu Lys Thr Phe Ser Val Cys Leu Lys Ala Ala Trp Ser Lys Ala
        35                  40                  45
Lys Glu Glu Val Glu Glu Ser Lys Glu Glu Ser Lys His Ile Ala Lys
    50                  55                  60
Ser Glu Glu Leu Lys Ala Trp Asn Trp Ala Glu Arg Lys Leu Gly Leu
65                  70                  75                  80
His Phe Asn Ile Ser Asp Asp Glu Lys Phe Thr Ser Val Lys Asp Glu
                85                  90                  95
Thr Lys Ile Asn Phe Gly Leu Ser Val Trp Ala Cys Ala Met Lys Ala
            100                 105                 110
Val Lys Leu His Asn Asp Leu Phe Pro Gln Thr Ala Ala
        115                 120                 125

<210> SEQ ID NO 120
<211> LENGTH: 125
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 120

Met Tyr Asn Lys Ala Glu Ile Met Lys Gln Ala Trp Asn Trp Phe Asn
1               5                   10                  15

Asn Ser Asn Val Trp Leu Ser Asp Ile Glu Trp Val Ser Tyr Thr Asp
            20                  25                  30

Lys Glu Lys Thr Phe Ser Val Cys Leu Arg Ala Ala Trp Ser Lys Ala
            35                  40                  45

Lys Glu Glu Val Glu Glu Ser Lys Glu Ser Lys His Ile Ala Lys
50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Ala Ala
            115                 120                 125

<210> SEQ ID NO 121
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 121

Met Phe Asn Lys Ala Glu Ile Met Lys Gln Ala Trp Asn Trp Phe Thr
1               5                   10                  15

Asp Ser Asn Val Trp Leu Ser Asp Ile Glu Trp Val Ser Tyr Thr Asp
            20                  25                  30

Lys Glu Lys Thr Phe Ser Val Cys Leu Lys Ala Ala Trp Ser Lys Ala
            35                  40                  45

Lys Glu Glu Val Lys Val Glu Lys Glu Ile Lys His Ile Ser Lys
50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Ala Ala
            115                 120                 125

<210> SEQ ID NO 122
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 122

Met Tyr Asn Lys Ala Glu Ile Met Lys Gln Ala Trp Asn Trp Phe Asn
1               5                   10                  15

Asp Ser Asn Val Trp Leu Ser Asp Ile Glu Trp Ala Ser Tyr Thr Asp
            20                  25                  30

Lys Glu Lys Thr Phe Ser Val Cys Leu Lys Ala Ala Trp Ser Lys Ala
            35                  40                  45

```
Lys Glu Glu Val Lys Glu Val Glu Lys Glu Ile Lys His Ile Ser Lys
    50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Ala Ala
        115                 120                 125
```

<210> SEQ ID NO 123
<211> LENGTH: 125
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 123

```
Met Phe Asn Lys Ala Glu Ile Met Lys Gln Ala Trp Asn Trp Phe Thr
1               5                   10                  15

Asp Ser Asn Val Trp Leu Ser Asp Ile Glu Trp Ala Ser Tyr Thr Asp
                20                  25                  30

Lys Glu Lys Thr Phe Ser Val Cys Leu Lys Ala Ala Trp Ser Lys Ala
            35                  40                  45

Lys Glu Glu Val Lys Glu Val Glu Lys Glu Ile Lys His Ile Ser Lys
        50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Ala Ala
        115                 120                 125
```

<210> SEQ ID NO 124
<211> LENGTH: 125
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 124

```
Met Tyr Asn Lys Ala Glu Ile Met Lys Gln Ala Trp Asn Trp Phe Thr
1               5                   10                  15

Asp Ser Asn Val Trp Leu Ser Asp Ile Glu Trp Ala Ser Tyr Thr Asp
                20                  25                  30

Lys Glu Lys Thr Phe Ser Val Cys Leu Lys Ala Ala Trp Ser Lys Ala
            35                  40                  45

Lys Glu Glu Val Lys Glu Val Glu Lys Glu Ile Lys His Ile Ser Lys
        50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95
```

Thr Lys Ile Asn Phe Gly Leu Ser Val Trp Ala Cys Ala Met Lys Ala
            100                 105                 110

Val Lys Leu His Asn Asp Leu Phe Pro Gln Thr Ala Ala
        115                 120                 125

<210> SEQ ID NO 125
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 125

Met Phe Asn Lys Ala Glu Ile Met Lys Gln Ala Trp Asn Trp Phe Thr
1               5                   10                  15

Asp Ser Asn Val Trp Leu Ser Asp Ile Glu Trp Val Ser Tyr Thr Asp
            20                  25                  30

Lys Glu Lys Thr Phe Ser Val Cys Leu Lys Ala Ala Trp Ser Lys Ala
        35                  40                  45

Lys Glu Glu Phe Lys Glu Val Glu Lys Glu Ile Lys His Ile Ser Lys
    50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asn Glu
                85                  90                  95

Thr Lys Met Asn Phe Gly Leu Ser Val Trp Ala Cys Ala Met Lys Ala
            100                 105                 110

Val Lys Leu His Asn Asp Leu Phe Pro Gln Thr Ala Ala
        115                 120                 125

<210> SEQ ID NO 126
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 126

Met Tyr Asn Lys Ala Glu Ile Met Lys Gln Ala Trp Asn Trp Phe Thr
1               5                   10                  15

Asp Ser Asn Val Trp Leu Ser Asp Ile Glu Trp Ala Ser Tyr Thr Asp
            20                  25                  30

Lys Glu Lys Thr Phe Ser Val Cys Leu Lys Ala Ala Trp Ser Lys Ala
        35                  40                  45

Lys Glu Glu Val Lys Glu Val Glu Lys Glu Ile Lys His Ile Ser Lys
    50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Val Ala
        115                 120                 125

<210> SEQ ID NO 127
<211> LENGTH: 125

```
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 127
```

Met Tyr Asn Lys Ala Glu Ile Met Lys Gln Ala Trp Asn Trp Phe Asn
1               5                   10                  15

Asp Ser Asn Val Trp Leu Ser Asp Ile Glu Trp Ala Ser Tyr Thr Asp
                20                  25                  30

Lys Glu Lys Thr Phe Ser Val Cys Leu Lys Ala Ala Trp Ser Lys Ala
            35                  40                  45

Lys Glu Glu Val Lys Glu Val Glu Lys Glu Ile Lys His Ile Ser Lys
        50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Ser His Leu Phe Pro Gln Thr Ala Ala
        115                 120                 125

```
<210> SEQ ID NO 128
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 128
```

Met Tyr Asn Lys Ala Glu Ile Met Lys Gln Ala Trp Asn Trp Phe Thr
1               5                   10                  15

Asp Ser Asn Val Trp Leu Ser Asp Ile Glu Trp Ala Ser Tyr Thr Asp
                20                  25                  30

Lys Glu Lys Thr Phe Ser Val Cys Leu Lys Ala Ala Trp Ser Lys Ala
            35                  40                  45

Lys Glu Glu Val Lys Glu Val Glu Lys Glu Ile Lys His Ile Ser Lys
        50                  55                  60

Arg Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Val Ala
        115                 120                 125

```
<210> SEQ ID NO 129
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 129
```

Met Phe Asn Lys Ala Glu Ile Met Lys Gln Ala Trp Asn Trp Phe Thr

```
                1               5                  10                  15
Asp Ser Asn Val Trp Leu Ser Asp Ile Glu Trp Val Ser Tyr Thr Asp
                20                  25                  30

Lys Glu Lys Thr Phe Ser Val Cys Leu Lys Ala Ala Trp Ser Lys Ala
            35                  40                  45

Lys Glu Glu Val Lys Glu Val Glu Lys Glu Ile Lys His Ile Ser Lys
        50                  55                  60

Ser Glu Glu Leu Lys Ala Trp Asn Trp Ala Glu Arg Lys Leu Gly Leu
65                  70                  75                  80

Arg Phe Asn Ile Ser Asp Asp Glu Lys Phe Thr Ser Val Lys Asp Glu
                85                  90                  95

Thr Lys Gln His Phe Gly Leu Ser Val Trp Ala Cys Ala Met Lys Ala
            100                 105                 110

Val Lys Leu His Asn Asp Leu Phe Pro Gln Thr Ala Ala
        115                 120                 125

<210> SEQ ID NO 130
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 130

Met Tyr Asn Lys Ala Glu Ile Met Lys Gln Ala Trp Asn Trp Phe Asn
1               5                  10                  15

Asp Ser Asn Ile Trp Leu Ser Asp Ile Glu Trp Val Ser Tyr Thr Asp
                20                  25                  30

Lys Glu Lys Ser Phe Ser Val Cys Leu Lys Ala Ala Trp Ser Lys Ala
            35                  40                  45

Lys Glu Glu Val Glu Glu Ser Lys Lys Glu Ser Lys His Ile Ala Lys
        50                  55                  60

Ser Glu Glu Leu Lys Ala Trp Asn Trp Ala Glu Ile Lys Leu Gly Leu
65                  70                  75                  80

Arg Phe Asn Ile Ser Asp Asp Glu Lys Phe Thr Ser Val Lys Asp Glu
                85                  90                  95

Thr Lys Met Asn Phe Asp Leu Asn Val Trp Ala Cys Ala Met Lys Ala
            100                 105                 110

Val Lys Leu His Asn Asp Leu Phe Pro Gln Thr Ala Ala
        115                 120                 125

<210> SEQ ID NO 131
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 131

Met Tyr Asn Lys Ala Glu Ile Met Lys Gln Ala Trp Asn Trp Phe Thr
1               5                  10                  15

Asp Ser Asn Val Trp Leu Ser Asp Ile Glu Trp Val Ser Tyr Thr Asp
                20                  25                  30

Lys Glu Lys Thr Phe Ser Val Cys Leu Lys Ala Ala Trp Ser Lys Ala
            35                  40                  45

Lys Glu Glu Val Lys Glu Val Glu Lys Glu Ile Lys His Ile Ser Lys
```

```
            50                  55                  60
Ser Glu Glu Leu Lys Ala Trp Asn Trp Ala Glu Arg Lys Leu Gly Leu
 65                  70                  75                  80

Arg Phe Asn Ile Ser Asp Asp Glu Lys Phe Thr Ser Val Lys Asp Glu
                     85                  90                  95

Thr Lys Gln His Phe Gly Leu Ser Val Trp Ala Cys Ala Met Lys Ala
                100                 105                 110

Val Lys Leu His Asn Asp Leu Phe Pro Gln Thr Ala Ala
            115                 120                 125

<210> SEQ ID NO 132
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 132

Met Tyr Asn Lys Ala Glu Ile Met Lys Gln Ala Trp Asn Cys Phe Asn
 1               5                  10                  15

Asp Ser Asn Val Trp Leu Ser Asp Ile Glu Trp Val Ser Tyr Thr Asp
                20                  25                  30

Lys Glu Lys Thr Phe Ser Val Cys Leu Lys Ala Ala Trp Ser Lys Ala
            35                  40                  45

Lys Glu Glu Ile Glu Lys Ser Lys Lys Glu Ser Lys His Ile Ala Lys
        50                  55                  60

Ser Glu Glu Leu Lys Ala Trp Asn Trp Ala Glu Arg Lys Leu Gly Leu
 65                  70                  75                  80

Arg Phe Asn Ile Ser Asp Asp Glu Lys Phe Thr Ser Val Lys Asp Glu
                     85                  90                  95

Thr Lys Gln His Phe Gly Leu Ser Val Trp Ala Cys Ala Met Lys Ala
                100                 105                 110

Val Lys Leu His Asn Asp Leu Phe Pro Gln Thr Ala Ala
            115                 120                 125

<210> SEQ ID NO 133
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 133

Met Tyr Asn Lys Ala Glu Ile Met Lys Gln Ala Trp Asn Cys Phe Asn
 1               5                  10                  15

Asp Ser Asn Val Trp Leu Ser Asp Ile Glu Trp Val Ser Tyr Thr Asp
                20                  25                  30

Lys Glu Lys Thr Phe Ser Val Cys Leu Lys Ala Ala Trp Ser Lys Ala
            35                  40                  45

Lys Glu Glu Ile Glu Glu Ser Lys Lys Glu Ser Lys His Ile Ala Lys
        50                  55                  60

Ser Glu Glu Leu Lys Ala Trp Asn Trp Ala Glu Arg Lys Leu Gly Leu
 65                  70                  75                  80

Arg Phe Asn Ile Ser Asp Asp Glu Lys Phe Thr Ser Val Lys Asp Glu
                     85                  90                  95

Thr Lys Gln His Phe Gly Leu Ser Val Trp Ala Cys Ala Met Lys Ala
```

```
                100                 105                 110
Val Lys Leu His Asn Asp Leu Phe Pro Gln Thr Ala Ala
        115                 120                 125

<210> SEQ ID NO 134
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 134

Met Tyr Asn Lys Ser Glu Ile Met Gln Gln Ala Trp Asn Trp Phe Arg
1               5                   10                  15

Asp Ser Ser Val Trp Leu Ser Asp Ile Glu Trp Val Ser Tyr Thr Asp
            20                  25                  30

Lys Glu Lys Thr Phe Ser Val Cys Leu Lys Ala Ala Trp Ser Lys Ala
        35                  40                  45

Lys Glu Glu Val Glu Glu Ser Lys Leu Glu Ser Lys His Ile Ala Lys
    50                  55                  60

Ser Glu Glu Leu Lys Ala Trp Asn Trp Ala Glu Ser Lys Leu Gly Leu
65                  70                  75                  80

Arg Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Ala Ala
        115                 120                 125

<210> SEQ ID NO 135
<211> LENGTH: 125
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 135

Met Tyr Asn Lys Ala Glu Ile Met Lys Gln Ala Trp Asn Trp Phe Thr
1               5                   10                  15

Asp Ser Asn Val Trp Leu Ser Asp Ile Glu Trp Ala Ser Tyr Thr Asp
            20                  25                  30

Lys Glu Lys Thr Phe Ser Val Cys Leu Lys Ala Ala Trp Ser Lys Ala
        35                  40                  45

Lys Glu Glu Val Lys Glu Val Glu Lys Glu Ile Lys His Ile Ser Lys
    50                  55                  60

Arg Glu Glu Leu Lys Ala Trp Asn Leu Ala Glu Arg Lys Leu Gly Leu
65                  70                  75                  80

His Phe Asn Ile Ser Asp Asp Gly Lys Phe Thr Ser Val Lys Asp Glu
                85                  90                  95

Thr Lys Ile Asn Phe Gly Leu Ser Val Trp Ala Cys Ala Met Lys Ala
            100                 105                 110

Val Lys Leu His Asn Asp Leu Phe Pro Gln Thr Val Ala
        115                 120                 125

<210> SEQ ID NO 136
<211> LENGTH: 117
<212> TYPE: PRT
```

<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 136

Met Phe Asn Lys Ala Glu Ile Met Lys Gln Ala Trp Asn Trp Phe Thr
1               5                   10                  15

Asp Ser Asn Val Trp Leu Ser Asp Ile Glu Trp Ala Ser Tyr Thr Asp
                20                  25                  30

Lys Glu Lys Thr Phe Ser Val Cys Leu Lys Ala Ala Trp Ser Lys Ala
            35                  40                  45

Lys Glu Glu Val Lys Glu Val Glu Lys Glu Ile Lys His Ile Ser Lys
        50                  55                  60

Ser Glu Glu Leu Lys Ala Trp Asn Trp Ala Glu Arg Lys Leu Gly Leu
65                  70                  75                  80

His Phe Asn Ile Ser Asp Asp Glu Lys Phe Thr Ser Val Lys Asp Glu
                85                  90                  95

Thr Lys Ile Asn Phe Gly Leu Ser Val Trp Ala Cys Ala Met Lys Ala
                100                 105                 110

Val Lys Leu His Asn
            115

<210> SEQ ID NO 137
<211> LENGTH: 128
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 137

Met Lys Lys Val Thr Tyr Asp Lys Ser Gly Ile Met Lys Glu Ala Trp
1               5                   10                  15

Asn Leu Phe Asn Asn Asp Asp Ile Thr Leu Ala Asp Phe Glu His Leu
                20                  25                  30

Gly Trp Met Glu Trp Lys Ser Glu Lys Thr Phe Ala Leu Cys Leu Lys
            35                  40                  45

Glu Ala Trp Gly Arg Glu Lys Glu Val Val Glu Arg Val Asn Gln Lys
        50                  55                  60

Phe Ala Asn Ala Glu Thr Ser Glu Glu Ala Lys Ala Trp Asp Trp Ala
65                  70                  75                  80

Cys Lys Lys Leu Gly Val Ala Phe Glu Met Asp Ala Tyr Thr Lys Met
                85                  90                  95

Thr Asn Val Glu Asp Met Glu Lys Glu Ala Trp Pro Gly Thr Ser Val
                100                 105                 110

Trp Ser Leu Ala Met Arg Ala Val Lys Leu His Met Glu Val Ala Ala
            115                 120                 125

<210> SEQ ID NO 138
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 138

Met Arg Tyr Asn Lys Ser Glu Ile Met Lys Asn Ala Trp Ala Met Phe
1               5                   10                  15

-continued

```
Asn Ser Cys Asn Trp Gly Ala Glu Asn Phe Lys Phe Val Ser Val Glu
            20                  25                  30

Glu Lys Thr Phe Ala Ala Cys Leu Lys Glu Ala Trp Ala Glu Glu Lys
        35                  40                  45

Glu Tyr Val Glu Glu Lys Ile Lys Glu Ser Ala Asn Ala Pro Lys Ser
 50                  55                  60

Glu Glu Ala Lys Ala Trp Asp Trp Ala Cys Arg Lys Leu Asn Ala Asn
 65                  70                  75                  80

Lys Leu Gln Asn Val Glu Ala Thr Asp Lys Val Ala Trp Val Ser Glu
            85                  90                  95

Met Ala Lys Glu Met Trp Ser Ser Asn Ile Trp Ala Gln Ala Ile Lys
        100                 105                 110

Ala Val Lys Leu His Ile Lys Leu Phe Ala Ala
        115                 120

<210> SEQ ID NO 139
<211> LENGTH: 126
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 139

Met Lys Tyr Asn Lys Ser Glu Ile Met Lys Asn Ala Trp Thr Met Phe
 1               5                  10                  15

Asn Asp Asp Asn Phe Asp Thr Ser Tyr Tyr Glu Tyr Ala Thr Ala Glu
            20                  25                  30

Val Tyr Gly Gln Lys Thr Phe Ser Glu Cys Leu Lys Glu Ser Trp Gly
        35                  40                  45

Arg Glu Lys Ala Tyr Gln Glu Lys Glu Lys Arg Leu Val Asp Ala
 50                  55                  60

Pro Lys Ser Glu Glu Ala Lys Ala Trp Asp Trp Ala Cys Arg Lys Leu
 65                  70                  75                  80

Asn Val Asn Glu Leu Gln Asn Ile Asp Ala Thr Asp Lys Val Phe Tyr
            85                  90                  95

Val Glu Gly Met Ala Lys Glu Met Trp Ser Ser Asn Val Trp Ala Gln
        100                 105                 110

Ala Ile Lys Ala Val Lys Leu His Ile Glu Leu Phe Val Ala
        115                 120                 125

<210> SEQ ID NO 140
<211> LENGTH: 129
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 140

Met Lys Lys Val Ala Tyr Asp Lys Ser Gly Ile Met Lys Glu Ala Trp
 1               5                  10                  15

Glu Met Phe Asn Arg Asn Tyr Gln Ile Cys Phe Glu Tyr Ala Asp
            20                  25                  30

Phe Ser Gly Arg Glu Tyr Phe Glu Tyr Ala Ser Phe Ala Asp Cys Leu
        35                  40                  45

Lys Glu Ala Trp Ala His Glu Lys Glu Val Val Glu Arg Val Asn Gln
 50                  55                  60
```

```
Lys Tyr Ala Asp Ala Glu Thr Ser Glu Glu Val Lys Ala Trp Asp Trp
 65                  70                  75                  80

Ala Cys Lys Lys Leu Gly Val Ala Phe Glu Met Asp Ala Tyr Thr Lys
                 85                  90                  95

Ile Thr Asn Val Glu Gly Met Glu Lys Glu Ala Trp Pro Gly Thr Ser
            100                 105                 110

Val Trp Ser Leu Ala Met Arg Ala Val Lys Leu His Met Glu Val Ala
        115                 120                 125

Ala

<210> SEQ ID NO 141
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 141

Met Ala Lys Tyr Asn Lys Ser Glu Ile Met Thr Gln Ala Trp Thr Leu
1                5                  10                  15

Phe Asn Ser Asp Asn Phe Asp Thr Cys Asp Tyr Glu Tyr Thr Thr Ala
                 20                  25                  30

Leu Val Tyr Gly Gln Lys Asn Phe Ser Asp Cys Leu Lys Glu Ala Trp
             35                  40                  45

Gly Arg Glu Lys Ala Ile Val Glu Arg Met Ala Glu Gln Glu Ala Asn
         50                  55                  60

Ala Pro Leu Ser Glu Glu Ala Lys Ala Trp Asp Trp Ala Cys Arg Lys
 65                  70                  75                  80

Leu Gly Val Thr Ala Glu Val Thr Ala Val Glu Lys Val Arg Tyr Val
                 85                  90                  95

Asp Asp Met Ala Lys Glu Met Trp Ser Ala Asn Val Trp Lys Gln Ala
            100                 105                 110

Ile Lys Ala Val Gln Leu Tyr Ala Thr Val Ala
        115                 120

<210> SEQ ID NO 142
<211> LENGTH: 123
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 142

Met Ala Lys Tyr Asn Lys Ser Glu Ile Met Thr Gln Ala Trp Thr Leu
1                5                  10                  15

Phe Asn Ser Asp Asn Phe Asp Thr Cys Asp Tyr Glu Tyr Ala Thr Ala
                 20                  25                  30

Leu Val Tyr Gly Gln Lys Thr Phe Ser Asp Cys Leu Lys Glu Ala Trp
             35                  40                  45

Gly Arg Glu Lys Ala Ile Val Glu Arg Met Ala Glu Lys Glu Ala Asn
         50                  55                  60

Ala Pro Leu Ser Glu Glu Ala Lys Ala Trp Asp Trp Ala Cys Arg Lys
 65                  70                  75                  80

Leu Gly Val Thr Ala Glu Val Thr Ala Val Glu Lys Val Arg Tyr Val
                 85                  90                  95
```

```
Asp Asp Met Ala Lys Glu Met Trp Ser Thr Asn Val Trp Lys Gln Ala
                100                 105                 110

Ile Lys Ala Val Gln Leu Tyr Ala Thr Val Ala
        115                 120
```

<210> SEQ ID NO 143
<211> LENGTH: 124
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 143

```
Met Ala Lys Tyr Asn Lys Ser Glu Ile Met Lys Asn Ala Trp Ala Met
1               5                   10                  15

Phe Asn Ser Tyr Glu Trp Asp Val Glu Asn Phe Lys Phe Val Ser Ala
                20                  25                  30

Glu Asn Lys Thr Phe Ser Asn Cys Leu Lys Glu Ala Trp Ala Glu Glu
            35                  40                  45

Lys Glu Tyr Val Glu Arg Lys Ala Lys Glu Thr Ala Glu Ala Pro Lys
        50                  55                  60

Ser Glu Glu Ala Lys Ala Trp Asp Trp Ala Cys Arg Lys Leu Asn Val
65                  70                  75                  80

Asn Asp Leu Gln Asn Ile Asp Ala Thr Asp Lys Val Phe Tyr Val Val
                85                  90                  95

Asp Met Gln Lys Glu Met Trp Thr Ser Asn Val Trp Ala Gln Ala Ile
                100                 105                 110

Lys Ala Val Glu Leu Tyr Val Lys Leu Gly Leu Ala
        115                 120
```

<210> SEQ ID NO 144
<211> LENGTH: 124
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 144

```
Met Thr Lys Tyr Asn Lys Ser Glu Ile Met Lys Asn Ala Trp Ala Met
1               5                   10                  15

Phe Asn Ser Tyr Glu Trp Asp Val Glu Asn Phe Lys Phe Val Ser Ala
                20                  25                  30

Glu Asn Lys Thr Phe Ser Asn Cys Leu Lys Glu Ala Trp Ala Glu Glu
            35                  40                  45

Lys Glu Tyr Val Glu Arg Lys Ala Lys Glu Thr Ala Glu Ala Pro Arg
        50                  55                  60

Ser Glu Glu Ala Lys Ala Trp Asp Trp Ala Cys Arg Lys Leu Asn Val
65                  70                  75                  80

Asn Asp Leu Gln Asn Ile Asp Ala Thr Asp Lys Val Phe Tyr Val Val
                85                  90                  95

Asp Met Gln Lys Glu Met Trp Thr Ser Asn Val Trp Ala Gln Ala Ile
                100                 105                 110

Lys Ala Val Glu Leu Tyr Val Lys Leu Gly Leu Ala
        115                 120
```

<210> SEQ ID NO 145
<211> LENGTH: 124

```
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 145
```

Met Thr Lys Tyr Asn Lys Ser Glu Ile Met Lys Asn Ala Trp Ala Met
1               5                   10                  15

Phe Asn Ser Tyr Glu Trp Asp Val Glu Asn Phe Lys Phe Val Ser Ala
            20                  25                  30

Glu Asn Lys Thr Phe Ser Asn Cys Leu Lys Glu Ala Trp Ala Glu Glu
        35                  40                  45

Lys Glu Tyr Val Glu Arg Lys Ala Lys Glu Thr Ala Glu Ala Pro Lys
    50                  55                  60

Ser Glu Glu Ala Lys Ala Trp Asp Trp Ala Cys Arg Lys Leu Asn Val
65                  70                  75                  80

Asn Asp Leu Gln Asn Ile Asp Ala Thr Asp Lys Val Phe Tyr Val Val
                85                  90                  95

Asp Met Gln Lys Glu Met Trp Thr Ser Asn Ile Trp Ala Gln Ala Ile
            100                 105                 110

Lys Ala Val Glu Leu Tyr Val Lys Leu Gly Leu Ala
        115                 120

```
<210> SEQ ID NO 146
<211> LENGTH: 124
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 146
```

Met Thr Lys Tyr Asn Lys Ser Glu Ile Met Lys Asn Ala Trp Ala Met
1               5                   10                  15

Phe Asn Ser Tyr Glu Trp Asp Val Glu Asn Phe Lys Phe Val Ser Ala
            20                  25                  30

Glu Asn Lys Thr Phe Ser Asn Cys Leu Lys Glu Ala Trp Ala Glu Glu
        35                  40                  45

Lys Glu Tyr Val Glu Arg Lys Ala Lys Glu Ala Glu Ala Ser Lys
    50                  55                  60

Ser Glu Glu Ala Lys Ala Trp Asp Trp Ala Cys Arg Lys Leu Asn Val
65                  70                  75                  80

Asn Asp Leu Gln Asn Ile Asp Ala Thr Asn Lys Val Phe Tyr Val Val
                85                  90                  95

Asp Met Gln Lys Glu Met Trp Thr Ser Asn Val Trp Ala Gln Ala Ile
            100                 105                 110

Lys Ala Val Glu Leu Tyr Val Lys Leu Gly Leu Ala
        115                 120

```
<210> SEQ ID NO 147
<211> LENGTH: 87
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 147
```

Met Asn Ile Asn Asp Leu Ile Arg Glu Ile Lys Asn Lys Asp Tyr Thr

```
1               5                   10                  15
Val Lys Leu Ser Gly Thr Asp Ser Asn Ser Ile Thr Gln Leu Ile Ile
                20                  25                  30

Arg Val Asn Asn Asp Gly Asn Glu Tyr Val Ile Ser Glu Ser Glu Asn
                35                  40                  45

Glu Ser Ile Val Glu Lys Phe Ile Ser Ala Phe Lys Asn Gly Trp Asn
            50                  55                  60

Gln Glu Tyr Glu Asp Glu Glu Phe Tyr Asn Asp Met Gln Thr Ile
65                  70                  75                  80

Thr Leu Lys Ser Glu Leu Asn
                85
```

<210> SEQ ID NO 148
<211> LENGTH: 87
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 148

```
Met Asn Ile Asn Glu Leu Ile Arg Glu Ile Lys Asn Lys Asp Tyr Thr
1               5                   10                  15

Ala Lys Leu Ser Gly Thr Asp Ser Asn Ser Ile Thr Gln Leu Ile Ile
                20                  25                  30

Arg Val Asn Asn Asp Gly Asn Glu Tyr Val Ile Ser Glu Ser Glu Asn
                35                  40                  45

Glu Ser Ile Val Glu Lys Phe Ile Ser Ala Phe Lys Asn Gly Trp Asn
            50                  55                  60

Gln Glu Tyr Glu Asp Glu Glu Phe Tyr Asn Asp Met Gln Thr Ile
65                  70                  75                  80

Thr Leu Lys Ser Glu Leu Asn
                85
```

<210> SEQ ID NO 149
<211> LENGTH: 87
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 149

```
Met Asn Ile Asn Glu Leu Ile Arg Glu Val Lys Asn Lys Asp Tyr Thr
1               5                   10                  15

Ala Lys Leu Ser Gly Thr Asp Ser Asn Ser Ile Thr Gln Leu Ile Ile
                20                  25                  30

Arg Val Asn Asn Asp Gly Asn Glu Tyr Val Ile Ser Glu Ser Glu Asn
                35                  40                  45

Glu Ser Ile Val Glu Lys Phe Ile Ser Ala Phe Lys Asn Gly Trp Asn
            50                  55                  60

Gln Glu Tyr Glu Asp Glu Glu Phe Tyr Asn Asp Met Gln Thr Ile
65                  70                  75                  80

Thr Leu Lys Ser Glu Leu Asn
                85
```

<210> SEQ ID NO 150
<211> LENGTH: 87
<212> TYPE: PRT

```
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 150

Met Asn Ile Asn Glu Leu Ile Arg Glu Ile Lys Asn Lys Asp Tyr Thr
1               5                   10                  15

Ala Lys Leu Ser Gly Thr Asp Ser Asn Ser Ile Ala Gln Leu Ile Ile
            20                  25                  30

Arg Val Asn Asn Asp Gly Asn Glu Tyr Val Ile Ser Glu Ser Glu Asn
        35                  40                  45

Glu Ser Ile Val Glu Lys Phe Ile Ser Ala Phe Lys Asn Gly Trp Asn
    50                  55                  60

Gln Glu Tyr Glu Asp Glu Glu Phe Tyr Asn Asp Met Gln Thr Ile
65                  70                  75                  80

Thr Leu Lys Ser Glu Leu Asn
                85

<210> SEQ ID NO 151
<211> LENGTH: 87
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 151

Met Asn Ile Asn Glu Leu Ile Arg Glu Ile Lys Asn Lys Asp Tyr Thr
1               5                   10                  15

Ala Lys Leu Ser Gly Thr Asp Ser Asn Ser Ile Thr Gln Leu Ile Ile
            20                  25                  30

His Val Asn Asn Asp Gly Asn Glu Tyr Val Ile Ser Glu Ser Glu Asn
        35                  40                  45

Glu Ser Ile Val Glu Lys Phe Ile Ser Ala Phe Lys Asn Gly Trp Asn
    50                  55                  60

Gln Glu Tyr Glu Asp Glu Glu Phe Tyr Asn Asp Met Gln Thr Ile
65                  70                  75                  80

Thr Leu Lys Ser Glu Leu Asn
                85

<210> SEQ ID NO 152
<211> LENGTH: 87
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 152

Met Asn Ile Asn Asp Leu Ile Arg Glu Ile Lys Asn Lys Asp Tyr Thr
1               5                   10                  15

Val Lys Leu Ser Gly Thr Asp Ser Asn Ser Ile Thr Gln Leu Ile Ile
            20                  25                  30

Asn Val Asn Asn Asp Gly Asn Glu Tyr Gly Ile Ser Glu Ser Asn Phe
        35                  40                  45

Glu Ser Ile Val Glu Lys Phe Val Ser Asn Phe Glu Asn Gly Trp Asp
    50                  55                  60

Gly Ala Tyr Glu Asp Glu Glu Phe Tyr Asn Asp Met Gln Ala Ile
65                  70                  75                  80
```

Ile Leu Lys Ser Glu Leu Asn
            85

<210> SEQ ID NO 153
<211> LENGTH: 87
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 153

Met Asn Ile Asn Asp Leu Ile Arg Glu Ile Lys Asn Lys Asp Tyr Thr
1               5                   10                  15

Val Lys Leu Ser Gly Thr Asp Ser Asn Ser Ile Thr Gln Leu Ile Ile
            20                  25                  30

Asn Val Asn Asn Asp Gly Asn Glu Tyr Gly Ile Ser Glu Ser Asn Phe
        35                  40                  45

Glu Ser Ile Val Glu Lys Phe Val Ser Asn Phe Glu Asn Gly Trp Asp
    50                  55                  60

Gly Ala Tyr Glu Asp Glu Glu Phe Tyr Asn Asp Met Gln Ala Ile
65                  70                  75                  80

Ile Leu Lys Ser Glu Ser Asn
            85

<210> SEQ ID NO 154
<211> LENGTH: 87
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 154

Met Asn Ile Ser Glu Leu Ile Arg Glu Ile Lys Asn Lys Asp Tyr Thr
1               5                   10                  15

Val Arg Leu Glu Gly Thr Asp Asp Asn Ser Ile Thr Lys Leu Ile Ile
            20                  25                  30

Asp Val Asp Asn Asp Gly Asn Glu Tyr Val Ile Ser Glu Ser Lys Asn
        35                  40                  45

Glu Ser Ile Ala Glu Lys Phe Ala Ser Thr Phe Lys Asn Gly Trp Asn
    50                  55                  60

Lys Glu Tyr Glu Asp Glu Glu Phe Tyr Asn Asp Met Gln Ser Ile
65                  70                  75                  80

Ile Leu Lys Ser Glu Leu Asn
            85

<210> SEQ ID NO 155
<211> LENGTH: 87
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 155

Met Asn Ile Ser Glu Leu Ile Arg Glu Ile Lys Asn Lys Asp Tyr Ala
1               5                   10                  15

Val Arg Leu Glu Gly Thr Asp Asp Asn Ser Ile Thr Lys Leu Ile Ile
            20                  25                  30

-continued

Asp Val Asp Asn Asp Gly Asn Glu Tyr Val Ile Ser Glu Ser Lys Asn
             35                  40                  45

Glu Ser Ile Ala Glu Lys Phe Ala Ser Thr Phe Lys Asn Gly Trp Asn
 50                  55                  60

Lys Glu Tyr Glu Asp Glu Glu Phe Tyr Asn Asp Met Gln Ser Ile
 65                  70                  75                  80

Ile Leu Lys Ser Glu Leu Asn
             85

<210> SEQ ID NO 156
<211> LENGTH: 160
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 156

Met Ala Gly Tyr Leu Lys Arg Tyr Ala Glu Asp Arg Gly Trp Thr Leu
 1               5                  10                  15

Tyr Arg Leu Ala Lys Glu Ser His Leu Ser Asp Ser Thr Leu Arg Thr
             20                  25                  30

Ala Asp Leu Thr Thr Leu Asn Lys Leu Ser Val Ile Asn Ile Lys Lys
             35                  40                  45

Ile Ser Glu Ala Val Gly Glu Thr Pro Gly Glu Val Leu Asp Asp Leu
 50                  55                  60

Ile Lys Phe Glu Glu Arg Val Glu Lys Met Asn Ile Ser Glu Leu Ile
 65                  70                  75                  80

Arg Glu Ile Lys Asn Lys Asp Tyr Ala Val Arg Leu Glu Gly Thr Asp
             85                  90                  95

Asp Asn Ser Ile Thr Lys Leu Ile Ile Asp Val Asp Asn Asp Gly Asn
             100                 105                 110

Glu Tyr Val Ile Ser Glu Ser Lys Asn Glu Ser Ile Ala Glu Lys Phe
             115                 120                 125

Ala Ser Thr Phe Lys Asn Gly Trp Asn Lys Glu Tyr Glu Asp Glu Glu
             130                 135                 140

Glu Phe Tyr Asn Asp Met Gln Ser Ile Ile Leu Lys Ser Glu Leu Asn
145                 150                 155                 160

<210> SEQ ID NO 157
<211> LENGTH: 86
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 157

Met Asn Leu Lys Glu Leu Val Arg Glu Ile Lys Asn Lys Asp Tyr Thr
 1               5                  10                  15

Ala Lys Leu Ser Gly Thr Asp Ser Asn Ser Ile Thr Gln Leu Ile Ile
             20                  25                  30

His Val Asn Asn Asp Gly Asn Glu Tyr Gly Ile Ser Glu Ser Asn Phe
             35                  40                  45

Glu Ser Ile Val Glu Lys Phe Val Ser Thr Phe Glu Asn Gly Trp Asp
 50                  55                  60

Gly Ala Tyr Glu Asp Glu Glu Phe Tyr Asn Asp Met Gln Asp Ile
 65                  70                  75                  80

```
Val Asn Arg His Phe Lys
            85

<210> SEQ ID NO 158
<211> LENGTH: 86
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 158

Met Asn Leu Lys Glu Leu Val Arg Glu Ile Lys Asn Lys Asp Tyr Thr
1               5                   10                  15

Ala Lys Leu Ser Gly Thr Asp Ser Asn Ser Ile Thr Gln Leu Ile Ile
            20                  25                  30

His Val Asn Asn Asp Gly Asn Glu Tyr Gly Ile Ser Glu Ser Asn Phe
        35                  40                  45

Glu Ser Ile Val Glu Lys Phe Val Ser Asn Phe Glu Asn Gly Trp Asp
    50                  55                  60

Gly Ala Tyr Glu Asp Glu Glu Phe Tyr Asn Asp Met Gln Asp Ile
65                  70                  75                  80

Val Asn Arg His Phe Lys
            85

<210> SEQ ID NO 159
<211> LENGTH: 151
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 159

Met Lys Ile Asn Glu Leu Val Arg Glu Ile Lys Ser Arg Asp Tyr Thr
1               5                   10                  15

Val Arg Leu Asn Gly Thr Asp Ser Asn Ser Ile Thr Lys Leu Ile Ile
            20                  25                  30

Asp Val Asn Asn Asp Gly Asn Glu Tyr Val Ile Ser Glu Arg Gln Asp
        35                  40                  45

Thr Ser Ile Val Glu Ser Phe Ala Asp Ser Phe Ile Asp Gly Trp Thr
    50                  55                  60

Gly Thr Tyr Glu Asp Glu Glu Asp Phe Tyr Asn Asp Met Gln Glu Ile
65                  70                  75                  80

Ala Gln Asp Ile Ile Leu Glu Thr Leu Lys Glu Ala Phe Glu Asn Asn
            85                  90                  95

Asn Tyr Asn Thr Asp Glu Val Asp Thr Asp Leu Phe Asp Gly Tyr Gln
            100                 105                 110

Ile Lys Leu Ala Met Glu Tyr Asp Asn Ile Gly Glu Leu Ala Thr Ser
            115                 120                 125

Val Asn Lys Thr Lys His Phe Thr Ala Tyr Met Asp Ala Ser Thr Asp
            130                 135                 140

Phe Met Ile Ile Glu Lys Tyr
145                 150

<210> SEQ ID NO 160
<211> LENGTH: 147
<212> TYPE: PRT
<213> ORGANISM: Unknown
<220> FEATURE:
```

<223> OTHER INFORMATION: Unknown bacterial, unknown viral (phage), or
      synthetic Cas9-inhibiting polypeptide

<400> SEQUENCE: 160

Met Ser Ile Ile Ala Ile Lys Lys Glu Ile His Ala Lys Gly Tyr Lys
1               5                   10                  15

Val Thr Gly Thr His Gln Gly Tyr Ile Ala Gln Ile Asn Phe Asp Gly
            20                  25                  30

Thr Gly Asn Glu Tyr Pro Leu Pro Ala Thr Trp Asp Glu Phe Ile Glu
        35                  40                  45

Thr Phe Lys Asp Gly Trp Asn Gly Thr Tyr Glu Asp Glu Gln Ala Phe
    50                  55                  60

Phe Asn Asp Met Gln Glu Val Ala Leu Lys Glu Ile Leu Asp Glu Leu
65                  70                  75                  80

Thr Gly Ala Leu Phe Cys Gln Asp Ile Thr Thr Tyr Asp Phe Thr Ile
                85                  90                  95

Asp Asp Val Lys Lys Lys Val Ile Thr Leu Asp Lys Pro Thr Phe Glu
            100                 105                 110

Glu Asp Ala Glu Asp Leu Ile Ile Glu Phe Asp Ser Thr Cys Phe Trp
        115                 120                 125

Asp Ala Thr Val Glu Asn Asp Lys Ile Lys Ile Thr Val Arg Asn Lys
    130                 135                 140

Ser Arg Tyr
145

<210> SEQ ID NO 161
<211> LENGTH: 99
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 161

Met Ser Ile Ile Ala Ile Lys Lys Glu Ile His Ala Lys Gly Tyr Lys
1               5                   10                  15

Val Thr Gly Thr His Gln Gly Tyr Ile Ala Gln Ile Asn Phe Asp Gly
            20                  25                  30

Thr Gly Asn Glu Tyr Pro Leu Pro Ala Thr Trp Asp Glu Phe Ile Glu
        35                  40                  45

Thr Phe Lys Asp Gly Trp Asn Gly Thr Tyr Glu Asp Glu Gln Ala Phe
    50                  55                  60

Phe Asn Asp Met Gln Glu Ile Ala Leu Asp Glu Ile Leu Asp Glu Leu
65                  70                  75                  80

Ile Asp Val Leu Tyr Asn Leu Asp Ile Thr Thr Tyr Asn Phe Thr Ile
                85                  90                  95

Asp Asp Ser

<210> SEQ ID NO 162
<211> LENGTH: 147
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 162

Met Ser Ile Ile Ala Ile Lys Lys Glu Ile His Ala Lys Gly Tyr Lys
1               5                   10                  15

```
Val Thr Gly Thr His Gln Gly Tyr Ile Ala Gln Ile Asn Phe Asp Gly
             20                  25                  30

Thr Gly Asn Glu Tyr Pro Leu Pro Ala Thr Trp Asp Glu Phe Ile Glu
         35                  40                  45

Thr Phe Lys Asp Gly Trp Asn Gly Thr Tyr Glu Asp Glu Gln Ala Phe
 50                  55                  60

Phe Asn Asp Met Gln Glu Ile Ala Leu Glu Glu Ile Leu Asp Glu Leu
 65                  70                  75                  80

Thr Gly Ala Leu Phe Cys Gln Asp Ile Thr Thr Tyr Asp Phe Thr Ile
                 85                  90                  95

Asp Asp Val Lys Lys Val Ile Thr Leu Asp Lys Pro Thr Phe Glu
                100                 105                 110

Glu Asp Ala Glu Asp Leu Ile Ile Glu Phe Asp Ser Thr Cys Phe Trp
            115                 120                 125

Asp Ala Thr Val Glu Asn Asp Lys Ile Lys Ile Thr Val Arg Asn Lys
        130                 135                 140

Ser Arg Tyr
145

<210> SEQ ID NO 163
<211> LENGTH: 149
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 163

Met Ser Ile Ile Ala Ile Asn Lys Glu Ile Arg Ala Lys Gly Tyr Lys
1               5                   10                  15

Val Thr Gly Thr His Gln Gly Tyr Ile Ala Gln Ile Asn Phe Glu Gly
             20                  25                  30

Thr Gly Asn Glu Tyr Pro Leu Pro Ala Thr Trp Asp Glu Phe Ile Glu
         35                  40                  45

Thr Phe Lys Asp Gly Trp Asn Gly Thr Tyr Glu Asp Glu Gln Ala Phe
 50                  55                  60

Phe Asn Asp Met Gln Glu Ile Ala Leu Asp Glu Ile Leu Asp Glu Leu
 65                  70                  75                  80

Ile Asp Val Leu Tyr Asn Leu Asp Ile Thr Thr Tyr Asn Phe Thr Ile
                 85                  90                  95

Asp Asp Val Lys Lys Val Ile Thr Leu Asn Lys Pro Ile Asp Glu
                100                 105                 110

Glu Glu Thr Glu Asp Leu Val Gln Glu Phe Asn Val Thr Cys Phe Trp
            115                 120                 125

Asp Ala Thr Val Glu Asp Lys Val Lys Val Thr Ile Arg Asn Lys
        130                 135                 140

Asn Arg Ala Ile Ser
145

<210> SEQ ID NO 164
<211> LENGTH: 146
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 164
```

Met Ser Thr Thr Ala Ile Asn Lys Glu Ile His Ala Lys Gly Tyr Lys
1               5                   10                  15

Val Thr Gly Thr His Gln Gly Tyr Ile Ala Gln Ile Asn Phe Asp Gly
                20                  25                  30

Thr Gly Asn Glu Tyr Pro Leu Pro Ala Thr Trp Glu Lys Phe Ile Glu
            35                  40                  45

Thr Phe Lys Asp Gly Trp Asp Gly Thr Tyr Glu Asp Glu Gln Ala Phe
        50                  55                  60

Phe Asn Asp Met Gln Glu Ile Ala Leu Asp Glu Ile Leu Asp Glu Leu
65                  70                  75                  80

Ile Asp Val Leu Tyr Asn Leu Asp Ile Thr Thr Tyr Asn Phe Thr Ile
                85                  90                  95

Asp Asp Val Lys Lys Lys Val Ile Thr Leu Asn Lys Pro Ile Asp Glu
                100                 105                 110

Glu Glu Thr Glu Asp Leu Val Gln Glu Phe Asn Val Thr Cys Phe Trp
            115                 120                 125

Asn Ala Ile Val Glu Asp Asp Lys Val Lys Ile Thr Val Arg Asn Lys
        130                 135                 140

Ser Lys
145

<210> SEQ ID NO 165
<211> LENGTH: 146
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 165

Met Ser Thr Thr Ala Ile Asn Lys Glu Ile His Ala Lys Gly Tyr Lys
1               5                   10                  15

Val Thr Gly Thr His Gln Gly Tyr Ile Ala Gln Ile Asn Phe Asp Gly
                20                  25                  30

Thr Gly Asn Glu Tyr Pro Leu Pro Ala Thr Trp Glu Glu Phe Ile Glu
            35                  40                  45

Thr Phe Lys Asp Gly Trp Asp Gly Thr Tyr Glu Asp Glu Gln Ala Phe
        50                  55                  60

Phe Asn Asp Met Gln Glu Ile Ala Leu Asp Glu Ile Leu Asp Glu Leu
65                  70                  75                  80

Ile Asp Val Leu Tyr Asn Leu Asp Ile Thr Thr Tyr Asn Phe Thr Ile
                85                  90                  95

Asp Asp Val Lys Lys Lys Val Ile Thr Leu Asn Lys Pro Ile Asp Glu
                100                 105                 110

Glu Glu Thr Glu Asp Leu Val Gln Glu Phe Asn Val Thr Cys Phe Trp
            115                 120                 125

Asn Ala Ile Val Glu Asp Asp Lys Val Lys Ile Thr Val Arg Asn Lys
        130                 135                 140

Ser Lys
145

<210> SEQ ID NO 166
<211> LENGTH: 146
<212> TYPE: PRT
<213> ORGANISM: Unknown
<220> FEATURE:
<223> OTHER INFORMATION: Unknown bacterial, unknown viral (phage), or synthetic Cas9-inhibiting polypeptide

<400> SEQUENCE: 166

Met Ser Thr Thr Ala Ile Asn Lys Glu Ile His Ala Lys Gly Tyr Lys
1               5                   10                  15

Val Thr Gly Thr His Gln Gly Tyr Val Ala Gln Ile Asn Phe Asp Gly
            20                  25                  30

Thr Gly Asn Glu Tyr Pro Leu Pro Ala Thr Trp Glu Glu Phe Ile Glu
        35                  40                  45

Thr Phe Lys Asp Gly Trp Asp Gly Thr Tyr Lys Asp Glu Gln Ala Phe
    50                  55                  60

Phe Asn Asp Met Gln Glu Ile Ala Leu Asp Glu Ile Leu Asp Glu Leu
65                  70                  75                  80

Ile Asp Thr Leu Tyr Asn Leu Asp Ile Thr Thr Tyr Asp Phe Thr Ile
                85                  90                  95

Asp Asp Ile Lys Lys Lys Val Ile Thr Leu Asp Lys Pro Thr Asp Arg
            100                 105                 110

Glu Glu Thr Glu Asp Leu Val Gln Glu Phe Asn Val Thr Cys Phe Trp
        115                 120                 125

Asn Ala Ile Val Glu Asp Lys Val Lys Val Thr Val Arg Asn Lys
    130                 135                 140

Ser Lys
145

<210> SEQ ID NO 167
<211> LENGTH: 130
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide
<220> FEATURE:
<221> NAME/KEY: MISC_FEATURE
<222> LOCATION: (112)..(112)
<223> OTHER INFORMATION: Xaa is any amino acid

<400> SEQUENCE: 167

Met Thr Gly Thr His Gln Gly Tyr Ile Ala Gln Ile Asn Phe Asp Gly
1               5                   10                  15

Thr Gly Asn Glu Tyr Pro Leu Pro Ala Thr Trp Asp Glu Phe Ile Glu
            20                  25                  30

Thr Phe Lys Asp Gly Trp Asn Gly Thr Tyr Glu Asp Glu Gln Ala Phe
        35                  40                  45

Phe Asn Asp Met Gln Glu Val Ala Leu Lys Glu Ile Leu Asp Glu Leu
    50                  55                  60

Ile Asp Val Leu Tyr Asn Leu Asp Ile Thr Thr Tyr Asn Phe Thr Ile
65                  70                  75                  80

Asp Asp Val Lys Lys Lys Val Ile Thr Leu Asn Lys Pro Thr Asp Glu
                85                  90                  95

Glu Asp Ala Glu Asp Leu Val Ile Glu Phe Asp Ser Thr Cys Phe Xaa
            100                 105                 110

Asp Ala Thr Val Glu Asn Asp Lys Ile Lys Val Thr Val Arg Asn Lys
        115                 120                 125

Ser Lys
    130

<210> SEQ ID NO 168
<211> LENGTH: 149

```
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 168

Met Ser Thr Thr Ala Ile Asn Lys Glu Ile His Ala Lys Gly Tyr Lys
1               5                   10                  15

Val Thr Gly Thr His Gln Gly Tyr Met Ala Gln Ile Asn Phe Asp Gly
            20                  25                  30

Thr Gly Asn Glu Phe Pro Leu Pro Ala Thr Trp Glu Glu Phe Ile Glu
        35                  40                  45

Thr Phe Lys Asp Gly Trp Asp Gly Thr Tyr Glu Asp Glu Gln Ala Phe
    50                  55                  60

Phe Asn Asp Met Gln Glu Val Ala Leu Glu Glu Leu Leu Asp Glu Leu
65                  70                  75                  80

Thr Asp Val Phe Tyr Asn Leu Asp Ile Thr Ala Tyr Asp Phe Thr Val
                85                  90                  95

Asp Asp Val Lys Lys Lys Val Ile Thr Leu Asp Lys Pro Thr Asp Arg
            100                 105                 110

Glu Glu Thr Glu Asp Leu Val Gln Glu Phe Lys Ala Thr Cys Phe Trp
        115                 120                 125

Asn Ala Val Val Glu Asp Asp Lys Val Lys Val Thr Ile Arg Asn Lys
    130                 135                 140

Asn Arg Ala Ile Ser
145

<210> SEQ ID NO 169
<211> LENGTH: 119
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 169

Met Gln Phe Val Val Thr Asn Lys Ser Glu Leu Phe Lys Phe Ala Trp
1               5                   10                  15

Lys Ile Phe Lys Ala Asn Lys Asp Ile Ala Phe Ser Glu Cys Leu Gln
            20                  25                  30

Asn Ala Trp Phe Gln Tyr Lys Arg Tyr Leu Asn Arg Glu Ala Ile Lys
        35                  40                  45

Ala Ala Gln Gln Arg Lys Leu Ala Lys Phe Ile Ala Asp Thr Glu Asn
    50                  55                  60

Glu Glu Val Lys Ala Trp Asn Trp Ala Glu Lys Lys Leu Gly Val Ala
65                  70                  75                  80

Leu Asn Leu Thr Asp Ala Glu Lys Glu Arg Asn Val Arg Asn Met Tyr
                85                  90                  95

Lys Glu Met Trp Asn Ala Asn Val Trp Ala Thr Ala Ile Lys Ala Val
            100                 105                 110

Lys Leu His Met Glu Ile Gly
        115

<210> SEQ ID NO 170
<211> LENGTH: 148
<212> TYPE: PRT
<213> ORGANISM: Unknown
<220> FEATURE:
```

<223> OTHER INFORMATION: Unknown bacterial, unknown viral (phage), or
      synthetic Cas9-inhibiting polypeptide

<400> SEQUENCE: 170

```
Met Asn Glu Leu Arg Ser Leu Glu Met Ser Ile Asn Ala Lys Lys Tyr
1               5                   10                  15

Asp Thr Arg Leu Glu Ser Gly Asn Arg Val Leu Asn Ile Gly Phe Gly
            20                  25                  30

Asp Gly Glu Asp Tyr Pro Val Cys Ser Ser Arg Tyr Ser Leu Lys
        35                  40                  45

Glu Ser Phe Ile Glu Cys Phe Lys Asp Gly Trp Ser Gly Thr Tyr Arg
    50                  55                  60

Asp Glu Lys Glu Leu Met Glu Asp Met Gln Glu Ile Ala Gln Glu Leu
65                  70                  75                  80

Ile Leu Glu Glu Leu Thr Asp Ile Phe Glu Tyr Glu Phe Asn Thr
                85                  90                  95

Asp Glu Ile Asp Thr Asp Leu Phe Lys Gly Phe Thr Phe Asp Val Asp
            100                 105                 110

Ser Asp Leu Glu Asp Ser Met Ala Leu Met Lys Ala Ile Asn Ala Thr
        115                 120                 125

Lys Tyr Phe Glu Ala Arg Ser Ser Ser Trp Tyr Ala Ser Phe Glu Val
130                 135                 140

Ser Tyr Ile Gly
145
```

<210> SEQ ID NO 171
<211> LENGTH: 28
<212> TYPE: RNA
<213> ORGANISM: Artificial Sequence
<220> FEATURE:
<223> OTHER INFORMATION: synthetic crRNA spacer sequence

<400> SEQUENCE: 171
gauagcaaga uggauaguua guuuuaga                                      28

<210> SEQ ID NO 172
<211> LENGTH: 36
<212> TYPE: DNA
<213> ORGANISM: Artificial Sequence
<220> FEATURE:
<223> OTHER INFORMATION: synthetic protospacer sequence (phiJ0161a
      prophage))

<400> SEQUENCE: 172
acgctccgta actatccatc ttgctatctg tatatg                             36

<210> SEQ ID NO 173
<211> LENGTH: 36
<212> TYPE: DNA
<213> ORGANISM: Artificial Sequence
<220> FEATURE:
<223> OTHER INFORMATION: synthetic protospacer sequence (phiJ0161a
      prophage)) - complement

<400> SEQUENCE: 173
catatacaga tagcaagatg gatagttacg gagcgt                             36

<210> SEQ ID NO 174
<211> LENGTH: 30
<212> TYPE: DNA
<213> ORGANISM: Artificial Sequence
<220> FEATURE:

```
<223> OTHER INFORMATION: synthetic spacer sequence from FIG. 7B

<400> SEQUENCE: 174
tggttctttc gctttcacaa gatacttttg                                      30

<210> SEQ ID NO 175
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 175
acccgtttct gatgaacgat acactgttgt                                      30

<210> SEQ ID NO 176
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 176
catctatcaa gctacaaatt ggatgtacac                                      30

<210> SEQ ID NO 177
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 177
aagacgaagt gaacgaagag tctttcccag                                      30

<210> SEQ ID NO 178
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 178
taacgtttgg aaccctaggc attatgttgc                                      30

<210> SEQ ID NO 179
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 179
gagaatgcaa gaattaatta atgagtacag                                      30

<210> SEQ ID NO 180
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 180
tgttgttata aacactgtta actgttgttc                                      30
```

```
<210> SEQ ID NO 181
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 181
tctatgcctt gatattttaa atgaccgagt                                              30

<210> SEQ ID NO 182
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 182
taagcaagtt gcagataaga aaaccatgtc                                              30

<210> SEQ ID NO 183
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 183
ttttgatgat gaaccagaat ggatttatta                                              30

<210> SEQ ID NO 184
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 184
ctatccgcaa acacatgttg atggcgtcgt                                              30

<210> SEQ ID NO 185
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 185
aaaaaaatat taacacgaat tagatactaa                                              30

<210> SEQ ID NO 186
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 186
caaggcactt ttcattttt gaacacgcca                                               30

<210> SEQ ID NO 187
<211> LENGTH: 30
<212> TYPE: DNA
<213> ORGANISM: Artificial Sequence
<220> FEATURE:
<223> OTHER INFORMATION: synthetic spacer sequence from FIG. 7B
```

<400> SEQUENCE: 187
aactgttgtg ccttcctttg cgtgcacttg           30

<210> SEQ ID NO 188
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 188 tcttttttgat gtattcattt attgttagaa           30

<210> SEQ ID NO 189
<211> LENGTH: 30
<212> TYPE: DNA
<213> ORGANISM: Artificial Sequence
<220> FEATURE:
<223> OTHER INFORMATION: synthetic spacer sequence from FIG. 7B;
      includes self-targeting spacer

<400> SEQUENCE: 189
agcatataca gatagcaaga tggatagtta           30

<210> SEQ ID NO 190
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 190
ttcaaggtca agatcaagag caagaatgcc           30

<210> SEQ ID NO 191
<211> LENGTH: 30
<212> TYPE: DNA
<213> ORGANISM: Artificial Sequence
<220> FEATURE:
<223> OTHER INFORMATION: synthetic spacer sequence from FIG. 7B

<400> SEQUENCE: 191
cgtcgcataa tactgttcct ctgccgttcg           30

<210> SEQ ID NO 192
<211> LENGTH: 29
<212> TYPE: DNA
<213> ORGANISM: Artificial Sequence
<220> FEATURE:
<223> OTHER INFORMATION: synthetic spacer sequence from FIG. 7B

<400> SEQUENCE: 192
gaatattctt cccccatga ctaacaggg           29

<210> SEQ ID NO 193
<211> LENGTH: 36
<212> TYPE: DNA
<213> ORGANISM: Artificial Sequence
<220> FEATURE:
<223> OTHER INFORMATION: synthetic spacer sequence from FIG. 7B

<400> SEQUENCE: 193
gttttagagc tatgttattt tgaatgctac caaaac           36

<210> SEQ ID NO 194

```
<211> LENGTH: 38
<212> TYPE: RNA
<213> ORGANISM: Artificial Sequence
<220> FEATURE:
<223> OTHER INFORMATION: synthetic crRNA spacer sequence

<400> SEQUENCE: 194
agcauauaca gauagcaaga uggauaguua guuuuaga                                   38

<210> SEQ ID NO 195
<211> LENGTH: 46
<212> TYPE: DNA
<213> ORGANISM: Artificial Sequence
<220> FEATURE:
<223> OTHER INFORMATION: synthetic target DNA sequence

<400> SEQUENCE: 195
acgctccgta actatccatc ttgctatctg tatatgcttt tgcaga                          46

<210> SEQ ID NO 196
<211> LENGTH: 46
<212> TYPE: DNA
<213> ORGANISM: Artificial Sequence
<220> FEATURE:
<223> OTHER INFORMATION: synthetic target DNA sequence (complement)

<400> SEQUENCE: 196
tctgcaaaag catatacaga tagcaagatg gatagttacg gagcgt                          46

<210> SEQ ID NO 197
<211> LENGTH: 154
<212> TYPE: DNA
<213> ORGANISM: Streptocococcus pyogenes

<400> SEQUENCE: 197
tatggctgat aaatttcttt gaatttctcc ttgattattt gttataaaag ttataaaata          60
atcttgttgg aaccattcaa aacagcatag caagttaaaa taaggctagt ccgttatcaa         120
cttgaaaaag tggcaccgag tcggtgcttt tttt                                     154

<210> SEQ ID NO 198
<211> LENGTH: 157
<212> TYPE: DNA
<213> ORGANISM: Listeria monocytogenes

<400> SEQUENCE: 198
catattcttc atcccttcaa cctgttttta gttgcattct ttttataatt tggtacaatg          60
tatatattgt tagtattcaa ataacatag caagttaaaa taaggctttg tccgttatca         120
acttttaatt aagtagcgct gtttcggcgc tttttttt                                 157

<210> SEQ ID NO 199
<211> LENGTH: 157
<212> TYPE: DNA
<213> ORGANISM: Listeria monocytogenes

<400> SEQUENCE: 199
catattcttc atcccttcaa cctgttttta gttgcattct ttttataatt tggtacaatg          60
tatatattgt tagtattcaa ataacatag caagttaaaa taaggctttg tccgttatca         120
acttttaatt aagtagcgct gtttcggcgc tttttttt                                 157

<210> SEQ ID NO 200
<211> LENGTH: 157
```

```
<212> TYPE: DNA
<213> ORGANISM: Listeria innocua

<400> SEQUENCE: 200
catattcttc atcccttcaa cctatttta gttgcattct ttttataatt tggtacaatg    60
tatatattgt tagtattcaa ataacatag caagttaaaa taaggctttg tccgttatca   120
acttttaatt aagtagcgct gtttcggcgc ttttttt                           157

<210> SEQ ID NO 201
<211> LENGTH: 246
<212> TYPE: DNA
<213> ORGANISM: Streptocococcus pyogenes

<400> SEQUENCE: 201
ttagatgaag attatttctt aataactaaa aatatggtat aatactctta ataaatgcag    60
taatacaggg gcttttcaag actgaagtct agctgagaca aatagtgcga ttacgaaatt   120
ttttagacaa aaatagtcta cgaggtttta gagctatgct gttttgaatg gtcccaaaac   180
tgcgctggtt gatttcttct tgcgcttttt gttttagagc tatgctgttt tgaatggtcc   240
caaaac                                                              246

<210> SEQ ID NO 202
<211> LENGTH: 233
<212> TYPE: DNA
<213> ORGANISM: Listeria monocytogenes

<400> SEQUENCE: 202
taaggtaacc gctgttcttt gaaaacaaaa taaattttat gtaaaccata aaatagcatt    60
caaaattgaa atcttgctat ggatgaatgg cgcgattacg gaatcttgga ggaaagaaaa   120
aattctgcga ggttttagag ctatgttatt ttgaatgcta ccaaaactcg tgatttcttc   180
ctcatgcgcg cttttgagtt ttagagctat gttattttga atgctaccaa aac          233

<210> SEQ ID NO 203
<211> LENGTH: 233
<212> TYPE: DNA
<213> ORGANISM: Listeria monocytogenes

<400> SEQUENCE: 203
taaggtaacc gctgttcttt gaaaacaaaa taaattttat gtaaaccata aaatagcatt    60
caaaattgaa atcttgctat ggatgaatgg cgcgattacg gaatcttgga ggaaagaaaa   120
aattctgcga ggttttagag ctatgttatt ttgaatgcta ccaaaactgg ttctttcgct   180
ttcacaagat acttttggtt ttagagctat gttattttga atgctaccaa aac          233

<210> SEQ ID NO 204
<211> LENGTH: 231
<212> TYPE: DNA
<213> ORGANISM: Listeria innocua

<400> SEQUENCE: 204
tagagttcaa atgatctttg aaaactaaat agattttatg tgaaccataa aataagcatt    60
caaaattgaa atcttgctat ggatgaatgg cgcgattacg aaatctagga gaataaaaaa   120
ttctacgagg ttttagagct atgttatttt gaatgctaac aaaaccgtag cgctttggta   180
actttgccta ggatagtttt agagctatgt tattttgaat gctaacaaaa c            231

<210> SEQ ID NO 205
```

```
<211> LENGTH: 1368
<212> TYPE: PRT
<213> ORGANISM: Streptococcus pyogenes

<400> SEQUENCE: 205
```

| | | | | | | | | | | | | | | |
|---|---|---|---|---|---|---|---|---|---|---|---|---|---|---|
| Met | Asp | Lys | Lys | Tyr | Ser | Ile | Gly | Leu | Asp | Ile | Gly | Thr | Asn | Ser | Val |
| 1 | | | | 5 | | | | | 10 | | | | | 15 | |
| Gly | Trp | Ala | Val | Ile | Thr | Asp | Glu | Tyr | Lys | Val | Pro | Ser | Lys | Lys | Phe |
| | | | 20 | | | | | 25 | | | | | 30 | | |
| Lys | Val | Leu | Gly | Asn | Thr | Asp | Arg | His | Ser | Ile | Lys | Lys | Asn | Leu | Ile |
| | | | | 35 | | | | | 40 | | | | | 45 | |
| Gly | Ala | Leu | Leu | Phe | Asp | Ser | Gly | Glu | Thr | Ala | Glu | Ala | Thr | Arg | Leu |
| | 50 | | | | | 55 | | | | | 60 | | | | |
| Lys | Arg | Thr | Ala | Arg | Arg | Arg | Tyr | Thr | Arg | Arg | Lys | Asn | Arg | Ile | Cys |
| 65 | | | | | 70 | | | | | 75 | | | | | 80 |
| Tyr | Leu | Gln | Glu | Ile | Phe | Ser | Asn | Glu | Met | Ala | Lys | Val | Asp | Asp | Ser |
| | | | | 85 | | | | | 90 | | | | | 95 | |
| Phe | Phe | His | Arg | Leu | Glu | Glu | Ser | Phe | Leu | Val | Glu | Glu | Asp | Lys | Lys |
| | | | 100 | | | | | 105 | | | | | 110 | | |
| His | Glu | Arg | His | Pro | Ile | Phe | Gly | Asn | Ile | Val | Asp | Glu | Val | Ala | Tyr |
| | | | | 115 | | | | | 120 | | | | | 125 | |
| His | Glu | Lys | Tyr | Pro | Thr | Ile | Tyr | His | Leu | Arg | Lys | Lys | Leu | Val | Asp |
| | | | 130 | | | | | 135 | | | | | 140 | | |
| Ser | Thr | Asp | Lys | Ala | Asp | Leu | Arg | Leu | Ile | Tyr | Leu | Ala | Leu | Ala | His |
| 145 | | | | | 150 | | | | | 155 | | | | | 160 |
| Met | Ile | Lys | Phe | Arg | Gly | His | Phe | Leu | Ile | Glu | Gly | Asp | Leu | Asn | Pro |
| | | | | 165 | | | | | 170 | | | | | 175 | |
| Asp | Asn | Ser | Asp | Val | Asp | Lys | Leu | Phe | Ile | Gln | Leu | Val | Gln | Thr | Tyr |
| | | | 180 | | | | | 185 | | | | | 190 | | |
| Asn | Gln | Leu | Phe | Glu | Glu | Asn | Pro | Ile | Asn | Ala | Ser | Gly | Val | Asp | Ala |
| | | | | 195 | | | | | 200 | | | | | 205 | |
| Lys | Ala | Ile | Leu | Ser | Ala | Arg | Leu | Ser | Lys | Ser | Arg | Arg | Leu | Glu | Asn |
| | | | 210 | | | | | 215 | | | | | 220 | | |
| Leu | Ile | Ala | Gln | Leu | Pro | Gly | Glu | Lys | Lys | Asn | Gly | Leu | Phe | Gly | Asn |
| 225 | | | | | 230 | | | | | 235 | | | | | 240 |
| Leu | Ile | Ala | Leu | Ser | Leu | Gly | Leu | Thr | Pro | Asn | Phe | Lys | Ser | Asn | Phe |
| | | | | 245 | | | | | 250 | | | | | 255 | |
| Asp | Leu | Ala | Glu | Asp | Ala | Lys | Leu | Gln | Leu | Ser | Lys | Asp | Thr | Tyr | Asp |
| | | | 260 | | | | | 265 | | | | | 270 | | |
| Asp | Asp | Leu | Asp | Asn | Leu | Leu | Ala | Gln | Ile | Gly | Asp | Gln | Tyr | Ala | Asp |
| | | | | 275 | | | | | 280 | | | | | 285 | |
| Leu | Phe | Leu | Ala | Ala | Lys | Asn | Leu | Ser | Asp | Ala | Ile | Leu | Leu | Ser | Asp |
| | | | 290 | | | | | 295 | | | | | 300 | | |
| Ile | Leu | Arg | Val | Asn | Thr | Glu | Ile | Thr | Lys | Ala | Pro | Leu | Ser | Ala | Ser |
| 305 | | | | | 310 | | | | | 315 | | | | | 320 |
| Met | Ile | Lys | Arg | Tyr | Asp | Glu | His | His | Gln | Asp | Leu | Thr | Leu | Leu | Lys |
| | | | | 325 | | | | | 330 | | | | | 335 | |
| Ala | Leu | Val | Arg | Gln | Gln | Leu | Pro | Glu | Lys | Tyr | Lys | Glu | Ile | Phe | Phe |
| | | | 340 | | | | | 345 | | | | | 350 | | |
| Asp | Gln | Ser | Lys | Asn | Gly | Tyr | Ala | Gly | Tyr | Ile | Asp | Gly | Gly | Ala | Ser |
| | | | | 355 | | | | | 360 | | | | | 365 | |
| Gln | Glu | Glu | Phe | Tyr | Lys | Phe | Ile | Lys | Pro | Ile | Leu | Glu | Lys | Met | Asp |
| | | | 370 | | | | | 375 | | | | | 380 | | |
| Gly | Thr | Glu | Glu | Leu | Leu | Val | Lys | Leu | Asn | Arg | Glu | Asp | Leu | Leu | Arg |

```
             385                 390                 395                 400
Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                    420                 425                 430

Leu Lys Asp Asn Arg Glu Lys Ile Glu Lys Ile Leu Thr Phe Arg Ile
                    435                 440                 445

Pro Tyr Tyr Val Gly Pro Leu Ala Arg Gly Asn Ser Arg Phe Ala Trp
                    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                    500                 505                 510

Leu Leu Tyr Glu Tyr Phe Thr Val Tyr Asn Glu Leu Thr Lys Val Lys
                    515                 520                 525

Tyr Val Thr Glu Gly Met Arg Lys Pro Ala Phe Leu Ser Gly Glu Gln
                    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                    580                 585                 590

Thr Tyr His Asp Leu Leu Lys Ile Ile Lys Asp Lys Asp Phe Leu Asp
                    595                 600                 605

Asn Glu Glu Asn Glu Asp Ile Leu Glu Asp Ile Val Leu Thr Leu Thr
                    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
                    660                 665                 670

Lys Gln Ser Gly Lys Thr Ile Leu Asp Phe Leu Lys Ser Asp Gly Phe
                    675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                    740                 745                 750

Arg His Lys Pro Glu Asn Ile Val Ile Glu Met Ala Arg Glu Asn Gln
                    755                 760                 765

Thr Thr Gln Lys Gly Gln Lys Asn Ser Arg Glu Arg Met Lys Arg Ile
                    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                    805                 810                 815
```

-continued

```
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
            835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
            1010                1015                1020
Lys Ser Glu Gln Glu Ile Gly Lys Ala Thr Ala Lys Tyr Phe Phe
            1025                1030                1035
Tyr Ser Asn Ile Met Asn Phe Phe Lys Thr Glu Ile Thr Leu Ala
            1040                1045                1050
Asn Gly Glu Ile Arg Lys Arg Pro Leu Ile Glu Thr Asn Gly Glu
            1055                1060                1065
Thr Gly Glu Ile Val Trp Asp Lys Gly Arg Asp Phe Ala Thr Val
            1070                1075                1080
Arg Lys Val Leu Ser Met Pro Gln Val Asn Ile Val Lys Lys Thr
            1085                1090                1095
Glu Val Gln Thr Gly Gly Phe Ser Lys Glu Ser Ile Leu Pro Lys
            1100                1105                1110
Arg Asn Ser Asp Lys Leu Ile Ala Arg Lys Lys Asp Trp Asp Pro
            1115                1120                1125
Lys Lys Tyr Gly Gly Phe Asp Ser Pro Thr Val Ala Tyr Ser Val
            1130                1135                1140
Leu Val Val Ala Lys Val Glu Lys Gly Lys Ser Lys Lys Leu Lys
            1145                1150                1155
Ser Val Lys Glu Leu Leu Gly Ile Thr Ile Met Glu Arg Ser Ser
            1160                1165                1170
Phe Glu Lys Asn Pro Ile Asp Phe Leu Glu Ala Lys Gly Tyr Lys
            1175                1180                1185
Glu Val Lys Lys Asp Leu Ile Ile Lys Leu Pro Lys Tyr Ser Leu
            1190                1195                1200
Phe Glu Leu Glu Asn Gly Arg Lys Arg Met Leu Ala Ser Ala Gly
            1205                1210                1215
```

Glu Leu Gln Lys Gly Asn Glu Leu Ala Leu Pro Ser Lys Tyr Val
1220              1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 206
<211> LENGTH: 1334
<212> TYPE: PRT
<213> ORGANISM: Listeria monocytogenes

<400> SEQUENCE: 206

Met Lys Asn Pro Tyr Thr Ile Gly Leu Asp Ile Gly Thr Asn Ser
1               5                   10                  15

Gly Trp Ala Val Leu Thr Asn Gln Tyr Asp Leu Val Lys Arg Lys Met
            20                  25                  30

Lys Val Ala Gly Asn Ser Asp Lys Lys Gln Ile Lys Lys Asn Phe Trp
        35                  40                  45

Gly Val Arg Leu Phe Asp Asp Gly Gln Thr Ala Val Asp Arg Arg Met
    50                  55                  60

Asn Arg Thr Ala Arg Arg Arg Ile Glu Arg Arg Asn Arg Ile Ser
65                  70                  75                  80

Tyr Leu Gln Glu Ile Phe Ala Val Glu Met Ala Asn Ile Asp Ala Asn
                85                  90                  95

Phe Phe Cys Arg Leu Asn Asp Ser Phe Tyr Val Asp Ser Glu Lys Arg
            100                 105                 110

Asn Ser Arg His Pro Phe Phe Ala Thr Ile Glu Glu Glu Val Ala Tyr
        115                 120                 125

His Lys Asn Tyr Arg Thr Ile Tyr His Leu Arg Glu Glu Leu Val Asn
    130                 135                 140

Ser Ser Glu Lys Ala Asp Leu Arg Leu Val Tyr Leu Ala Leu Ala His
145                 150                 155                 160

Ile Ile Lys Tyr Arg Gly Asn Phe Leu Ile Glu Gly Ala Leu Asp Thr
                165                 170                 175

Lys Asn Thr Ser Val Asp Gly Val Tyr Glu Gln Phe Ile Gln Thr Tyr
            180                 185                 190

Asn Gln Val Phe Met Ser Asn Ile Glu Glu Gly Thr Leu Ala Lys Val
        195                 200                 205

Glu Glu Asn Ile Glu Val Ala Asn Ile Leu Ala Gly Lys Phe Thr Arg
    210                 215                 220

```
Arg Glu Lys Phe Glu Arg Ile Leu Gln Leu Tyr Pro Gly Glu Lys Ser
225                 230                 235                 240

Thr Gly Met Phe Ala Gln Phe Ile Ser Leu Ile Val Gly Ser Lys Gly
            245                 250                 255

Asn Phe Gln Lys Val Phe Asp Leu Ile Glu Lys Thr Asp Ile Glu Cys
        260                 265                 270

Ala Lys Asp Ser Tyr Glu Glu Asp Leu Glu Ala Leu Leu Ala Ile Ile
    275                 280                 285

Gly Asp Glu Tyr Ala Glu Leu Phe Val Ala Ala Lys Asn Thr Tyr Asn
290                 295                 300

Ala Val Val Leu Ser Ser Ile Ile Thr Val Thr Ala Thr Glu Thr Asn
305                 310                 315                 320

Ala Lys Leu Ser Ala Ser Met Ile Glu Arg Phe Asp Ala His Glu Lys
            325                 330                 335

Asp Leu Gly Glu Leu Lys Ala Phe Ile Lys Leu His Leu Pro Lys Gln
        340                 345                 350

Tyr Gln Glu Ile Phe Asn Asn Ala Ala Ile Asp Gly Tyr Ala Gly Tyr
    355                 360                 365

Ile Asp Gly Lys Thr Lys Gln Val Asp Phe Tyr Lys Tyr Leu Lys Thr
370                 375                 380

Ile Leu Glu Asn Ile Glu Gly Ala Asp Tyr Phe Ile Ala Lys Ile Glu
385                 390                 395                 400

Glu Glu Asn Phe Leu Arg Lys Gln Arg Thr Phe Asp Asn Gly Ala Ile
            405                 410                 415

Pro His Gln Leu His Leu Glu Glu Leu Glu Ala Ile Ile His Gln Gln
        420                 425                 430

Ala Lys Tyr Tyr Pro Phe Leu Arg Glu Asp Tyr Glu Lys Ile Lys Ser
    435                 440                 445

Leu Val Thr Phe Arg Ile Pro Tyr Phe Val Gly Pro Leu Ala Lys Gly
450                 455                 460

Gln Ser Glu Phe Ala Trp Leu Thr Arg Lys Ala Asp Gly Glu Ile Arg
465                 470                 475                 480

Pro Trp Asn Ile Glu Glu Lys Val Asp Phe Gly Lys Ser Ala Val Asp
            485                 490                 495

Phe Ile Glu Lys Met Thr Asn Lys Asp Thr Tyr Leu Pro Lys Glu Asn
        500                 505                 510

Val Leu Pro Lys His Ser Leu Cys Tyr Gln Lys Tyr Met Val Tyr Asn
    515                 520                 525

Glu Leu Thr Lys Val Arg Tyr Ile Asp Asp Gln Gly Lys Thr Asn Tyr
530                 535                 540

Phe Ser Gly Gln Glu Lys Gln Gln Ile Phe Asn Asp Leu Phe Lys Gln
545                 550                 555                 560

Lys Arg Lys Val Lys Lys Asp Leu Glu Leu Phe Leu Arg Asn Ile
            565                 570                 575

Asn His Ile Glu Ser Pro Thr Ile Glu Gly Leu Glu Asp Ser Phe Asn
        580                 585                 590

Ala Ser Tyr Ala Thr Tyr His Asp Leu Leu Lys Val Gly Met Lys Gln
    595                 600                 605

Glu Ile Leu Asp Asn Pro Leu Asn Thr Glu Met Leu Glu Asp Ile Val
610                 615                 620

Lys Ile Leu Thr Val Phe Glu Asp Lys Pro Met Ile Lys Glu Gln Leu
625                 630                 635                 640
```

-continued

Gln Gln Phe Ser Asp Val Leu Asp Gly Gly Val Leu Lys Lys Leu Glu
            645                 650                 655

Arg Arg His Tyr Thr Gly Trp Gly Arg Leu Ser Ala Lys Leu Leu Val
            660                 665                 670

Gly Ile Arg Glu Lys Gln Ser His Leu Thr Ile Leu Asp Tyr Leu Met
            675                 680                 685

Asn Asp Asp Gly Leu Asn Arg Asn Leu Met Gln Leu Ile Asn Asp Ser
            690                 695                 700

Asn Leu Ser Phe Lys Ser Ile Ile Glu Lys Glu Gln Val Ser Thr Thr
705                 710                 715                 720

Asp Lys Asp Leu Gln Ser Ile Val Ala Asp Leu Ala Gly Ser Pro Ala
            725                 730                 735

Ile Lys Lys Gly Ile Leu Gln Ser Leu Lys Ile Val Asp Glu Leu Val
            740                 745                 750

Ser Ile Met Gly Tyr Pro Pro Gln Thr Ile Val Val Glu Met Ala Arg
            755                 760                 765

Glu Asn Gln Thr Thr Gly Lys Gly Lys Asn Asn Ser Lys Pro Arg Tyr
            770                 775                 780

Lys Ser Leu Glu Lys Ala Ile Lys Glu Phe Gly Ser Lys Ile Leu Lys
785                 790                 795                 800

Glu His Pro Thr Asp Asn Gln Glu Leu Lys Asn Asn Arg Leu Tyr Leu
            805                 810                 815

Tyr Tyr Leu Gln Asn Gly Lys Asp Met Tyr Thr Gly Gln Glu Leu Asp
            820                 825                 830

Ile His Asn Leu Ser Asn Tyr Asp Ile Asp His Ile Val Pro Gln Ser
            835                 840                 845

Phe Ile Thr Asp Asn Ser Ile Asp Asn Leu Val Leu Thr Ser Ser Ala
            850                 855                 860

Gly Asn Arg Glu Lys Gly Gly Asp Val Pro Pro Leu Glu Ile Val Arg
865                 870                 875                 880

Lys Arg Lys Val Phe Trp Glu Lys Leu Tyr Gln Gly Asn Leu Met Ser
            885                 890                 895

Lys Arg Lys Phe Asp Tyr Leu Thr Lys Ala Glu Arg Gly Gly Leu Thr
            900                 905                 910

Asp Ala Asp Lys Ala Arg Phe Ile His Arg Gln Leu Val Glu Thr Arg
            915                 920                 925

Gln Ile Thr Lys Asn Val Ala Asn Ile Leu His Gln Arg Phe Asn Asn
            930                 935                 940

Glu Thr Asp Asn His Gly Asn Thr Met Glu Gln Val Arg Ile Val Thr
945                 950                 955                 960

Leu Lys Ser Ala Leu Val Ser Gln Phe Arg Lys Gln Phe Gln Leu Tyr
            965                 970                 975

Lys Val Arg Glu Val Asn Asp Tyr His His Ala His Asp Ala Tyr Leu
            980                 985                 990

Asn Gly Val Val Ala Asn Thr Leu Leu Lys Val Tyr Pro Gln Leu Glu
            995                 1000                1005

Pro Glu Phe Val Tyr Gly Glu Tyr His Gln Phe Asp Trp Phe Lys
            1010                1015                1020

Ala Asn Lys Ala Thr Ala Lys Lys Gln Phe Tyr Thr Asn Ile Met
            1025                1030                1035

Leu Phe Phe Gly Gln Lys Glu Arg Ile Ile Asp Glu Asn Gly Glu
            1040                1045                1050

Ile Leu Trp Asp Lys Lys Tyr Leu Glu Thr Ile Lys Lys Val Leu

```
                1055                1060                1065

Asp Tyr Arg Gln Met Asn Ile Val Lys Lys Thr Glu Ile Gln Lys
        1070                1075                1080

Gly Glu Phe Ser Lys Ala Thr Ile Lys Pro Lys Gly Asn Ser Ser
    1085                1090                1095

Lys Leu Ile Pro Arg Lys Glu Asn Trp Asp Pro Met Lys Tyr Gly
1100                1105                1110

Gly Leu Asp Ser Pro Asn Met Ala Tyr Ala Val Ile Ile Glu His
        1115                1120                1125

Ala Lys Gly Lys Lys Leu Ile Phe Glu Lys Lys Ile Ile Arg
    1130                1135                1140

Ile Thr Ile Met Glu Arg Lys Met Phe Glu Lys Asp Glu Glu Ala
1145                1150                1155

Phe Leu Glu Glu Lys Gly Tyr Arg His Pro Lys Val Leu Thr Lys
        1160                1165                1170

Leu Pro Lys Tyr Thr Leu Tyr Glu Cys Glu Lys Gly Arg Arg Arg
    1175                1180                1185

Met Leu Ala Ser Ala Asn Glu Ala Gln Lys Gly Asn Gln Leu Val
1190                1195                1200

Leu Ser Asn His Leu Val Ser Leu Leu Tyr His Ala Lys Asn Cys
        1205                1210                1215

Glu Ala Ser Asp Gly Lys Ser Leu Lys Tyr Ile Glu Ala His Arg
    1220                1225                1230

Glu Thr Phe Ser Glu Leu Leu Ala Gln Val Ser Glu Phe Ala Thr
1235                1240                1245

Arg Tyr Thr Leu Ala Asp Ala Asn Leu Ser Lys Ile Asn Asn Leu
        1250                1255                1260

Phe Glu Gln Asn Lys Glu Gly Asp Ile Gln Ala Ile Ala Gln Ser
    1265                1270                1275

Phe Val Asp Leu Met Ala Phe Asn Ala Met Gly Ala Pro Ala Ser
1280                1285                1290

Phe Lys Phe Phe Glu Ala Thr Ile Asp Arg Lys Arg Tyr Thr Asn
        1295                1300                1305

Leu Lys Glu Leu Leu Ser Ser Thr Ile Ile Tyr Gln Ser Ile Thr
    1310                1315                1320

Gly Leu Tyr Glu Ser Arg Lys Arg Leu Asp Asp
1325                1330

<210> SEQ ID NO 207
<211> LENGTH: 1334
<212> TYPE: PRT
<213> ORGANISM: Listeria monocytogenes

<400> SEQUENCE: 207

Met Lys Asn Pro Tyr Thr Ile Gly Leu Asp Ile Gly Thr Asn Ser Val
1               5                   10                  15

Gly Trp Ala Val Leu Thr Asn Gln Tyr Asp Leu Val Lys Arg Lys Met
            20                  25                  30

Lys Val Ala Gly Asn Ser Asp Lys Lys Gln Ile Lys Lys Asn Phe Trp
        35                  40                  45

Gly Val Arg Leu Phe Asp Asp Gly Gln Thr Ala Val Asp Arg Arg Met
    50                  55                  60

Asn Arg Thr Ala Arg Arg Arg Ile Glu Arg Arg Arg Asn Arg Ile Ser
65                  70                  75                  80
```

-continued

```
Tyr Leu Gln Glu Ile Phe Ala Val Glu Met Ala Asn Ile Asp Ala Asn
                 85                  90                  95

Phe Phe Cys Arg Leu Asn Asp Ser Phe Tyr Val Asp Ser Glu Lys Arg
            100                 105                 110

Asn Ser Arg His Pro Phe Phe Ala Thr Ile Glu Glu Val Ala Tyr
        115                 120                 125

His Asp Asn Tyr Arg Thr Ile Tyr His Leu Arg Glu Lys Leu Val Asn
    130                 135                 140

Ser Ser Glu Lys Ala Asp Leu Arg Leu Val Tyr Leu Ala Leu Ala His
145                 150                 155                 160

Ile Ile Lys Tyr Arg Gly Asn Phe Leu Ile Glu Gly Ala Leu Asp Thr
                165                 170                 175

Lys Asn Thr Ser Val Asp Glu Val Tyr Lys Gln Phe Ile Glu Thr Tyr
            180                 185                 190

Asn Gln Val Phe Met Ser Asn Ile Glu Glu Gly Ala Leu Ala Lys Val
        195                 200                 205

Glu Glu Asn Ile Glu Val Ala Asn Ile Leu Ala Gly Lys Phe Thr Arg
    210                 215                 220

Arg Glu Lys Phe Glu Arg Ile Leu Gln Leu Tyr Pro Gly Glu Lys Ser
225                 230                 235                 240

Thr Gly Met Phe Ala Gln Phe Ile Ser Leu Ile Val Gly Ser Lys Gly
                245                 250                 255

Asn Phe Gln Lys Val Phe Asp Leu Ile Glu Lys Thr Asp Ile Glu Cys
            260                 265                 270

Ala Lys Asp Ser Tyr Glu Glu Asp Leu Glu Thr Leu Leu Ala Ile Ile
        275                 280                 285

Gly Asp Glu Tyr Ala Glu Leu Phe Val Ala Ala Lys Asn Thr Tyr Asn
    290                 295                 300

Ala Val Val Leu Ser Ser Ile Ile Thr Val Thr Asp Thr Glu Thr Asn
305                 310                 315                 320

Ala Lys Leu Ser Ala Ser Met Ile Glu Arg Phe Asp Ala His Glu Lys
                325                 330                 335

Asp Leu Val Glu Leu Lys Ala Phe Ile Lys Leu Asn Leu Pro Lys Gln
            340                 345                 350

Tyr Glu Glu Ile Phe Ser Asn Ala Ala Ile Asp Gly Tyr Ala Gly Tyr
        355                 360                 365

Ile Asp Gly Lys Thr Lys Gln Val Asp Phe Tyr Lys Tyr Leu Lys Thr
    370                 375                 380

Ile Leu Glu Asn Ile Glu Gly Ser Asp Tyr Phe Ile Ala Lys Ile Glu
385                 390                 395                 400

Glu Glu Asn Phe Leu Arg Lys Gln Arg Thr Phe Asp Asn Gly Ala Ile
                405                 410                 415

Pro His Gln Leu His Leu Glu Glu Leu Glu Ala Ile Ile His Gln Gln
            420                 425                 430

Ala Lys Tyr Tyr Pro Phe Leu Lys Glu Asp Tyr Asp Lys Ile Lys Ser
        435                 440                 445

Leu Val Thr Phe Arg Ile Pro Tyr Phe Val Gly Pro Leu Ala Asn Gly
    450                 455                 460

Gln Ser Glu Phe Ala Trp Leu Thr Arg Lys Ala Asp Gly Glu Ile Arg
465                 470                 475                 480

Pro Trp Asn Ile Glu Glu Lys Val Asp Phe Gly Lys Ser Ala Val Asp
                485                 490                 495

Phe Ile Glu Lys Met Thr Asn Lys Asp Thr Tyr Leu Pro Lys Glu Asn
```

-continued

```
                500             505             510
Val Leu Pro Lys His Ser Leu Cys Tyr Gln Lys Tyr Met Val Tyr Asn
            515                 520             525

Glu Leu Thr Lys Ile Arg Tyr Ile Asp Asp Gln Gly Lys Thr Asn Tyr
            530                 535             540

Phe Ser Gly Arg Glu Lys Gln Gln Val Phe Asn Asp Leu Phe Lys Gln
545                 550                 555                 560

Lys Arg Lys Val Lys Lys Asp Leu Glu Leu Phe Leu Arg Asn Ile
                565                 570                 575

Asn His Ile Glu Ser Pro Thr Ile Glu Gly Leu Glu Asp Ser Phe Asn
            580                 585                 590

Ala Ser Tyr Ala Thr Tyr His Asp Leu Leu Lys Val Gly Met Lys Gln
            595                 600                 605

Glu Ile Leu Asp Asn Pro Leu Asn Thr Glu Met Leu Glu Asp Ile Val
            610                 615                 620

Lys Ile Leu Thr Val Phe Glu Asp Lys Pro Met Ile Lys Glu Gln Leu
625                 630                 635                 640

Gln Gln Phe Ser Asp Val Leu Asp Gly Gly Val Leu Lys Lys Leu Glu
                645                 650                 655

Arg Arg His Tyr Thr Gly Trp Gly Arg Leu Ser Ala Lys Leu Leu Val
            660                 665                 670

Gly Ile Arg Glu Lys Gln Ser His Leu Thr Ile Leu Asp Tyr Leu Met
            675                 680                 685

Asn Asp Asp Gly Leu Asn Arg Asn Leu Met Gln Leu Ile Asn Asp Ser
            690                 695                 700

Asn Leu Ser Phe Lys Ser Ile Ile Glu Lys Glu Gln Val Ser Thr Thr
705                 710                 715                 720

Asp Lys Asp Leu Gln Ser Ile Val Ala Glu Leu Ala Gly Ser Pro Ala
                725                 730                 735

Ile Lys Lys Gly Ile Leu Gln Ser Leu Lys Ile Val Asp Glu Leu Val
                740                 745                 750

Ser Ile Met Gly Tyr Pro Pro Gln Thr Ile Val Val Glu Met Ala Arg
            755                 760                 765

Glu Asn Gln Thr Thr Gly Lys Gly Lys Asn Asn Ser Lys Pro Arg Tyr
            770                 775                 780

Lys Ser Leu Glu Lys Ala Ile Lys Glu Phe Gly Ser Gln Ile Leu Lys
785                 790                 795                 800

Glu His Pro Thr Asp Asn Gln Glu Leu Lys Asn Asn Arg Leu Tyr Leu
            805                 810                 815

Tyr Tyr Leu Gln Asn Gly Lys Asp Met Tyr Thr Gly Gln Glu Leu Asp
            820                 825                 830

Ile His Asn Leu Ser Asn Tyr Asp Ile Asp His Ile Val Pro Gln Ser
            835                 840                 845

Phe Ile Thr Asp Asn Ser Ile Asp Asn Leu Val Leu Thr Ser Ser Ala
            850                 855                 860

Gly Asn Arg Glu Lys Gly Gly Asp Val Pro Pro Leu Glu Ile Val Arg
865                 870                 875                 880

Lys Arg Lys Val Phe Trp Glu Lys Leu Tyr Gln Gly Asn Leu Met Ser
                885                 890                 895

Lys Arg Lys Phe Asp Tyr Leu Thr Lys Ala Glu Arg Gly Gly Leu Thr
                900                 905                 910

Glu Ala Asp Lys Ala Arg Phe Ile His Arg Gln Leu Val Glu Thr Arg
            915                 920                 925
```

```
Gln Ile Thr Lys Asn Val Ala Asn Ile Leu Tyr Gln Arg Phe Asn Lys
    930                 935                 940

Glu Thr Asp Asn His Gly Asn Thr Met Glu Gln Val Arg Ile Val Thr
945                 950                 955                 960

Leu Lys Ser Ala Leu Val Ser Gln Phe Arg Lys Gln Phe Gln Leu Tyr
                965                 970                 975

Lys Val Arg Glu Val Asn Gly Tyr His His Ala His Asp Ala Tyr Leu
                980                 985                 990

Asn Gly Val Val Ala Asn Thr Leu Leu Lys Val Tyr Pro Gln Leu Glu
            995                 1000                1005

Pro Glu Phe Val Tyr Gly Tyr His Gln Phe Asp Trp Phe Lys
    1010                1015                1020

Ala Asn Lys Ala Thr Ala Lys Lys Gln Phe Tyr Thr Asn Ile Met
    1025                1030                1035

Leu Phe Phe Ala Gln Lys Glu Arg Ile Ile Asp Glu Asn Gly Glu
    1040                1045                1050

Ile Leu Trp Asp Lys Lys Tyr Leu Glu Thr Ile Lys Lys Val Leu
    1055                1060                1065

Asp Tyr Arg Gln Met Asn Ile Val Lys Lys Thr Glu Ile Gln Lys
    1070                1075                1080

Gly Glu Phe Ser Lys Ala Thr Ile Lys Pro Lys Gly Asn Ser Ser
    1085                1090                1095

Lys Leu Ile Pro Arg Lys Glu Asn Trp Asp Pro Met Lys Tyr Gly
    1100                1105                1110

Gly Leu Asp Ser Pro Asn Met Ala Tyr Ala Val Ile Ile Glu His
    1115                1120                1125

Ala Lys Gly Lys Lys Ile Val Ile Glu Lys Lys Leu Ile Gln
    1130                1135                1140

Ile Asn Ile Met Glu Arg Lys Met Phe Glu Lys Asp Glu Glu Ala
    1145                1150                1155

Phe Leu Glu Glu Lys Gly Tyr Arg His Pro Lys Val Leu Thr Lys
    1160                1165                1170

Leu Pro Lys Tyr Thr Leu Tyr Glu Cys Glu Lys Gly Arg Arg Arg
    1175                1180                1185

Met Leu Ala Ser Ala Asn Glu Ala Gln Lys Gly Asn Gln Leu Val
    1190                1195                1200

Leu Ser Asn His Leu Val Ser Leu Leu Tyr His Ala Lys Asn Cys
    1205                1210                1215

Glu Ala Ser Asp Gly Lys Ser Leu Lys Tyr Ile Glu Ala His Arg
    1220                1225                1230

Glu Thr Phe Ser Glu Leu Leu Ala Gln Val Ser Glu Phe Ala Thr
    1235                1240                1245

Arg Tyr Thr Leu Ala Asp Ala Asn Leu Ser Lys Ile Asn Asn Leu
    1250                1255                1260

Phe Glu Gln Asn Lys Glu Gly Asp Ile Lys Ala Ile Ala Gln Ser
    1265                1270                1275

Phe Val Asp Leu Met Ala Phe Asn Ala Met Gly Ala Pro Ala Ser
    1280                1285                1290

Phe Lys Phe Phe Glu Ala Thr Ile Asp Arg Lys Arg Tyr Thr Asn
    1295                1300                1305

Leu Lys Glu Leu Leu Ser Ser Thr Ile Ile Tyr Gln Ser Ile Thr
    1310                1315                1320
```

-continued

```
Gly Leu Tyr Glu Ser Arg Lys  Arg Leu Asp Asp
    1325                1330
```

<210> SEQ ID NO 208
<211> LENGTH: 1334
<212> TYPE: PRT
<213> ORGANISM: Listeria innocua

<400> SEQUENCE: 208

```
Met Lys Lys Pro Tyr Thr Ile Gly Leu Asp Ile Gly Thr Asn Ser Val
1               5                   10                  15

Gly Trp Ala Val Leu Thr Asp Gln Tyr Asp Leu Val Lys Arg Lys Met
            20                  25                  30

Lys Ile Ala Gly Asp Ser Glu Lys Gln Ile Lys Lys Asn Phe Trp
        35                  40                  45

Gly Val Arg Leu Phe Asp Glu Gly Gln Thr Ala Ala Asp Arg Arg Met
    50                  55                  60

Ala Arg Thr Ala Arg Arg Arg Ile Glu Arg Arg Arg Asn Arg Ile Ser
65              70                  75                  80

Tyr Leu Gln Gly Ile Phe Ala Glu Glu Met Ser Lys Thr Asp Ala Asn
                85                  90                  95

Phe Phe Cys Arg Leu Ser Asp Ser Phe Tyr Val Asp Asn Glu Lys Arg
            100                 105                 110

Asn Ser Arg His Pro Phe Phe Ala Thr Ile Glu Glu Val Glu Tyr
        115                 120                 125

His Lys Asn Tyr Pro Thr Ile Tyr His Leu Arg Glu Glu Leu Val Asn
    130                 135                 140

Ser Ser Glu Lys Ala Asp Leu Arg Leu Val Tyr Leu Ala Leu Ala His
145             150                 155                 160

Ile Ile Lys Tyr Arg Gly Asn Phe Leu Ile Glu Gly Ala Leu Asp Thr
                165                 170                 175

Gln Asn Thr Ser Val Asp Gly Ile Tyr Lys Gln Phe Ile Gln Thr Tyr
            180                 185                 190

Asn Gln Val Phe Ala Ser Gly Ile Glu Asp Gly Ser Leu Lys Lys Leu
        195                 200                 205

Glu Asp Asn Lys Asp Val Ala Lys Ile Leu Val Glu Lys Val Thr Arg
    210                 215                 220

Lys Glu Lys Leu Glu Arg Ile Leu Lys Leu Tyr Pro Gly Glu Lys Ser
225             230                 235                 240

Ala Gly Met Phe Ala Gln Phe Ile Ser Leu Ile Val Gly Ser Lys Gly
                245                 250                 255

Asn Phe Gln Lys Pro Phe Asp Leu Ile Glu Lys Ser Asp Ile Glu Cys
            260                 265                 270

Ala Lys Asp Ser Tyr Glu Glu Asp Leu Glu Ser Leu Leu Ala Leu Ile
        275                 280                 285

Gly Asp Glu Tyr Ala Glu Leu Phe Val Ala Ala Lys Asn Ala Tyr Ser
    290                 295                 300

Ala Val Val Leu Ser Ser Ile Ile Thr Val Ala Glu Thr Glu Thr Asn
305             310                 315                 320

Ala Lys Leu Ser Ala Ser Met Ile Glu Arg Phe Asp Thr His Glu Glu
                325                 330                 335

Asp Leu Gly Glu Leu Lys Ala Phe Ile Lys Leu His Leu Pro Lys His
            340                 345                 350

Tyr Glu Glu Ile Phe Ser Asn Thr Glu Lys His Gly Tyr Ala Gly Tyr
        355                 360                 365
```

```
Ile Asp Gly Lys Thr Lys Gln Ala Asp Phe Tyr Lys Tyr Met Lys Met
    370                 375                 380

Thr Leu Glu Asn Ile Glu Gly Ala Asp Tyr Phe Ile Ala Lys Ile Glu
385                 390                 395                 400

Lys Glu Asn Phe Leu Arg Lys Gln Arg Thr Phe Asp Asn Gly Ala Ile
                405                 410                 415

Pro His Gln Leu His Leu Glu Glu Leu Glu Ala Ile Leu His Gln Gln
            420                 425                 430

Ala Lys Tyr Tyr Pro Phe Leu Lys Glu Asn Tyr Asp Lys Ile Lys Ser
        435                 440                 445

Leu Val Thr Phe Arg Ile Pro Tyr Phe Val Gly Pro Leu Ala Asn Gly
    450                 455                 460

Gln Ser Glu Phe Ala Trp Leu Thr Arg Lys Ala Asp Gly Glu Ile Arg
465                 470                 475                 480

Pro Trp Asn Ile Glu Glu Lys Val Asp Phe Gly Lys Ser Ala Val Asp
                485                 490                 495

Phe Ile Glu Lys Met Thr Asn Lys Asp Thr Tyr Leu Pro Lys Glu Asn
            500                 505                 510

Val Leu Pro Lys His Ser Leu Cys Tyr Gln Lys Tyr Leu Val Tyr Asn
        515                 520                 525

Glu Leu Thr Lys Val Arg Tyr Ile Asn Asp Gln Gly Lys Thr Ser Tyr
    530                 535                 540

Phe Ser Gly Gln Glu Lys Glu Gln Ile Phe Asn Asp Leu Phe Lys Gln
545                 550                 555                 560

Lys Arg Lys Val Lys Lys Asp Leu Glu Leu Phe Leu Arg Asn Met
                565                 570                 575

Ser His Val Glu Ser Pro Thr Ile Glu Gly Leu Glu Asp Ser Phe Asn
            580                 585                 590

Ser Ser Tyr Ser Thr Tyr His Asp Leu Leu Lys Val Gly Ile Lys Gln
        595                 600                 605

Glu Ile Leu Asp Asn Pro Val Asn Thr Glu Met Leu Glu Asn Ile Val
    610                 615                 620

Lys Ile Leu Thr Val Phe Glu Asp Lys Arg Met Ile Lys Glu Gln Leu
625                 630                 635                 640

Gln Gln Phe Ser Asp Val Leu Asp Gly Val Val Leu Lys Lys Leu Glu
                645                 650                 655

Arg Arg His Tyr Thr Gly Trp Gly Arg Leu Ser Ala Lys Leu Leu Met
            660                 665                 670

Gly Ile Arg Asp Lys Gln Ser His Leu Thr Ile Leu Asp Tyr Leu Met
        675                 680                 685

Asn Asp Asp Gly Leu Asn Arg Asn Leu Met Gln Leu Ile Asn Asp Ser
    690                 695                 700

Asn Leu Ser Phe Lys Ser Ile Ile Glu Lys Glu Gln Val Thr Thr Ala
705                 710                 715                 720

Asp Lys Asp Ile Gln Ser Ile Val Ala Asp Leu Ala Gly Ser Pro Ala
                725                 730                 735

Ile Lys Lys Gly Ile Leu Gln Ser Leu Lys Ile Val Asp Glu Leu Val
            740                 745                 750

Ser Val Met Gly Tyr Pro Pro Gln Thr Ile Val Val Glu Met Ala Arg
        755                 760                 765

Glu Asn Gln Thr Thr Gly Lys Gly Lys Asn Asn Ser Arg Pro Arg Tyr
    770                 775                 780
```

```
Lys Ser Leu Glu Lys Ala Ile Lys Glu Phe Gly Ser Gln Ile Leu Lys
785                 790                 795                 800

Glu His Pro Thr Asp Asn Gln Glu Leu Arg Asn Asn Arg Leu Tyr Leu
            805                 810                 815

Tyr Tyr Leu Gln Asn Gly Lys Asp Met Tyr Thr Gly Gln Asp Leu Asp
            820                 825                 830

Ile His Asn Leu Ser Asn Tyr Asp Ile Asp His Ile Val Pro Gln Ser
            835                 840                 845

Phe Ile Thr Asp Asn Ser Ile Asp Asn Leu Val Leu Thr Ser Ser Ala
850                 855                 860

Gly Asn Arg Glu Lys Gly Asp Asp Val Pro Pro Leu Glu Ile Val Arg
865                 870                 875                 880

Lys Arg Lys Val Phe Trp Glu Lys Leu Tyr Gln Gly Asn Leu Met Ser
            885                 890                 895

Lys Arg Lys Phe Asp Tyr Leu Thr Lys Ala Glu Arg Gly Gly Leu Thr
            900                 905                 910

Glu Ala Asp Lys Ala Arg Phe Ile His Arg Gln Leu Val Glu Thr Arg
            915                 920                 925

Gln Ile Thr Lys Asn Val Ala Asn Ile Leu His Gln Arg Phe Asn Tyr
930                 935                 940

Glu Lys Asp Asp His Gly Asn Thr Met Lys Gln Val Arg Ile Val Thr
945                 950                 955                 960

Leu Lys Ser Ala Leu Val Ser Gln Phe Arg Lys Gln Phe Gln Leu Tyr
            965                 970                 975

Lys Val Arg Asp Val Asn Asp Tyr His His Ala His Asp Ala Tyr Leu
            980                 985                 990

Asn Gly Val Val Ala Asn Thr Leu Leu Lys Val Tyr Pro Gln Leu Glu
            995                 1000                1005

Pro Glu Phe Val Tyr Gly Asp Tyr His Gln Phe Asp Trp Phe Lys
1010                1015                1020

Ala Asn Lys Ala Thr Ala Lys Lys Gln Phe Tyr Thr Asn Ile Met
1025                1030                1035

Leu Phe Phe Ala Gln Lys Asp Arg Ile Ile Asp Glu Asn Gly Glu
1040                1045                1050

Ile Leu Trp Asp Lys Lys Tyr Leu Asp Thr Val Lys Lys Val Met
1055                1060                1065

Ser Tyr Arg Gln Met Asn Ile Val Lys Lys Thr Glu Ile Gln Lys
1070                1075                1080

Gly Glu Phe Ser Lys Ala Thr Ile Lys Pro Lys Gly Asn Ser Ser
1085                1090                1095

Lys Leu Ile Pro Arg Lys Thr Asn Trp Asp Pro Met Lys Tyr Gly
1100                1105                1110

Gly Leu Asp Ser Pro Asn Met Ala Tyr Ala Val Val Ile Glu Tyr
1115                1120                1125

Ala Lys Gly Lys Asn Lys Leu Val Phe Glu Lys Lys Ile Ile Arg
1130                1135                1140

Val Thr Ile Met Glu Arg Lys Ala Phe Glu Lys Asp Glu Lys Ala
1145                1150                1155

Phe Leu Glu Glu Gln Gly Tyr Arg Gln Pro Lys Val Leu Ala Lys
1160                1165                1170

Leu Pro Lys Tyr Thr Leu Tyr Glu Cys Glu Glu Gly Arg Arg Arg
1175                1180                1185

Met Leu Ala Ser Ala Asn Glu Ala Gln Lys Gly Asn Gln Gln Val
```

```
                        1190                 1195                 1200
Leu Pro Asn His Leu Val Thr Leu Leu His His Ala Ala Asn Cys
    1205                 1210                 1215

Glu Val Ser Asp Gly Lys Ser Leu Asp Tyr Ile Glu Ser Asn Arg
    1220                 1225                 1230

Glu Met Phe Ala Glu Leu Leu Ala His Val Ser Glu Phe Ala Lys
    1235                 1240                 1245

Arg Tyr Thr Leu Ala Glu Ala Asn Leu Asn Lys Ile Asn Gln Leu
    1250                 1255                 1260

Phe Glu Gln Asn Lys Glu Gly Asp Ile Lys Ala Ile Ala Gln Ser
    1265                 1270                 1275

Phe Val Asp Leu Met Ala Phe Asn Ala Met Gly Ala Pro Ala Ser
    1280                 1285                 1290

Phe Lys Phe Phe Glu Thr Thr Ile Glu Arg Lys Arg Tyr Asn Asn
    1295                 1300                 1305

Leu Lys Glu Leu Leu Asn Ser Thr Ile Ile Tyr Gln Ser Ile Thr
    1310                 1315                 1320

Gly Leu Tyr Glu Ser Arg Lys Arg Leu Asp Asp
    1325                 1330

<210> SEQ ID NO 209
<211> LENGTH: 132
<212> TYPE: PRT
<213> ORGANISM: Unknown
<220> FEATURE:
<223> OTHER INFORMATION: Unknown bacterial, unknown viral (phage), or
      synthetic Cas9-inhibiting polypeptide

<400> SEQUENCE: 209

Met Gly Met Thr Thr Ala Arg Lys Lys Phe Tyr Gln Ala Ile Ser Glu
1               5                   10                  15

Phe Glu Ala Met Thr Gly Lys Asp Val Glu Arg Thr Pro Gln Ile Ala
                20                  25                  30

Asp Glu Val Leu Asn Asp Ala Glu Tyr Ile Ala Phe Thr Lys Thr Glu
            35                  40                  45

Lys Tyr Ala Leu Tyr Leu Cys Thr Ser Asn Val Glu Gly Leu Glu Asp
    50                  55                  60

Arg Tyr Phe Leu Asp Glu Glu Cys Leu Asp Ser Thr Phe Leu Glu Thr
65                  70                  75                  80

Glu Asp Asn Glu Thr Tyr Tyr Ile His Phe Leu Gln Glu Thr Glu Phe
                85                  90                  95

Ser Glu Asp Asn Glu Asp Glu Leu Pro Leu Ala Thr Glu Glu Gln
            100                 105                 110

Ile Glu Ala Tyr Asp Lys Gln Glu Glu Leu Lys Ala Val Ile Leu Lys
        115                 120                 125

Lys Glu Leu Asn
    130
```